(12) United States Patent
Luckow et al.

(10) Patent No.: US 12,630,844 B2
(45) Date of Patent: May 19, 2026

(54) HEPATITIS E VIRUS-LIKE PARTICLES (VLPS) DERIVED FROM CONSENSUS SEQUENCES

(71) Applicant: Novo Capsid Technologies LLC, Carmichael, CA (US)

(72) Inventors: Verne A. Luckow, Chesterfield, MO (US); Chun-Chieh Chen, Rocklin, CA (US); David Hedin, Carmichael, CA (US)

(73) Assignee: Novo Capsid Technologies LLC, Carmichael, CA (US)

( * ) Notice: Subject to any disclaimer, the term of this patent is extended or adjusted under 35 U.S.C. 154(b) by 0 days.

(21) Appl. No.: 18/970,024

(22) Filed: Dec. 5, 2024

(65) Prior Publication Data
US 2025/0236885 A1     Jul. 24, 2025

Related U.S. Application Data

(60) Provisional application No. 63/609,538, filed on Dec. 13, 2023.

(51) Int. Cl.
| | |
|---|---|
| *C12N 15/86* | (2006.01) |
| *C07K 14/005* | (2006.01) |
| *C07K 14/08* | (2006.01) |
| *C12N 7/00* | (2006.01) |
| *C12N 7/02* | (2006.01) |
| *C12N 15/11* | (2006.01) |

(52) U.S. Cl.
CPC .............. *C12N 15/86* (2013.01); *C07K 14/08* (2013.01); *C12N 7/02* (2013.01); *C12N 15/11* (2013.01); *C12N 2710/14041* (2013.01); *C12N 2770/28041* (2013.01); *C12N 2799/026* (2013.01)

(58) Field of Classification Search
None
See application file for complete search history.

(56) References Cited

U.S. PATENT DOCUMENTS

| | | | |
|---|---|---|---|
| 8,906,863 | B2 | 12/2014 | Cheng et al. |
| 2012/0064169 | A1 | 3/2012 | Cheng et al. |
| 2017/0107261 | A1 | 4/2017 | Cheng et al. |
| 2021/0038697 | A1 | 2/2021 | Cheng et al. |
| 2023/0159959 | A1 | 5/2023 | Zhang et al. |

FOREIGN PATENT DOCUMENTS

| | | | | |
|---|---|---|---|---|
| CN | 112292150 | A | * 1/2021 | .............. C12N 7/00 |
| WO | 2015/179321 | A3 | 11/2015 | |

OTHER PUBLICATIONS

Li TC, Suzaki Y, Ami Y, Dhole TN, Miyamura T, Takeda N. Protection of cynomolgus monkeys against HEV infection by oral administration of recombinant hepatitis E virus-like particles. Vaccine. Jan. 2, 2004;22(3-4):370-7. doi: 10.1016/j.vaccine.2003.08. 004. PMID: 14670318. (Year: 2004).*

Shi, Y, Van Der Meel, R, Chen, X, and Lammers, T (2020). "The EPR effect and beyond: Strategies to improve tumor targeting and cancer nanomedicine treatment efficacy." Theranostics 10(17): 7921-7924.

Shizuo G. Kamita, M A B, Luis M. De La Maza and R. Holland Cheng (2019). Abstract Only—A Noninvasive, Orally Stable, Mucosa-Penetrating Polyvalent Vaccine Platform Based on Hepatitis E Virus Nanoparticle.

Sievers, F, Wilm, A, Dineen, D, Gibson, T J, Karplus, K, Li, W, Lopez, R, McWilliam, H, Remmert, M, Soding, J, Thompson, J D, and Higgins, D G (2011). "Fast, scalable generation of high-quality protein multiple sequence alignments using Clustal Omega." Mol Syst Biol 7: 539.

Stark, M, and Cheng, R H (2016). "Surface modulatable nanocapsids for targeting and tracking toward nanotheranostic delivery." Pharm Pat Anal 5(5): 307-317.

Stark, M C, Baikoghli, M A, Lahtinen, T, Malola, S, Xing, L, Nguyen, M, Nguyen, M, Sikaroudi, A, Marjomaki, V, Hakkinen, H, and Cheng, R H (2017). "Structural characterization of site-modified nanocapsid with monodispersed gold clusters." Sci Rep 7(1): 17048.

Sun, X, Yan, X, Zhuo, W, Gu, J, Zuo, K, Liu, W, Liang, L, Gan, Y, He, G, Wan, H, Gou, X, Shi, H, and Hu, J (2018). "PD-L1 Nanobody Competitively Inhibits the Formation of the PD-1/PD-L1 Complex: Comparative Molecular Dynamics Simulations." Int J Mol Sci 19(7).

(Continued)

*Primary Examiner* — Anna Skibinsky
*Assistant Examiner* — Catherine L McCormick
(74) *Attorney, Agent, or Firm* — The IP Law Office of Verne A. Luckow, LLC

(57) ABSTRACT

Virus-Like Particles derived from the subfamilies, Parahepevirinae, which infect trout and salmon, and the Orthohepevirinae, which infect mammals and birds, particularly those of the species Paslahepevirus balayani, which can cause acute hepatitis in humans and several mammalian species, and chronic conditions in immunocompromised patients are also disclosed. Major aspects of the invention relate to compositions of Virus-Like Particles comprising viral capsid proteins capable of assembly in cultured cells that may be purified, disassembled, and reassembled in the presence of other molecules suitable for use as therapeutic drug products to facilitate the targeting and delivery of cargo molecules to specific cells or tissues, or as antigenic agents designed to stimulate responses to heterologous epitopes exposed on the surfaces of Virus-Like Particles. Preferred aspects relate to functional capsids comprising polypeptide sequences comprising one or more amino acid substitutions, insertions, or deletions of amino acid encoded by a consensus of ORF2 genes, wherein said variant polypeptides are functionally-similar or have enhanced properties compared to capsid polypeptides encoded by naturally-occurring viruses obtained from clinical samples or prototype Hepatitis E Viruses (HEV). Other aspects include the design and assembly of modified vectors to facilitate the basic and applied studies leading to the development and commercialization of novel drug products, and as tools advancing the interests of institutions involved in animal and human healthcare.

30 Claims, 42 Drawing Sheets

Specification includes a Sequence Listing.

(56)          References Cited

OTHER PUBLICATIONS

Takamura, S, Niikura, M, Li, T C, Takeda, N, Kusagawa, S, Takebe, Y, Miyamura, T, and Yasutomi, Y (2004). "DNA vaccine-encapsulated virus-like particles derived from an orally transmissible virus stimulate mucosal and systemic immune responses by oral administration." Gene Ther 11(7): 628-635.

Tam, A W, Smith, M M, Guerra, M E, Huang, C C, Bradley, D W, Fry, K E, and Reyes, G R (1991). "Hepatitis E virus (HEV): molecular cloning and sequencing of the full-length viral genome." Virology 185(1): 120-131.

Vargason, A M, Anselmo, A C, and Mitragotri, S (2021). "The evolution of commercial drug delivery technologies." Nat Biomed Eng 5(9): 951-967.

Wang, C Y, Miyazaki, N, Yamashita, T, Higashiura, A, Nakagawa, A, Li, T C, Takeda, N, Xing, L, Hjalmarsson, E, Friberg, C, Liou, D M, Sung, Y J, Tsukihara, T, Matsuura, Y, Miyamura, T, and Cheng, R H (2008). "Crystallization and preliminary X-ray diffraction analysis of recombinant hepatitis E virus-like particle." Acta Crystallogr Sect F Struct Biol Cryst Commun 64(Pt 4): 318-322.

Ward, K, and Fan, Z H (2015). "Mixing in microfluidic devices and enhancement methods." J Micromech Microeng 25(9).

Wu, Z, Zhuo, Z, Cai, D, Wu, J, Wang, J, and Tang, J (2015). "An induction heating device using planar coil with high amplitude alternating magnetic fields for magnetic hyperthermia." Technol Health Care 23 Suppl 2: S203-209.

Xia, W, Wang, Y, Yang, A, and Yang, G (2017). "DNA Compaction and Charge Inversion Induced by Organic Monovalent Ions." Polymers (Basel) 9(4).

Xiao, W, Li, T, Bononi, F C, Lac, D, Kekessie, I A, Liu, Y, Sanchez, E, Mazloom, A, Ma, A H, Lin, J, Tran, J, Yang, K, Lam, K S, and Liu, R (2016). "Discovery and characterization of a high-affinity and high-specificity peptide ligand LXY30 for in vivo targeting of alpha3 integrin-expressing human tumors." EJNMMI Res 6(1): 18.

Xing, L, Kato, K, Li, T, Takeda, N, Miyamura, T, Hammar, L, and Cheng, R H (1999). "Recombinant hepatitis E capsid protein self-assembles into a dual-domain T = 1 particle presenting native virus epitopes." Virology 265(1): 35-45.

Xing, L, Li, T C, Mayazaki, N, Simon, M N, Wall, J S, Moore, M, Wang, C Y, Takeda, N, Wakita, T, Miyamura, T, and Cheng, R H (2010). "Structure of hepatitis E virion-sized particle reveals an RNA-dependent viral assembly pathway." J Biol Chem 285(43): 33175-33183.

Xing, L, Wang, J C, Li, T C, Yasutomi, Y, Lara, J, Khudyakov, Y, Schofield, D, Emerson, S U, Purcell, R H, Takeda, N, Miyamura, T, and Cheng, R H (2011). "Spatial configuration of hepatitis E virus antigenic domain." J Virol 85(2): 1117-1124.

Yamashita, T, Mori, Y, Miyazaki, N, Cheng, R H, Yoshimura, M, Unno, H, Shima, R, Moriishi, K, Tsukihara, T, Li, T C, Takeda, N, Miyamura, T, and Matsuura, Y (2009). "Biological and immunological characteristics of hepatitis E virus-like particles based on the crystal structure." Proc Natl Acad Sci U S A 106(31): 12986-12991.

Yu, H, Li, S, Yang, C, Wei, M, Song, C, Zheng, Z, Gu, Y, Du, H, Zhang, J, and Xia, N (2011). "Abstract Only—Homology model and potential virus-capsid binding site of a putative HEV receptor Grp78." J Mol Model 17(5): 987-995.

Zafrullah, M, Khursheed, Z, Yadav, S, Sahgal, D, Jameel, S, and Ahmad, F (2004). "Acidic pH enhances structure and structural stability of the capsid protein of hepatitis E virus." Biochem Biophys Res Commun 313(1): 67-73.

Zeng, C, Zhang, C, Walker, P G, and Dong, Y (2022). "Formulation and Delivery Technologies for mRNA Vaccines." Curr Top Microbiol Immunol 440: 71-110.

Kim, Y S (2015). "Advances in MR image-guided high-intensity focused ultrasound therapy." Int J Hyperthermia 31 (3): 225-232.

Kitts, P A, Ayres, M D, and Possee, R D (1990). "Linearization of baculovirus DNA enhances the recovery of recombinant virus expression vectors." Nucleic Acids Res 18(19): 5667-5672.

Kosheleva, O K, Lai, T C, Chen, N G, Hsiao, M, and Chen, C H (2016). "Selective killing of cancer cells by nanoparticle-assisted ultrasound." J Nanobiotechnology 14(1): 46.

Lambidis, E, Chen, C C, Baikoghli, M, Imlimthan, S, Khng, Y C, Sarparanta, M, Cheng, R H, and Airaksinen, A J (2022). "Development of (68)Ga-Labeled Hepatitis E Virus Nanoparticles for Targeted Drug Delivery and Diagnostics with PET." Mol Pharm 19(8): 2971-2979.

Lambidis, E, Chen, C C, Lumen, D, Sanchez, A I F, Sarparanta, M, Cheng, R H, and Airaksinen, A J (2023). "Biological evaluation of integrin alpha(3)beta(1)-targeted (68)Ga-labeled HEVNPs in HCT 116 colorectal tumor-bearing mice." Eur J Pharm Sci 180: 106336.

Li, T C, Suzaki, Y, Ami, Y, Dhole, T N, Miyamura, T, and Takeda, N (2004). "Abstract Only—Protection of cynomolgus monkeys against HEV infection by oral administration of recombinant hepatitis E virus-like particles." Vaccine 22(3-4): 370-377.

Li, T C, Takeda, N, Miyamura, T, Matsuura, Y, Wang, J C, Engvall, H, Hammar, L, Xing, L, and Cheng, R H (2005). "Essential elements of the capsid protein for self-assembly into empty virus-like particles of hepatitis E virus." J Virol 79(20): 12999-13006.

Li, T C, Yamakawa, Y, Suzuki, K, Tatsumi, M, Razak, M A, Uchida, T, Takeda, N, and Miyamura, T (1997). "Expression and self-assembly of empty virus-like particles of hepatitis E virus." J Virol 71(10): 7207-7213.

Luckow, V A, Lee, S C, Barry, G F, and Olins, P O (1993). "Efficient generation of infectious recombinant baculoviruses by site-specific transposon-mediated insertion of foreign genes into a baculovirus genome propagated in *Escherichia coli*." J Virol 67(8): 4566-4579.

Ludwig, C, and Wagner, R (2007). "Virus-like particles-universal molecular toolboxes." Curr Opin Biotechnol 18 (6): 537-545.

Ma, Y, Nolte, R J, and Cornelissen, J J (2012). "Abstract Only—Virus-based nanocarriers for drug delivery." Adv Drug Deliv Rev 64(9): 811-825.

McIntire, J J, Umetsu, S E, Macaubas, C, Hoyte, E G, Cinnioglu, C, Cavalli-Sforza, L L, Barsh, G S, Hallmayer, J F, Underhill, P A, Risch, N J, Freeman, G J, Dekruyff, R H, and Umetsu, D T (2003). "Abstract Only—Immunology: hepatitis A virus link to atopic disease." Nature 425(6958): 576.

Mulvania, T, Hayes, B, and Hedin, D (2004). "A flow cytometric assay for rapid, accurate determination of baculovirus titers." BioProcessing journal 3(3): 47.

Ndeupen, S, Qin, Z, Jacobsen, S, Estanbouli, H, Bouteau, A, and Igyarto, B Z (2021). "The mRNA-LNP platform's lipid nanoparticle component used in preclinical vaccine studies is highly inflammatory." bioRxiv.

Niikura, M, Takamura, S, Kim, G, Kawai, S, Saijo, M, Morikawa, S, Kurane, I, Li, T C, Takeda, N, and Yasutomi, Y (2002). "Chimeric recombinant hepatitis E virus-like particles as an oral vaccine vehicle presenting foreign epitopes." Virology 293(2): 273-280.

Nilsson, J, Miyazaki, N, Xing, L, Wu, B, Hammar, L, Li, T C, Takeda, N, Miyamura, T, and Cheng, R H (2005). "Structure and assembly of a T=1 virus-like particle in BK polyomavirus." J Virol 79(9): 5337-5345.

Olsen, H B, Leuenberger-Fisher, M R, Kadima, W, Borchardt, D, Kaarsholm, N C, and Dunn, M F (2003). "Structural signatures of the complex formed between 3-nitro-4-hydroxybenzoate and the Zn(II)-substituted R (6) insulin hexamer." Protein Sci 12(9): 1902-1913.

O'Reilly, D R, Miller, L K, and Luckow, V A (1994). Baculovirus expression vectors: a laboratory manual, Oxford University Press.\.

Panda, S K, Kapur, N, Paliwal, D, and Durgapal, H (2015). "Recombinant Hepatitis E virus like particles can function as RNA nanocarriers." J Nanobiotechnology 13: 44.

Peyret, H (2015). "A protocol for the gentle purification of virus-like particles produced in plants." J Virol Methods 225: 59-63.

Possee, R D, Chambers, A C, Graves, L P, Aksular, M, and King, L A (2019). "Recent developments in the use of baculovirus expression vectors." Current Issues in Molecular Biology 34(1): 215-230.

52. Purcell, R H (1996). Hepatitis E virus. Fields Virology: 2831-2843. Unavailable.

R. Holland Cheng, C-C C, Mohammad Ali Baikoghli (2017). Mucosal Delivery of Macromolecules to Target Metabolic Disorders. UC Case No. 2018-316. Unavailable.

Richaud, A D, Zhao, G, Hobloss, S, and Roche, S P (2021). "Folding in Place: Design of beta-Strap Motifs to Stabilize the Folding of Hairpins with Long Loops." J Org Chem 86(19): 13535-13547.

(56)            References Cited

OTHER PUBLICATIONS

Roemer, R B (1999). "Abstract Only—Engineering aspects of hyperthermia therapy." Annu Rev Biomed Eng 1: 347-376.

Roy, P, and Noad, R (2012). "Use of bacterial artificial chromosomes in baculovirus research and recombinant protein expression: current trends and future perspectives." ISRN Microbiol 2012: 628797.

Russell, L M, Hultz, M, and Searson, P C (2018). "Leakage kinetics of the liposomal chemotherapeutic agent Doxil: The role of dissolution, protonation, and passive transport, and implications for mechanism of action." J Control Release 269: 171-176.

Schofield, D J, Glamann, J, Emerson, S U, and Purcell, R H (2000). "Identification by phage display and characterization of two neutralizing chimpanzee monoclonal antibodies to the hepatitis E virus capsid protein." J Virol 74(12): 5548-5555.

Sebestik, J, Niederhafner, P, and Jezek, J (2011). "Abstract Only—Peptide and glycopeptide dendrimers and analogous dendrimeric structures and their biomedical applications." Amino Acids 40(2): 301-370.

Serkova, N J (2017). "Nanoparticle-Based Magnetic Resonance Imaging on Tumor-Associated Macrophages and Inflammation." Front Immunol 8: 590.

Anselmo, A C, and Mitragotri, S (2016). "Nanoparticles in the clinic." Bioeng Transl Med 1(1): 10-29.

Anselmo, A C, and Mitragotri, S (2021). "Nanoparticles in the clinic: An update post COVID-19 vaccines." Bioeng Transl Med 6(3): e10246.

Attar, M M, and Haghpanahi, M (2016). "Abstract Only—Effect of heat dissipation of superparamagnetic nanoparticles in alternating magnetic field on three human cancer cell lines in magnetic fluid hyperthermia." Electromagn Biol Med 35(4): 305-320.

Barr, S M, Keck, K, and Aposhian, H V (1979). "Abstract Only—Cell-free assembly of a polyoma-like particle from empty capsids and DNA." Virology 96(2): 656-659.

Buehler, D C, Marsden, M D, Shen, S, Toso, D B, Wu, X, Loo, J A, Zhou, Z H, Kickhoefer, V A, Wender, P A, Zack, J A, and Rome, L H (2014). "Bioengineered vaults: self-assembling protein shell-lipophilic core nanoparticles for drug delivery." ACS Nano 8(8): 7723-7732.

Cassim, S M, Giustini, A J, Baker, I, and Hoopes, P J (2011). "Development of Novel Magnetic Nanoparticles for Hyperthermia Cancer Therapy." Proc SPIE Int Soc Opt Eng 7901: 790115.

Chen, C C, Baikoghli, M A, and Cheng, R H (2018). "Tissue targeted nanocapsids for oral insulin delivery via drink." Pharm Pat Anal 7(3): 121-127.

Chen, C C, Baikoghli, M A, and Cheng, R H (2021). "Protein-based nanoplatform for detection of tumorigenic polyps in the colon via noninvasive mucosal routes." Pharm Pat Anal 10(1): 13-24.

Chen, C C, Stark, M, Baikoghli, M, and Cheng, R H (2018). "Surface Functionalization of Hepatitis E Virus Nanoparticles Using Chemical Conjugation Methods." J Vis Exp(135).

Cheng, R (2017). "Hepatitis E Virus Nanoparticle Encapsulating Nano-Theranostic Reagent as Modularized Capsule." Adv. Res. Gastroenterol. Hepatol 5(555674.10): 19080.

Cheng, R H (2017). "Hepatitis E Virus Nanoparticle Encapsulating Nano-Theranostic Reagent as Modularized Capsule." Advanced Research in Gastroenterology & Hepatology 5(5): 555674.

Devarakonda, S B, Myers, M R, and Banerjee, R K (2018). "Comparison of Heat Transfer Enhancement Between Magnetic and Gold Nanoparticles During HIFU Sonication." J Biomech Eng 140(8).

Devarakonda, S B, Myers, M R, Giridhar, D, Dibaji, S A, and Banerjee, R K (2017). "Enhanced thermal effect using magnetic nano-particles during high-intensity focused ultrasound." PLoS One 12(4): e0175093.

Devarakonda, S B, Myers, M R, Lanier, M, Dumoulin, C, and Banerjee, R K (2017). "Assessment of Gold Nanoparticle-Mediated-Enhanced Hyperthermia Using MR-Guided High-Intensity Focused Ultrasound Ablation Procedure." Nano Lett 17(4): 2532-2538.

Espinosa, A, Di Corato, R, Kolosnjaj-Tabi, J, Flaud, P, Pellegrino, T, and Wilhelm, C (2016). "Abstract Only—Duality of Iron Oxide Nanoparticles in Cancer Therapy: Amplification of Heating Efficiency by Magnetic Hyperthermia and Photothermal Bimodal Treatment." ACS Nano 10(2): 2436-2446.

Fath-Goodin, A, Kroemer, J, Martin, S, Reeves, K, and Webb, B A (2006). "Abstract Only—Polydnavirus genes that enhance the baculovirus expression vector system." Adv Virus Res 68: 75-90.

Galaway, F A, and Stockley, P G (2013). "Abstract Only—MS2 viruslike particles: a robust, semisynthetic targeted drug delivery platform." Mol Pharm 10(1): 59-68.

Guu, T S, Liu, Z, Ye, Q, Mata, D A, Li, K, Yin, C, Zhang, J, and Tao, Y J (2009). "Structure of the hepatitis E virus-like particle suggests mechanisms for virus assembly and receptor binding." Proc Natl Acad Sci U S A 106(31): 12992-12997.

Holla, P, Baikoghli, M A, Soonsawad, P, and Cheng, R H (2017). Toward Mucosal DNA Delivery: Structural Modularity in Vaccine Platform Design. Micro and Nanotechnology in Vaccine Development. Skwarczynski, M., and Toth, I., William Andrew Publishing: 303-326.

Hughes, K A, Misra, B, Maghareh, M, and Bobbala, S (2023). "Use of stimulatory responsive soft nanoparticles for intracellular drug delivery." Nano Res 16(5): 6974-6990.

Ito, A, Honda, H, and Kobayashi, T (2006). "Cancer immunotherapy based on intracellular hyperthermia using magnetite nanoparticles: a novel concept of "heat-controlled necrosis" with heat shock protein expression." Cancer Immunol Immunother 55(3): 320-328.

Ito, A, Shinkai, M, Honda, H, Yoshikawa, K, Saga, S, Wakabayashi, T, Yoshida, J, and Kobayashi, T (2003). "Heat shock protein 70 expression induces antitumor immunity during intracellular hyperthermia using magnetite nanoparticles." Cancer Immunol Immunother 52(2): 80-88.

Jariyapong, P, Xing, L, Van Houten, Ne, Li, T C, Weerachatyanukul, W, Hsieh, B, Moscoso, C G, Chen, C C, Niikura, M, and Cheng, R H (2013). "Chimeric hepatitis E virus-like particle as a carrier for oral-delivery." Vaccine 31(2): 417-424.

Jeong, T-J, Lee, H-T, Gu, N, Jang, Y-J, Choi, S-B, Park, U-B, Lee, S-H, and Heo, Y-S (2022) "The High-Resolution Structure Reveals Remarkable Similarity in PD-1 Binding of Cemiplimab and Dostarlimab, the FDA-Approved Antibodies for Cancer Immunotherapy." Biomedicines 10 DOI: 10.3390/biomedicines 10123154.

Jian, F, Zhang, Y, Wang, J, Ba, K, Mao, R, Lai, W, and Lin, Y (2012). "Abstract Only—Toxicity of biodegradable nanoscale preparations." Curr Drug Metab 13(4): 440-446.

Kaba, S A, Salcedo, A M, Wafula, P O, Vlak, J M, and Van Oers, M M (2004). "Abstract Only—Development of a chitinase and v-cathepsin negative bacmid for improved integrity of secreted recombinant proteins." J Virol Methods 122(1): 113-118.

Kaczmarek, K, Hornowski, T, Dobosz, B, and Jozefczak, A (2018). "Influence of Magnetic Nanoparticles on the Focused Ultrasound Hyperthermia." Materials (Basel) 11(9).

Kaur, P, Aliru, M L, Chadha, A S, Asea, A, and Krishnan, S (2016). "Hyperthermia using nanoparticles—Promises and pitfalls." Int J Hyperthermia 32(1): 76-88.

Kawano, M, Xing, L, Lam, K S, Handa, H, Miyamura, T, Barnett, S, Srivastava, I K, and Cheng, R H (2011). Abstract Only—Design Platforms of Nanocapsules for Human Therapeutics or Vaccines. Development of Vaccines, John Wiley & Sons, Inc.: 125-139.

PCT International Searching Authority (2025). Invitation to pay additional fees under PCT Article 17(3)(a) and Rules 40.1 and 40.2(e).

PCT Search report (Written Opinion of the ISA) for PCT/US2025/058707 mailed Jun. 27, 2025.

Cancela et al (2023) Epidemiology of Hepatitis E Virus (HEV) in Uruguay: Subtyping, Environmental Surveillance and Zoonotic Transmission. Viruses 15:2006 (13 pages).

Aye TT, Uchida T, Max, Iida F, Shikata T, Ichikawa M, Rikihisa T, Win KM. (1993) Sequence and gene structure of the hepatitis E virus isolated from Myanmar. Virus genes. Feb. 1993;7(1):95-109.

Albert W. Tam, Matthew M. Smith, Martha E. Guerra, Chiao-Chain Huang, Daniel W. Bradley*, Kirk E. Fry, and Gregory R. Reyes' Hepatitis E Virus (HEV): Molecular Cloning and Sequencing of the Full-Length Viral Genome. Virology 185, 120-131 (1991).

* cited by examiner

Classes of Therapeutic and Delivery Paradigms

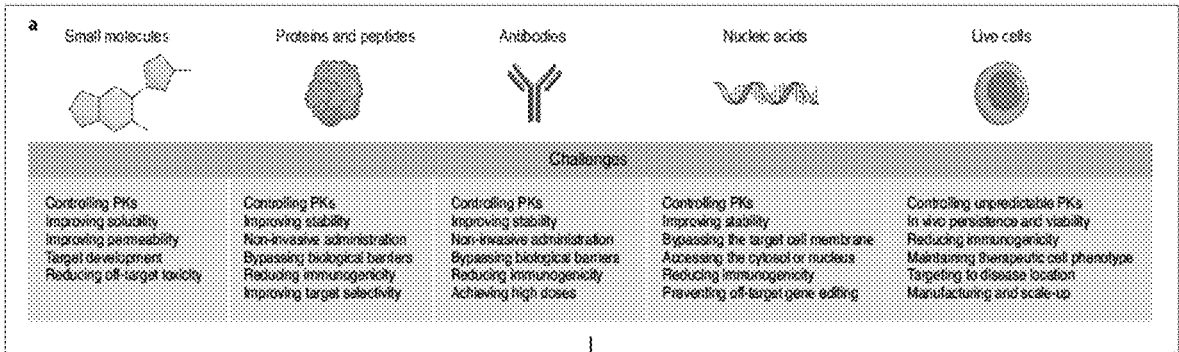

- This figure is based on Vargason (2021).
- Pharmacokinetics (PK) relates to studies of how an organism affects a drug product, such as the uptake of a drug product by the body, their biotransformation as substrates into other products, the distribution of drug products and their metabolites in tissues, and elimination of the drugs and their metabolites from the body over a period of time.
- Pharmacodynamics (PD) relates to studies of how a drug product affects an organism.
- Data from PK and PD model systems both influence decisions concerning dosing, benefit, and adverse effects of compositions comprising one or more drug products.

Fig. 1

Crystal Structure of Hepatitis E Virus-Like Particles (HEV-VLPs) and

Ribbon Diagram of Capsid Protein Subunits

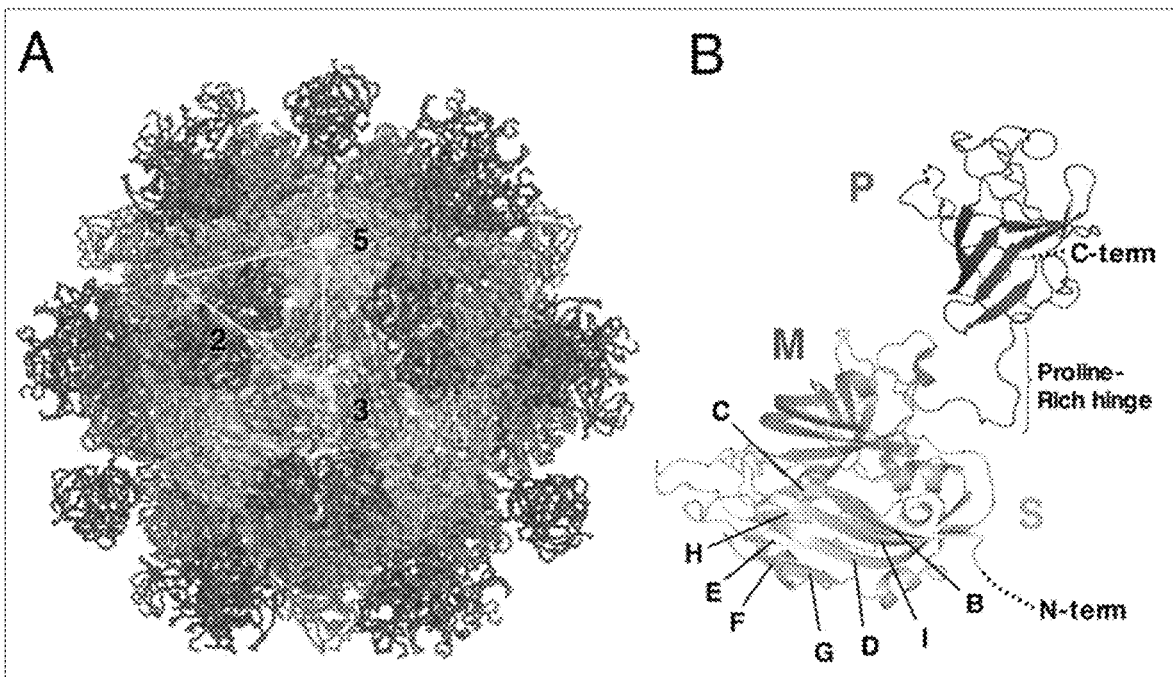

- Panel A: The S, M, and P domains of the HEV capsid protein are indicated by pink, green, and blue, respectively. (A) HEV-LP is composed of sixty capsid subunits forming icosahedral 2-, 3-, and 5-fold axes and indicating a T = 1 symmetry.
- Panel B: The ribbon diagram of a capsid subunit (PORF2) of HEV-VLP (PDB accession code: 2ZTN) shows P, M, and S domains at the top, middle, and bottom, respectively. The disordered regions are shown with dashed lines. The S domain shows a jerry roll-like beta-barrel structure.
- Both panels are based on illustrations by Yamashita et al (2009).

Fig. 2

Modifications to the Surfaces of HEV-VLPs

Encapsulation of Payloads by HEV-VLPs

Pretreatment of Expression Cells Before Purification for HEV-VLPs

That Are Not Secreted From Cultured Cells

Purification Process with Capture/Purification Steps by pH-Gradient-Based Cation Exchange Methods Purification Process with Capture/Purification Steps by Salt-Gradient-Based Ion Exchange Methods

General Process for Encapsulating Payloads in HEV-VLPs

Frequencies of Amino Acid Substitutions Considered One Position at a Time in 124 Related HEV ORF2 Capsid Sequences Used to Generate a Consensus Capsid Sequence Frequencies of Amino Acid Substitutions Considered One Position at a Time in 124 Related HEV ORF2 Capsid Sequences Used to Generate a Consensus Capsid Sequence Distances in Number of Amino Acid Changes Across 124 HEV Sequences (Green is Lower, Red is Higher)

Distances in Number of Amino Acid Changes Across 124 HEV Sequences (Green is Lower, Red is Higher)

Distances in Number of Amino Acid Changes Across 124 HEV Sequences (Green is Lower, Red is Higher)

Distances in Number of Amino Acid Changes Across 124 HEV Sequences (Green is Lower, Red is Higher)

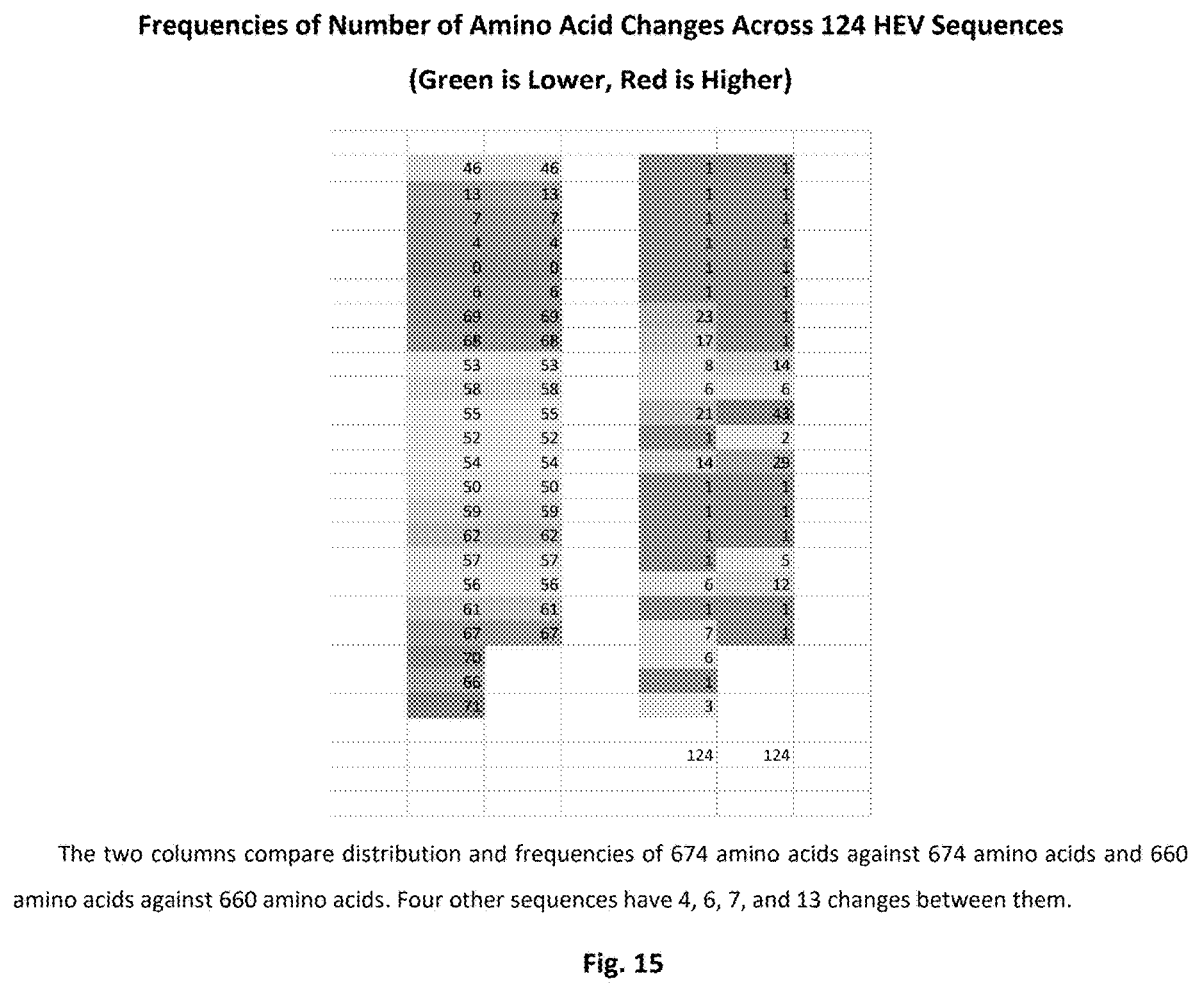

Frequencies of Number of Amino Acid Changes Across 124 HEV Sequences

(Green is Lower, Red is Higher)

The two columns compare distribution and frequencies of 674 amino acids against 674 amino acids and 660 amino acids against 660 amino acids. Four other sequences have 4, 6, 7, and 13 changes between them.

Fig. 15

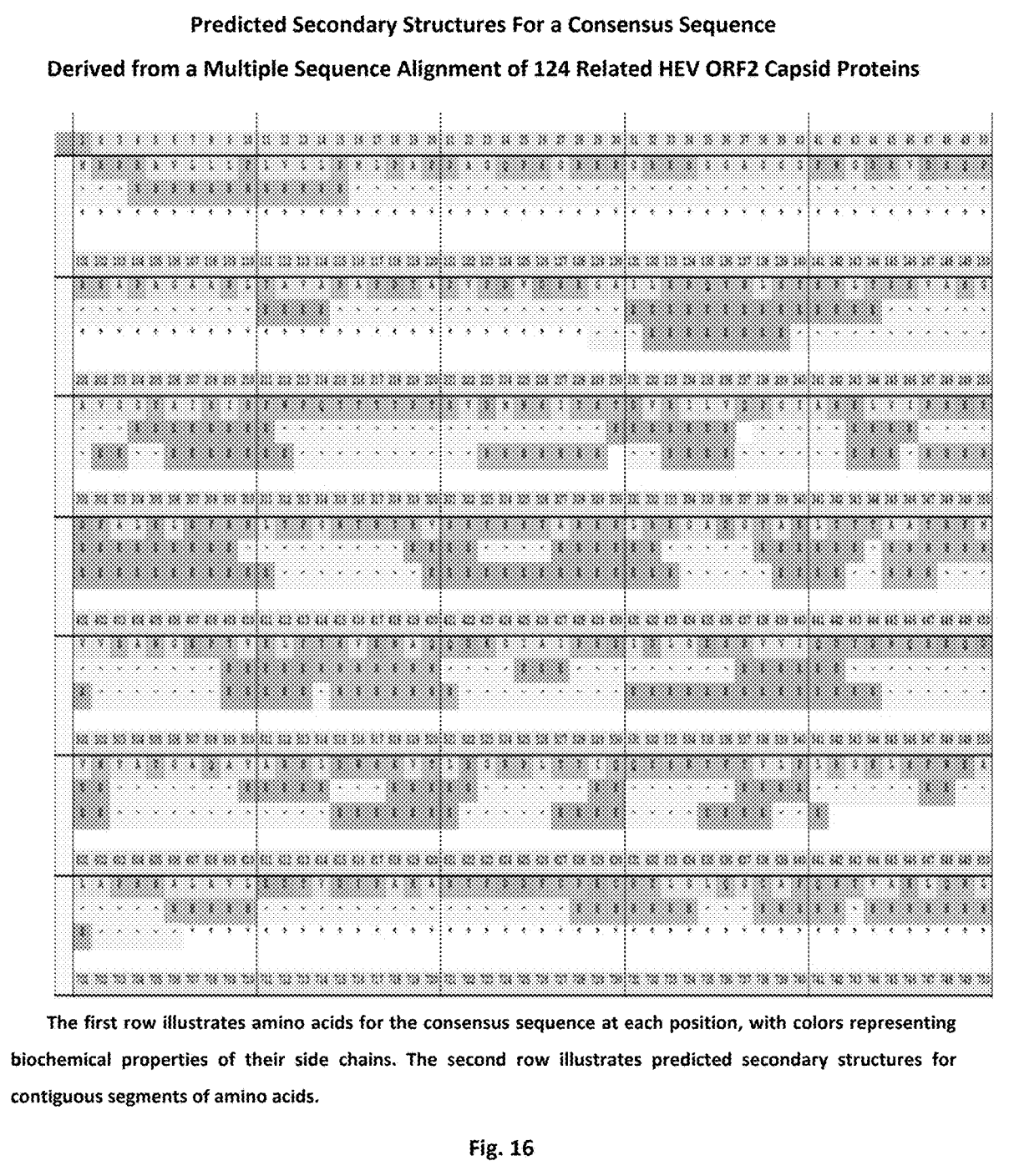

Predicted Secondary Structures For a Consensus Sequence

Derived from a Multiple Sequence Alignment of 124 Related HEV ORF2 Capsid Proteins The first row illustrates amino acids for the consensus sequence at each position, with colors representing biochemical properties of their side chains. The second row illustrates predicted secondary structures for contiguous segments of amino acids.

Fig. 16

Predicted Secondary Structures For a Consensus Sequence

Derived from a Multiple Sequence Alignment of 124 Related HEV ORF2 Capsid Proteins

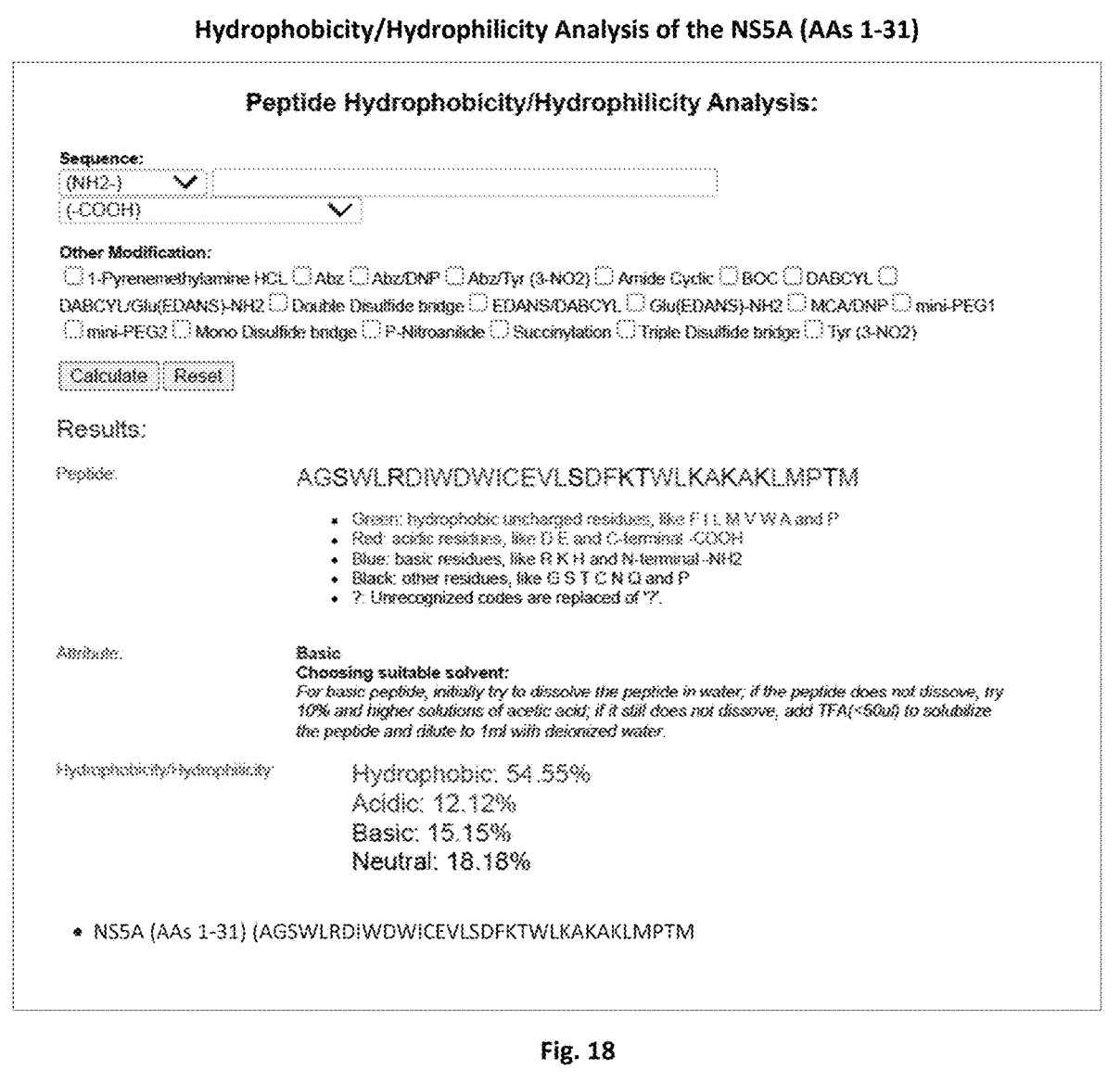

Hydrophobicity/Hydrophilicity Analysis of the NS5A (AAs 1-31)

Peptide Hydrophobicity/Hydrophilicity Analysis:

Sequence:

(NH2-) ▾

(-COOH) ▾

Other Modification:

☐ 1-Pyrenemethylamine HCL ☐ Abz ☐ Abz/DNP ☐ Abz/Tyr (3-NO2) ☐ Amide Cyclic ☐ BOC ☐ DABCYL ☐ DABCYL/Glu(EDANS)-NH2 ☐ Double Disulfide bridge ☐ EDANS/DABCYL ☐ Glu(EDANS)-NH2 ☐ MCA/DNP ☐ mini-PEG1 ☐ mini-PEG2 ☐ Mono Disulfide bridge ☐ P-Nitroanilide ☐ Succinylation ☐ Triple Disulfide bridge ☐ Tyr (3-NO2)

[ Calculate ] [ Reset ]

Results:

| | |
|---|---|
| Peptide: | AGSWLRDIWDWICEVLSDFKTWLKAKAKLMPTM |

- Green: hydrophobic uncharged residues, like F I L M V W A and P
- Red: acidic residues, like D E and C-terminal -COOH
- Blue: basic residues, like R K H and N-terminal -NH2
- Black: other residues, like G S T C N Q and P
- ?: Unrecognized codes are replaced of '?'.

Attribute:
Basic
Choosing suitable solvent:
*For basic peptide, initially try to dissolve the peptide in water; if the peptide does not dissove, try 10% and higher solutions of acetic acid; if it still does not dissove, add TFA(<50ul) to solubilize the peptide and dilute to 1ml with deionized water.*

Hydrophobicity/Hydrophilicity
Hydrophobic: 54.55%
Acidic: 12.12%
Basic: 15.15%
Neutral: 18.18%

- NS5A (AAs 1-31) (AGSWLRDIWDWICEVLSDFKTWLKAKAKLMPTM

Fig. 18

HEV ORF2 Capsid Variant With Truncated Amino and Carboxy Termini

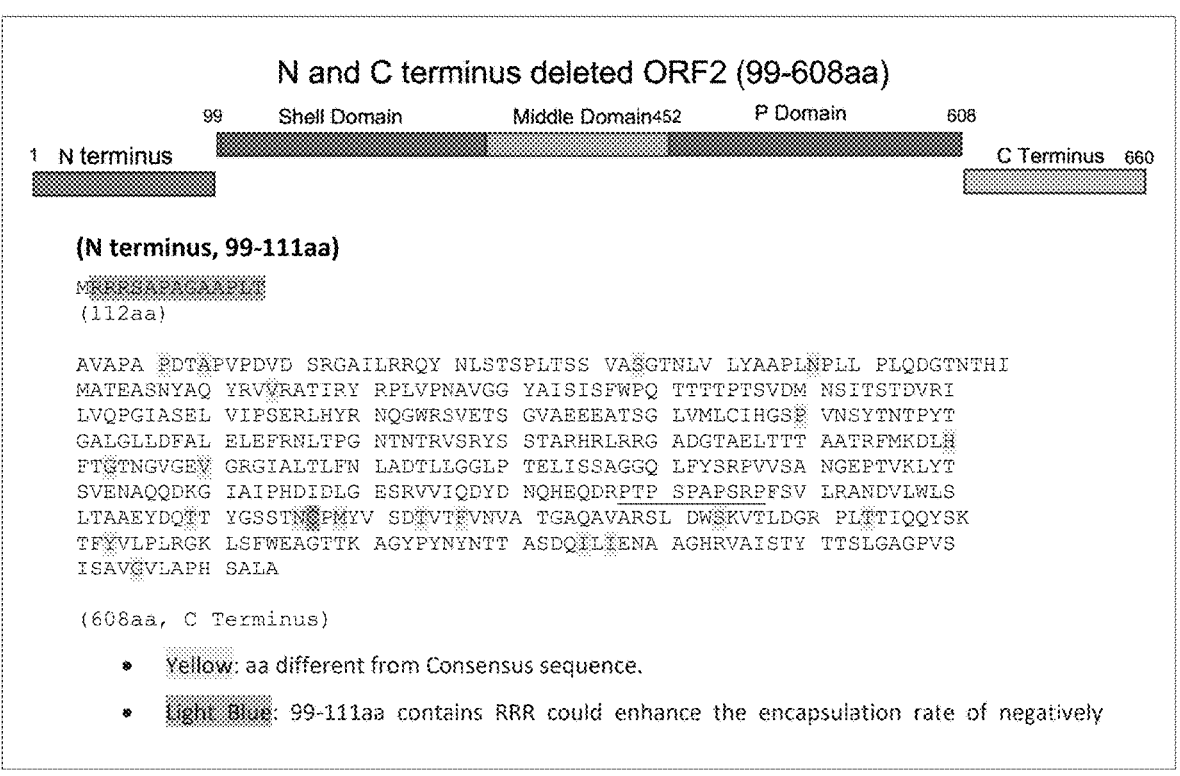

N and C terminus deleted ORF2 (99-608aa)

(N terminus, 99-111aa)

M
(112aa)

```
AVAPA PDTAPVPDVD SRGAILRRQY NLSTSPLTSS VASGTNLV LYAAPLNPLL PLQDGTNTHI
MATEASNYAQ YRVVRATIRY RPLVPNAVGG YAISISFWPQ TTTTPTSVDM NSITSTDVRI
LVQPGIASEL VIPSERLHYR NQGWRSVETS GVAEEEATSG LVMLCIHGSP VNSYTNTPYT
GALGLLDFAL ELEFRNLTPG NTNTRVSRYS STARHRLRRG ADGTAELTTT AATRFMKDLH
FTGTNGVGEY GRGIALTLFN LADTLLGGLP TELISSAGGQ LFYSRPVVSA NGEPTVKLYT
SVENAQQDKG IAIPHDIDLG ESRVVIQDYD NQHEQDRPTP SPAPSRPFSV LRANDVLWLS
LTAAEYDQT YGSSTNSPMYV SDTVTFVNVA TGAQAVARSL DWSKVTLDGR PLTTIQQYSK
TFYVLPLRGK LSFWEAGTTK AGYPYNYNTT ASDQILIENA AGHRVAISTY TTSLGAGPVS
ISAVGVLAPH SALA
```

(608aa, C Terminus)

* Yellow: aa different from Consensus sequence.

* Light Blue: 99-111aa contains RRR could enhance the encapsulation rate of negatively

Fig. 19

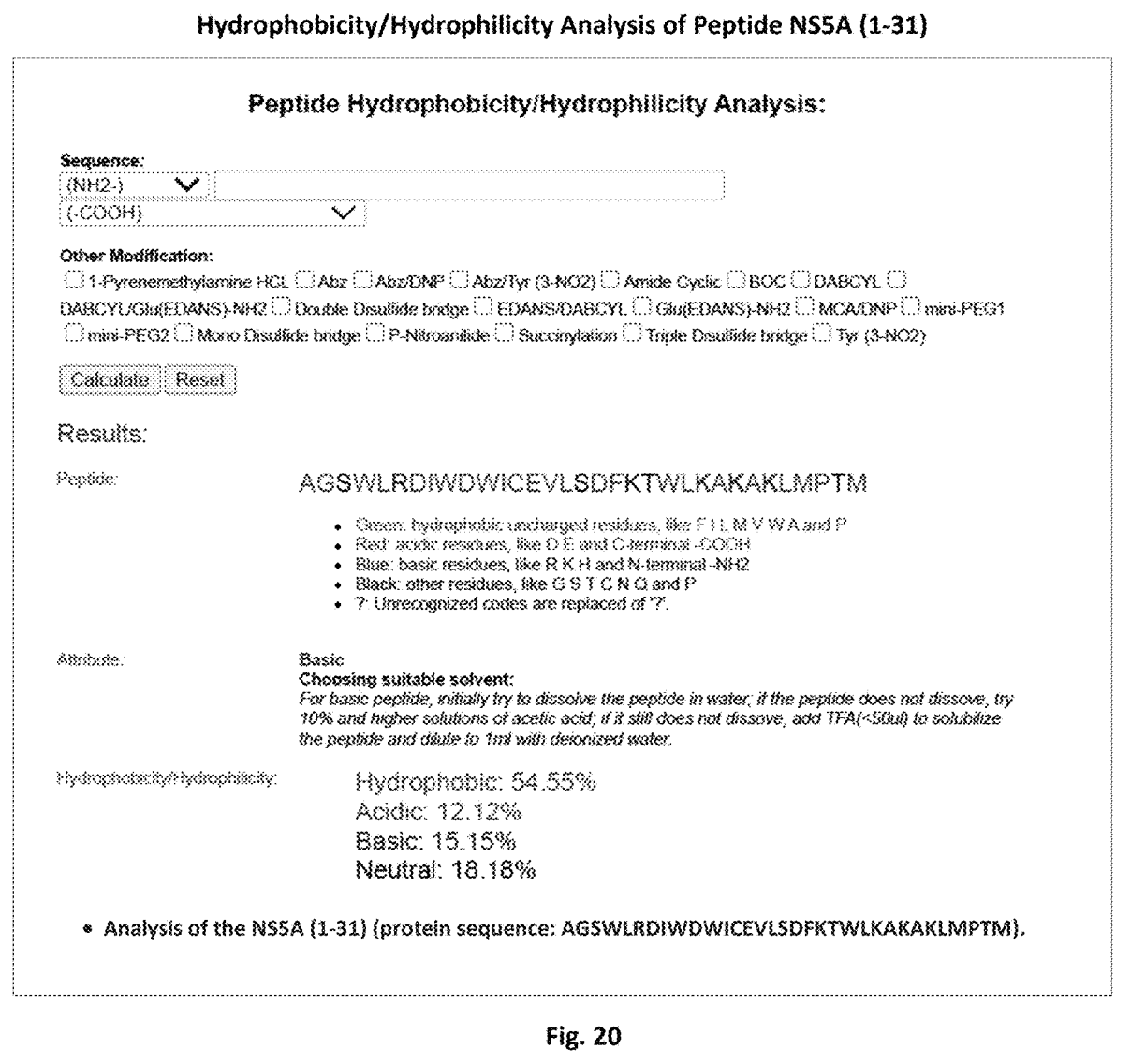

Hydrophobicity/Hydrophilicity Analysis of Peptide NS5A (1-31)

Peptide Hydrophobicity/Hydrophilicity Analysis:

Sequence:
(NH2-)

(-COOH)

Other Modification:
☐ 1-Pyrenemethylamine HCL ☐ Abz ☐ Abz/DNP ☐ Abz/Tyr (3-NO2) ☐ Amide Cyclic ☐ BOC ☐ DABCYL ☐
DABCYL/Glu(EDANS)-NH2 ☐ Double Disulfide bridge ☐ EDANS/DABCYL ☐ Glu(EDANS)-NH2 ☐ MCA/DNP ☐ mini-PEG1
☐ mini-PEG2 ☐ Mono Disulfide bridge ☐ P-Nitroanilide ☐ Succinylation ☐ Triple Disulfide bridge ☐ Tyr (3-NO2)

[ Calculate ] [ Reset ]

Results:

Peptide:
AGSWLRDIWDWICEVLSDFKTWLKAKAKLMPTM

- Green: hydrophobic uncharged residues, like F I L M V W A and P
- Red: acidic residues, like D E and C-terminal -COOH
- Blue: basic residues, like R K H and N-terminal -NH2
- Black: other residues, like G S T C N Q and P
- ?: Unrecognized codes are replaced of '?'.

Attribute:
Basic
Choosing suitable solvent:
*For basic peptide, initially try to dissolve the peptide in water; if the peptide does not dissolve, try 10% and higher solutions of acetic acid; if it still does not dissolve, add TFA(<50ul) to solubilize the peptide and dilute to 1ml with deionized water.*

Hydrophobicity/Hydrophilicity:
Hydrophobic: 54.55%
Acidic: 12.12%
Basic: 15.15%
Neutral: 18.18%

- Analysis of the NS5A (1-31) (protein sequence: AGSWLRDIWDWICEVLSDFKTWLKAKAKLMPTM).

Fig. 20

NCT-002: HEV-NS5A-VLP

AA sequence of the proposed NovoCapsid No. 002: HEV-NS5A-VLP (N terminus)

MAGSWLRDIWDWICEVLSDFKTWLKAKAKLMPTM
LTAVAPA PDTAPVPDVD SRGAILRRQY NLSTSPLTSS VASGTNLV LYAAPLNPLL PLQDGTNTHI MATEASNYAQ
YRVVRATIRY RPLVPNAVGG YAISISFWPQ TTTTPTSVDM NSITSTDVRI LVQPGIASEL VIPSERLHYR
NQGWRSVETS GVAEEEATSG LVMLCIHGSP VNSYTNTPYT GALGLLDFAL ELEFRNLTPG NTNTRVSRYS
STARHRLRRG ADGTAELTTT AATRFMKDLH FTGTNGVGEV GRGIALTLFN LADTLLGGLP TELISSAGGQ
LFYSRPVVSA NGEPTVKLYT SVENAQQDKG IAIPHDIDLG ESRVVIQDYD NQHEQDRPTP SPAPSRPFSV
LRANDVLWLS LTAAEYDQTT YGSSTN🔲PMYV SDTVTFVNVA TGAQAVARSL DWSKVTLDGR PLTTIQQYSK
TFYVLPLRGK LSFWEAGTTK AGYPYNYNTT ASDQILIENA AGHRVAISTY TTSLGAGPVS ISAVGVLAPH SALA
(C Terminus)

- Yellow: Hydrophobic peptides derived from reference published in Nanomedicine 2018.

- ▓▓▓▓▓▓: Cys is inserted between 490aa N and 491aa as Chemical conjugation site

Fig. 21

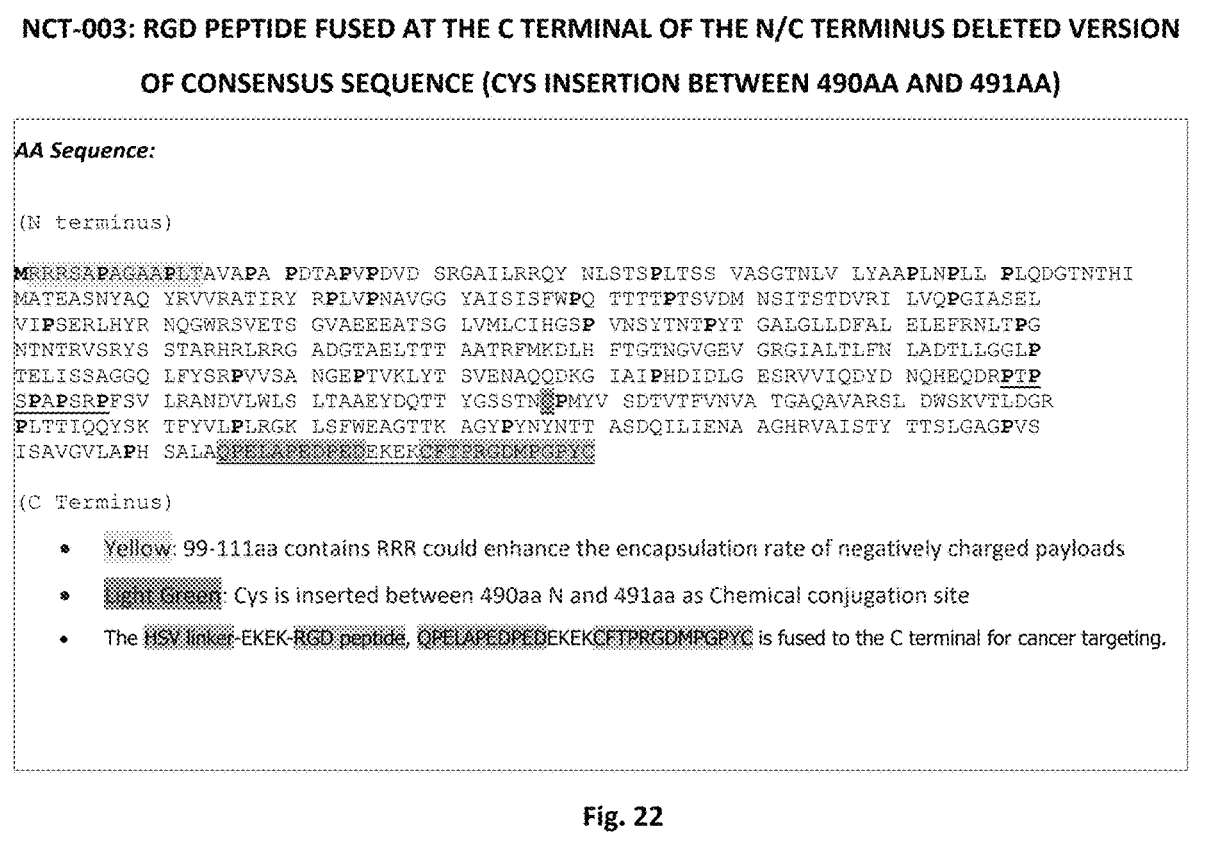

NCT-003: RGD PEPTIDE FUSED AT THE C TERMINAL OF THE N/C TERMINUS DELETED VERSION

OF CONSENSUS SEQUENCE (CYS INSERTION BETWEEN 490AA AND 491AA)

*AA Sequence:*

(N terminus)

MRRRSAPAGAAPLTAVAPA PDTAPVPDVD SRGAILRRQY NLSTSPLTSS VASGTNLV LYAAPLNPLL PLQDGTNTHI
MATEASNYAQ YRVVRATIRY RPLVPNAVGG YAISISFWPQ TTTTPTSVDM NSITSTDVRI LVQPGIASEL
VIPSERLHYR NQGWRSVETS GVAEEEATSG LVMLCIHGSP VNSYTNTPYT GALGLLDFAL ELEFRNLTPG
NTNTRVSRYS STARHRLRRG ADGTAELTTT AATRFMKDLH FTGTNGVGEV GRGIALTLFN LADTLLGGLP
TELISSAGGQ LFYSRPVVSA NGEPTVKLYT SVENAQQDKG IAIPHDIDLG ESRVVIQDYD NQHEQDRPTP
SPAPSRPFSV LRANDVLWLS LTAAEYDQTT YGSSTNSPMYV SDTVTFVNVA TGAQAVARSL DWSKVTLDGR
PLTTIQQYSK TFYVLPLRGK LSFWEAGTTK AGYPYNYNTT ASDQILIENA AGHRVAISTY TTSLGAGPVS
ISAVGVLAPH SALASPPPPPPPPPPPPEKEKCFTPRGDMFGPYK (C Terminus)

- Yellow: 99-111aa contains RRR could enhance the encapsulation rate of negatively charged payloads
- Light Green: Cys is inserted between 490aa N and 491aa as Chemical conjugation site
- The HSV linker-EKEK-RGD peptide, QPELAPEDPEDEKEKCFTPRGDMFGPYK is fused to the C terminal for cancer targeting.

Fig. 22

NCT-004: 13aa deleted N terminus of Full Length of Proposed Consensus sequence derived from 160 sequences (14aa-660aa, Cys insertion between 490aa and 491aa)

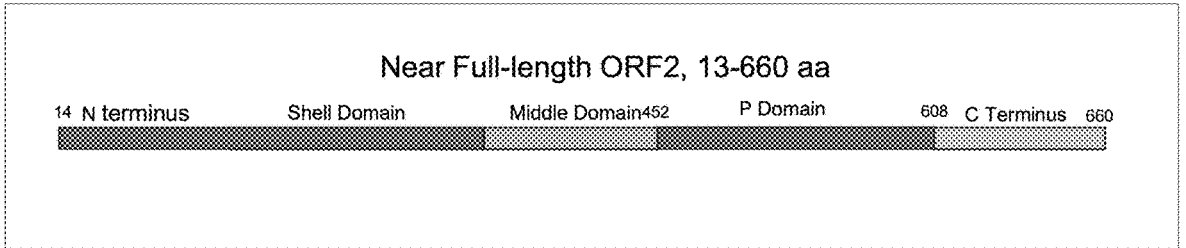

(N terminus, 14aa)

MLPMLPAP PAGQPSGRRR GRRSGGAGGG FWGDRVDSQ PFALPYIHPTN PFASDVYSQS GAGARPRQPA RPLGSAWRDQ

SQRPAAAPRR RSAPAGAAPL TAVAPA PDTAPVPDVD SRGAILRRQY NLSTSPLTSS VASGTNLV LYAAPLNPLL

PLQDGTNTHI MATEASNYAQ YRVVRATIRY RPLVPNAVGG YAISISFWPQ TTTTPTSVDM NSITSTDVRI
LVQPGIASEL VIPSERLHYR NQGWRSVETS GVAEEEATSG LVMLCIHGSP VNSYTNTPYT GALGLLDFAL
ELEFRNLTPG NTNTRVSRYS STARHRLRRG ADGTAELTTT AATRFMKDLH FTGTNGVGEY GRGIALTLFN
LADTLLGGLP TELISSAGGQ LFYSRPVVSA NGEPTVKLYT SVENAQQDKG IAIPHDIDLG ESRVVIQDYD
NQHEQDRPTP SPAPSRPFSV LRANDVLWLS LTAAEYDQTT YGSSTNPMYV SDIVTIVNVA TGAQAVARSL
DWSKVTLDGR PLITIQQYSK TFIVLPLRGK LSFWEAGTTK AGYPYNYNTT ASDQILIENA AGHRVAISTY
TTSLGAGPVS ISAVGVLAPH SALAVLEDTV

DYPARAHTFD DFCPECRILG LQGCAFQSTV AELQRLKMKV GKTREY

(C Terminus)

*   Yellow: aa different from Consensus sequence. Green: Cys mutated site: N573C
*   Light Green: Cys is inserted between 490aa N and 491aa as Chemical conjugation site

Fig. 23

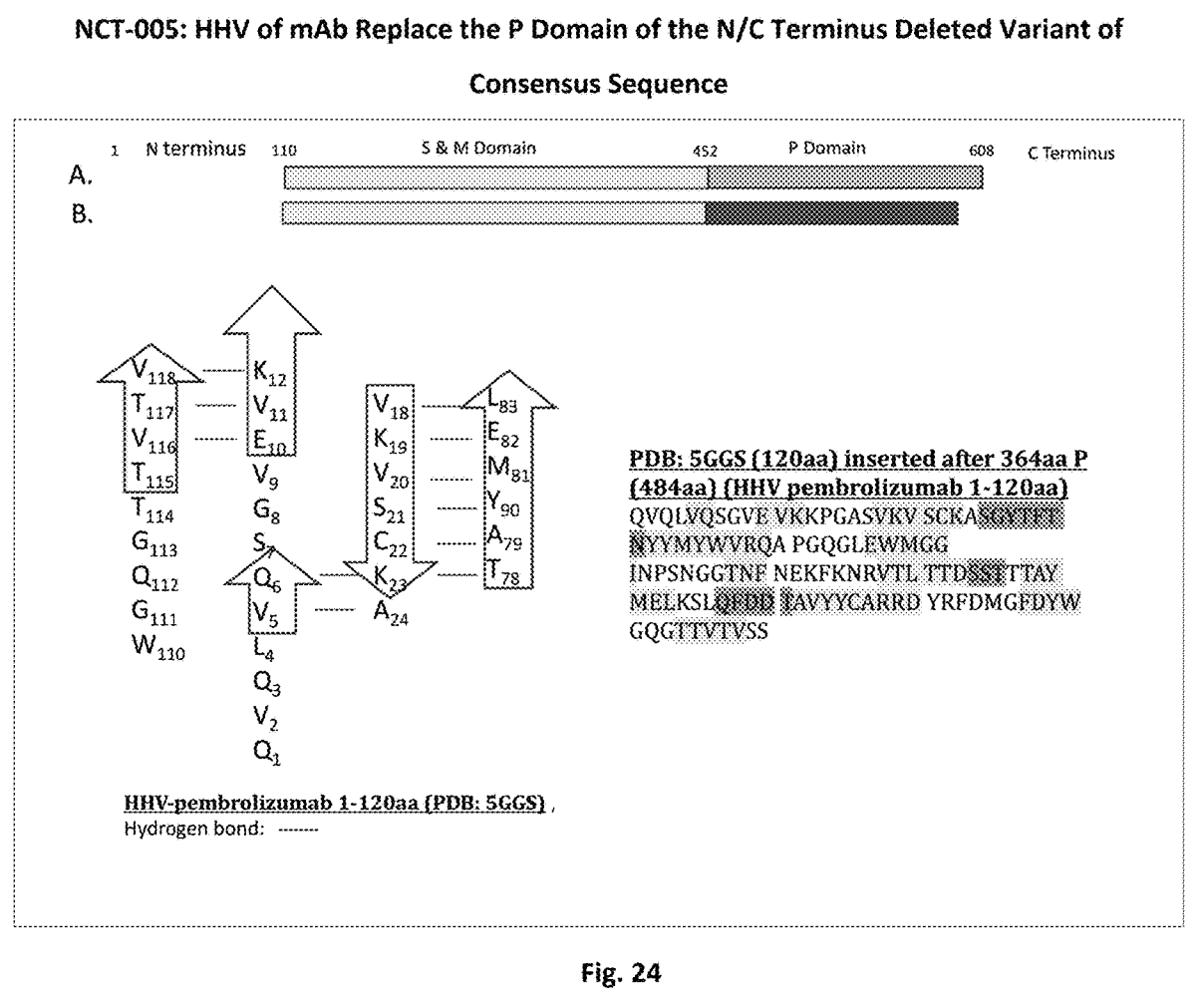

NCT-005: HHV of mAb Replace the P Domain of the N/C Terminus Deleted Variant of Consensus Sequence

PDB: 5GGS (120aa) inserted after 364aa P (484aa) (HHV pembrolizumab 1-120aa)
QVQLVQSGVE VKKPGASVKV SCKA▒▒▒▒▒ ▒YYMYWVRQA PGQGLEWMGG INPSNGGTNF NEKFKNRVTL TTD▒▒TTAY MELKSL▒▒▒▒ ▒AVYYCARRD YRFDMGFDYW GQGTTVTVSS HHV-pembrolizumab 1-120aa (PDB: 5GGS) ,
Hydrogen bond: ------

Fig. 24

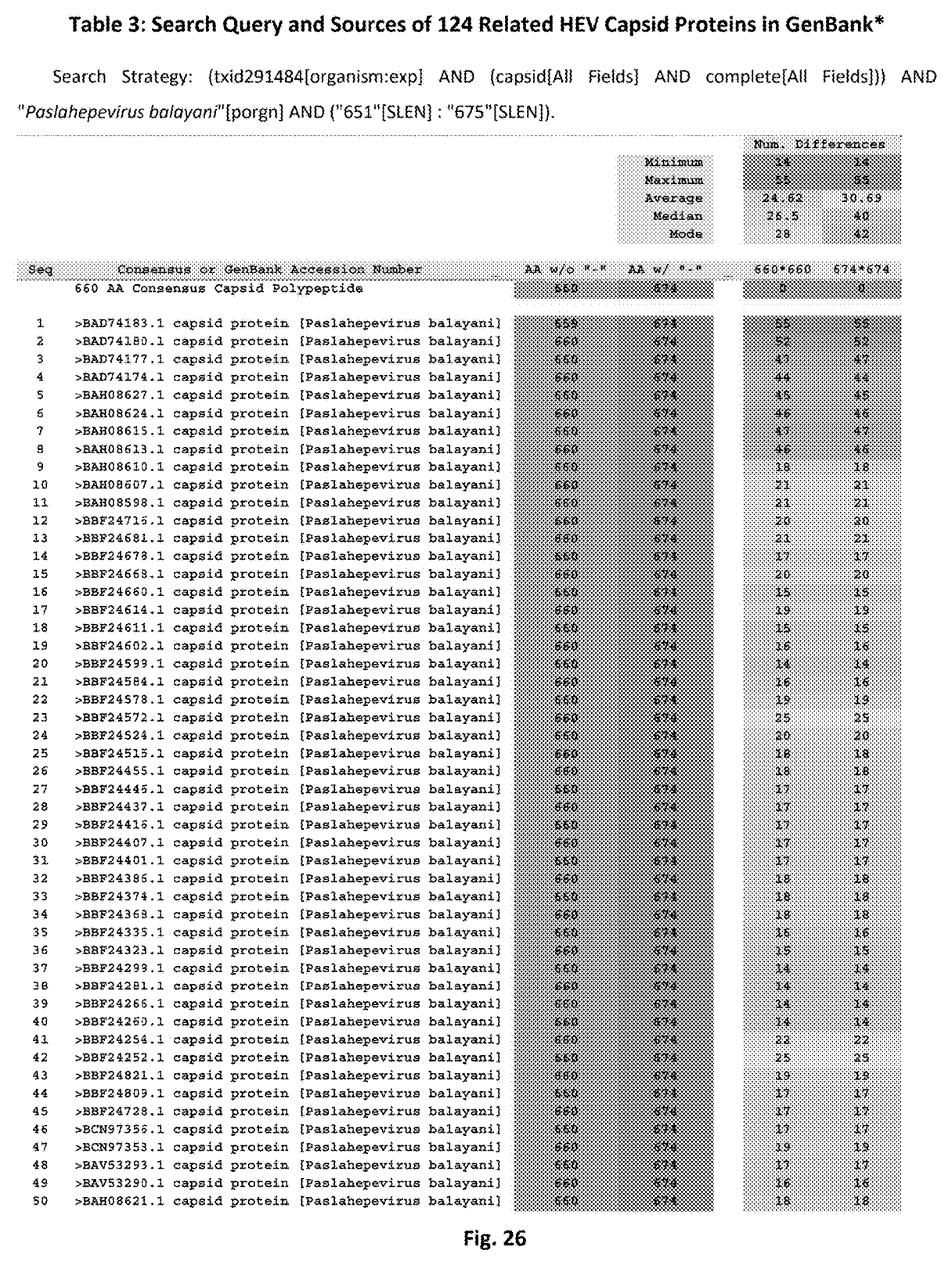

Table 3: Search Query and Sources of 124 Related HEV Capsid Proteins in GenBank\*

Search Strategy: (txid291484[organism:exp] AND (capsid[All Fields] AND complete[All Fields])) AND *Paslahepevirus balayani*"[porgn] AND ("651"[SLEN] : "675"[SLEN]).

|  |  | Num. Differences | |
|---|---|---|---|
| Minimum |  |  |  |
| Maximum |  |  |  |
| Average |  | 24.62 | 30.69 |
| Median |  | 26.5 | 40 |
| Mode |  | 28 | 42 |

| Seq | Consensus or GenBank Accession Number | AA w/o "-" | AA w/ "-" | 660*660 | 674*674 |
|---|---|---|---|---|---|
|  | 660 AA Consensus Capsid Polypeptide | 660 | 674 | 0 | 0 |
| 1 | >BAD74183.1 capsid protein [Paslahepevirus balayani] | 660 | 674 |  |  |
| 2 | >BAD74180.1 capsid protein [Paslahepevirus balayani] | 660 | 674 |  |  |
| 3 | >BAD74177.1 capsid protein [Paslahepevirus balayani] | 660 | 674 | 47 | 47 |
| 4 | >BAD74174.1 capsid protein [Paslahepevirus balayani] | 660 | 674 | 44 | 44 |
| 5 | >BAH08627.1 capsid protein [Paslahepevirus balayani] | 660 | 674 | 45 | 45 |
| 6 | >BAH08624.1 capsid protein [Paslahepevirus balayani] | 660 | 674 | 46 | 46 |
| 7 | >BAH08615.1 capsid protein [Paslahepevirus balayani] | 660 | 674 | 47 | 47 |
| 8 | >BAH08613.1 capsid protein [Paslahepevirus balayani] | 660 | 674 | 46 | 46 |
| 9 | >BAH08610.1 capsid protein [Paslahepevirus balayani] | 660 | 674 | 18 | 18 |
| 10 | >BAH08607.1 capsid protein [Paslahepevirus balayani] | 660 | 674 | 21 | 21 |
| 11 | >BAH08598.1 capsid protein [Paslahepevirus balayani] | 660 | 674 | 21 | 21 |
| 12 | >BBF24715.1 capsid protein [Paslahepevirus balayani] | 660 | 674 | 20 | 20 |
| 13 | >BBF24681.1 capsid protein [Paslahepevirus balayani] | 660 | 674 | 21 | 21 |
| 14 | >BBF24678.1 capsid protein [Paslahepevirus balayani] | 660 | 674 | 17 | 17 |
| 15 | >BBF24668.1 capsid protein [Paslahepevirus balayani] | 660 | 674 | 20 | 20 |
| 16 | >BBF24660.1 capsid protein [Paslahepevirus balayani] | 660 | 674 | 15 | 15 |
| 17 | >BBF24614.1 capsid protein [Paslahepevirus balayani] | 660 | 674 | 19 | 19 |
| 18 | >BBF24611.1 capsid protein [Paslahepevirus balayani] | 660 | 674 | 15 | 15 |
| 19 | >BBF24602.1 capsid protein [Paslahepevirus balayani] | 660 | 674 | 16 | 16 |
| 20 | >BBF24599.1 capsid protein [Paslahepevirus balayani] | 660 | 674 | 14 | 14 |
| 21 | >BBF24584.1 capsid protein [Paslahepevirus balayani] | 660 | 674 | 16 | 16 |
| 22 | >BBF24578.1 capsid protein [Paslahepevirus balayani] | 660 | 674 | 19 | 19 |
| 23 | >BBF24572.1 capsid protein [Paslahepevirus balayani] | 660 | 674 | 25 | 25 |
| 24 | >BBF24524.1 capsid protein [Paslahepevirus balayani] | 660 | 674 | 20 | 20 |
| 25 | >BBF24515.1 capsid protein [Paslahepevirus balayani] | 660 | 674 | 18 | 18 |
| 26 | >BBF24455.1 capsid protein [Paslahepevirus balayani] | 660 | 674 | 18 | 18 |
| 27 | >BBF24446.1 capsid protein [Paslahepevirus balayani] | 660 | 674 | 17 | 17 |
| 28 | >BBF24437.1 capsid protein [Paslahepevirus balayani] | 660 | 674 | 17 | 17 |
| 29 | >BBF24416.1 capsid protein [Paslahepevirus balayani] | 660 | 674 | 17 | 17 |
| 30 | >BBF24407.1 capsid protein [Paslahepevirus balayani] | 660 | 674 | 17 | 17 |
| 31 | >BBF24401.1 capsid protein [Paslahepevirus balayani] | 660 | 674 | 17 | 17 |
| 32 | >BBF24386.1 capsid protein [Paslahepevirus balayani] | 660 | 674 | 18 | 18 |
| 33 | >BBF24374.1 capsid protein [Paslahepevirus balayani] | 660 | 674 | 18 | 18 |
| 34 | >BBF24368.1 capsid protein [Paslahepevirus balayani] | 660 | 674 | 18 | 18 |
| 35 | >BBF24335.1 capsid protein [Paslahepevirus balayani] | 660 | 674 | 16 | 16 |
| 36 | >BBF24323.1 capsid protein [Paslahepevirus balayani] | 660 | 674 | 15 | 15 |
| 37 | >BBF24299.1 capsid protein [Paslahepevirus balayani] | 660 | 674 | 14 | 14 |
| 38 | >BBF24281.1 capsid protein [Paslahepevirus balayani] | 660 | 674 | 14 | 14 |
| 39 | >BBF24266.1 capsid protein [Paslahepevirus balayani] | 660 | 674 | 14 | 14 |
| 40 | >BBF24260.1 capsid protein [Paslahepevirus balayani] | 660 | 674 | 14 | 14 |
| 41 | >BBF24254.1 capsid protein [Paslahepevirus balayani] | 660 | 674 | 22 | 22 |
| 42 | >BBF24252.1 capsid protein [Paslahepevirus balayani] | 660 | 674 | 25 | 25 |
| 43 | >BBF24821.1 capsid protein [Paslahepevirus balayani] | 660 | 674 | 19 | 19 |
| 44 | >BBF24809.1 capsid protein [Paslahepevirus balayani] | 660 | 674 | 17 | 17 |
| 45 | >BBF24728.1 capsid protein [Paslahepevirus balayani] | 660 | 674 | 17 | 17 |
| 46 | >BCN97356.1 capsid protein [Paslahepevirus balayani] | 660 | 674 | 17 | 17 |
| 47 | >BCN97353.1 capsid protein [Paslahepevirus balayani] | 660 | 674 | 19 | 19 |
| 48 | >BAV53293.1 capsid protein [Paslahepevirus balayani] | 660 | 674 | 17 | 17 |
| 49 | >BAV53290.1 capsid protein [Paslahepevirus balayani] | 660 | 674 | 16 | 16 |
| 50 | >BAH08621.1 capsid protein [Paslahepevirus balayani] | 660 | 674 | 18 | 18 |

Fig. 26

Table 3: Search Query and Sources of 124 Related HEV Capsid Proteins in GenBank\*

|  | | | | Num. Differences | |
|---|---|---|---|---|---|
| Minimum | | | | 14 | 14 |
| Maximum | | | | 55 | 55 |
| Average | | | | 24.62 | 30.69 |
| Median | | | | 26.5 | 40 |
| Mode | | | | 28 | 43 |

| Seq | Consensus or GenBank Accession Number | AA w/o "-" | AA w/ "-" | 660*660 | 674*674 |
|---|---|---|---|---|---|
|  | 660 AA Consensus Capsid Polypeptide | 660 | 674 | 0 | 0 |
| 51 | >BAH08618.1 capsid protein [Paslahepevirus balayani] | 660 | 674 | 18 | 18 |
| 52 | >BAH08604.1 capsid protein [Paslahepevirus balayani] | 660 | 674 | 17 | 17 |
| 53 | >BAH08600.1 capsid protein [Paslahepevirus balayani] | 660 | 674 | 17 | 17 |
| 54 | >BAH08595.1 capsid protein [Paslahepevirus balayani] | 660 | 674 | 17 | 17 |
| 55 | >BAH08592.1 capsid protein [Paslahepevirus balayani] | 660 | 674 | 19 | 19 |
| 56 | >BAH08589.1 capsid protein [Paslahepevirus balayani] | 660 | 674 | 19 | 19 |
| 57 | >BAH08586.1 capsid protein [Paslahepevirus balayani] | 660 | 674 | 15 | 15 |
| 58 | >BAH08583.1 capsid protein [Paslahepevirus balayani] | 660 | 674 | 15 | 15 |
| 59 | >BAH08580.1 capsid protein [Paslahepevirus balayani] | 660 | 674 | 15 | 15 |
| 60 | >BAH08577.1 capsid protein [Paslahepevirus balayani] | 660 | 674 | 15 | 15 |
| 61 | >BAH03573.1 capsid protein [Paslahepevirus balayani] | 660 | 674 | 15 | 15 |
| 62 | >BAH03570.1 capsid protein [Paslahepevirus balayani] | 660 | 674 | 16 | 16 |
| 63 | >BAH03567.1 capsid protein [Paslahepevirus balayani] | 660 | 674 | 17 | 17 |
| 64 | >BAH03564.1 capsid protein [Paslahepevirus balayani] | 660 | 674 | 16 | 16 |
| 65 | >BAH03561.1 capsid protein [Paslahepevirus balayani] | 660 | 674 | 16 | 16 |
| 66 | >BAF92627.1 capsid protein [Paslahepevirus balayani] | 660 | 674 | 16 | 16 |
| 67 | >BAE79668.1 capsid protein [Paslahepevirus balayani] | 660 | 674 | 15 | 15 |
| 68 | >BAE79665.1 capsid protein [Paslahepevirus balayani] | 660 | 674 | 15 | 15 |
| 69 | >BAE79662.1 capsid protein [Paslahepevirus balayani] | 660 | 674 | 15 | 15 |
| 70 | >BAE79659.1 capsid protein [Paslahepevirus balayani] | 656 | 674 | 43 | 43 |
| 71 | >BAE79656.1 capsid protein [Paslahepevirus balayani] | 674 | 674 | 32 | 46 |
| 72 | >BAE79653.1 capsid protein [Paslahepevirus balayani] | 674 | 674 | 30 | 44 |
| 73 | >BAE79650.1 capsid protein [Paslahepevirus balayani] | 674 | 674 | 32 | 46 |
| 74 | >BAE79647.1 capsid protein [Paslahepevirus balayani] | 674 | 674 | 30 | 44 |
| 75 | >BAE79644.1 capsid protein [Paslahepevirus balayani] | 674 | 674 | 30 | 44 |
| 76 | >BAH22721.1 capsid protein [Swine hepatitis E virus] | 674 | 674 | 30 | 44 |
| 77 | >BAH22718.1 capsid protein [Swine hepatitis E virus] | 674 | 674 | 30 | 44 |
| 78 | >BAH22714.1 capsid protein [Swine hepatitis E virus] | 674 | 674 | 31 | 45 |
| 79 | >BAH22712.1 capsid protein [Swine hepatitis E virus] | 674 | 674 | 31 | 45 |
| 80 | >BAD74171.1 capsid protein [Paslahepevirus balayani] | 674 | 674 | 30 | 44 |
| 81 | >BAD74168.1 capsid protein [Paslahepevirus balayani] | 674 | 674 | 31 | 45 |
| 82 | >ACJ54949.1 capsid protein [Swine hepatitis E virus] | 674 | 674 | 31 | 45 |
| 83 | >ACJ54946.1 capsid protein [Swine hepatitis E virus] | 674 | 674 | 30 | 44 |
| 84 | >BBL78146.1 capsid protein [Paslahepevirus balayani] | 674 | 674 | 30 | 44 |
| 85 | >BBH72275.1 capsid protein [Paslahepevirus balayani] | 674 | 674 | 29 | 43 |
| 86 | >BBE29389.1 capsid protein [Paslahepevirus balayani] | 674 | 674 | 28 | 42 |
| 87 | >BAV57607.1 capsid protein [Paslahepevirus balayani] | 674 | 674 | 26 | 40 |
| 88 | >BAK52238.1 capsid protein [Paslahepevirus balayani] | 674 | 674 | 31 | 45 |
| 89 | >BAK52235.1 capsid protein [Paslahepevirus balayani] | 674 | 674 | 31 | 45 |
| 90 | >BAE02704.1 capsid protein [Paslahepevirus balayani] | 674 | 674 | 30 | 44 |
| 91 | >BAE02701.1 capsid protein [Paslahepevirus balayani] | 674 | 674 | 30 | 44 |
| 92 | >AXL93752.1 capsid protein [Paslahepevirus balayani] | 674 | 674 | 28 | 42 |
| 93 | >AXJ21463.1 capsid protein [Paslahepevirus balayani] | 674 | 674 | 29 | 43 |
| 94 | >AOG18225.1 capsid protein [Hepatitis E virus type 3] | 674 | 674 | 29 | 43 |
| 95 | >AOG18222.1 capsid protein [Hepatitis E virus type 3] | 674 | 674 | 28 | 42 |
| 96 | >AOG18219.1 capsid protein [Hepatitis E virus type 3] | 674 | 674 | 28 | 42 |
| 97 | >AOG18216.1 capsid protein [Hepatitis E virus type 3] | 674 | 674 | 28 | 42 |
| 98 | >AOG18213.1 capsid protein [Hepatitis E virus type 3] | 674 | 674 | 28 | 42 |
| 99 | >AOG18210.1 capsid protein [Hepatitis E virus type 3] | 674 | 674 | 28 | 42 |
| 100 | >ART85721.1 capsid protein [Swine hepatitis E virus] | 674 | 674 | 28 | 42 |

Fig. 27

Table 3: Search Query and Sources of 124 Related HEV Capsid Proteins in GenBank\*

|  |  |  |  | Num. Differences | |
|---|---|---|---|---|---|
|  |  | Minimum |  | 14 | 14 |
|  |  | Maximum |  | 55 | 55 |
|  |  | Average |  | 24.62 | 30.69 |
|  |  | Median |  | 26.5 | 40 |
|  |  | Mode |  | 28 | 42 |

| Seq | Consensus or GenBank Accession Number | AA w/o "-" | AA w/ "-" | 660*660 | 674*674 |
|---|---|---|---|---|---|
|  | 660 AA Consensus Capsid Polypeptide | 660 | 674 | 0 | 0 |
| 101 | >AMH40419.1 capsid protein [Swine hepatitis E virus] | 674 | 674 | 28 | 42 |
| 102 | >BAS32610.1 capsid protein [Hepatitis E virus type 4] | 674 | 674 | 28 | 42 |
| 103 | >AHZ44449.1 capsid protein [Swine hepatitis E virus] | 674 | 674 | 28 | 42 |
| 104 | >AHZ44446.1 capsid protein [Swine hepatitis E virus] | 674 | 674 | 28 | 42 |
| 105 | >AHI87595.1 capsid protein [Swine hepatitis E virus] | 674 | 674 | 27 | 41 |
| 106 | >ACY66855.1 capsid protein [Swine hepatitis E virus] | 674 | 674 | 28 | 42 |
| 107 | >ACY66852.1 capsid protein [Swine hepatitis E virus] | 674 | 674 | 28 | 42 |
| 108 | >ACM68932.1 capsid protein [Swine hepatitis E virus] | 674 | 674 | 28 | 42 |
| 109 | >ABB88701.2 capsid protein [Swine hepatitis E virus] | 674 | 674 | 28 | 42 |
| 110 | >ACH87960.1 capsid protein [Swine hepatitis E virus] | 674 | 674 | 28 | 42 |
| 111 | >ACH87954.1 capsid protein [Swine hepatitis E virus] | 674 | 674 | 28 | 42 |
| 112 | >BAB79306.1 capsid protein [Swine hepatitis E virus] | 674 | 674 | 28 | 42 |
| 113 | >ACH87966.1 capsid protein [Swine hepatitis E virus] | 674 | 674 | 28 | 42 |
| 114 | >ACH87963.1 capsid protein [Swine hepatitis E virus] | 674 | 674 | 30 | 44 |
| 115 | >ACH87957.1 capsid protein [Swine hepatitis E virus] | 674 | 674 | 31 | 45 |
| 116 | >sp\|P33426.1\|CAPSD_HEVPA | 674 | 674 | 30 | 44 |
| 117 | >sp\|P29326.1\|CAPSD_HEVBU | 674 | 674 | 27 | 41 |
| 118 | >sp\|Q81871.1\|CAPSD_HEVCH | 674 | 674 | 28 | 42 |
| 119 | >sp\|Q68985.1\|CAPSD_HEVHY | 674 | 674 | 28 | 42 |
| 120 | >sp\|Q9IVZ8.2\|CAPSD_HEVCT | 674 | 674 | 30 | 44 |
| 121 | >sp\|Q9YLQ9.1\|CAPSD_HEVUS | 674 | 674 | 29 | 43 |
| 122 | >sp\|Q6J8F7.1\|CAPSD_HEVMG | 671 | 674 | 29 | 40 |
| 123 | >sp\|Q04611.1\|CAPSD_HEVMY | 674 | 674 | 31 | 45 |
| 124 | >sp\|Q03500.1\|CAPSD_HEVME | 674 | 674 | 31 | 45 |

Column 1 provides the sequence number in the multiple sequence alignment used to generate the consensus sequence. Column 2 provides the GenBank Accession Number and its description. Column 3 shows the number of amino acids, removing dashes, in the aligned sequences, and column 4 shows the number of amino acids in the aligned amino acids, with dashes, primarily at the amino terminal end of the polypeptide. Columns 5 and 6 show the number of differences between any individual sequence and the consensus sequence derived from 124 aligned sequences, when compared as 660 against 660 amino acids, or as 674 against 674 amino acids.

Without padding, HEV capsid sequences 1, 70, and 122 have 659, 658, and 671 amino acids, respectively, while 68 of 124 sequences have 660 amino acids, and 53 sequences have 674 amino acids.

Fig. 28

Table 4: Positions of Islands of Variability for 674 and 660 AA

HEV Capsid Polypeptides Used to Determine a Consensus Derived from 124 Sequences

| Positions | | Consensus and Variant Amino Acids | | | | Frequencies of Alterations | | | | Positions of Islands | |
|---|---|---|---|---|---|---|---|---|---|---|---|
| 674 | 660 | | | | | | | | | 674 | 660 |
| 1 | | 0 | - | M | | 75 | 71 | 53 | | 1 | |
| 2 | | - | N | 0 | | 71 | 53 | 1 | | 2 | |
| 3 | | - | N | | | 71 | 53 | | | 3 | |
| 4 | | - | M | | | 70 | 54 | | | 4 | |
| 5 | | - | F | | | 70 | 54 | | | 5 | |
| 6 | | - | F | S | | 70 | 52 | 2 | | 6 | |
| 7 | | - | C | | | 70 | 54 | | | 7 | |
| 8 | | - | S | | | 70 | 54 | | | 8 | |
| 9 | | - | V | L | | 70 | 51 | 3 | | 9 | |
| 10 | | - | H | | | 70 | 54 | | | 10 | |
| 11 | | - | G | | | 70 | 54 | | | 11 | |
| 12 | | - | D | N | | 70 | 53 | 1 | | 12 | |
| 13 | | - | A | | | 70 | 54 | | | 13 | |
| 14 | | - | T | A | | 70 | 50 | 4 | | 14 | |
| 15 | 1 | M | | | | 124 | | | | | |
| 16 | 2 | R | C | G | | 115 | 8 | 1 | | 16 | 2 |
| 17 | 3 | P | S | T | | 67 | 55 | 2 | | 17 | 3 |
| 18 | 4 | R | | | | 124 | | | | | |
| 19 | 5 | A | P | V | | 114 | 6 | 4 | | 19 | 5 |
| 20 | 6 | V | P | L | I | 61 | 31 | 25 | 7 | 20 | 6 |
| 21 | 7 | L | | | | 124 | | | | | |
| 22 | 8 | L | F | | | 69 | 55 | | | 22 | 8 |
| 23 | 9 | L | | | | 124 | | | | | |
| 24 | 10 | P | L | | | 73 | 51 | | | 24 | 10 |
| 25 | 11 | L | P | I | | 67 | 56 | 1 | | 25 | 11 |
| 26 | 12 | V | L | M | | 113 | 6 | 5 | | 26 | 12 |
| 27 | 13 | L | P | | | 95 | 29 | | | 27 | 13 |
| 28 | 14 | L | | | | 124 | | | | | |
| 29 | 15 | P | | | | 124 | | | | | |
| 30 | 16 | M | | | | 124 | | | | | |
| 31 | 17 | L | | | | 124 | | | | | |
| 32 | 18 | P | L | | | 123 | 1 | | | 32 | 18 |
| 33 | 19 | A | | | | 124 | | | | | |
| 34 | 20 | P | | | | 124 | | | | | |
| 35 | 21 | P | | | | 124 | | | | | |
| 36 | 22 | A | P | T | | 118 | 5 | 1 | | 36 | 22 |
| 37 | 23 | G | S | | | 123 | 1 | | | 37 | 23 |
| 38 | 24 | Q | | | | 124 | | | | | |
| 39 | 25 | P | S | | | 113 | 11 | | | 39 | 25 |
| 40 | 26 | S | P | | | 123 | 1 | | | 40 | 26 |
| 41 | 27 | G | S | | | 122 | 3 | | | 41 | 27 |
| 42 | 28 | R | | | | 124 | | | | | |
| 43 | 29 | R | | | | 124 | | | | | |
| 44 | 30 | R | | | | 124 | | | | | |
| 45 | 31 | G | | | | 124 | | | | | |
| 46 | 32 | R | Q | | | 123 | 1 | | | 46 | 32 |
| 47 | 33 | R | - | | | 123 | 1 | | | 47 | 33 |
| 48 | 34 | S | N | G | - | 119 | 3 | 1 | 1 | 48 | 34 |
| 49 | 35 | G | S | A | | 120 | 3 | 1 | | 49 | 35 |
| 50 | 36 | G | S | | | 116 | 8 | | | 50 | 36 |

Fig. 29

Table 4: Positions of Islands of Variability for 674 and 660 AA

HEV Capsid Polypeptides Used to Determine a Consensus Derived from 124 Sequences

| Positions | | Consensus and | | | | Frequencies of | | | | | Positions of Islands | |
|---|---|---|---|---|---|---|---|---|---|---|---|---|
| 674 | 660 | Variant Amino Acids | | | | Alterations | | | | | 674 | 660 |
| 51 | 37 | A | T | S | C | 98 | 15 | 10 | 1 | | 51 | 37 |
| 52 | 38 | G | S | | | 120 | 4 | | | | 52 | 38 |
| 53 | 39 | G | S | | | 110 | 14 | | | | 53 | 39 |
| 54 | 40 | G | | | | 124 | | | | | | |
| 55 | 41 | F | | | | 124 | | | | | | |
| 56 | 42 | N | R | | | 123 | 1 | | | | 56 | 42 |
| 57 | 43 | G | | | | 124 | | | | | | |
| 58 | 44 | D | | | | 124 | | | | | | |
| 59 | 45 | R | | | | 124 | | | | | | |
| 60 | 46 | V | I | A | | 109 | 14 | 1 | | | 60 | 46 |
| 61 | 47 | D | | | | 124 | | | | | | |
| 62 | 48 | S | X | | | 123 | 1 | | | | 62 | 48 |
| 63 | 49 | Q | | | | 124 | | | | | | |
| 64 | 50 | P | | | | 124 | | | | | | |
| 65 | 51 | F | | | | 124 | | | | | | |
| 66 | 52 | A | | | | 124 | | | | | | |
| 67 | 53 | L | I | | | 117 | 7 | | | | 67 | 53 |
| 68 | 54 | P | S | | | 123 | 1 | | | | 68 | 54 |
| 69 | 55 | T | | | | 124 | | | | | | |
| 70 | 56 | I | | | | 124 | | | | | | |
| 71 | 57 | H | | | | 124 | | | | | | |
| 72 | 58 | P | | | | 124 | | | | | | |
| 73 | 59 | T | | | | 124 | | | | | | |
| 74 | 60 | N | | | | 124 | | | | | | |
| 75 | 61 | P | | | | 124 | | | | | | |
| 76 | 62 | F | | | | 124 | | | | | | |
| 77 | 63 | A | V | | | 122 | 2 | | | | 77 | 63 |
| 78 | 64 | S | A | P | T | 59 | 57 | 7 | 1 | | 78 | 64 |
| 79 | 65 | D | N | | | 123 | 1 | | | | 79 | 65 |
| 80 | 66 | V | I | | | 67 | 57 | | | | 80 | 66 |
| 81 | 67 | V | P | T | L | S | 55 | 52 | 7 | 4 | 3 | 81 | 67 |
| 82 | 68 | S | A | T | P | 61 | 53 | 8 | 2 | | 82 | 68 |
| 83 | 69 | Q | A | S | T | 61 | 60 | 2 | 1 | | 83 | 69 |
| 84 | 70 | S | A | P | T | 45 | 45 | 19 | 15 | | 84 | 70 |
| 85 | 71 | G | | | | 124 | | | | | | |
| 86 | 72 | A | T | S | G | 115 | 5 | 3 | 1 | | 86 | 72 |
| 87 | 73 | G | | | | 124 | | | | | | |
| 88 | 74 | A | T | P | V | 98 | 11 | 8 | 7 | | 88 | 74 |
| 89 | 75 | R | | | | 124 | | | | | | |
| 90 | 76 | P | V | S | L | 114 | 5 | 4 | 1 | | 90 | 76 |
| 91 | 77 | R | | | | 124 | | | | | | |
| 92 | 78 | Q | | | | 124 | | | | | | |
| 93 | 79 | P | | | | 124 | | | | | | |
| 94 | 80 | A | P | V | T | S | 68 | 50 | 3 | 2 | 1 | 94 | 80 |
| 95 | 81 | R | | | | 124 | | | | | | |
| 96 | 82 | P | | | | 124 | | | | | | |
| 97 | 83 | L | P | | | 123 | 1 | | | | 97 | 83 |
| 98 | 84 | G | | | | 124 | | | | | | |
| 99 | 85 | S | T | | | 122 | 2 | | | | 99 | 85 |
| 100 | 86 | A | S | T | | 107 | 15 | 2 | | | 100 | 86 |

Fig. 30

Table 4: Positions of Islands of Variability for 674 and 660 AA

HEV Capsid Polypeptides Used to Determine a Consensus Derived from 124 Sequences

| Positions | | Consensus and Variant Amino Acids | | | | | Frequencies of Alterations | | | | | Positions of Islands | |
|---|---|---|---|---|---|---|---|---|---|---|---|---|---|
| 674 | 660 | | | | | | | | | | | 674 | 660 |
| 101 | 87 | N | | | | | 124 | | | | | | |
| 102 | 88 | R | | | | | 124 | | | | | | |
| 103 | 89 | D | G | | | | 123 | 1 | | | | 103 | 89 |
| 104 | 90 | Q | | | | | 124 | | | | | | |
| 105 | 91 | S | A | | | | 118 | 6 | | | | 105 | 91 |
| 106 | 92 | Q | | | | | 124 | | | | | | |
| 107 | 93 | R | | | | | 124 | | | | | | |
| 108 | 94 | P | | | | | 124 | | | | | | |
| 109 | 95 | A | P | S | T | | 59 | 37 | 26 | 2 | | 109 | 95 |
| 110 | 96 | A | T | V | I | | 79 | 41 | 3 | 1 | | 110 | 96 |
| 111 | 97 | A | S | T | P | V | 62 | 54 | 3 | 1 | 2 | 111 | 97 |
| 112 | 98 | P | A | S | T | | 50 | 50 | 21 | 3 | | 112 | 98 |
| 113 | 99 | R | | | | | 124 | | | | | | |
| 114 | 100 | R | | | | | 124 | | | | | | |
| 115 | 101 | R | | | | | 124 | | | | | | |
| 116 | 102 | S | P | | | | 112 | 12 | | | | 116 | 102 |
| 117 | 103 | A | T | S | | | 103 | 20 | 1 | | | 117 | 103 |
| 118 | 104 | P | T | | | | 118 | 6 | | | | 118 | 104 |
| 119 | 105 | A | T | S | V | | 113 | 8 | 8 | 1 | | 119 | 105 |
| 120 | 106 | G | | | | | 124 | | | | | | |
| 121 | 107 | A | | | | | 124 | | | | | | |
| 122 | 108 | A | S | T | | | 66 | 55 | 3 | | | 122 | 108 |
| 123 | 109 | P | A | | | | 123 | 1 | | | | 123 | 109 |
| 124 | 110 | L | | | | | 124 | | | | | | |
| 125 | 111 | T | K | | | | 123 | 1 | | | | 125 | 111 |
| 126 | 112 | A | | | | | 124 | | | | | | |
| 127 | 113 | V | T | I | M | | 83 | 22 | 18 | 1 | | 127 | 113 |
| 128 | 114 | A | S | | | | 63 | 61 | | | | 128 | 114 |
| 129 | 115 | P | | | | | 124 | | | | | | |
| 130 | 116 | A | | | | | 124 | | | | | | |
| 131 | 117 | P | R | S | | | 116 | 6 | 2 | | | 131 | 117 |
| 132 | 118 | D | G | | | | 122 | 2 | | | | 132 | 118 |
| 133 | 119 | T | A | | | | 123 | 1 | | | | 133 | 119 |
| 134 | 120 | A | V | P | S | T | 104 | 10 | 5 | 4 | 1 | 134 | 120 |
| 135 | 121 | P | | | | | 124 | | | | | | |
| 136 | 122 | V | | | | | 124 | | | | | | |
| 137 | 123 | P | | | | | 124 | | | | | | |
| 138 | 124 | D | | | | | 124 | | | | | | |
| 139 | 125 | V | I | A | | | 121 | 2 | 1 | | | 139 | 125 |
| 140 | 126 | D | | | | | 124 | | | | | | |
| 141 | 127 | S | | | | | 124 | | | | | | |
| 142 | 128 | R | | | | | 124 | | | | | | |
| 143 | 129 | G | A | | | | 123 | 1 | | | | 143 | 129 |
| 144 | 130 | A | | | | | 124 | | | | | | |
| 145 | 131 | I | | | | | 124 | | | | | | |
| 146 | 132 | L | | | | | 124 | | | | | | |
| 147 | 133 | R | | | | | 124 | | | | | | |
| 148 | 134 | R | | | | | 124 | | | | | | |
| 149 | 135 | Q | | | | | 124 | | | | | | |
| 150 | 136 | Y | | | | | 124 | | | | | | |

Fig. 31

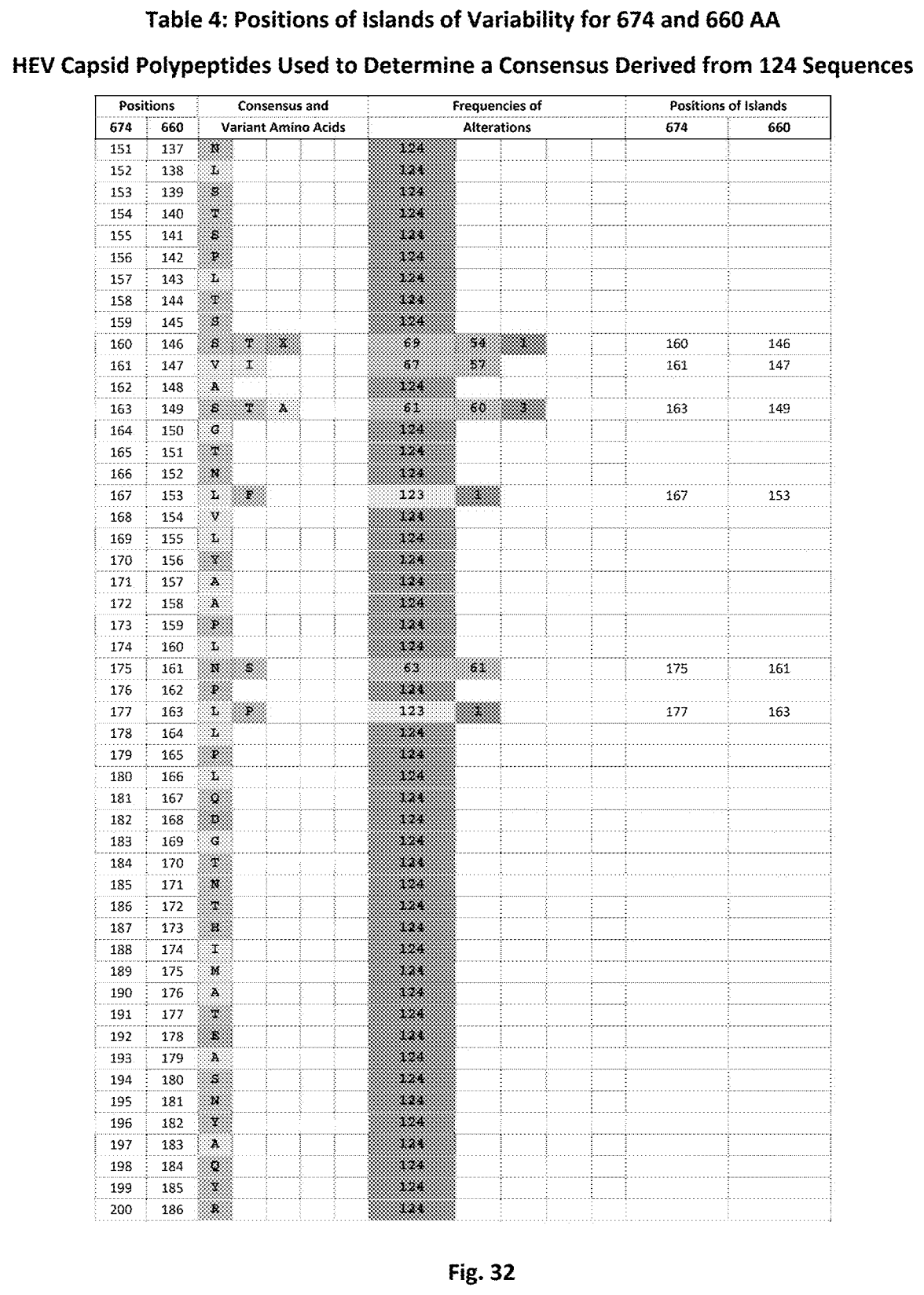

Table 4: Positions of Islands of Variability for 674 and 660 AA

HEV Capsid Polypeptides Used to Determine a Consensus Derived from 124 Sequences

| Positions | | Consensus and Variant Amino Acids | | | | Frequencies of Alterations | | | | Positions of Islands | |
|---|---|---|---|---|---|---|---|---|---|---|---|
| 674 | 660 | | | | | | | | | 674 | 660 |
| 151 | 137 | N | | | | 124 | | | | | |
| 152 | 138 | L | | | | 124 | | | | | |
| 153 | 139 | S | | | | 124 | | | | | |
| 154 | 140 | T | | | | 124 | | | | | |
| 155 | 141 | S | | | | 124 | | | | | |
| 156 | 142 | P | | | | 124 | | | | | |
| 157 | 143 | L | | | | 124 | | | | | |
| 158 | 144 | T | | | | 124 | | | | | |
| 159 | 145 | S | | | | 124 | | | | | |
| 160 | 146 | S | T | X | | 69 | 54 | 1 | | 160 | 146 |
| 161 | 147 | V | I | | | 67 | 57 | | | 161 | 147 |
| 162 | 148 | A | | | | 124 | | | | | |
| 163 | 149 | S | T | A | | 61 | 60 | 3 | | 163 | 149 |
| 164 | 150 | G | | | | 124 | | | | | |
| 165 | 151 | T | | | | 124 | | | | | |
| 166 | 152 | N | | | | 124 | | | | | |
| 167 | 153 | L | P | | | 123 | 1 | | | 167 | 153 |
| 168 | 154 | V | | | | 124 | | | | | |
| 169 | 155 | L | | | | 124 | | | | | |
| 170 | 156 | Y | | | | 124 | | | | | |
| 171 | 157 | A | | | | 124 | | | | | |
| 172 | 158 | A | | | | 124 | | | | | |
| 173 | 159 | P | | | | 124 | | | | | |
| 174 | 160 | L | | | | 124 | | | | | |
| 175 | 161 | N | S | | | 63 | 61 | | | 175 | 161 |
| 176 | 162 | P | | | | 124 | | | | | |
| 177 | 163 | L | P | | | 123 | 1 | | | 177 | 163 |
| 178 | 164 | L | | | | 124 | | | | | |
| 179 | 165 | P | | | | 124 | | | | | |
| 180 | 166 | L | | | | 124 | | | | | |
| 181 | 167 | Q | | | | 124 | | | | | |
| 182 | 168 | D | | | | 124 | | | | | |
| 183 | 169 | G | | | | 124 | | | | | |
| 184 | 170 | T | | | | 124 | | | | | |
| 185 | 171 | N | | | | 124 | | | | | |
| 186 | 172 | T | | | | 124 | | | | | |
| 187 | 173 | H | | | | 124 | | | | | |
| 188 | 174 | I | | | | 124 | | | | | |
| 189 | 175 | M | | | | 124 | | | | | |
| 190 | 176 | A | | | | 124 | | | | | |
| 191 | 177 | T | | | | 124 | | | | | |
| 192 | 178 | S | | | | 124 | | | | | |
| 193 | 179 | A | | | | 124 | | | | | |
| 194 | 180 | S | | | | 124 | | | | | |
| 195 | 181 | N | | | | 124 | | | | | |
| 196 | 182 | Y | | | | 124 | | | | | |
| 197 | 183 | A | | | | 124 | | | | | |
| 198 | 184 | Q | | | | 124 | | | | | |
| 199 | 185 | Y | | | | 124 | | | | | |
| 200 | 186 | R | | | | 124 | | | | | |

Fig. 32

Table 4: Positions of Islands of Variability for 674 and 660 AA

HEV Capsid Polypeptides Used to Determine a Consensus Derived from 124 Sequences

| Positions 674 | Positions 660 | Consensus and Variant Amino Acids | | | | | Frequencies of Alterations | | | | | Positions of Islands 674 | Positions of Islands 660 |
|---|---|---|---|---|---|---|---|---|---|---|---|---|---|
| 201 | 187 | V | | | | | 124 | | | | | | |
| 202 | 188 | V | A | X | | | 106 | 17 | 1 | | | 202 | 188 |
| 203 | 189 | R | | | | | 124 | | | | | | |
| 204 | 190 | A | | | | | 124 | | | | | | |
| 205 | 191 | T | | | | | 124 | | | | | | |
| 206 | 192 | I | | | | | 124 | | | | | | |
| 207 | 193 | R | | | | | 124 | | | | | | |
| 208 | 194 | Y | | | | | 124 | | | | | | |
| 209 | 195 | R | | | | | 124 | | | | | | |
| 210 | 196 | P | | | | | 124 | | | | | | |
| 211 | 197 | L | | | | | 124 | | | | | | |
| 212 | 198 | V | | | | | 124 | | | | | | |
| 213 | 199 | P | | | | | 124 | | | | | | |
| 214 | 200 | N | | | | | 124 | | | | | | |
| 215 | 201 | A | | | | | 124 | | | | | | |
| 216 | 202 | V | | | | | 124 | | | | | | |
| 217 | 203 | G | | | | | 124 | | | | | | |
| 218 | 204 | G | | | | | 124 | | | | | | |
| 219 | 205 | Y | | | | | 124 | | | | | | |
| 220 | 206 | A | | | | | 124 | | | | | | |
| 221 | 207 | I | V | | | | 123 | 1 | | | | 221 | 207 |
| 222 | 208 | S | | | | | 124 | | | | | | |
| 223 | 209 | I | | | | | 124 | | | | | | |
| 224 | 210 | S | | | | | 124 | | | | | | |
| 225 | 211 | F | | | | | 124 | | | | | | |
| 226 | 212 | W | | | | | 124 | | | | | | |
| 227 | 213 | P | | | | | 124 | | | | | | |
| 228 | 214 | Q | | | | | 124 | | | | | | |
| 229 | 215 | T | | | | | 124 | | | | | | |
| 230 | 216 | T | | | | | 124 | | | | | | |
| 231 | 217 | T | P | | | | 123 | 1 | | | | 231 | 217 |
| 232 | 218 | T | | | | | 124 | | | | | | |
| 233 | 219 | P | | | | | 124 | | | | | | |
| 234 | 220 | T | | | | | 124 | | | | | | |
| 235 | 221 | S | | | | | 124 | | | | | | |
| 236 | 222 | V | | | | | 124 | | | | | | |
| 237 | 223 | D | | | | | 124 | | | | | | |
| 238 | 224 | M | I | | | | 123 | 1 | | | | 238 | 224 |
| 239 | 225 | N | | | | | 124 | | | | | | |
| 240 | 226 | S | | | | | 124 | | | | | | |
| 241 | 227 | I | | | | | 124 | | | | | | |
| 242 | 228 | T | | | | | 124 | | | | | | |
| 243 | 229 | S | | | | | 124 | | | | | | |
| 244 | 230 | T | | | | | 124 | | | | | | |
| 245 | 231 | D | | | | | 124 | | | | | | |
| 246 | 232 | V | | | | | 124 | | | | | | |
| 247 | 233 | R | | | | | 124 | | | | | | |
| 248 | 234 | I | | | | | 124 | | | | | | |
| 249 | 235 | L | | | | | 124 | | | | | | |
| 250 | 236 | V | | | | | 124 | | | | | | |

Fig. 33

Table 4: Positions of Islands of Variability for 674 and 660 AA

HEV Capsid Polypeptides Used to Determine a Consensus Derived from 124 Sequences

| Positions | | Consensus and | | | | | Frequencies of | | | | | Positions of Islands | |
|---|---|---|---|---|---|---|---|---|---|---|---|---|---|
| 674 | 660 | Variant Amino Acids | | | | | Alterations | | | | | 674 | 660 |
| 251 | 237 | Q | | | | | 124 | | | | | | |
| 252 | 238 | P | | | | | 124 | | | | | | |
| 253 | 239 | G | | | | | 124 | | | | | | |
| 254 | 240 | I | V | | | | 122 | 2 | | | | 254 | 240 |
| 255 | 241 | A | | | | | 124 | | | | | | |
| 256 | 242 | S | | | | | 124 | | | | | | |
| 257 | 243 | E | | | | | 124 | | | | | | |
| 258 | 244 | L | H | | | | 123 | 1 | | | | 258 | 244 |
| 259 | 245 | V | | | | | 124 | | | | | | |
| 260 | 246 | I | T | | | | 123 | 1 | | | | 260 | 246 |
| 261 | 247 | P | | | | | 124 | | | | | | |
| 262 | 248 | S | | | | | 124 | | | | | | |
| 263 | 249 | E | | | | | 124 | | | | | | |
| 264 | 250 | R | | | | | 124 | | | | | | |
| 265 | 251 | L | | | | | 124 | | | | | | |
| 266 | 252 | H | | | | | 124 | | | | | | |
| 267 | 253 | Y | | | | | 124 | | | | | | |
| 268 | 254 | R | | | | | 124 | | | | | | |
| 269 | 255 | N | | | | | 124 | | | | | | |
| 270 | 256 | Q | | | | | 124 | | | | | | |
| 271 | 257 | G | | | | | 124 | | | | | | |
| 272 | 258 | W | | | | | 124 | | | | | | |
| 273 | 259 | R | | | | | 124 | | | | | | |
| 274 | 260 | S | | | | | 124 | | | | | | |
| 275 | 261 | V | | | | | 124 | | | | | | |
| 276 | 262 | E | | | | | 124 | | | | | | |
| 277 | 263 | T | | | | | 124 | | | | | | |
| 278 | 264 | S | T | | | | 77 | 47 | | | | 278 | 264 |
| 279 | 265 | G | | | | | 124 | | | | | | |
| 280 | 266 | V | | | | | 124 | | | | | | |
| 281 | 267 | A | | | | | 124 | | | | | | |
| 282 | 268 | E | | | | | 124 | | | | | | |
| 283 | 269 | E | | | | | 124 | | | | | | |
| 284 | 270 | E | | | | | 124 | | | | | | |
| 285 | 271 | A | | | | | 124 | | | | | | |
| 286 | 272 | T | | | | | 124 | | | | | | |
| 287 | 273 | S | | | | | 124 | | | | | | |
| 288 | 274 | G | | | | | 124 | | | | | | |
| 289 | 275 | L | | | | | 124 | | | | | | |
| 290 | 276 | V | | | | | 124 | | | | | | |
| 291 | 277 | M | | | | | 124 | | | | | | |
| 292 | 278 | L | | | | | 124 | | | | | | |
| 293 | 279 | C | | | | | 124 | | | | | | |
| 294 | 280 | I | | | | | 124 | | | | | | |
| 295 | 281 | H | | | | | 124 | | | | | | |
| 296 | 282 | G | | | | | 124 | | | | | | |
| 297 | 283 | S | | | | | 124 | | | | | | |
| 298 | 284 | P | L | | | | 122 | 2 | | | | 298 | 284 |
| 299 | 285 | V | | | | | 124 | | | | | | |
| 300 | 286 | N | | | | | 124 | | | | | | |

Fig. 34

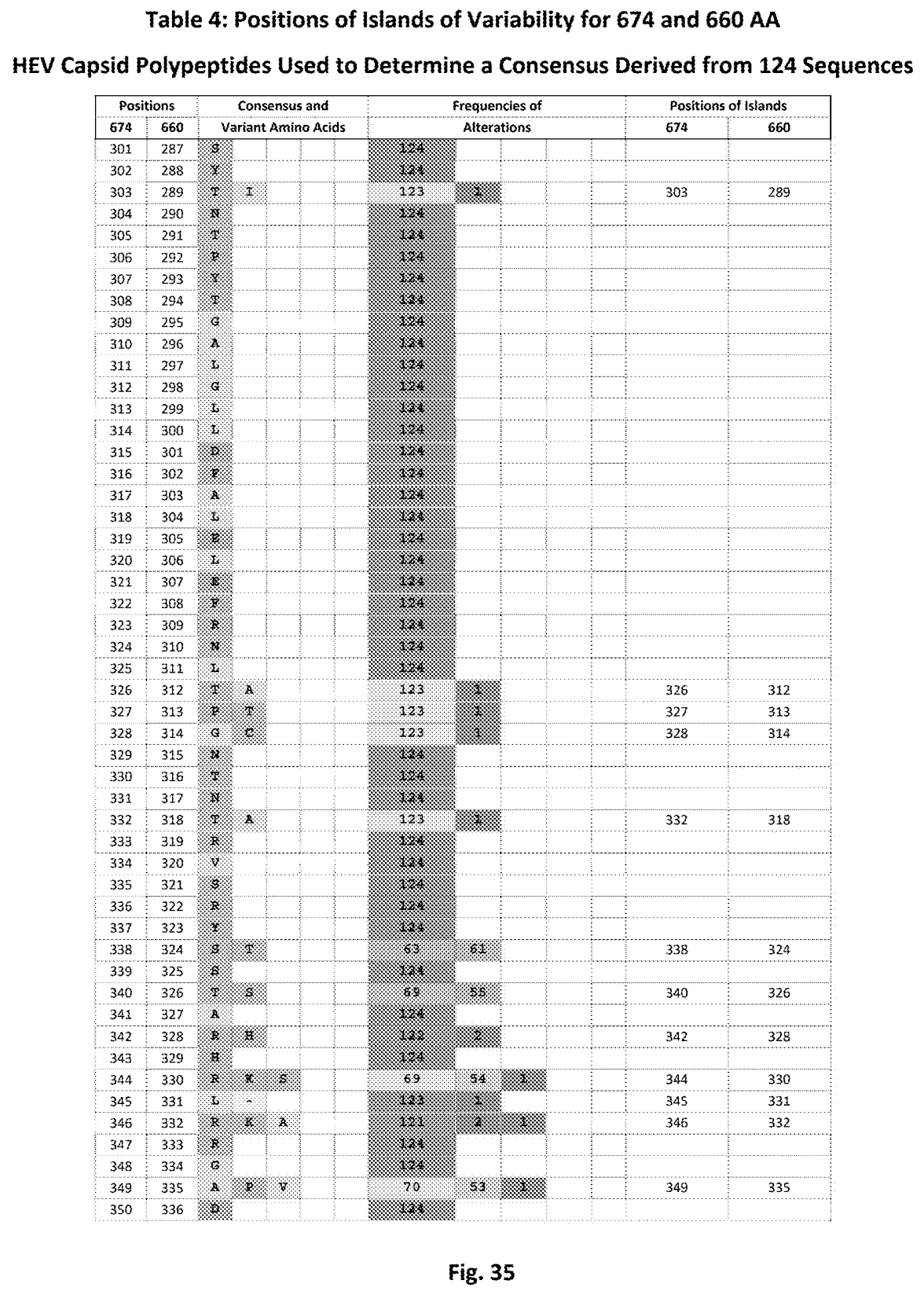

Table 4: Positions of Islands of Variability for 674 and 660 AA

HEV Capsid Polypeptides Used to Determine a Consensus Derived from 124 Sequences

| Positions | | Consensus and | | | | | Frequencies of | | | | | Positions of Islands | |
|---|---|---|---|---|---|---|---|---|---|---|---|---|---|
| 674 | 660 | Variant Amino Acids | | | | | Alterations | | | | | 674 | 660 |
| 301 | 287 | S | | | | | 124 | | | | | | |
| 302 | 288 | Y | | | | | 124 | | | | | | |
| 303 | 289 | T | I | | | | 123 | 1 | | | | 303 | 289 |
| 304 | 290 | N | | | | | 124 | | | | | | |
| 305 | 291 | T | | | | | 124 | | | | | | |
| 306 | 292 | P | | | | | 124 | | | | | | |
| 307 | 293 | Y | | | | | 124 | | | | | | |
| 308 | 294 | T | | | | | 124 | | | | | | |
| 309 | 295 | G | | | | | 124 | | | | | | |
| 310 | 296 | A | | | | | 124 | | | | | | |
| 311 | 297 | L | | | | | 124 | | | | | | |
| 312 | 298 | G | | | | | 124 | | | | | | |
| 313 | 299 | L | | | | | 124 | | | | | | |
| 314 | 300 | L | | | | | 124 | | | | | | |
| 315 | 301 | D | | | | | 124 | | | | | | |
| 316 | 302 | F | | | | | 124 | | | | | | |
| 317 | 303 | A | | | | | 124 | | | | | | |
| 318 | 304 | L | | | | | 124 | | | | | | |
| 319 | 305 | E | | | | | 124 | | | | | | |
| 320 | 306 | L | | | | | 124 | | | | | | |
| 321 | 307 | E | | | | | 124 | | | | | | |
| 322 | 308 | F | | | | | 124 | | | | | | |
| 323 | 309 | R | | | | | 124 | | | | | | |
| 324 | 310 | N | | | | | 124 | | | | | | |
| 325 | 311 | L | | | | | 124 | | | | | | |
| 326 | 312 | T | A | | | | 123 | 1 | | | | 326 | 312 |
| 327 | 313 | P | T | | | | 123 | 1 | | | | 327 | 313 |
| 328 | 314 | G | C | | | | 123 | 1 | | | | 328 | 314 |
| 329 | 315 | N | | | | | 124 | | | | | | |
| 330 | 316 | T | | | | | 124 | | | | | | |
| 331 | 317 | N | | | | | 124 | | | | | | |
| 332 | 318 | T | A | | | | 123 | 1 | | | | 332 | 318 |
| 333 | 319 | R | | | | | 124 | | | | | | |
| 334 | 320 | V | | | | | 124 | | | | | | |
| 335 | 321 | S | | | | | 124 | | | | | | |
| 336 | 322 | R | | | | | 124 | | | | | | |
| 337 | 323 | Y | | | | | 124 | | | | | | |
| 338 | 324 | S | T | | | | 63 | 61 | | | | 338 | 324 |
| 339 | 325 | S | | | | | 124 | | | | | | |
| 340 | 326 | T | S | | | | 69 | 55 | | | | 340 | 326 |
| 341 | 327 | A | | | | | 124 | | | | | | |
| 342 | 328 | R | H | | | | 122 | 2 | | | | 342 | 328 |
| 343 | 329 | R | | | | | 124 | | | | | | |
| 344 | 330 | R | K | S | | | 69 | 54 | 1 | | | 344 | 330 |
| 345 | 331 | L | - | | | | 123 | 1 | | | | 345 | 331 |
| 346 | 332 | R | K | A | | | 121 | 2 | 1 | | | 346 | 332 |
| 347 | 333 | R | | | | | 124 | | | | | | |
| 348 | 334 | G | | | | | 124 | | | | | | |
| 349 | 335 | A | P | V | | | 70 | 53 | 1 | | | 349 | 335 |
| 350 | 336 | D | | | | | 124 | | | | | | |

Fig. 35

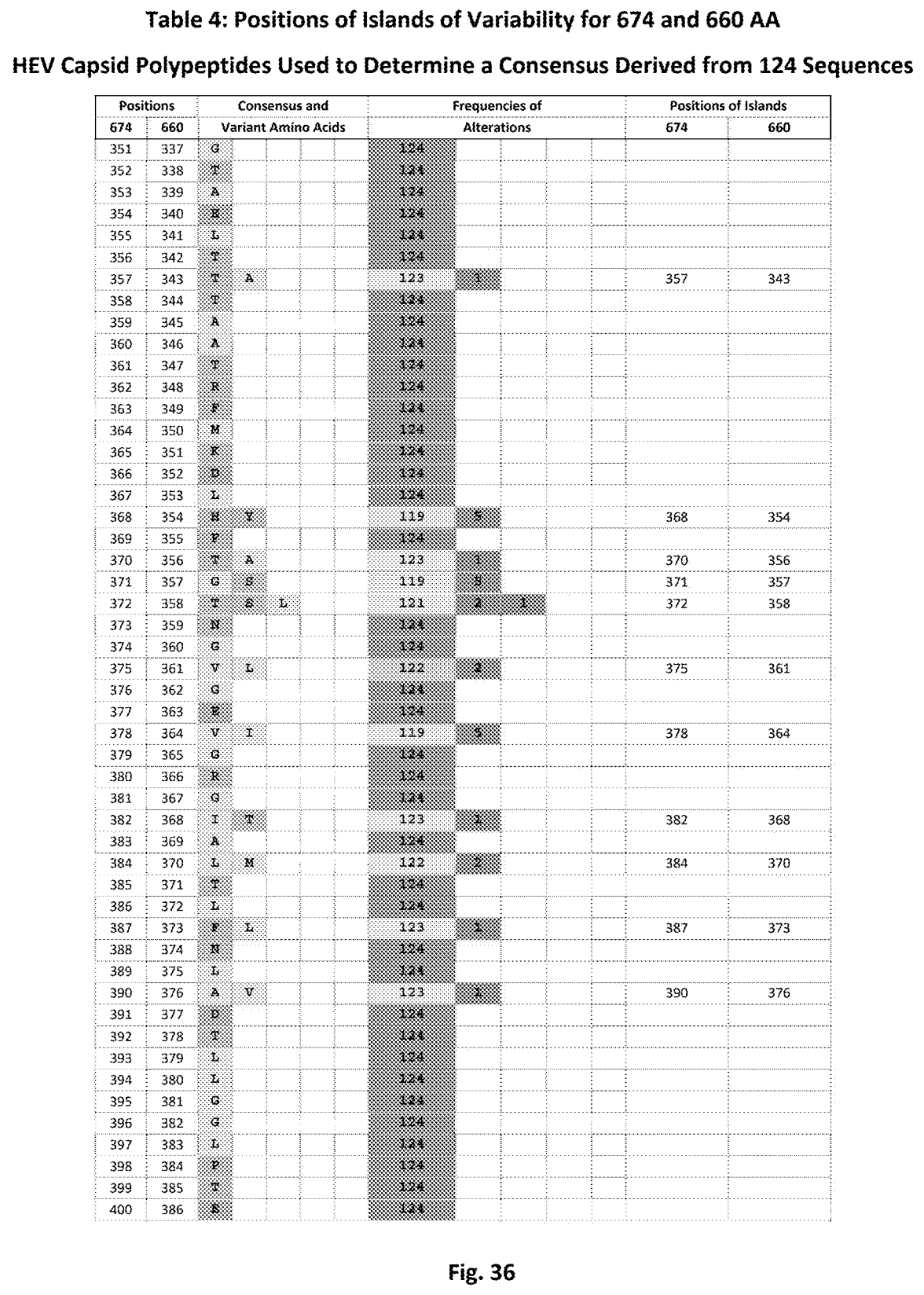

Table 4: Positions of Islands of Variability for 674 and 660 AA

HEV Capsid Polypeptides Used to Determine a Consensus Derived from 124 Sequences

| Positions | | Consensus and | | | | Frequencies of | | | | Positions of Islands | |
|---|---|---|---|---|---|---|---|---|---|---|---|
| 674 | 660 | Variant Amino Acids | | | | Alterations | | | | 674 | 660 |
| 351 | 337 | G | | | | 124 | | | | | |
| 352 | 338 | T | | | | 124 | | | | | |
| 353 | 339 | A | | | | 124 | | | | | |
| 354 | 340 | E | | | | 124 | | | | | |
| 355 | 341 | L | | | | 124 | | | | | |
| 356 | 342 | T | | | | 124 | | | | | |
| 357 | 343 | T | A | | | 123 | 1 | | | 357 | 343 |
| 358 | 344 | T | | | | 124 | | | | | |
| 359 | 345 | A | | | | 124 | | | | | |
| 360 | 346 | A | | | | 124 | | | | | |
| 361 | 347 | T | | | | 124 | | | | | |
| 362 | 348 | R | | | | 124 | | | | | |
| 363 | 349 | F | | | | 124 | | | | | |
| 364 | 350 | M | | | | 124 | | | | | |
| 365 | 351 | K | | | | 124 | | | | | |
| 366 | 352 | D | | | | 124 | | | | | |
| 367 | 353 | L | | | | 124 | | | | | |
| 368 | 354 | H | V | | | 119 | 5 | | | 368 | 354 |
| 369 | 355 | P | | | | 124 | | | | | |
| 370 | 356 | T | A | | | 123 | 1 | | | 370 | 356 |
| 371 | 357 | G | S | | | 119 | 5 | | | 371 | 357 |
| 372 | 358 | T | S | L | | 121 | 2 | 1 | | 372 | 358 |
| 373 | 359 | N | | | | 124 | | | | | |
| 374 | 360 | G | | | | 124 | | | | | |
| 375 | 361 | V | L | | | 122 | 2 | | | 375 | 361 |
| 376 | 362 | G | | | | 124 | | | | | |
| 377 | 363 | E | | | | 124 | | | | | |
| 378 | 364 | V | I | | | 119 | 5 | | | 378 | 364 |
| 379 | 365 | G | | | | 124 | | | | | |
| 380 | 366 | R | | | | 124 | | | | | |
| 381 | 367 | G | | | | 124 | | | | | |
| 382 | 368 | I | T | | | 123 | 1 | | | 382 | 368 |
| 383 | 369 | A | | | | 124 | | | | | |
| 384 | 370 | L | M | | | 122 | 2 | | | 384 | 370 |
| 385 | 371 | T | | | | 124 | | | | | |
| 386 | 372 | L | | | | 124 | | | | | |
| 387 | 373 | F | L | | | 123 | 1 | | | 387 | 373 |
| 388 | 374 | N | | | | 124 | | | | | |
| 389 | 375 | L | | | | 124 | | | | | |
| 390 | 376 | A | V | | | 123 | 1 | | | 390 | 376 |
| 391 | 377 | D | | | | 124 | | | | | |
| 392 | 378 | T | | | | 124 | | | | | |
| 393 | 379 | L | | | | 124 | | | | | |
| 394 | 380 | L | | | | 124 | | | | | |
| 395 | 381 | G | | | | 124 | | | | | |
| 396 | 382 | G | | | | 124 | | | | | |
| 397 | 383 | L | | | | 124 | | | | | |
| 398 | 384 | P | | | | 124 | | | | | |
| 399 | 385 | T | | | | 124 | | | | | |
| 400 | 386 | E | | | | 124 | | | | | |

Fig. 36

Table 4: Positions of Islands of Variability for 674 and 660 AA

HEV Capsid Polypeptides Used to Determine a Consensus Derived from 124 Sequences

| Positions | | Consensus and | | | | | Frequencies of | | | | | | Positions of Islands | |
|---|---|---|---|---|---|---|---|---|---|---|---|---|---|---|
| 674 | 660 | Variant Amino Acids | | | | | Alterations | | | | | | 674 | 660 |
| 401 | 387 | L | | | | | 124 | | | | | | | |
| 402 | 388 | I | | | | | 124 | | | | | | | |
| 403 | 389 | S | | | | | 124 | | | | | | | |
| 404 | 390 | S | | | | | 124 | | | | | | | |
| 405 | 391 | A | | | | | 124 | | | | | | | |
| 406 | 392 | G | S | | | | 123 | 1 | | | | | 406 | 392 |
| 407 | 393 | G | | | | | 124 | | | | | | | |
| 408 | 394 | Q | | | | | 124 | | | | | | | |
| 409 | 395 | L | M | | | | 123 | 1 | | | | | 409 | 395 |
| 410 | 396 | F | | | | | 124 | | | | | | | |
| 411 | 397 | Y | | | | | 124 | | | | | | | |
| 412 | 398 | S | | | | | 124 | | | | | | | |
| 413 | 399 | R | | | | | 124 | | | | | | | |
| 414 | 400 | P | R | | | | 123 | 1 | | | | | 414 | 400 |
| 415 | 401 | V | | | | | 124 | | | | | | | |
| 416 | 402 | V | A | | | | 123 | 1 | | | | | 416 | 402 |
| 417 | 403 | S | | | | | 124 | | | | | | | |
| 418 | 404 | A | | | | | 124 | | | | | | | |
| 419 | 405 | N | H | | | | 123 | 1 | | | | | 419 | 405 |
| 420 | 406 | G | | | | | 124 | | | | | | | |
| 421 | 407 | R | | | | | 124 | | | | | | | |
| 422 | 408 | P | L | | | | 123 | 1 | | | | | 422 | 408 |
| 423 | 409 | T | A | | | | 121 | 1 | | | | | 423 | 409 |
| 424 | 410 | V | R | | | | 123 | 1 | | | | | 424 | 410 |
| 425 | 411 | R | | | | | 124 | | | | | | | |
| 426 | 412 | L | | | | | 124 | | | | | | | |
| 427 | 413 | Y | | | | | 124 | | | | | | | |
| 428 | 414 | T | | | | | 124 | | | | | | | |
| 429 | 415 | S | | | | | 124 | | | | | | | |
| 430 | 416 | V | | | | | 124 | | | | | | | |
| 431 | 417 | R | | | | | 124 | | | | | | | |
| 432 | 418 | N | | | | | 124 | | | | | | | |
| 433 | 419 | A | | | | | 124 | | | | | | | |
| 434 | 420 | Q | | | | | 124 | | | | | | | |
| 435 | 421 | Q | | | | | 124 | | | | | | | |
| 436 | 422 | D | | | | | 124 | | | | | | | |
| 437 | 423 | K | | | | | 124 | | | | | | | |
| 438 | 424 | G | | | | | 124 | | | | | | | |
| 439 | 425 | I | V | | | | 122 | 2 | | | | | 439 | 425 |
| 440 | 426 | A | T | | | | 77 | 47 | | | | | 440 | 426 |
| 441 | 427 | I | | | | | 124 | | | | | | | |
| 442 | 428 | P | | | | | 124 | | | | | | | |
| 443 | 429 | H | N | | | | 123 | 1 | | | | | 443 | 429 |
| 444 | 430 | D | | | | | 124 | | | | | | | |
| 445 | 431 | I | | | | | 124 | | | | | | | |
| 446 | 432 | D | | | | | 124 | | | | | | | |
| 447 | 433 | L | | | | | 124 | | | | | | | |
| 448 | 434 | G | | | | | 124 | | | | | | | |
| 449 | 435 | E | D | | | | 62 | 62 | | | | | 449 | 435 |
| 450 | 436 | S | | | | | 124 | | | | | | | |

Fig. 37

Table 4: Positions of Islands of Variability for 674 and 660 AA

HEV Capsid Polypeptides Used to Determine a Consensus Derived from 124 Sequences

| Positions | | Consensus and | | | | Frequencies of | | | Positions of Islands | |
|---|---|---|---|---|---|---|---|---|---|---|
| 674 | 660 | Variant Amino Acids | | | | Alterations | | | 674 | 660 |
| 451 | 43 | G | | | | 124 | | | | |
| 452 | 44 | D | | | | 124 | | | | |
| 453 | 45 | R | | | | 124 | | | | |
| 454 | 46 | V | I | A | | 109 | 14 | 1 | 60 | 46 |
| 455 | 437 | R | | | | 124 | | | | |
| 456 | 438 | V | | | | 124 | | | | |
| 457 | 439 | V | | | | 124 | | | | |
| 458 | 440 | I | | | | 124 | | | | |
| 459 | 441 | Q | | | | 124 | | | | |
| 460 | 442 | D | | | | 124 | | | | |
| 461 | 443 | Y | | | | 124 | | | | |
| 462 | 444 | D | | | | 124 | | | | |
| 463 | 445 | N | | | | 124 | | | | |
| 464 | 446 | Q | | | | 124 | | | | |
| 465 | 447 | H | | | | 124 | | | | |
| 466 | 448 | E | G | | | 123 | 1 | | 462 | 448 |
| 467 | 449 | Q | | | | 124 | | | | |
| 468 | 450 | D | | | | 124 | | | | |
| 469 | 451 | R | | | | 124 | | | | |
| 470 | 452 | P | X | | | 123 | 1 | | 466 | 452 |
| 471 | 453 | T | | | | 124 | | | | |
| 472 | 454 | F | | | | 124 | | | | |
| 473 | 455 | R | | | | 124 | | | | |
| 474 | 456 | P | | | | 124 | | | | |
| 475 | 457 | A | | | | 124 | | | | |
| 476 | 458 | P | | | | 124 | | | | |
| 477 | 459 | S | | | | 124 | | | | |
| 478 | 460 | R | | | | 124 | | | | |
| 479 | 461 | P | | | | 124 | | | | |
| 480 | 462 | F | | | | 124 | | | | |
| 481 | 463 | S | | | | 124 | | | | |
| 482 | 464 | V | | | | 124 | | | | |
| 483 | 465 | L | | | | 124 | | | | |
| 484 | 466 | R | | | | 124 | | | | |
| 485 | 467 | A | | | | 124 | | | | |
| 486 | 468 | N | | | | 124 | | | | |
| 487 | 469 | D | | | | 124 | | | | |
| 488 | 470 | V | | | | 124 | | | | |
| 489 | 471 | L | | | | 124 | | | | |
| 490 | 472 | W | | | | 124 | | | | |
| 491 | 473 | L | | | | 124 | | | | |
| 492 | 474 | S | | | | 124 | | | | |
| 493 | 475 | L | | | | 124 | | | | |
| 494 | 476 | T | | | | 124 | | | | |
| 495 | 477 | A | V | | | 123 | 1 | | 491 | 477 |
| 496 | 478 | A | | | | 124 | | | | |
| 497 | 479 | E | G | D | | 122 | 1 | 1 | 493 | 479 |
| 498 | 480 | T | | | | 124 | | | | |
| 499 | 481 | D | | | | 124 | | | | |
| 500 | 482 | Q | | | | 124 | | | | |

Fig. 38

Table 4: Positions of Islands of Variability for 674 and 660 AA

HEV Capsid Polypeptides Used to Determine a Consensus Derived from 124 Sequences

| Positions | | Consensus and Variant Amino Acids | | | | | Frequencies of Alterations | | | | | Positions of Islands | |
|---|---|---|---|---|---|---|---|---|---|---|---|---|---|
| 674 | 660 | | | | | | | | | | | 674 | 660 |
| 501 | 487 | S | | | | | 124 | | | | | | |
| 502 | 488 | S | T | | | | 122 | 2 | | | | 502 | 488 |
| 503 | 489 | T | | | | | 124 | | | | | | |
| 504 | 490 | N | G | A | | | 118 | 5 | 1 | | | 504 | 490 |
| 505 | 491 | P | | | | | 124 | | | | | | |
| 506 | 492 | M | V | | | | 118 | 6 | | | | 506 | 492 |
| 507 | 493 | Y | | | | | 124 | | | | | | |
| 508 | 494 | V | I | | | | 123 | 1 | | | | 508 | 494 |
| 509 | 495 | S | | | | | 124 | | | | | | |
| 510 | 496 | D | | | | | 124 | | | | | | |
| 511 | 497 | T | S | | | | 118 | 6 | | | | 511 | 497 |
| 512 | 498 | V | A | | | | 123 | 1 | | | | 512 | 498 |
| 513 | 499 | T | | | | | 124 | | | | | | |
| 514 | 500 | F | L | | | | 103 | 21 | | | | 514 | 500 |
| 515 | 501 | V | I | A | | | 121 | 2 | 1 | | | 515 | 501 |
| 516 | 502 | N | | | | | 124 | | | | | | |
| 517 | 503 | V | | | | | 124 | | | | | | |
| 518 | 504 | A | | | | | 124 | | | | | | |
| 519 | 505 | T | | | | | 124 | | | | | | |
| 520 | 506 | G | | | | | 124 | | | | | | |
| 521 | 507 | A | | | | | 124 | | | | | | |
| 522 | 508 | Q | | | | | 124 | | | | | | |
| 523 | 509 | A | G | | | | 67 | 57 | | | | 523 | 509 |
| 524 | 510 | V | | | | | 124 | | | | | | |
| 525 | 511 | A | S | | | | 70 | 54 | | | | 525 | 511 |
| 526 | 512 | R | | | | | 124 | | | | | | |
| 527 | 513 | S | T | | | | 122 | 2 | | | | 527 | 513 |
| 528 | 514 | L | | | | | 124 | | | | | | |
| 529 | 515 | D | | | | | 124 | | | | | | |
| 530 | 516 | W | | | | | 124 | | | | | | |
| 531 | 517 | S | T | | | | 119 | 5 | | | | 531 | 517 |
| 532 | 518 | K | | | | | 124 | | | | | | |
| 533 | 519 | V | | | | | 124 | | | | | | |
| 534 | 520 | T | A | | | | 123 | 1 | | | | 534 | 520 |
| 535 | 521 | L | F | | | | 123 | 1 | | | | 535 | 521 |
| 536 | 522 | D | | | | | 124 | | | | | | |
| 537 | 523 | G | | | | | 124 | | | | | | |
| 538 | 524 | R | | | | | 124 | | | | | | |
| 539 | 525 | P | | | | | 124 | | | | | | |
| 540 | 526 | L | | | | | 124 | | | | | | |
| 541 | 527 | T | M | S | A | P | 74 | 41 | 5 | 2 | 1 | 541 | 527 |
| 542 | 528 | T | | | | | 124 | | | | | | |
| 543 | 529 | I | V | T | | | 121 | 2 | 1 | | | 543 | 529 |
| 544 | 530 | Q | H | R | | | 121 | 3 | 1 | | | 544 | 530 |
| 545 | 531 | Q | L | | | | 123 | 1 | | | | 545 | 531 |
| 546 | 532 | Y | | | | | 124 | | | | | | |
| 547 | 533 | S | P | | | | 123 | 1 | | | | 547 | 533 |
| 548 | 534 | K | | | | | 124 | | | | | | |
| 549 | 535 | T | I | | | | 123 | 1 | | | | 549 | 535 |
| 550 | 536 | F | | | | | 124 | | | | | | |

Fig. 39

Table 4: Positions of Islands of Variability for 674 and 660 AA

HEV Capsid Polypeptides Used to Determine a Consensus Derived from 124 Sequences

| Positions 674 | Positions 660 | Consensus and Variant Amino Acids | | | Frequencies of Alterations | | | Positions of Islands 674 | Positions of Islands 660 |
|---|---|---|---|---|---|---|---|---|---|
| 551 | 537 | Y | F | L | 69 | 54 | 1 | 551 | 537 |
| 552 | 538 | V | | | 124 | | | | |
| 553 | 539 | L | | | 124 | | | | |
| 554 | 540 | P | | | 124 | | | | |
| 555 | 541 | L | | | 124 | | | | |
| 556 | 542 | R | | | 124 | | | | |
| 557 | 543 | G | | | 124 | | | | |
| 558 | 544 | K | | | 124 | | | | |
| 559 | 545 | L | | | 124 | | | | |
| 560 | 546 | S | | | 124 | | | | |
| 561 | 547 | F | | | 124 | | | | |
| 562 | 548 | W | | | 124 | | | | |
| 563 | 549 | E | | | 124 | | | | |
| 564 | 550 | A | | | 124 | | | | |
| 565 | 551 | G | | | 124 | | | | |
| 566 | 552 | T | | | 124 | | | | |
| 567 | 553 | T | V | | 123 | 1 | | 567 | 553 |
| 568 | 554 | K | R | | 123 | 1 | | 568 | 554 |
| 569 | 555 | A | S | P | 122 | 1 | 1 | 569 | 555 |
| 570 | 556 | G | | | 124 | | | | |
| 571 | 557 | T | | | 124 | | | | |
| 572 | 558 | F | | | 124 | | | | |
| 573 | 559 | T | | | 124 | | | | |
| 574 | 560 | M | | | 124 | | | | |
| 575 | 561 | Y | | | 124 | | | | |
| 576 | 562 | N | D | | 123 | 1 | | 576 | 562 |
| 577 | 563 | T | | | 124 | | | | |
| 578 | 564 | T | A | | 123 | 1 | | 578 | 564 |
| 579 | 565 | A | | | 124 | | | | |
| 580 | 566 | S | | | 124 | | | | |
| 581 | 567 | D | | | 124 | | | | |
| 582 | 568 | Q | | | 124 | | | | |
| 583 | 569 | I | L | | 119 | 5 | | 583 | 569 |
| 584 | 570 | L | | | 124 | | | | |
| 585 | 571 | I | V | | 113 | 11 | | 585 | 571 |
| 586 | 572 | E | G | | 123 | 1 | | 586 | 572 |
| 587 | 573 | N | | | 124 | | | | |
| 588 | 574 | A | | | 124 | | | | |
| 589 | 575 | A | S | | 122 | 2 | | 589 | 575 |
| 590 | 576 | G | | | 124 | | | | |
| 591 | 577 | H | | | 124 | | | | |
| 592 | 578 | R | | | 124 | | | | |
| 593 | 579 | V | | | 124 | | | | |
| 594 | 580 | A | C | T | 68 | 55 | 1 | 594 | 580 |
| 595 | 581 | I | | | 124 | | | | |
| 596 | 582 | S | | | 124 | | | | |
| 597 | 583 | T | | | 124 | | | | |
| 598 | 584 | Y | | | 124 | | | | |
| 599 | 585 | T | | | 124 | | | | |
| 600 | 586 | T | | | 124 | | | | |

Fig. 40

Table 4: Positions of Islands of Variability for 674 and 660 AA

HEV Capsid Polypeptides Used to Determine a Consensus Derived from 124 Sequences

| Positions | | Consensus and Variant Amino Acids | | | | | Frequencies of Alterations | | | | | Positions of Islands | |
|---|---|---|---|---|---|---|---|---|---|---|---|---|---|
| 674 | 660 | | | | | | | | | | | 674 | 660 |
| 601 | 587 | S | N | R | | | 68 | 55 | 1 | | | 601 | 587 |
| 602 | 588 | L | | | | | 124 | | | | | | |
| 603 | 589 | G | S | | | | 123 | 1 | | | | 603 | 589 |
| 604 | 590 | A | S | V | | | 67 | 55 | 2 | | | 604 | 590 |
| 605 | 591 | G | S | | | | 123 | 1 | | | | 605 | 591 |
| 606 | 592 | P | | | | | 124 | | | | | | |
| 607 | 593 | V | T | | | | 77 | 47 | | | | 607 | 593 |
| 608 | 594 | S | A | | | | 123 | 1 | | | | 608 | 594 |
| 609 | 595 | I | V | | | | 111 | 13 | | | | 609 | 595 |
| 610 | 596 | S | | | | | 124 | | | | | | |
| 611 | 597 | A | S | C | | | 120 | 2 | 2 | | | 611 | 597 |
| 612 | 598 | V | A | | | | 123 | 1 | | | | 612 | 598 |
| 613 | 599 | G | A | | | | 118 | 6 | | | | 613 | 599 |
| 614 | 600 | V | | | | | 124 | | | | | | |
| 615 | 601 | L | | | | | 124 | | | | | | |
| 616 | 602 | A | G | | | | 123 | 1 | | | | 616 | 602 |
| 617 | 603 | P | | | | | 124 | | | | | | |
| 618 | 604 | H | R | | | | 123 | 1 | | | | 618 | 604 |
| 619 | 605 | S | T | | | | 123 | 1 | | | | 619 | 605 |
| 620 | 606 | A | V | | | | 115 | 9 | | | | 620 | 606 |
| 621 | 607 | L | | | | | 124 | | | | | | |
| 622 | 608 | A | | | | | 124 | | | | | | |
| 623 | 609 | V | A | L | M | I | 61 | 51 | 7 | 3 | 2 | 623 | 609 |
| 624 | 610 | L | | | | | 124 | | | | | | |
| 625 | 611 | R | | | | | 124 | | | | | | |
| 626 | 612 | D | | | | | 124 | | | | | | |
| 627 | 613 | T | | | | | 124 | | | | | | |
| 628 | 614 | V | I | A | T | L | 80 | 18 | 16 | 4 | 3 | 628 | 614 |
| 629 | 615 | D | | | | | 124 | | | | | | |
| 630 | 616 | Y | F | | | | 123 | 1 | | | | 630 | 616 |
| 631 | 617 | P | | | | | 124 | | | | | | |
| 632 | 618 | A | G | | | | 123 | 1 | | | | 632 | 618 |
| 633 | 619 | R | C | | | | 122 | 2 | | | | 633 | 619 |
| 634 | 620 | A | | | | | 124 | | | | | | |
| 635 | 621 | R | | | | | 124 | | | | | | |
| 636 | 622 | T | | | | | 124 | | | | | | |
| 637 | 623 | P | X | | | | 123 | 1 | | | | 637 | 623 |
| 638 | 624 | D | | | | | 124 | | | | | | |
| 639 | 625 | D | | | | | 124 | | | | | | |
| 640 | 626 | F | | | | | 124 | | | | | | |
| 641 | 627 | C | | | | | 124 | | | | | | |
| 642 | 628 | P | X | | | | 123 | 1 | | | | 642 | 628 |
| 643 | 629 | R | | | | | 124 | | | | | | |
| 644 | 630 | C | | | | | 124 | | | | | | |
| 645 | 631 | R | N | | | | 122 | 2 | | | | 645 | 631 |
| 646 | 632 | T | A | N | P | S | 57 | 44 | 13 | 5 | 2 | 646 | 632 |
| 647 | 633 | L | | | | | 124 | | | | | | |
| 648 | 634 | G | | | | | 124 | | | | | | |
| 649 | 635 | L | F | | | | 123 | 1 | | | | 649 | 635 |
| 650 | 636 | Q | | | | | 124 | | | | | | |

Fig. 41

Table 4: Positions of Islands of Variability for 674 and 660 AA

HEV Capsid Polypeptides Used to Determine a Consensus Derived from 124 Sequences

| Positions | | Consensus and | | | | | Frequencies of | | | | | Positions of Islands | |
|---|---|---|---|---|---|---|---|---|---|---|---|---|---|
| 674 | 660 | Variant Amino Acids | | | | | Alterations | | | | | 674 | 660 |
| 651 | 637 | G | | | | | 124 | | | | | | |
| 652 | 638 | C | | | | | 124 | | | | | | |
| 653 | 639 | A | | | | | 124 | | | | | | |
| 654 | 640 | F | X | | | | 123 | 1 | | | | 654 | 640 |
| 655 | 641 | Q | | | | | 124 | | | | | | |
| 656 | 642 | S | | | | | 124 | | | | | | |
| 657 | 643 | T | | | | | 124 | | | | | | |
| 658 | 644 | V | I | | | | 77 | 47 | | | | 658 | 644 |
| 659 | 645 | A | X | G | | | 122 | 1 | 1 | | | 659 | 645 |
| 660 | 646 | R | | | | | 124 | | | | | | |
| 661 | 647 | L | I | | | | 122 | 2 | | | | 661 | 647 |
| 662 | 648 | Q | | | | | 124 | | | | | | |
| 663 | 649 | R | | | | | 124 | | | | | | |
| 664 | 650 | L | X | | | | 123 | 1 | | | | 664 | 650 |
| 665 | 651 | K | R | | | | 121 | 3 | | | | 665 | 651 |
| 666 | 652 | M | T | V | | | 119 | 4 | 1 | | | 666 | 652 |
| 667 | 653 | R | | | | | 124 | | | | | | |
| 668 | 654 | V | | | | | 124 | | | | | | |
| 669 | 655 | G | | | | | 124 | | | | | | |
| 670 | 656 | R | | | | | 124 | | | | | | |
| 671 | 657 | T | | | | | 124 | | | | | | |
| 672 | 658 | R | | | | | 124 | | | | | | |
| 673 | 659 | R | | | | | 124 | | | | | | |
| 674 | 660 | Y | S | F | L | | 55 | 53 | 10 | 6 | | 674 | 660 |

Amino acids are colored by the biochemical properties of their side chains, as shown in columns 3-7 of the table. Relative positions of amino acids across a consensus capsid polypeptide from positions 1-674 or 1-660, where position 1 of a 660 amino acid polypeptide corresponds to position 15 of a 674 amino acid polypeptide. The consensus polypeptide derived from a multiple sequence alignment of 124 HEV capsid polypeptide sequences is in column 3 of the table, with variant amino acids shown in columns 4-7, and the frequencies of each are in columns 8-12. The positions of islands of variability for the 674 and 660 amino acid consensus sequences, where there is at least one variant shown in column 4, are shown in columns 13 and 14, respectively. This data was extracted from Figures 9 and 10 and transposed to illustrate the consensus sequence vertically in rows, with observed variant amino acids and their frequencies in adjacent columns.

Fig. 42

HEPATITIS E VIRUS-LIKE PARTICLES (VLPS) DERIVED FROM CONSENSUS SEQUENCES

PRIORITY CLAIMS

This application claims priority to United States Provisional Application U.S. 63/609,538 filed on Dec. 13, 2023.

INCORPORATION-BY-REFERENCE OF A SEQUENCE LISTING

The sequence listing contained in file "762_196_008_US_01_Sequence_Listing_2023_12_11.xml" created on 2023 Nov. 6, modified on 2023 Dec. 11, file size 32,173 bytes, and any original and amended sequence listings are incorporated by reference in their entirety herein.

FIELD OF THE INVENTION

Virus-Like Particles (VLPs) comprising capsid proteins derived from viruses of the family Hepeviridae that are capable of encapsulating or being conjugated to nucleic acids, polypeptides, or small molecules for use in a variety of diagnostic and therapeutic applications are disclosed. Virus-Like Particles derived from the subfamilies, Parahepevirinae, which infect trout and salmon, and the Orthohepevirinae, which infect mammals and birds, particularly those of the species Paslahepevirus balayani, which can cause acute hepatitis in humans and several other mammalian species, and chronic conditions in immunocompromised patients are also disclosed. Major aspects of the invention relate to compositions of Virus-Like Particles comprising viral capsid proteins capable of assembly in cultured cells that may be purified, disassembled, and reassembled in the presence of other molecules suitable for use as therapeutic drug products to facilitate the targeting and delivery of cargo molecules to specific cells or tissues, or as antigenic agents designed to stimulate responses to heterologous epitopes exposed on the surfaces of Virus-Like Particles. Preferred aspects relate to functional capsids derived from polypeptide sequences comprising one or more amino acid substitutions, insertions, or deletions of amino acid encoded by a consensus of ORF2 genes, wherein said variant polypeptides are functionally-similar or have enhanced properties compared to capsid polypeptides encoded by naturally-occurring viruses obtained from clinical samples or prototype Hepatitis E Viruses (HEV).

BACKGROUND OF THE INVENTION

The design and assembly of nucleic acids comprising one or more genetic elements in a desired order typically requires a variety of techniques, including cloning of one or more isolated DNA sequences into vectors which propagate in bacteria, sequencing of the cloned inserts, introduction of the vector into an appropriate host cell, and expression of polypeptides under the control of a promoters operably-linked to the inserted sequences. Structural and functional analyses of the expressed polypeptides accelerate research, often leading to the development and commercialization of therapeutic drug products, such as small and large molecules, vaccines, components of cell and gene therapy vector systems, and research tools, promoting the interests of institutions having a wide variety of strong interests in the life sciences.

Virus-Like Particles Derived From Viral Capsid Systems

Virus-like particles (VLPs) have been used as nanocarriers to encapsulate nucleic acids or small molecule drug products, or to display epitopes on their surfaces to facilitate the targeting and delivery of molecules to cells for the detection and treatment of a wide variety of diseases. The discovery, development, and commercialization of commercial drug delivery technologies, including VLPs, was reported in an extensive review (Vargason et al (2021).

FIG. 1: Sets Forth an Illustration Entitled "Classes of Therapeutic and Delivery Paradigms".

Hepatitis E Virus-Like Particles (HEV-VLPs)

Hepatitis E virus (HEV) has a non-enveloped icosahedral capsid, enclosing a 7.2 kb single-stranded RNA (ssRNA) genome. The major capsid protein is encoded by the second open reading frame (ORF2), which is essential for virus assembly, immunogenicity, and host cell interactions (Purcell 1996; Tam et al. 1991; Xing et al. 2011; Schofield et al. 2000; Yu et al. 2010). HEV-VLP forms a hollow, T=1 icosahedral capsid composed of 60 identical units (Xing et al. 1999), rendering it highly stable in both storage and harsh physiological conditions. HEV-VLP have a surface-exposed protrusion (P) domain connected through a flexible hinge to a stable icosahedral base. The P domain forms surface-exposed spikes atop the icosahedral base. The shell(S) and middle (M) domains can assemble into the stable icosahedral shell of HEV-VLP, while the P-domain protrudes as a surface spike that carried profoundly determines HEV antigenicity (Yamashita et al. 2009; Xing et al. 2011). The modular nature of the three-domains facilitates assembly of particles that are antigenic, while reducing their size from a T3 to T1 icosahedral particles (Xing et al. 1999), with or without sequence modifications on the P-domain without interference with HEV-VLP assembly steps (Niikura et al. 2002; Jariyapong et al. 2013).

FIG. 2: Sets Forth Panel a which Illustrates the Crystal Structure of HEV VLPs, and Panel B Illustrates a Ribbon Diagram Capsid Subunit.

Recombinant capsid proteins (PORF2) are able to self-assemble into virus-like particles when expressed in insect cells that have deletions of 111 amino acids from the N-terminal end and 52 amino acids from the C-terminal end (Li et al. 2005b; Li et al. 1997). PORF2 folds into shell, middle, and protruding domains, corresponding to amino acids 118-317, 318-451, and 452-606, respectively (Guu et al. 2009; Xing, Li, Miyazaki, et al. 2010; Yamashita et al. 2009). A flexible hinge makes it possible to modify the P domain by inserting a foreign peptide (Jariyapong et al. 2013) or by conjugating chemicals to residues in it without compromising its basic icosahedral structure (Chen et al. 2016). Three variable loops and the C terminal end of the P domain can also be modified to contain conjugation sites for bioactive agents that are exposed on the surface of HEV-VLP (Cheng et al. 2015; Chen et al. 2016; Cheng 2017). Replacing other amino acids with cysteine residues, or adding new cysteine residues to the P domain reduces responses of pre-existing antibodies to HEV-VLPs, addressing shortcomings of many other protein-based delivery vector systems (Chen et al. 2016).

Nanotheranostic and Diagnostic Agents Based on HEV-VLPs

Nanotheranostic agents have accelerated the delivery of therapeutic drug products and diagnostic agents to specific kinds of cells and tissues (Ludwig and Wagner 2007). These systems rely on delivery of Virus-Like Particles conjugated to theranostic moieties to modulate the activities of regulatory and structural molecules in impaired host cell systems (Galaway and Stockley 2013; Ma, Nolte, and Cornelissen 2012; Chen et al. 2016). Many of these are subject to issues relating to passive cell uptake, pre-mature degradation, toxicity, and insufficient association with theranostic molecules. VLP-based systems, however, overcome many of these obstacles, by enhancing ways to display foreign epitopes on their surfaces, or to deliver small molecules to a cell (Ludwig and Wagner 2007).

Modularized theranostic and diagnostic agents derived from HEV virus-like particles have been proposed as platforms for vaccine, cancer targeting, diagnostic, and therapeutic applications (Chen et al. 2016; Cheng et al. 2017; Holla et al. 2017; Stark et al. 2017; Chen, Baikoghli, and Cheng 2018; Jariyapong et al. 2013; Niikura et al. 2002). The flexible domain in HEV-VLPs can be used to conjugate functional peptides or compounds to their surfaces (Chen et al. 2016; Stark et al. 2017; Niikura et al. 2002; Jariyapong et al. 2013), which permit the encapsulation of small molecule drug products (Chen, Baikoghli, and Cheng 2018), DNA and RNA molecules (Takamura et al. 2004), and inorganic beads (Chen CC 2017).

FIG. 3: Sets Forth an Illustration Entitled "Surface Modification Capability of HEV-VLP".

HEV-VLPs retain many of the biophysical attributes of the native virion, including structural stability, antigenicity, and cell binding capabilities. These particles, like the native virus, are stable in acidic environments (Zafrullah et al. 2004) and resistant to digestion by proteolytic enzymes (Jariyapong et al. 2013; Chen, Baikoghli, and Cheng 2018), allowing delivery by oral routes. Administration of chimeric HEV-VLPs displaying foreign epitopes can stimulate systemic and mucosal immunological responses (Niikura et al. 2002) with undetectable tolerance, and provide protection against HEVs in non-human primates (Li et al. 2004). Orally-delivered HEV-VLPs can also deliver plasmid DNAs to epithelial cells of the small intestine, stimulating antibody and cytotoxic T lymphocyte responses against plasmid-encoded antigens (Takamura et al. 2004).

HEV-VLPs with modified surface protruding domains can also be used as diagnostic agents or as targetable drug delivery vehicles to treat cancer and other illnesses. HEV-VLPs conjugated to ligand peptides, such as LXY30, which have high affinities for malignant breast tumor cells, bound to tumor cells in in vitro and in vivo assays, suggesting that routes of administration can be manipulated to facilitate delivery of diagnostic or therapeutic agents to pathologic foci (Chen et al. 2016; Stark et al. 2017).

Negatively-charged nucleic acids, such as DNA and mRNA, can also be encapsulated for use in vaccines (Takamura et al. 2004), or as carriers for gene therapy vector systems (Panda et al. 2015). HEV-VLPs have also been proposed as carriers for the delivery of proteins by oral means, such as insulin, to treat diabetes (Chen, Baikoghli, and Cheng 2018). Magnetic particles such as ferrite can also be encapsulated and used as contrasting agents for magnetic resonance imaging or tumor-targeted hyperthermia applications (Roemer 1999; Chen CC 2017).

HEV-VLPs can also be used in cell-specific drug targeting and delivery systems (DDSs) by combining surface modifications and payload encapsulation capabilities, to deliver epitope and DNA vaccines, MRI/PET imaging enhancing agents, and in gene therapy, genome editing, and cancer drug delivery systems. Scalable, low-cost expression and purification of stable, functional particles are required for all of these applications.

HEV-VLPs have also been proposed as nano-platforms for the development of theranostic agents by replacing or adding amino acids such as cysteine to incorporate reaction sites that facilitate the conjugation of ligands or small molecules, such as maleimide-linked peptides or molecules, to the protrusion domain. Structural analyses of HEV-VLP and well-studied immunogenic epitopes, identified residues within the flexible loops and exposed sites within the C terminus that can be replaced with or allow insertion of cysteine residues as chemical conjugation sites (Xing, Li, Mayazaki, et al. 2010; Xing et al. 2011; Chen et al. 2016).

Theranostic and diagnostic agents targeting cancer cells require a targeting ligand that will facilitate the binding and uptake of the agent by the malignant cell. HEV-VLPs conjugated to LXY30 bound to breast tumor cells in vitro and in vivo assays systems, suggesting that HEV-VLPs can be manipulated in other ways to facilitate the delivery of agents to pathologic foci (Xiao et al. 2016; Chen et al. 2016). HEV-VLPs were also observed to accumulate at abdominal organs, including liver (Chen et al. 2016), inspiring perhaps, the development of liver-specific Positron emission tomography (PET) imaging agents chemically conjugated to radio-active gallium-68 [68Ga] (Lambidis, Chen, Lumen, et al. 2022; Lambidis, Chen, Baikoghli, et al. 2022), supporting the development of HEV-VLPs as nanotheranostic agents, particularly for those affecting liver and related cells and tissues.

Reports describing targeted drug delivery systems based on VLPs have dramatically increased in recent years. While nanocarriers comprising synthetic polymers, liposomes, or telodendrimers have been studied extensively over the last 20 years, many limitations remain to be addressed, such as toxicity, inability to accumulate a sufficient number of molecules to the cytoplasm, and lack of biodegradability (Sebestik, Niederhafner, and Jezek 2011; Jian et al. 2012). Liposomal carriers, such as Doxil®, do not possess tumor-targeting abilities, but tend to accumulate in solid tumors due to the features of the tumor region, such as large pore spaces in newly-synthesized blood vessels (EPR effect) (Shi et al. 2020). Drug leakage during circulation, stimulating undesirable side effects, is another significant concern (Russell, Hultz, and Searson 2018).

Modularized theranostic and diagnostic HEV-VLPs can also be designed to take advantage of chemical moieties that are exposed on the interior of a capsid, as well as moieties exposed on its surface. HEV-VLPs have been designed to encapsulate viral RNAs, that form highly stable non-infectious capsids capable of reversible in vitro assembly mediated by cation exchanges (Xing, Li, Mayazaki, et al. 2010), suggesting that they can also be switched back and forth in self-assembly reactions through a series of steps involving chemical reduction and cation chelation, mediated by reducing and chelating reagents such as dithiothreitol (DTT), ethylenediaminetetraacetic acid (EDTA), or ethylene glycol-bis(β-aminoethyl ether)-N,N,N',N'-tetraacetic acid (EGTA), and calcium or magnesium ions.

FIG. 4: Sets Forth an Illustration Entitled "Encapsulation Capability of HEV-VLPs".

While HEV capsids normally encapsulate ssRNA molecules mediated primarily by interactions based on charge, modified capsids should be able to encapsulate small proteins or small molecules for therapeutic drug product applications. HEV-VLPs were used to orally deliver plasmid DNAs encoding antigens to epithelial cells of the small intestine for transient expression (Takamura et al. 2004; Cheng and Xing 2014). Negatively-charged mRNAs could also be encapsulated into the interior of HEV-VLPs for gene delivery. HEV-VLPs were also shown to be capable of encapsulating magnetic Virus-Like Particles such as citric-coated ferrite, suitable for diagnosis under MRI and by tumor-targeted hyperthermia induced by ultrasonic or radio frequency electromagnetic radiation (Chen CC 2017). HEV-VLPs comprising surface-bound cancer cell targeting ligands could have many applications in gene therapy applications (Stark and Cheng 2016).

Theranostic and diagnostic agents derived from HEV-VLPs should be capable of encapsulating a variety of molecules, including other types of inorganic nanoparticles, including metal nanoparticles, such as gold nanoparticles, in addition to ferrite ($Fe_3O_4$) nanoparticles noted above.

Key issues to be addressed when designing and optimizing methods for the disassembly and reassembly of VLPs, include the concentrations and ratios of chelating agents and calcium or magnesium ions, concentration, charge, and other properties of the payload molecules. Issues relating to administration also need to be addressed, which include dosing of encapsulated molecules, delivery and release of molecules at target sites, and cost effectiveness, which are all critical to produce larger scale quantities of GMP-quality materials needed for clinical trials.

Immunomodulatory Agents Based on HEV-VLPs

Atopic diseases, such as asthma, allergic rhinitis, and atopic dermatitis, are caused by environmental and genetic factors. Exposure to Hepatitis A Virus (HAV) associated with poor hygiene, large family sizes, and attendance at day-care centers, are all factors that are inversely associated with atopy. Individuals infected with HAV may be protected from atopy, if they carry a variant (designated HAVcr-1) of the gene that encodes TIM-1, a cell-surface receptor used by HAV to infect human cells (McIntire et al. 2003). These results suggest that interactions between HAV and cells expressing TIM-1 variants are somehow involved in the etiology of atopic diseases, supporting the poor hygiene hypothesis.

Orally-transmitted Hepatitis E Virus is also recognized as a pathogen associated with the poor hygiene. HEV-VLPs can also be used to induce expression of many genes in THP-1 cells derived from monocytes isolated from an acute leukemia patient, which are often used in immune system disorder research, immunology research, and toxicology research. In vivo effects of HEV VLPs as oral immune modulators can also be studied in a variety of animal models, by measuring immune responses and weight gains, such as chickens inoculated with avian-flu vaccines.

SUMMARY OF THE INVENTION

A major aspect of the invention relates to a nucleotide sequence encoding a polypeptide sequence derived from a consensus of Hepeviridae capsid proteins comprising one or more amino acid substitutions, insertions, or deletions, capable of forming a functional Virus-Like Particle, wherein said Virus-Like Particle encapsulates or is conjugated to one or more molecules selected from the group consisting of a nucleic acid, a polypeptide, an inorganic nanoparticle, and a small molecule drug product.

Major aspects of the invention also relate to a vector comprising a nucleotide sequence noted above, encoding a functional Virus-Like Particle, including a vector selected from the group consisting of a cloning vector and an expression vector, including an expression vector that comprises a nucleotide sequence encoding a functional Virus-Like Particle operably-linked to a promoter at its 5' end, and optionally a transcriptional termination signal at its 3' end, more preferably wherein said expression vector is baculo-virus expression vector, and most preferably wherein said baculovirus expression vector comprises a baculovirus promoter operably-linked to a nucleotide sequence encoding a functional Virus-Like Particle, such as a vector comprising a nucleotide sequence represented by SEQ ID NOs: 01, 03, 05, 07, 09, 11, and 13.

Major aspects of the invention relate to a prokaryotic or eukaryotic cell harboring a vector noted above, preferably, a eukaryotic cell, an insect cell, a lepidopteran insect cell, and most preferably a Lepidopteran insect cell selected from the group consisting of *Spodoptera frugiperda, Trichoplusia ni*, and *Bombyx mori*, plus other eukaryotic cell lines including fungal cells, such as yeast cells, and prokaryotic cells, such as *Escherichia coli* cells.

A major aspect of the invention relate to a method of isolating functional Virus-Like Particles derived from a consensus of Hepeviridae capsid proteins comprising one or more amino acid substitutions, insertions, or deletions comprising the steps of (a): infecting susceptible insect cells with a baculovirus expression vector comprising a nucleotide sequence encoding a functional Virus-Like Particle under the control of a polyhedrin promoter; (2) monitoring the expression of capsid protein over time; (3) concentrating, binding, and eluting purified capsid proteins; and (4) forming functional Virus-Like Particles.

A major aspect of the invention relates to a polypeptide sequence derived from a consensus of Hepeviridae capsid proteins comprising one or more amino acid substitutions, insertions, or deletions, capable of forming a functional Virus-Like Particle, wherein said Virus-Like Particle encapsulates or is conjugated to a molecule selected from the group consisting of a nucleic acid, a polypeptide, an inorganic nanoparticle, and a small molecule drug product. Related aspects include a polypeptide sequence, wherein said consensus of Hepeviridae capsid proteins are derived from the subfamily Orthohepevirinae, including those derived from the subfamily Orthohepevirinae, species *Paslahepevirus balayani*.

A major aspect of the invention is a functional Virus-Like Particle derived from a consensus of Hepeviridae capsid proteins comprising one or more amino acid substitutions, insertions, or deletions, wherein said Virus-Like Particle encapsulates or is conjugated to a molecule selected from the group consisting of a nucleic acid, a polypeptide, or a small molecule drug product.

A better understanding of the invention will be obtained from the following detailed descriptions and accompanying drawings, which set forth illustrative embodiments that are indicative of the various ways in which the principals of the invention may be employed.

BRIEF DESCRIPTION OF THE DRAWINGS

Statement Concerning Aspects of the Invention Understood by Reference to the Drawings The foregoing aspects and many of the attendant advantages of this invention will become more readily appreciated as the same become better understood by reference to the following detailed description, when taken in conjunction with the accompanying drawings, wherein:

FIG. 1: sets forth an illustration entitled "Classes of therapeutic and delivery paradigms".

FIG. 2: sets forth Panel A which illustrates the crystal structure of HEV VLPs, and Panel B illustrates a ribbon diagram capsid subunit.

FIG. 15: sets forth an illustration entitled "Frequencies of Number of Amino Acid Changes Across 124 HEV Sequences (Green is Lower, Red is Higher)".

FIG. 16 and FIG. 17: set forth illustrations entitled "Frequencies of Number of Amino Acid Changes Across 124 HEV Sequences (Green is Lower, Red is Higher)

FIG. 18: sets forth an illustration entitled "Hydrophobicity/Hydrophilicity Analysis of the NS5A (AAs 1-31)".

FIG. 19: sets forth an illustration entitled "HEV ORF2 Capsid Variant With Truncated Amino and Carboxy Termini".

FIG. 20: sets forth an illustration entitled "Hydrophobicity/Hydrophilicity Analysis of Peptide NS5A (1-31)".

FIG. 21: sets forth an illustration entitled "NCT-002: HEV-NS5A-VLP".

FIG. 22: sets forth an illustration entitled "Nct-003: RGD Peptide Fused at the C Terminal of the N/C Terminus Deleted Version of Consensus Sequence (Cys Insertion Between 490aa and 491aa)".

FIG. 23: sets forth an illustration entitled "NCT-004: 13aa deleted N terminus of Full Length of Proposed Consensus sequence derived from 160 sequences (14aa-660aa, Cys insertion between 490aa and 491aa)".

FIG. 24: sets forth an illustration entitled "NCT-005: HHV of mAb Replace the P Domain of the N/C Terminus Deleted Variant of Consensus Sequence".

FIGS. 26-28: set forth illustrations entitled "Table 3: Search Query and Sources of 124 Related HEV Capsid Proteins in GenBank*".

FIGS. 29-42: set forth illustrations entitled "Table 4: Positions of Islands of Variability for 674 and 660 AA HEV Capsid Polypeptides Used to Determine a Consensus Derived from 124 Sequences" in groups of 50 amino acids from 1-674 of the 674 aa consensus HEV capsid polypeptide, or the corresponding positions from 1-660 where position 1 of the 660 aa polypeptide corresponds to amino acid 15 of the 674 aa consensus HEV capsid polypeptide.

ABBREVIATIONS, TERMS AND THEIR DEFINITIONS

Figure 3:
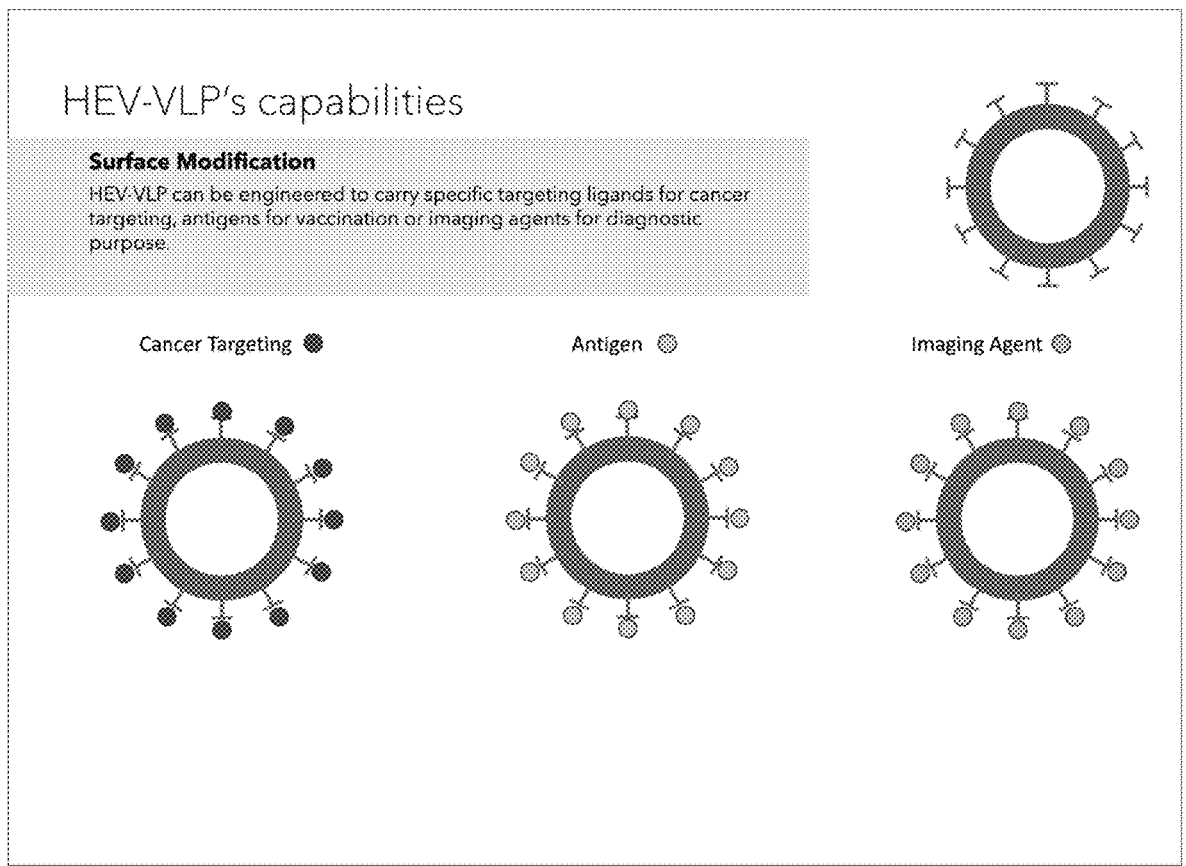
FIG. 3: sets forth an illustration entitled "Surface modification capability of HEV-VLPs".
Figure 4:
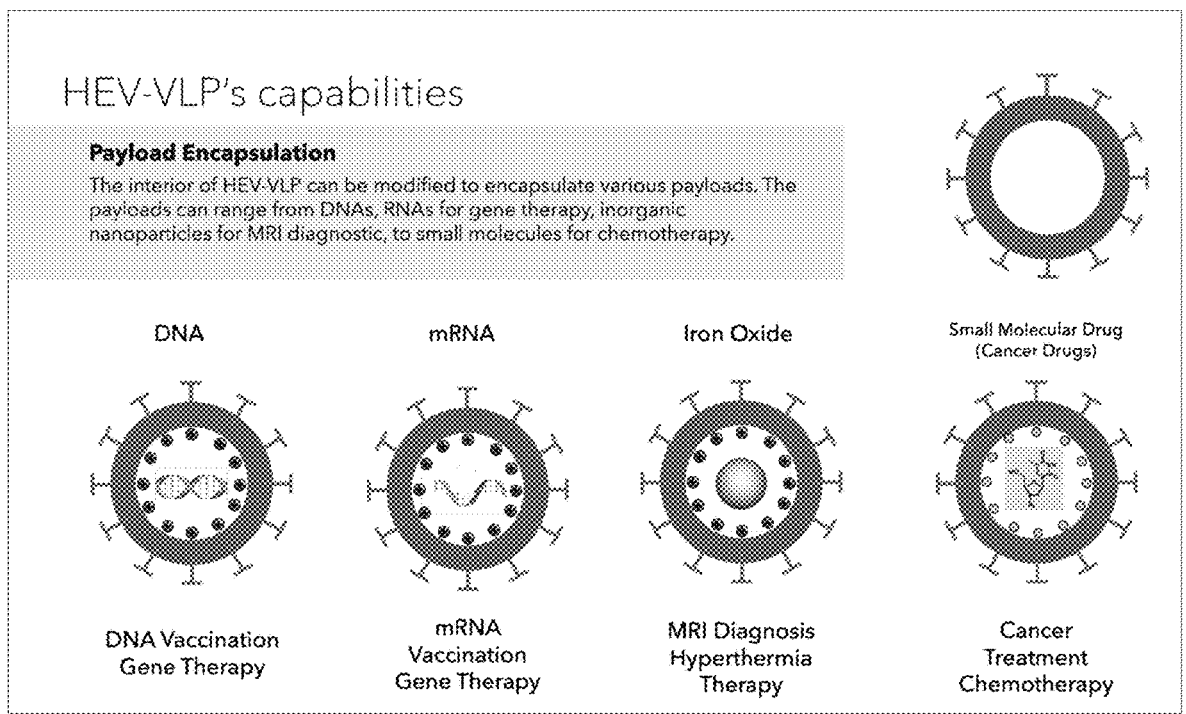
FIG. 4: sets forth an illustration entitled "Encapsulation capability of HEV-VLPs".

The following is a list of abbreviations, plus terms and their definitions, used throughout the text of the specification, the figures, the sequence listing, supplementary data tables (if any), and the claims:

TABLE 1

| List of Abbreviations | |
|---|---|
| A = adenosine; | PAGE = PA-gel electrophoresis; |
| A = absorbance (1 cm); | PCR = polymerase chain reaction, a gene amplification |
| aa or AA = amino acid; | procedure; |
| Ab = antibody(ies); | PEG = poly(ethylene glycol); |
| AcNPV = *Autographa californica* Nuclear Polyhedrosis | PEP = phosphoenolpyruvate; |
| Virus, a member of the Baculoviridae family of insect | pfu = plaque-forming unit(s); |
| viruses; | Pi = inorganic phosphate; |
| Amp, Ap = ampicillin; | pmol = picomole(s); |
| ATP = Adenosine triphosphate; | PMSF = phenylmethylsulfonyl fluoride; |
| bla = beta lactamase gene conferring resistance to | ppm = parts per million; |
| beta-lactam antibiotics, particularly ampicillin; | R = purine (or restriction); |
| Bluo-gal = halogenated indolyl-β-D-galactoside; | r or R or superscripted r or R = resistant or resistance |
| bp, Bp = base pair(s); | RBS = ribosome-binding site(s); |
| BSA = bovine serum albumin; | rDNA = DNA coding for rRNA; |
| C = cytidine; | RNase = ribonuclease; |
| Cam, Cm or CM = chloramphenicol; | RP-HPLC = reverse phase high performance liquid |
| cAMP = cyclic adenosine 3',5'-monophosphate; | chromatograph; |
| cDNA = DNA complementary to RNA; | rRNA = ribosomal RNA; |
| CMP = cytidine monophosphate; | RT = reverse transcriptase; |
| cpm = counts per minute; | RT = room temperature; |
| CTP = cytidine triphosphate; | RT-PCR = reverse transcriptase polymerase chain |
| Δ = deletion; | reaction; |
| d = deoxyribo; | s or S = (superscript) sensitivity/sensitive; |
| dd = dideoxyribo; | S = sedimentation constant; |
| DMF = N,N-dimethylformamide; | SD = Shine-Dalgarno (sequence); |
| DMSO = dimethylsulfoxide; | SDS = sodium dodecyl sulfate; |
| DNase = deoxyribonuclease; | SDS-PAGE = sodium dodecyl sulfate-polyacrylamide |
| dNTP = deoxyribonucleoside triphosphate; | gel electrophoresis; |
| ds = double strand(ed); | "::" = novel junction (fusion or insertion, transposon |
| DTT = dithiothreitol; | insertion); |
| ELISA = enzyme-linked immunosorbent assay; | ' (prime) = denotes a truncated gene at the indicated |
| EST = expressed sequence tag; | side; |
| EtBr, EtdBr = ethidium bromide; | Sf = *Spodoptera frugiperda*; |
| g = gram(s); | Sf9 = *Spodoptera frugiperda* (Sf9) cells/cell line; |

TABLE 1-continued

List of Abbreviations

| | |
|---|---|
| G = guanosine; | Sf21 = *Spodoptera frugiperda* (IPLB Sf21) cells/cell line; |
| GLC-MS = Gas-liquid chromatography-mass | SID or SIDNO or SID# = SEQ ID NO; |
| spectrometry; | ss = single strand(ed); |
| HEV = Hepatitis E Virus | SSC = 0.15M NaCl/0.015M Na3•citrate pH 7.6; |
| HPLC = high performance liquid chromatography; | T = thymidine; |
| IPTG = isopropyl β-D-thiogalactopyranoside; | t, T = terminator of transcription; |
| kb or kbp = kilobase(s) = 1000 bp(s); | Tc, TC = tetracycline; |
| kDa = kilodalton(s); | Tni, *T. ni* = *Trichoplusia ni* cells/cell line; |
| LTR = long terminal repeat(s); | Tni368 = *Trichoplusia ni* (Tni368) cells/cell line; |
| MAb, mAb = monoclonal Ab; | ts = temperature-sensitive; |
| Mb = megabase(s); | tsp = transcription start point(s); |
| MCS = multiple cloning site(s); | u or U = unit(s); |
| Me = methyl; | U = uridine; |
| mg = milligram(s); | p, P = promoter; |
| ml or mL = milliliter(s); | ug or μg = microgram(s); |
| mm = millimeter(s); | ul or μl = microliter(s); |
| mM = millimolar; | UV = ultraviolet; |
| moi, MOI = multiplicity of infection; | VLP(s) = virus-like particle(s) |
| Mr = relative molecular mass (dimensionless); | wt = wild-type; |
| N = any nucleoside; | Xgal, X-gal = 5-bromo-4-chloro-3-indolyl β-D- |
| NAD/NADH = nicotinamide-adenine dinucleotide, and | galactopyranoside; |
| its reduced form; | Y = pyrimidine; |
| nmol = nanomole(s); | [ ] = denotes plasmid-carrier state; |
| NMR = nuclear magnetic resonance; | Nucleotide symbol combinations: |
| NPV = Nuclear polyhedrosis virus; | Pairs: |
| nt = nucleotide(s); | K = G/T; M = A/C; R = A/G; S = C/G; W = A/T; Y = C/T; |
| oligo = oligodeoxyribonucleotide; | Triples: |
| ORF = open reading frame; | B = C/G/T; D = A/G/T; H = A/C/T; V = A/C/G; |
| ori = origin(s) of DNA replication; | N = A/C/G/T; |
| p = plasmid; | |

General abbreviations and their corresponding meanings include: aa or AA = amino acid; mg = milligram(s); ml or mL = milliliter(s); mm = millimeter(s); mM = millimolar; nmol = nanomole(s); pmol = picomole(s); ppm = parts per million; RT = room temperature; U = units; ug, μg = micro gram(s); ul, μl = micro liter(s); uM, μM = micromolar.

Specific abbreviations and their corresponding meanings include:

The terms "cell" and "cells," which are meant to be inclusive, refer to one or more cells which can be in an isolated or cultured state, as in a cell line comprising a homogeneous or heterogeneous population of cells, or in a tissue sample, or as part of an organism, such as a transgenic animal.

The term "amino acid" encompasses both naturally occurring and non-naturally occurring amino acids unless otherwise designated.

The term "pharmacokinetics" (PK) relates to studies of how an organism affects a drug product, such as the uptake of a drug product by the body, their biotransformation as substrates into other products, the distribution of drug products and their metabolites in tissues, and elimination of the drugs and their metabolites from the body over a period of time.

The term "pharmacodynamics" (PD) relates to studies of how a drug product affects an organism.

Data from PK and PD model systems both influence decisions concerning dosing, benefit, and adverse effects of compositions comprising one or more drug products

DETAILED DESCRIPTION OF THE INVENTION

The present invention relates to Virus-Like Particles derived from the subfamilies, Parahepevirinae, which infect trout and salmon, and the Orthohepevirinae, which infect mammals and birds, particularly those of the species *Paslahepevirus balayani*, which can cause acute hepatitis in humans and several mammalian species, and chronic conditions in immunocompromised patients are also disclosed.

Major aspects of the invention relate to compositions of Virus-Like Particles comprising viral capsid proteins capable of assembly in cultured cells that may be purified, disassembled, and reassembled in the presence of other molecules suitable for use as therapeutic drug products to facilitate the targeting and delivery of cargo molecules to specific cells or tissues, or as antigenic agents designed to stimulate responses to heterologous epitopes exposed on the surfaces of Virus-Like Particles.

Preferred aspects relate to functional capsids comprising polypeptide sequences comprising one or more amino acid substitutions, insertions, or deletions of amino acid encoded by a consensus of ORF2 genes, wherein said variant polypeptides are functionally-similar or have enhanced properties compared to capsid polypeptides encoded by naturally-occurring viruses obtained from clinical samples or prototype Hepatitis E Viruses (HEV).

Other aspects include the design and assembly of modified vectors to facilitate the basic and applied studies leading to the development and commercialization of novel drug products, and as tools advancing the interests of institutions involved in animal and human healthcare.

A nucleotide sequence encoding a polypeptide sequence derived from a consensus of Hepeviridae capsid proteins comprising one or more amino acid substitutions, insertions, or deletions, capable of forming a functional Virus-Like Particle (VLP), wherein said VLP encapsulates or is conjugated to one or more molecules selected from the group consisting of a nucleic acid, a polypeptide, an inorganic nanoparticle and a small molecule drug product.

A major aspect of the invention relates to a nucleotide sequence encoding a polypeptide sequence derived from a consensus of Hepeviridae capsid proteins comprising one or more amino acid substitutions, insertions, or deletions, capable of forming a functional Virus-Like Particle, wherein said Virus-Like Particle encapsulates or is conjugated to one or more molecules selected from the group consisting of a nucleic acid, a polypeptide, and a small molecule drug product.

Preferred aspects related to a nucleotide sequence wherein said consensus of Hepeviridae capsid proteins are derived from the subfamily Orthohepevirinae, and a nucleotide sequence wherein said consensus of Hepeviridae capsid proteins are derived from the subfamily Orthohepevirinae, species *Paslahepevirus balayani*.

Other preferred aspects relate to a nucleotide sequence wherein said polypeptide sequence comprises one or more conservative amino acid substitutions in variable or invariable domains of the consensus sequence, including a nucleotide sequence wherein said polypeptide sequence comprises one or more conservative amino acid substitutions in variable domains of the consensus sequence, or a nucleotide sequence, wherein said polypeptide sequence comprises one or more conservative amino acid substitutions in invariable domains of the consensus sequence.

Other preferred aspects relate to a nucleotide sequence wherein said polypeptide sequence comprises one or more amino acid deletions, including a nucleotide sequence wherein said polypeptide sequence comprises a deletion at the amino, carboxy, or amino and carboxy termini of the consensus sequence, or a nucleotide sequence wherein said polypeptide sequence comprises one or more deletions in variable domains of the consensus sequence.

Other preferred aspects relate to a nucleotide sequence wherein said polypeptide sequence comprises one or more amino acid insertions, including a nucleotide sequence wherein said polypeptide sequence comprises one or more insertions in variable domains of the consensus sequence, or wherein said polypeptide sequence comprises one or more insertions in invariable domains of the consensus sequence.

Other preferred aspects relate to a nucleotide sequence wherein said polypeptide sequence comprises one or more conservative amino acid substitutions, and one or more insertions or one or more deletions in variable or invariable domains of the consensus sequence, or wherein all of said conservative amino acid substitutions, insertions or deletions are in variable domains of the consensus sequence.

Other preferred aspects relate to nucleotide sequences noted above, further comprising one or more insertions of DNA segments encoding heterologous polypeptides selected from the group consisting of nucleic acid binding domains, hydrophobic binding domains, polypeptide binding domain, and antibody binding domains, preferably wherein said domain is a nucleic acid binding domain, a hydrophobic binding domain, a hydrophilic binding domain, a polypeptide binding domain, or an antibody binding domain.

Major aspects of the invention relate to a vector comprising a nucleotide sequence noted above, encoding a functional Virus-Like Particle, including a vector is selected from the group consisting of a cloning vector and an expression vector, including an expression vector comprises a nucleotide sequence encoding a functional Virus-Like Particle operably linked to a promoter at its 5' end and optionally a transcriptional termination signal at its 3' end, more preferably wherein said expression vector is baculovirus expression vector, and most preferably wherein said baculovirus expression vector comprises a baculovirus promoter, such as a polyhedrin or p10 promoter operably-linked to a nucleotide sequence encoding a functional Virus-Like Particle. Other aspects relate to bacterial expression vectors, mammalian expression vectors, and yeast expression vectors. Preferred aspects relate to any of the vectors noted above comprising a nucleotide sequence represented by SEQ ID NOs: 01, 03, 05, 07, 09, 11, and 13, which encode polypeptides represented by 02, 04, 06, 08, 10, 12, and 14, respectively.

Major aspects of the invention relate to a prokaryotic or eukaryotic cell harboring a vector noted above, preferably, a eukaryotic cell, an insect cell, a lepidopteran insect cell, and most preferably a Lepidopteran insect cell is selected from the group consisting of *Spodoptera frugiperda, Trichoplusia ni,* and *Bombyx mori.* Other aspects relate to mammalian cells, including primate and human cells, fungal cells, including filamentous and non-filamentous fungi, including yeast cells, and prokaryotic cells, including *Escherichia coli* cells.

A major aspect of the invention relates to a polypeptide sequence derived from a consensus of Hepeviridae capsid proteins comprising one or more amino acid substitutions, insertions, or deletions, capable of forming a functional Virus-Like Particle, wherein said Virus-Like Particle encapsulates or is conjugated to one or more molecules selected from the group consisting of one or more molecules selected from the group consisting of a nucleic acid, a polypeptide, an inorganic nanoparticle, and a small molecule drug product. Related aspects include a polypeptide sequence wherein said consensus of Hepeviridae capsid proteins are derived from the subfamily Orthohepevirinae, including those derived from the subfamily Orthohepevirinae, species *Paslahepevirus balayani.*

Related aspects include a polypeptide sequence which comprises one or more conservative amino acid substitutions in variable or invariable domains of the consensus sequence, wherein said polypeptide sequence comprises one or more conservative amino acid substitutions in variable domains of the consensus sequence, or wherein said polypeptide sequence comprises one or more conservative amino acid substitutions in invariable domains of the consensus sequence.

Related aspects include a polypeptide sequence comprises one or more amino acid deletions, including wherein said polypeptide sequence comprises a deletion at the amino, carboxy, or amino and carboxy termini of the consensus sequence, or wherein said polypeptide sequence comprises one or more deletions in variable domains of the consensus sequence.

Related aspects include a polypeptide sequence which comprises one or more amino acid insertions, including wherein said polypeptide sequence comprises one or more insertions in variable domains of the consensus sequence, or wherein said polypeptide sequence comprises one or more insertions in invariable domains of the consensus sequence.

Related aspects include a polypeptide sequence comprises one or more conservative amino acid substitutions, and one or more insertions or one or more deletions in variable or invariable domains of the consensus sequence, including wherein all of said conservative amino acid substitutions, insertions or deletions are in variable domains of the consensus sequence.

Other related aspects include a polypeptide sequence noted above, further comprising one or more insertions of DNA segments encoding heterologous polypeptides selected from the group consisting of nucleic acid binding domains, hydrophobic binding domains, polypeptide binding domain, and antibody binding domains, including a polypeptide sequence wherein said domain is a nucleic acid binding domain, a hydrophobic binding domain, hydrophilic binding domain, a polypeptide binding domain, or an antibody binding domain.

A major aspect of the invention is a functional Virus-Like Particle derived from a consensus of Hepeviridae capsid proteins comprising one or more amino acid substitutions, insertions, or deletions, wherein said Virus-Like Particle encapsulates or is conjugated to one or more molecules selected from the group consisting of a nucleic acid, a polypeptide, or a small molecule drug product.

Related aspects include a functional Virus-Like Particle wherein said Virus-Like Particle encapsulates one or more molecules selected from the group consisting of a nucleic acid, including a single-stranded RNA (ssRNA) molecule, a double-stranded RNA (dsRNA) molecule, a single-stranded DNA (ssDNA) molecule, a double-stranded DNA (dsDNA) molecule, a polypeptide, an inorganic nanoparticle, and a small molecule drug product.

Other related aspects include a functional Virus-Like Particle wherein said Virus-Like Particle encapsulates one or more molecules selected from the group consisting of a nucleic acid, a polypeptide, and an inorganic nanoparticle.

A major aspect of the invention relate to a method of isolating functional Virus-Like Particles derived from a consensus of Hepeviridae capsid proteins comprising one or more amino acid substitutions, insertions, or deletions comprising the steps of (a): infecting susceptible insect cells with a baculovirus expression vector comprising a nucleotide sequence encoding a functional Virus-Like Particle under the control of a baculovirus promoter; (2) monitoring the expression of capsid protein over time; (3) concentrating, binding, and eluting purified capsid proteins; and (4) forming functional Virus-Like Particles.

EXAMPLES

The foregoing discussion may be better understood in connection with the following representative examples which are presented for purposes of illustrating the principal methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods

All parts are by weight (e.g., % w/w), and temperatures are in degrees Centigrade (C), unless otherwise indicated.

The following table presents a summary of the nucleotide and amino acid sequences described in this application. Sequence Identifier Numbers (SEQ ID NOs) with even numbers generally represent polypeptide sequences, while SEQ ID NOs with odd numbers represent nucleotide sequences that encode corresponding polypeptide sequences, generally by back translation of the polypeptide sequence into a nucleotide sequence.

TABLE: 2

Summary Table of Sequence ID Numbers

| Name | Description | Len | Type | SEQ ID NO |
|---|---|---|---|---|
| Back translation of NCT-660-HEV ORF2-consensus | ATGAGACCCAGAGCAGTACTTCTGTTGTTCCTGGTACTGCTTCCAATGCT TCCTGCGCCGCCAGCTGGCCAACCGTCGGGTCGCCGTCGTGGTAGACGCT CTGGTGGAGCAGGTGGAGGCTTTTGGGGCGATAGGGTAGACAGCCAACCG TTTGCGCTCCCATATATCCACCCCACGAATCCATTCGCGTCAGACGTTGT CAGTCAATCGGGAGCAGGCGCCCGTCCAAGACAACCTGCGAGACCTTTGG GTTCCGCCTGGAGGGATCAATCACAGCGTCCGGCGGCTGCGCCGAGACGC AGATCTGCACCAGCGGGTGCCGCTCCCCTGACAGCTGTCGCGCCTGCACC GGATACAGCACCCGTCCCTGATGTCGATTCTAGAGGCGCGATATTGCGCA GGCAGTACAATCTTTCTACATCGCCTCTCACAAGCTCTGTAGCCAGTGGT ACTAACCTCGTACTTTACGCCGCGCCCCTGAATCCGTTGCTCCCCCTGCA AGACGGCACGAACACGCACATAATGGCTACGGAGGCCTCGAATTACGCGC AGTATCGCGTGGTCAGGGCCACGATTAGATACAGGCCTCTCGTACCTAAC GCAGTTGGAGGATACGCCATATCTATCTCGTTCTGGCCCCAGACTACGAC GACACCGACGAGTGTCGACATGAATTCTATTACCAGCACGGATGTACGCA TCCTCGTGCAGCCTGGAATCGCCTCGGAGCTGGTGATCCCTTCCGAAAGG CTGCATTACCGCAACCAGGGCTGGAGGAGTGTGGAAACCAGCGGTGTGGC AGAGGAGGAGGCAACGTCAGGACTCGTAATGCTGTGCATACACGGCAGCC CTGTAAATTCGTATACAAACACACCATACACCGGTGCATTGGGTCTGCTT GATTTTGCTCTCGAGCTGGAGTTCAGGAATCTCACTCCAGGTAATACAAA TACGCGCGTCAGCAGATATTCGAGTACGGCGCGCCATAGGCTCAGACGTG GTGCCGACGGCACAGCGGAACHCACAACCACCGCAGCCACGCGTTTTATG AAAGATCTTCATTTTACGGGTACCAATGGCGTCGGAGAAGTAGGTAGGGG TATTGCACTCACTCTTTTCAATCTTGCAGACACTCTGCTCGGAGGCCTTC CTACCGAACTTATTTCTAGCGCTGGTGGTCAGCTCTTTTATAGCAGGCCG GTGGTCTCTGCCAACGGAGAACCTACAGTAAAACTTTATACTTCTGTTGA GAATGCGCAGCAAGATAAGGGCATCGCTATACCACACGACATAGACCTCG GTGAGTCTCGTGTCGTAATCCAGGATTATGACAATCAGCACGAACAGGAT CGCCCTACTCCATCGCCAGCCCCTTCCCGTCCGTTTAGTGTCCTTCGCGC CAATGACGTATTGTGGCTTAGTCTCACTGCGGCAGAATACGATCAGACAA CATATGGATCGTCGACTAATCCTATGTACGTAAGCGACACGGTCACATTC GTAAATGTTGCTACCGGAGCCCAAGCTGTTGCAAGGTCTCTTGATTGGAG CAAGGTCACGTTGGACGGTCCCCCGTTGACTACCATTCAGCAGTACTCCA AGACCTTTTATGTCTTGCCTTTGCGCGGAAAACTTAGCTTTTGGGAGGCA GGAACGACCAAAGCAGGCTATCCTTACAACTACAACACCACCGCCAGCGA TCAGATACTTATAGAAACGCTGCCGGTCATAGAGTTGCAATCTCGACGT ATACCACTTCTTTGGGCGCAGGACCAGTGTCCATATCTGCTGTTGGTGTT TTGGCCCCACACTCAGCTCTCGCGGTCCTCGAGGACACAGTTGACTATCC CGCTAGGGCTCATACCTTCGACGATTTCTGTCCCGAGTGTCGTACGCTCG | 1983 | DNA | 01 |

TABLE: 2-continued

| | Summary Table of Sequence ID Numbers | | | |
|---|---|---|---|---|
| Name | Description | Len | Type | SEQ ID NO |
| | GACTTCAAGGCTGCGCTTTCCAATCTACTGTGGCCGAACTGCAGAGACTC AAGATGAAAGTGGGAAAAACGCGCGAGTACtaa | | | |
| NCT-660-HEV ORF2-consensus | MRPRAVLLLFLVLLPMLPAPPAGQPSGRRRGRRSGGAGGGFWGDRVDSQP FALPYIHPTNPFASDVVSQSGAGARPRQPARPLGSAWRDQSQRPAAAPRR RSAPAGAAPLTAVAPAPDTAPVPDVDSRGAILRRQYNLSTSPLTSSVASG TNLVLYAAPLNPLLPLQDGINTHIMATEASNYAQYRVVRATIRYRPLVPN AVGGYAISISFWPQTTTTPTSVDMNSITSIDVRILVQPGIASELVIPSER LHYRNQGWRSVETSGVAEEEATSGLVMLCIHGSPVNSYINTPYTGALGLL DFALELEFRNLTPGNTNTRVSRYSSTARHRLRRGADGTAELTTTAATRFM KDLHFTGINGVGEVGRGIALTLFNLADTLLGGLPTELISSAGGQLFYSRP VVSANGEPTVKLYTSVENAQQDKGIAIPHDIDLGESRVVIQDYDNQHEQD RPTPSPAPSRPFSVLRANDVLWLSLTAAEYDQTTYGSSINPMYVSDTVTF VNVATGAQAVARSLDWSKVTLDGRPLTTIQQYSKTFYVLPLRGKLSFWEA GTTKAGYPYNYNTTASDQILIENAAGHRVAISTYTTSLGAGPVSISAVGV LAPHSALAVLEDTVDYPARAHTFDDFCPECRTLGLQGCAFQSTVAELQRL KMKVGKTREY | 660 | PRT | 02 |
| Back translation of NCT-004-(649 aa)-(M1_R2_L13del_N490_P491insC)-(M1 -L14-Y660)-(Near-Full-Length) | ATGCTCCCCATGCTGCCGGCACCCCCTGCGGGCCAGCCATCTGGACGACG ACGCGGAAGGCGTAGTGGAGGCGCGGGCGGTGGTTTCTGGGGTGATAGAG TCGACTCACAACCTTTTGCTCTTCCGTATATACATCCTACAAACCCCTTC GCGTCTGATGTGGTGAGCCAGTCGGGCGCGGGCGCTCGTCCACGGCAACC AGCCAGACCTCTTGGGTCGGCATGGCGTGACCAGAGTCAACGGCCAGCTG CAGCACCTCGACGTAGGAGTGCACCTGCCGGAGCTGCCCCCTTGACTGCC GTGGCGCCTGCCCCTGACACCGCTCCGGTACCTGATGTTGATTCCAGAGG TGCGATTCTAAGACGCCAGTATAATTTGAGCACTTCGCCTTTGACTTCCA GTGTAGCGTCTGGAACTAACCTTGTTCTGTACGCCGCCCCGTTAAATCCG CTCCTTCCCTTACAGGACGGCACCAATACGCACATTATGGCGACTGAGGC TTCCAACTATGCTCAATATGAGTGGTGAGAGCAACGATCCGATACAGAC CACTGGTTCCGAATGCCGTTGGAGGGTATGCCATTTCAATAAGTTTCTGG CCACAAACCACGACAACCCCGACGTCAGTAGACATGAACTCCATAACCTC GACCGATGTGCGCATCTTGGTTCAGCCCGGTATTGCTTCTGAACTCGTGA TACCCAGCGAAAGACTGCATTATAGGAACCAAGGCTGGCGGTCAGTCGAA ACAAGCGGCGTCGCCGAGGAGGAAGCTACCTCCGGCCTGGTTATGTTGTG CATCCATGGTTCACCGGTCAACAGTTACACTAATACTCCCTACACGGGTG CGCTAGGGTTACTGGACTTCGCACTAGAATTGGAGTTTCGTAATTTAACG CCAGGAAATACCAACACTCGCGTATCCAGGTACAGTTCGACGGCTCGACA CCGGTTGCGCCGTGGTGCTGATGGAACGGCTGAGCTCACAACTACTGCAG CAACTCGCTTTATGAAGGACCTACACTTTACGGGCACAAATGGTGTCGGA GAAGTCGGCCGTGGAATCGCATTAACACTTTTTAATCTAGCTGATACTTT GCTAGGCGGGCTCCCAACGGAGCTGATCTCAAGCGCTGGGGGGCAGCTTT TCTATTCTCGGCCTGTGGTATCTGCGAATGGCGAACCCACGGTTAAACTT TATACATCCGTAGAAAACGCTCAACAGGATAAAGGCATAGCGATTCCACA TGATATAGATCTAGGGGAAAGTCGAGTTGTAATCCAGGACTATGATAACC AGCACGAGCAAGACCGGCCCACGCCGTCACCTGCCCCATCGCGACCATTC TCCGTGCTACGGGCGAATGACGTACTATGGCTCTCCCTCACAGCCGCGGA ATACGATCAAACCACATATGGAAGTAGCACGAATTGTCCCATGTACGTAA GCGACACCGTGACATTTGTTAACGTCGCAACTGGTGCACAAGCTGTTGCG AGGAGCTTAGACTGGTCAAAGGTCACATTGGATGGGCGCCCGCTCACTAC CATCCAACAATATTCTAAAACTTTCTACGTGCTGCCGCTGCGTGGGAAGC TCTCATTCTGGGAAGCTGGGACGACAAAGGCAGGATACCCTTAACTAT AACACGACGGCATCCGATCAGATTTTAATAGAGAACGCAGCCGGACATAG AGTCGCCATTTCGACATACACAACCTCGTTAGGTGCTGGACCTGTCTCGA TTTCTGCTGTTGGGGTCCTTGCGCCGCATTCTGCACTTGCAGTGCTTGAG GACACCGTAGATTACCCCGCCCGCGCGCACACCTTCGACGACTTTTGTCC AGAGTGTAGGACATTAGGGCTCCAAGGTTGCGCCTTTCAGAGCACCGTAG CGGAGCTGCAGCGGCTTAAAATGAAAGTTGGGAAGACCAGGGAATACtaa | 1950 | DNA | 03 |
| NCT-004-(649 aa)-(M1_R2_L13del_N490_P491insC)-(M1-L14-Y660)-(Near-Full-Length) | MLPMLPAPPAGQPSGRRRGRRSGGAGGGFWGDRVDSQPFA LPYIHPTNPFASDVVSQSGAGARPRQPARPLGSAWRDQSQRPAAAPRRRS APAGAAPLTAVAPAPDTAPVPDVDSRGAILRRQYNLSTSPLTSSVASGIN LVLYAAPLNPLLPLQDGINTHIMATEASNYAQYRVVRATIRYRPLVPNAV GGYAISISFWPQTTTTPTSVDMNSITSIDVRILVQPGIASELVIPSERLH YRNQGWRSVETSGVAEEEATSGLVMLCIHGSPVNSYINTPYTGALGLLDE ALELEFRNLTPGNINTRVSRYSSTARHRLRRGADGTAELTTTAATREMKD LHFTGINGVGEVGRGIALTLFNLADTLLGGLPTELISSAGGQLFYSRPVV SANGEPTVKLYTSVENAQQDKGIAIPHDIDLGESRVVIQDYDNQHEQDRP TPSPAPSRPFSVLRANDVLWLSLTAAEYDQTTYGSSTNCPMYVSDTVTEV NVATGAQAVARSLDWSKVTLDGRPLTTIQQYSKTFYVLPLRGKLSFWEAG TTKAGYPYNYNTTASDQILIENAAGHRVAISTYTTSLGAGPVSISAVGVL APHSALAVLEDTVDYPARAHTEDDFCPECRTLGLQGCAFQSTVAELQRLK MKVGKTREY | 649 | PRT | 04 |

TABLE: 2-continued

Summary Table of Sequence ID Numbers

| Name | Description | Len | Type | SEQ ID NO |
|------|-------------|-----|------|-----------|
| Back translation of NCT-000- (498 aa)- (M1_R2_ T110del_ misssense_ vars_V610_ Y660del | ATGGCCGTTGCTCCAGCTCACGACACGCCTCCGGTTCCAGACGTCGATTC GAGAGGGGCCATATTGCGAAGACAATATAATCTTTCAACGTCACCCCTAA CAAGTTCTGTGGCTACGGGAACAAATCIGGTACTCTACGCGGCGCCCCTT TCGCCACTACTACCCCTCCAAGACGGCACCAACACCCATATCATGGCCAC AGAAGCATCTAATTACGCACAATATCGCGTGGCACGCGCTACCATAAGAT ACAGGGCCTCTGGTACCGAACGCCGTAGGAGGTTACGCGATTTCCATTCA TTCTGGCCTCAGACAACAACTACGCCAACGTCAGTGGATATGAACTCAAT TACTAGCACGGATGTGCGGATTTTAGTCCAGCCTGGGATTGCTAGTGAGC TAGTAATCCCGAGCGAAAGGCTTCACTATCGAAACCAGGGCTGGCGGTCC GTTGAGACGAGCGGCGTAGCGGAAGAGGAGGCCACCTCCGGTTTGGTCAT GCTGTGTATACATGGATCATTGGTAAACAGTTACACTAACACACCGTATA CGGGTGCCCTAGGCCTACTTGATTTCGCGTTAGAGCTCGAGTTTAGGAAT CTCACGCCCGGAAATACTAATACACGGGTGTCCCGTTATTCTAGTACCGC AAGGCATCGACTGCGGCGTGGTGCAGATGGGACGGCCGAACTGACGACGA CCGCCGCAACACGCTTCATGAAGGACCTATACTTTACCAGCACCAATGGG GTCGGGGAAATTGGACGTGGGATTGCCCTCACCCTTTTTAACTTGGCTGA CACACTGTTGGGCGGGTTACCCACTGAACTAATATCTTCCGCAGGCGGTC AGCTTTTTTATTCTAGACCAGTAGTGTCTGCTAACGGTGAACCTACTGTG AAGTTGTACACGTCAGTCGAAAACGCTCAGCAAGACAAGGGTATCGCAAT ACCACATGACATCGATCTCGGCGAGAGTCGGGTAGTGATCCAGGATTACG ATAATCAACATGAGCAAGACCGTCCCACCCCGAGCCCCGCTCCTAGCCGC CCGTTCTCGGTGCTGCGTGCGAACGACGTTCTTTGGCTGAGTTTAACTGC GGCGGAGTATGACCAAAGTACTTATGGCTCTAGTACAGGGCCTGTTTACG TATCGGATAGCGTAACTTTGGTCAATGTTGCTACAGGCGCTCAGGCCGTG GCGAGGTCGCTTGACTGGACTAAGGTTACTCTCGATGGACGACCGCTATC GACTATACAACAGTATTCTAAAACCTTCTTTGTCCTGCCATTGCGAGGAA AATTATCATTTTGGGAAGCAGGTACAACCAAAGCCGGATATCCGTACAAT TATAATACCACAGCCTCCGATCAACTCTTAGTTGAGTGCGCCGCGGGACA CCGCGTCGCGATCAGCACTTACACGACTTCCTTAGGTGCAGGGCCCGTCT CGATATCGGCAGTGGCGGTTTTGGCTCCACACTCCGCATTAGCCtaa | 1497 | DNA | 05 |
| NCT-000- (498 aa)- (M1_R2_ T110del_ misssense_ vars_V610_ Y660del) | MAVAPAHDTPPVPDVDSRGAILRRQYNLSTSPLTSSVATGIN LVLYAAPLSPLLPLQDGINTHIMATEASNYAQYRVARATIRYRPLVPNAV GGYAISISFWPQTTTTPTSVDMNSITSIDVRILVQPGIASELVIPSERLH YRNQGWRSVETSGVAEEEATSGLVMLCIHGSLVNSYINTPYTGALGLLDF ALELEFRNLTPGNINTRVSRYSSTARHRLRRGADGTAELTTTAATREMKD LYFTSINGVGEIGRGIALTLENLADTLLGGLPTELISSAGGQLFYSRPVV SANGEPTVKLYTSVENAQQDKGIAIPHDIDLGESRVVIQDYDNQHEQDRP TPSPAPSRPFSVLRANDVLWLSLTAAEYDQSTYGSSTGPVYVSDSVTLVN VATGAQAVARSLDWTKVTLDGRPLSTIQQYSKTFFVLPLRGKLSFWEAGT TKAGYPYNYNTTASDQLLVECAAGHRVAISTYTTSLGAGPVSISAVAVLA PHSALA | 498 | PRT | 06 |
| Back translation of NCT-002- (534 aa)- (M1_R2_ P109delins_ HEVNS4A_13 aa_ peptide_N490_ P491insC_ V610_Y660del) (Hydrophobic) | ATGGCCGGTTCCTGGCTACGAGACATCTGGGACTGGATATGTGAAGTTTT GTCCGATTTCAAAACCTGGCTGAAGGCAAAAGCCAAACTTATGCCGACAA TGCTTACTGCGGTGGCTCCAGCACCCGATACCGCACCGGTGCCAGACGTT GATTCCAGAGGGGCTATTTTACGTCGCCAATACAACCTCTCTACATCGCC TCTAACAAGCTCAGTTGCTAGCGGGACTAACTTAGTACTATATGCTGCGC CTTTAAATCCCCTGCTGCCACTGCAGGATGGGACTAACACACATATAATG GCGACCGAGGCAAGTAACTACGCCCAATATCGCGTGGTAAGAGCAACCAT ACGGTACAGGCCTTTGGTGCCGAATGCTGTAGGCGGGTATGCTATATCTA TTTCGTTCTGGCCCCAGACGACAACTACCCCAACTTCTGTGGATATGAAC TCCATCACTTCTACTGATGTGCGTATACTCGTCCAACCCGGTATCGCTAG TGAACTAGTAATCCCCTCGGAGAGATTGCACTATCGCAATCAGGGTTGGC GAAGCGTCGAAACCTCAGGTGTAGCGGAAGAGGAAGCAACTTCCGGGTTA GTGATGCTGTGTATCCGGATCACCGGTGAATTCTTATACAAATACGCC GTATACGGGAGCCCTCGGACTCCTCGACTTCGCATTGGAGCTTGAATTCA GGAACCTAACTCCAGGAAATACAAACACCAGGGTTTCCCGCTACAGTTCC ACAGCCCGGCATCGGCTTCGGCGTGGTGCAGACGGCACTGCAGAGTTGAC CACAACAGCCGCTACTCGGTTTATGAAGGACCTTCATTTTACAGGGACGA ATGGAGTTGGAGAGGTTGGGCGTGGCATAGCCTTGACCTTGTTCAACTTA GCGGATACGCTCCTAGGAGGCCTCCCGACCGAACTTATTTCGTCGGCTGG CGGCCAGCTGTTCTATTCTCGACCAGTCGTCTCGGCAAACGGCGAACCTA CAGTGAAGCTCTATACGTCAGTTGAGAACGCCCAACAAGACAAAGGTATT GCTATCCCGCATGATATCGACCTTGGAGAGAGCCGAGTCGTAATTCAGGA TTATGACAACCAGCACGAACAGGATCGCCCCACGCCATCACCCGCTCCTA GCCGTCCGTTTAGCGTATTGCGAGCGAATGATGTACTCTGGTTAAGCCTA ACGGCCGCGGAATATGACCAAAGCGACGTACGGTTCATCCACTAACTGCC AATGTACGTATCAGACACAGTGACCTTTGTCAATGTCGCGACTGGAGCCC AAGCAGTCGCTAGGAGTCTTGACTGGAGTAAGGTCACGTTGGATGGCAGA CCTCTGACGACAATTCAGCAATACAGTAAAACCTTTTATGTACTACCACT TAGAGGTAAGTTATCGTTTTGGGAGGCAGGCACCCACGAAGGCGGGTTACC CCTACAATTACAAATACTACCGCCTCTGACCAGATACTGATCGAGAATGCC | 1605 | DNA | 07 |

TABLE: 2-continued

Summary Table of Sequence ID Numbers

| Name | Description | Len | Type | SEQ ID NO |
|---|---|---|---|---|
| | GCGGGACACAGGGTTGCCATAAGCACCTACACGACGTCTCTAGGCGCGGG GCCTGTTAGTATTAGTGCTGTTGGGGTATTAGCCCCTCATTCAGCACTCG CGtaa | | | |
| NCT-002- (534 aa)- (M1_R2_ P109delins_ HEVNS4A_13 aa_ peptide_N490_ P491insC_ V610_Y660del) (Hydrophobic) | MAGSWLRDIWDWICEVLSDFKTWLKAK AKLMPTMLTAVAPAPDTAPVPDVDSRGAILRRQYNLSTSPLTSSVASGTN LVLYAAPLNPLLPLQDGTNTHIMATEASNYAQYRVVRATIRYRPLVPNAV GGYAISISFWPQTTTTPTSVDMNSITSIDVRILVQPGIASELVIPSERLH YRNQGWRSVETSGVAEEEATSGLVMLCIHGSPVNSYTNTPYTGALGLLDF ALELEFRNLTPGNINTRVSRYSSTARHRLRRGADGTAELTTTAATRFMKD LHFTGINGVGEVGRGIALTLFNLADTLLGGLPTELISSAGGQLFYSRPVV SANGEPTVKLYTSVENAQQDKGIAIPHDIDLGESRVVIQDYDNQHEQDRP TPSPAPSRPFSVLRANDVLWLSLTAAEYDQTTYGSSTNCPMYVSDTVTFV NVATGAQAVARSLDWSKVTLDGRPLTTIQQYSKTFYVLPLRGKLSFWEAG TTKAGYPYNYNTTASDQILIENAAGHRVAISTYTTSLGAGPVSISAVGVL APHSALA | 534 | PRT | 08 |
| Back translation of NCT-001- (512 aa)- (M1_R2_ P98del_N490_ P491insC_V610_ Y660del) | ATGCGCCGTAGATCGGCGCCGGCCGGTGCGGCACCTCTAACAGCTGTCGC GCCGGCTCCGGATACAGCACCGGTTCCAGATGTAGATTCCCGTGGTGCAA TCCTACGACGTCAATATAATCTCTCCACGTCACCGCTCACTTCCAGCGTA GCAAGTGGAACGAATTTAGTTTTGTACGCTGCCCCCCTAAACCCCTTGTT ACCTTTACAAGACGGAACAAATACCCACATCATGGCTACTGAGGCTTCTA ACTATGCGCAATATAGGGTTGTAAGGGCAACTATTCGTTATAGACCTCTC GTACCTAATGCTGTTGGAGGTTATGCTATCAGCATCTCGTTTTGGCCCCA GACTACGACTACGCCCACTTCCGTAGATATGAACAGCATTACTTCAACTG ACGTGCGCATACTGGTACAGCCCGGCATCGCAAGTGAACTTGTCATCCCC AGCGAGCGTTTACATTACCGCAATCAGGGATGGAGATCAGTGGAAACATC TGGAGTGGCCGAAGAAGAGGCCACATCGGGGCTCGTTATGCTGTGCATTC ATGGGTCGCCGGTAAATAGTTACACTAACACGCCATATACCGGTGCGTTG GGGCTACTCGATTTCGCGCTGGAATTAGAATTTCGAAACCTCACGCCAGG TAACACTAATACGCGAGTATCCAGGTATAGTAGTACCGCACGCCATCGGC TGCGGAGGGGAGCTGATGGGACAGCTGAGCTGACCACAACTGCGGCCACC CGTTTCATGAAGGATCTTCACTTCACAGGAACCAACGGTGTCGGTGAGGT CGGCAGAGGGATAGCATTGACCTTATTCAATCTGGCGGACACCTTACTTG GAGGGCTTCCTACGGAACTGATAAGTAGTGCCGGGGGCCAGCTATTTTAC TCTAGACCAGTCGTCTCAGCGAATGGTGAACCTACTGTGAAGTTATATAC AAGCGTGGAGAACGCTCAGCAAGACAAAGGCATAGCTATTCCGCACGACA TAGACTTGGGCGAAAGCCGAGTTGTCATACAAGATTATGATAACCAACAC GAGCAGGACCGGCCAACCCCTTCTCCGGCGCCCTCAAGGCCCTTTTCGGT TTTGCGGGCCAATGACGTACTGTGGTTATCGCTTACGGCAGCGGGAATACG ATCAAACTACCTACGGTTCATCCACAAACTGTCCAATGTACGTCTCTGAT ACGGTAACCTTTGTGAATGTTGCGACGGGCGCCCAAGCGGTGGCTCGCTC ACTCGACTGGAGCAAAGTTACGCTAGACGGACGGCCACTAACGACAATTC AACAGTACTCCAAGACTTTCTACGTTCTCCCTTTGCGAGGAAAGCTTTCG TTCTGGGAGGCCGGGACAACCAAAGCCGGTTACCCGTATAACTACAACAC AACCGCATCTGACCAGATTCTAATAGAGAATGCCGCAGGCCATCGAGTGG CCATCTCAACATATACCACGTGTCTTGGCGCAGGGCCAGTCTCCATTTCG GCTGTGGGCGTGTTGGCACCTCATAGTGCCCTCGCGtaa | 1539 | DNA | 09 |
| NCT-001- (512 aa)- (M1_R2_ P98del_N490_ P491insC_V610_ Y660del) | MRR RSAPAGAAPLTAVAPAPDTAPVPDVDSRGAILRRQYNLSTSPLTSSVASG TNLVLYAAPLNPLLPLQDGTNTHIMATEASNYAQYRVVRATIRYRPLVPN AVGGYAISISFWPQTTTTPTSVDMNSITSIDVRILVQPGIASELVIPSER LHYRNQGWRSVETSGVAEEEATSGLVMLCIHGSPVNSYINTPYTGALGLL DFALELEFRNLTPGNINTRVSRYSSTARHRLRRGADGTAELTTTAATRFM KDLHFTGINGVGEVGRGIALTLFNLADTLLGGLPTELISSAGGQLFYSRP VVSANGEPTVKLYTSVENAQQDKGIAIPHDIDLGESRVVIQDYDNQHEQD RPTPSPAPSRPFSVLRANDVLWLSLTAAEYDQTTYGSSINCPMYVSDTVT FVNVATGAQAVARSLDWSKVTLDGRPLTTIQQYSKTFYVLPLRGKLSFWE AGTTKAGYPYNYNTTASDQILIENAAGHRVAISTYTTSLGAGPVSISAVG VLAPHSALA | 512 | PRT | 10 |
| Back translation of NCT-003- (540 aa)- (M1_R2_ P98del_N490_ P491insC- V610_ Y660delins_ HSVLinker_ EKEK_RGD_ 28 aa_peptide) | ATGAGACGACGAAGTGCCCCGGCCGGGGCGGCACCCCTCACGGCTGTCGC ACCTGCTCCCGACACAGCTCCCGTCCCTGATGTTGATTCCCGCGGAGCGA TCTTAAGGCGGCAGTATAACTTGTCCACTTCACCACTCACGAGCTCGGTG GCCAGCGGTACTAATCTGGTATTATACGCTGCACCGTTAAATCCGTTGCT GCCACTCCAGGATGGCACGAACACGCACATTATGGCTACAGAGGCATCAA ACTACGCGCAATACCGAGTAGTCCGGGCAACTATTAGATATCGTCCACTA GTCCCTAATGCTGTTGGCGGCTACGCTATATCGATCTCGTTCTGGCCCTA GACAACAACTACTCCGACCTCTGTGGATATGAACTCGATCACCTCCACCG ACGTGCGGATTCTAGTCCAACCAGGCATCGCCAGCGAACTGGTTATTCCC TCTGAACGTCTTCATTACAGGAACCAGGGGTGGAGATCGGTAGAGACAAG TGGTGTGGCGGAGGAAGAAGCGACCAGTGGCTTGGTAATGTTATGTATAC ACGGATCACCTGTAAACAGTTACACTAACACTCCCTATACTGGGGCTCTG | 1623 | DNA | 11 |

TABLE: 2-continued

Summary Table of Sequence ID Numbers

| Name | Description | Len | Type | SEQ ID NO |
|------|-------------|-----|------|-----------|
| | GGTCTGCTCGATTTCGCGCTGGAGCTAGAGTTCAGAAATCTGACGCCGGG GAACACAAATACGCGAGTATCCCGCTATAGCAGTACGGCCCGCCATAGGC TGCGCCGAGGGGCTGACGGGACGGCGGAGCTTACGACCACAGCCGCGACT CGTTTTATGAAGGACTTGCATTTTACCGGCACCAACGGAGTTGGGGAAGT CGGTCGTGGTATAGCCCTAACGCTATTTAATTTGGCGGACACCCTTCTTG GAGGACTACCGACAGAGCTCATAAGCAGTGCAGGCGGACAGTTATTCTAT TCACGCCCCGTAGTCTCTGCGAATGGTGAACCAACCGTTAAACTCTACAC CTCTGTAGAGAATGCGCAACAAGATAAGGGCATCGCCATACCGCACGACA TAGATCTTGGAGAATCCCGTGTTGTAATTCAAGACTACGACAACCAGCAC GAACAGGACAGGCCTACCCCCTCTCCAGCACCTTCCAGGCCATTCTCCGT GCTAAGAGCCAATGACGTCTTGTGGCTTTCATTAACTGCCGCTGAATACG ACCAAACCACATATGGCAGTTCCACGAATTGCCCCATGTATGTGTCAGAC ACGGTCACATTTGTGAATGTAGCTACTGGTGCTCAAGCGGTGGCGCGCTC ACTCGATTGGTCTAAAGTGACATTGGATGGACGGCCACTCACTACAATCC AACAGTATTCAAAGACTTTTTATGTTCTCCCATTGCGTGGTAAGCTTTCG TTTTGGGAGGCTGGAACGACTAAGGCAGGTTACCCGTACAACTACAACAC CACCGCAAGCGATCAAATTCTCATCGAAATGCTGCCGGTCACCGGGTTG CAATAAGTACATATACAACGTCTTTAGGCGCAGGGCCAGTTTCAATTTCG GCGGTGGGGTCTTGGCACCTCATAGCGCCTTAGCCCAGCCTGAGCTTGC GCCTGAGGACCCGGAGGATGAAAAAGAAAATGTTTCACCCCACGGGGAG ATATGCCGGGGCCCTATTGCtaa | | | |
| NCT-003-(540 aa)-(M1_R2_P98del_N490_P491insC-V610_Y660delins_HSVLinker_EKEK_RGD_28 aa_peptide) | MRRR SAPAGAAPLTAVAPAPDTAPVPDVDSRGAILRRQYNLSTSPLTSSVASGT NLVLYAAPLNPLLPLQDGINTHIMATEASNYAQYRVVRATIRYRPLVPNA VGGYAISISFWPQTTTTPTSVDMNSITSTDVRILVQPGIASELVIPSERL HYRNQGWRSVETSGVAEEEATSGLVMLCIHGSPVNSYINTPYTGALGLLD FALELEFRNLTPGNTNTRVSRYSSTARHRLRRGADGTAELTTTAATRFMK DLHFTGTNGVGEVGRGIALTLENLADTLLGGLPTELISSAGGQLFYSRPV VSANGEPTVKLYTSVENAQQDKGIAIPHDIDLGESRVVIQDYDNQHEQDR PTPSPAPSRPFSVLRANDVLWLSLTAAEYDQTTYGSSINCPMYVSDTVTF VNVATGAQAVARSLDWSKVTLDGRPLTTIQQYSKTFYVLPLRGKLSFWEA GTTKAGYPYNYNTTASDQILIENAAGHRVAISTYTTSLGAGPVSISAVGV LAPHSALAQPELAPEDPEDEKEKCFTPRGDMPGPYC | | PRT | 12 |
| Back translation of NCT-005-(484 aa)-(M1_R2_P98del_F461_Y660_delins_HHV_Pembrolizumab_120 aa peptide) | ATGAGAAGGAGGAGCGCTCCAGCGGGAGCGGCTCCTCTTACAGCCGTAGC ACCGGCACCTGACACAGCACCGGTGCCTGATGTTGACTCGCGTGGTGCCA TACTGAGGCGGCAGTATAATCTATCGACTTCGCCGCTCACCTCTAGTGTT GCATCGGGCACAAATCTCGTGCTATACGCCGCTCCATTGAACCCGTTATT GCCATTACAAGATGGGACGAATACGCATTATTATGGCGACTGAAGCAAGTA ATTACGCGCAATATAGAGTGGTCCGGGCAACCATCCGTTATCGCCCACTC GTGCCTAATGCTGTAGGGGGTTACGCGATCTCAATATCCTTTTGGCCCCA GACAACAACCACACCTACGTCCGTCGATATGAACAGTATTACTTCAACTG ATGTCCGAATATTAGTGCAACCCGGAATAGCGAGTGAACTGGTGATCCCC TCTGAGCGCCTTCACTATCGAAACCAAGGTTGGCGATCCGTCGAGACCTC CGGGGTTGCTGAGGAAGAGGCGACATCCGGCCTCGTTATGCTGTGTATCC ACGGAAGCCCCGTTAACAGTTACACGAACACCCCCTATACAGGAGCCTTA GGCTTGCTTGACTTTGCTCTGGAACTAGAATTCCGGAATCTAACGCCTGG AAATACCAACACCCGCGTTTCTAGGTACTCTTCTACCGCTAGGCATCGAC TCAGACGAGGCGCCGACGGAACGGCTGAGCTTACTACAACTGCTGCGACT CGCTTTATGAAAGACTTGCATTTCACCGGGACGAATGGCGTTGGGGAAGT CGGGAGAGAGGTATTGCCCTGACACTTTTCAATCTAGCAGATACTCTATTGG GTGGACTACCGACTGAGCTGATATCAAGTGCTGGAGGGCAACTTTTTTAC AGCCGACCTGTGGTATCTGCCAACGGAGAGCCAACAGTAAAGCTTTACAC GTCGGTAGAGAACGCCCAACAGGACAAAGGTATTGCAATACCACATGACA TTGACCTGGGTGAATCACGGGTGGTTATCCAGGACTATGATAACCAGCAC GAACAAGATCGTCCGACGCCCAGCCCGGCGCCATCCAGGCCACAAGTACA GTTGGTTCAGAGCGGCGTGGAAGTCAAGAAGCCCGGGGCATCGGTGAAAG TATCGTGCAAGGCATCCGGTTATACATTTACGAATTACTACATGTATTGG GTACGTCAGGCCCCGGGTCAAGGCTTGGAGTGGATGGGGGGGATCAATCC TTCAAATGGAGGTACGAACTTCAACGAAAAATTTAAGAACCGGGTCACTT TAACCACCGACTCCAGTACGACCACTGCGTACATGGAGCTCAAATCTTTA CAATTTGATGATACCGCGGTATATTACTGTGCCCGCCGTGATTATAGATT CGATATGGGCTTCGACTATTGGGGCCAGGGCACAACTGTCACGGTCAGCT CATaa | 1455 | DNA | 13 |
| NCT-005-(484 aa)-(M1_R2_P98del_F461_Y660_delins_HHV_Pembrolizumab_120 aa | MRR RSAPAGAAPLTAVAPAPDTAPVPDVDSRGAILRRQYNLSTSPLTSSVASG TNLVLYAAPLNPLLPLQDGINTHIMATEASNYAQYRVVRATIRYRPLVPN AVGGYAISISFWPQTTTTPTSVDMNSITSIDVRILVQPGIASELVIPSER LHYRNQGWRSVETSGVAEEEATSGLVMLCIHGSPVNSYTNTPYTGALGLL DFALELEFRNLTPGNINTRVSRYSSTARHRLRRGADGTAELTTTAATRFM KDLHFTGINGVGEVGRGIALTLFNLADTLLGGLPTELISSAGGQLFYSRP VVSANGEPTVKLYTSVENAQQDKGIAIPHDIDLGESRVVIQDYDNQHEQD | 484 | PRT | 14 |

TABLE: 2-continued

Summary Table of Sequence ID Numbers

| Name | Description | Len | Type | SEQ ID NO |
|---|---|---|---|---|
| peptide) | RPTPSPAPSRPQVQLVQSGVEVKKPGASVKVSCKASGYTFTNYYMYWVRQ APGQGLEWMGGINPSNGGTNFNEKFKNRVTLTIDSSTTTAYMELKSLQFD DTAVYYCARRDYRFDMGFDYWGQGTTVTVSS | | | |
| Back translation of the following sequence | ATGCGTAGGAGATCGGCGCCGGCAGGGGCCGCTCCTCTCACCGCTGTCGC TCCGGCACCGGACACAGCACCCGTGCCGGACGTAGACTCGCGAGGGGCAA TTCTGCGTAGGCAGTATAACCTGAGCACCTCCCCATTGACTTCCTCTGTT GCGAGTGGCACGAATTTGGTACTTTACGCAGCCCCACTAAACCCCCTACT ACCTCTCCAAGATGGAACGAACACACATATAATGGCTACGGAGGCGTCGA ATTACGCGCAGTACCGCGTAGTCCGCGCGACTATACGGTATAGGCCCTTG GTACCTAATGCGGTGGGGGGCTATGCGATCTCGATCAGTTTCTGGCCACA AACCACGACGACCCCCACATCTGTGGACATGAATTCAATTACGAGTACTG ACGTCCGCATACTGGTACAACCTGGGATTGCATCCGAGTTGGTTATCCCC AGCGAGCGGTTACACTATCGGAACCAAGGTTGGAGATCCGTGGAAACTTC CGGTGTGGCGGAGGAGGAAGCGACGAGTGGGTTGGTTATGTTATGTATAC ACGGCTCGCCGGTGAATTCTTATACTAATACACCTTATACTGGAGCACTG GGCCTTCTTGATTTCGCACTGGAACTCGAATTTCGTAATCTCACACCTGG CAACACAAACACCAGAGTGTCACGGTATTCGTCCACCGCTCGCCATCGCC TTCGACGAGGAGCCGATGGAACAGCGGAACTCACTACTACCGCAGCCACC AGATTTATGAAGGATCTTCACTTCACAGGCACCAACGGGGTTGGAGAAGT TGGGCGAGGTATCGCCTTGACCCTATTCAATTTAGCCGACACCCTACTAG GAGGTCTCCCTACAGAACTGATTAGCTCAGCTGGCGGACAGCTCTTCTAC TCACGCCCCGTTGTTTCTGCCAACGGGGAGCCAACAGTGAAATTATACAC GAGTGTAGAAAATGCCCAGCAGGATAAAGGCATTGCTATACCACACGATA TTGATTTAGGTGAGAGCCGTGTGGTCATCCAGGACTACGATAACCAGCAT GAGCAGGACAGGCCCACACCCTCACCGGCTCCAAGCCGGCCACAGGTGCA ATTACGCGTCCGGAGGCGAGTATGCGCAAGGCGTGTAGACTATCGATTCG ACATGGGTTTTGATTACTGGGGTGTCCAATCTGGTGTCGAGGTCAAGAAG CCAGGTGCTTCAGTAAAAGTTTCATGTAAAGCCTCGGGGTATACTTTCAC GAACTACTATATGTATTGGGTTCGTCAAGCCCCGGGTCAAGGCCTTGAAT GGATGGGGGGAATCAACCCGAGTAATGGAGGAACGAATTTTAATGAAAAG TTTAAGAACAGAGTAACCCTGACTACCGACAGCTCTACTACGACAGCATA CATGGAGCTAAAATCCTTGCAATTCGACGATACTGCTGTCTACTATTGCG CTAGACGGGATTACAGATTTGACATGGGCTTTGATTACTGGGGGCAGGGC ACAACTGTTACGGTCAGCTCTtaa | 1524 | DNA | 15 |
| NCT-006 22_12851-PL02087-2.7-NCT006-(507 aa)-(M1_R2_P98del_F461_Y660_delins_HHV_Pembrolizumab_plus_linker_143 aa peptide) | MRR RSAPAGAAPLTAVAPAPDTAPVPDVDSRGAILRRQYNLSTSPLTSSVASG TNLVLYAAPLNPLLPLQDGTNTHIMATEASNYAQYRVVRATIRYRPLVPN AVGGYAISISFWPQTTTTPTSVDMNSITSIDVRILVQPGIASELVIPSER LHYRNQGWRSVETSGVAEEEATSGLVMLCIHGSPVNSYTNTPYTGALGLL DFALELEFRNLTPGNINTRVSRYSSTARHRLRRGADGTAELTTTAATRFM KDLHFTGINGVGEVGRGIALTLFNLADTLLGGLPTELISSAGGQLFYSRP VVSANGEPTVKLYTSVENAQQDKGIAIPHDIDLGESRVVIQDYDNQHEQD RPTPSPAPSRPQVQLRVRRRVCARRVDYRFDMGFDYWGVQSGVEVKKPGA SVKVSCKASGYTFTNYYMYWVRQAPGQGLEWMGGINPSNGGTNFNEKFKN RVTLTTDSSTTTAYMELKSLQFDDTAVYYCARRDYRFDMGFDYWGQGTTV TVSS | 507 | PRT | 16 |

Expression and Assembly of HEV VLPs in Baculovirus Expression Vector Systems

Baculovirus expression vector systems (BEVS) have been widely used to facilitate the expression of heterologous proteins in cultured insect cells, most commonly based on the *Autographa californica* Nuclear Polyhedrosis Virus (AcNPV) or the *Bombyx mori* Nuclear Polyhedrosis Virus (BmNPV), which are used to infect *Spodoptera frugiperda* (fall armyworm), *Trichoplusia ni* (cabbage looper), or *Bombyx mori* (silkworm) cells [O'Reilly, Miller, and Luckow, 1992].

A variety of methods have been used to facilitate the generation of recombinant baculoviruses. The earliest methods were based on homologous recombination between a transfer vector and wild-type or modified baculovirus DNA samples transfected into cultured insect cells, replacing the polyhedrin gene to generate viruses that formed occlusion-minus plaques at a frequency of 0.1% to 1% on lawns of cultured cells under a layer of low melting point agarose [O'Reilly, Miller, and Luckow, 1992]. The frequency increased to about 30%, when a linearized parental virus was used, and later, up to 100% with improved parental virus variants were developed [Kitts et al, 1990; Roy et al 2012; Possee et al 2019]. Linearized viral backbones are now available from a variety of sources.

The development of the baculovirus shuttle vector (bacmid) system also improved the efficiency of the system, by using components of Tn7, a site-specific bacterial transposon, to insert a mini-transposon comprising one or more genes of interest under the control of a baculovirus promoter derived from a donor vector, in the presence of a helper vector which comprises four transposase genes, into a target vector comprising a gene fusion with an attachment site for the transposon propagated as a very low copy number plasmid (designated as a bacmid, or more generically as a baculovirus shuttle vector) in *E. coli* [Luckow et al 1993].

DNA samples isolated from bacterial cells harboring composite shuttle vectors comprising a cargo DNA segment derived from the transposon are infectious when transfected into susceptible insect cells, bypassing the need to perform plaque assays to purify recombinant viruses using tedious traditional or more rapid methods based on homologous recombination between a transfer vector and a circular or linearized parental viral DNA genome. Donor, helper, and target vectors are available from Thermo Fisher as components of their Bac-To-Bac™ system.

Thousands of proteins have been expressed in baculovirus-infected insect cells for a wide variety of applications, including therapeutic proteins, vaccines, and components of gene therapy vector systems, including viral capsid systems, used in basic and applied research and development, and as biopharmaceutical products reviewed and approved by the FDA and similar regulatory agencies around the world [Luckow et al 1993; Chen et al. 2016; Possee 2019].

*Spodoptera frugiperda* and *Trichoplusia ni* cells are commonly used as substrates for expression of proteins encoded by genes of interest on recombinant baculoviruses derived from AcNPV. These include Sf9, Sf21, Tn368 and High Five (*T. ni*) cell lines available from the biological material depositories, such as ATCC (Manassas, Virginia) and a variety of commercial sources. Products intended for use in healthcare applications need to be expressed in cells that are free of adventitious agents or byproducts of purification processes, which have the potential to compromise the activity or effectiveness of the product in its intended application, such as a patient receiving a therapeutic protein, vaccine, or gene therapy vector, more so perhaps, than a product used in a diagnostic assay or for basic structure/function assays. Rhabdovirus- and nodavirus-free *Spodoptera frugiperda* and *Trichoplusia ni* cell lines are now available from a variety of commercial sources.

Expression of VLPs in Baculovirus-Infected Insect Cell Lines

While baculovirus expression vector systems have been used to facilitate the expression and purification Virus-Like Particles used in human and animal vaccines at very large scales for many years (Kaba et al. 2004), there is a growing interest in using these systems to express HEV-VLPs at high levels as well, followed by procedures to efficiently concentrate and purify the particles (Kawano et al. 2011). Since methods involving ultracentrifugation are labor-intensive and not easily scalable, other approaches have been developed for use to produce GMP-quality materials, using cation exchange liquid chromatography (LC) and size-exclusion columns. Non-infectious HEV-VLPs with T=1 virus-like structures have been produced via baculovirus expression of the Hepatitis E capsid protein with N terminus and C terminus truncated, PORF2 (Xing et al. 1999; Xing, Li, Mayazaki, et al. 2010; Yamashita et al. 2009).

Construction of Recombinant Baculoviruses Comprising HEV-VLP Sequences

Recombinant baculoviruses comprising genes encoding HEV-VLP variant capsid proteins can be constructed by two basic methods: (1) insertion of a capsid variant gene into a transfer vector, which is then transfected into cultured insect cells with a circular or linearized viral backbone, where they recombine to generate infectious viruses that are capable of expressing the heterologous capsid proteins, typically under the control of the polyhedrin promoter; or (2) insertion of a capsid variant gene into a donor vector that is transformed into *E. coli* DH10Bac cells, harboring a shuttle vector, such as bMON14272, and a helper vector, such as pMON7124, and screening for cells that harbor a composite shuttle vector generated by transposition of the cargo segment of the donor into a target site within a disruptable lacZalpha gene fusion on the shuttle vector to generate a composite target vector that can be transfected directly as a pure virus into cultured insect cell lines.

Both approaches require synthesis of segments of DNA encoding the desired genes, that may be codon-optimized, and flanked by recognition sites for restriction enzymes or regulatory sequences, which are available from a variety of commercial vendors of synthetic DNA fragments and vectors. In the first approach, DNA fragments are cloned into a transfer vector such as pVL1392 or pVL1393, verified by sequencing, and transfected into insect cells with a linearized viral backbone, such as BestBac 2.0 ($\Delta$v-cath/chiA) (Expression Systems, Davis, CA) to generate viruses in a series designated AcBestBacORF2. In the second approach, DNA fragments are cloned onto a donor vector, such as pFastBac1 (Thermo Fisher), and transformed into competent, *E. coli* DH10Bac cells, screened, and composite DNA samples transfected into insect cells to generate AcBacTo-BacORF2 viral vectors. Stocks of AcBactoBac-ORF2 and AcBestBacORF2 can be prepared by repeated passages in Sf9 cells grown in ESF921 serum-free medium (Expression Systems) at 27° C. Viral titers can be measured using antibodies directed against gp64 (Mulvania, Hayes, and Hedin 2004).

The general parameters used for inoculation (by AcBactoBacORF2 or AcBestBacORF2) and harvest of the cell culture supernatants are described as follows. Day 1: Seed cell cultures of High Five cells in ESF921 at 1 million cells/ml; Day 2: Infect the cell cultures at an MOI=0.1-5.0, incubate by shaking for two hours; and determine the viable cell count and percent viability on a daily basis, staining cells for gp64 expression on days 1 and 2 post infection (pi). Days 3-7: pellet cells and store pellets from each culture at −80° C., while storing viral supernatant samples at 4° C. The yields and qualities of HEV-VLPs from each inoculation conditions are analyzed and compared after each purification step.

Stocks of pure virus at known titers can be used in subsequent studies to determine optimal conditions for expression under a variety of conditions. For example, High Five cells at 1-2 million cells per ml can be infected with titered viral samples to determine the time course for expression over a series of days, and samples of cells and clarified supernatants collected for analysis, to determine the optimal period to harvest cells which ensure that the desired protein is expressed at high levels without significant degradation or disassembly, into inactive fragments.

Purification of HEV-VLPs from Baculovirus-Infected Insect Cells

Levels of expression of heterologous proteins in baculovirus-infected insect cell lines will vary, typically starting around 48 hpi for genes under the control of the strong polyhedrin promoter. The nature of the protein being expressed will also affect its location, within the cell, or the accumulation of proteins or complex Virus-Like Particles actively secreted by intact cells, or exposed to the media when cells begin to lyse, late in infection (48-72 hpi). Cell fractionation studies can be performed to determine the relative amounts and activities of proteins of interest using a variety of assays, including immunoblotting or dye binding properties of proteins separated by electrophoresis on acrylamide gels.

If HEV-VLPs are secreted from infected cells, the medium and cells can be separated by centrifugation at low-speed centrifugation (e.g., 1500-3000 rpm for 15 min at 4° C.). The supernatant can be pre-treated with a detergent (e.g., 0.5-1% Nonidet P-40), and gently rocked at room temperature for >2 h), before adding 5-20 U/ml of Benzonase in 1 mM MgCl₂ at 37° C., 2.5 hours to be used to break down endogenous DNA.

If HEV-VLPs are not secreted from infected cells, the medium and cells can be separated by centrifugation at low-speed centrifugation (e.g., 3,000 rpm for 15 min at 4° C.). The pelleted cells can be pre-treated with a denaturation buffer (e.g., 50 mM sodium borate, 150 mM NaCl, 1% Nonidet P-40, 0.5% sodium deoxycholate, and 5% 2-mercaptoethanol, and gently rocked at room temperature for 2 h). The lysate will be diluted with cell medium before the purification process.

Figure 5:
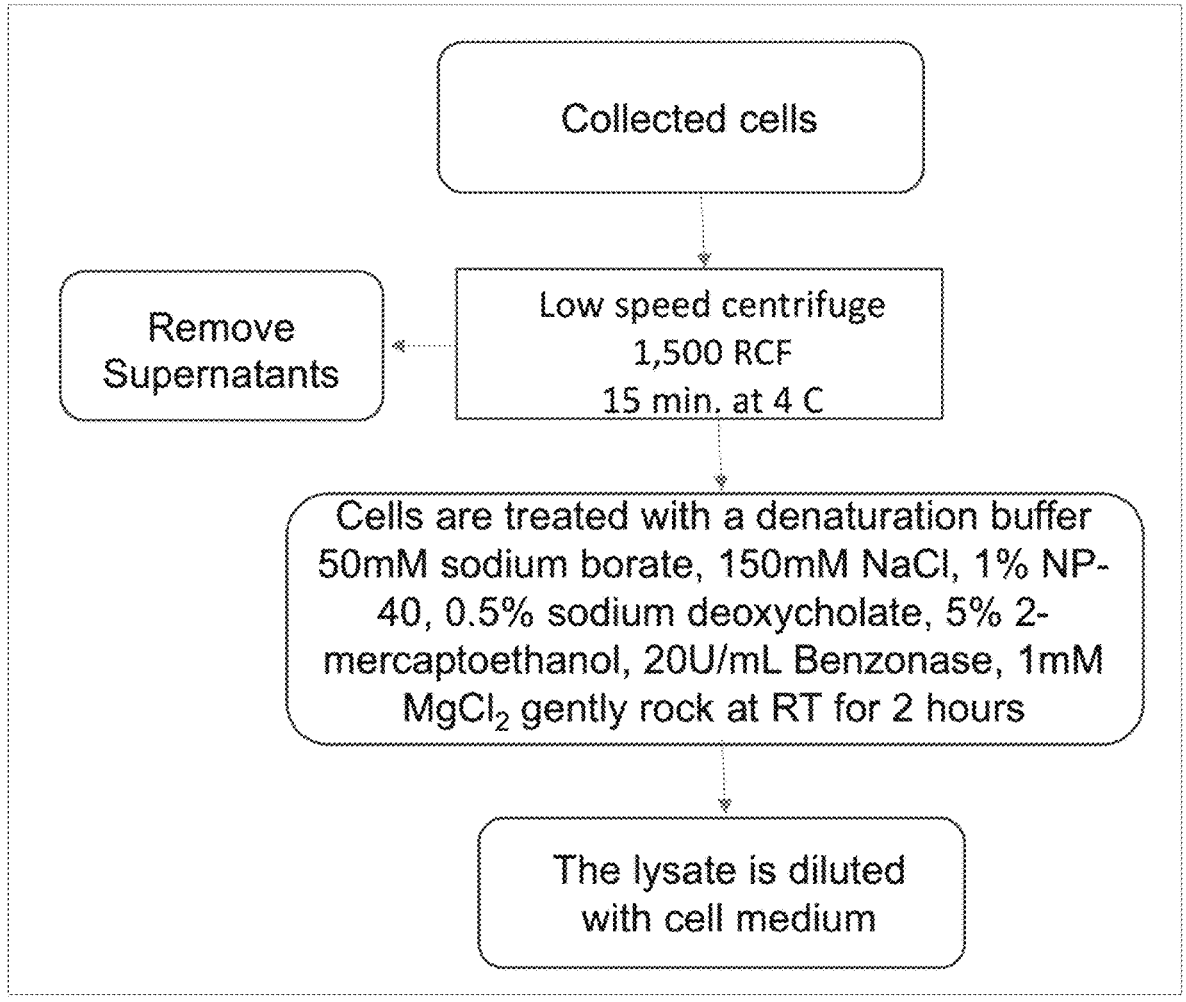
FIG. 5: sets forth an illustration entitled "Pretreatment of Expression Cells Before Purification for HEV-VLPs That Are Not Secreted From Cultured Cells".

FIG. 5: Sets Forth an Illustration Entitled "Pretreatment of Cells Before Purification for HEV-VLPs that are not Secreted from Cultured Cells".

Figure 6:
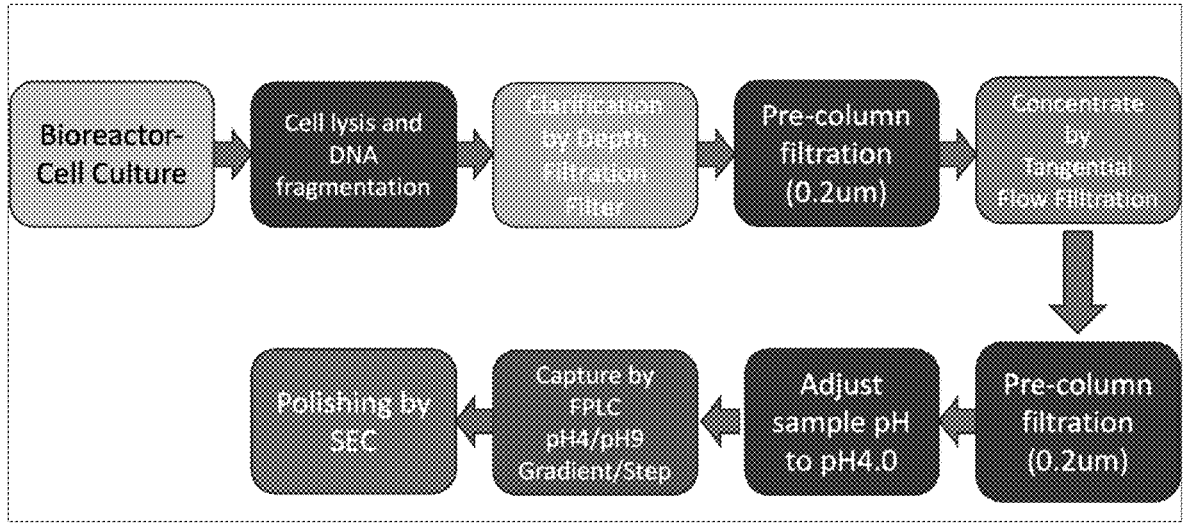
FIG. 6: sets forth an illustration entitled "Purification process with Capture/purification steps by pH-gradient-based ion exchange methods".

HEV-VLPs recovered by either method can purified further by several additional steps: (1) Clarification, to remove cell debris and large aggregates; (2) Concentration, to minimize investment in the equipment and consumable products; (3) Purification of the desired molecules; and (4) Polishing, to remove host-cell proteins and nucleic acids needed to reach acceptable thresholds for clinical grade biomaterials. FIG. 6: Sets Forth an Illustration Entitled "Purification Process with Capture/Purification Steps by pH-Gradient-Based Ion Exchange Methods".

Figure 7:
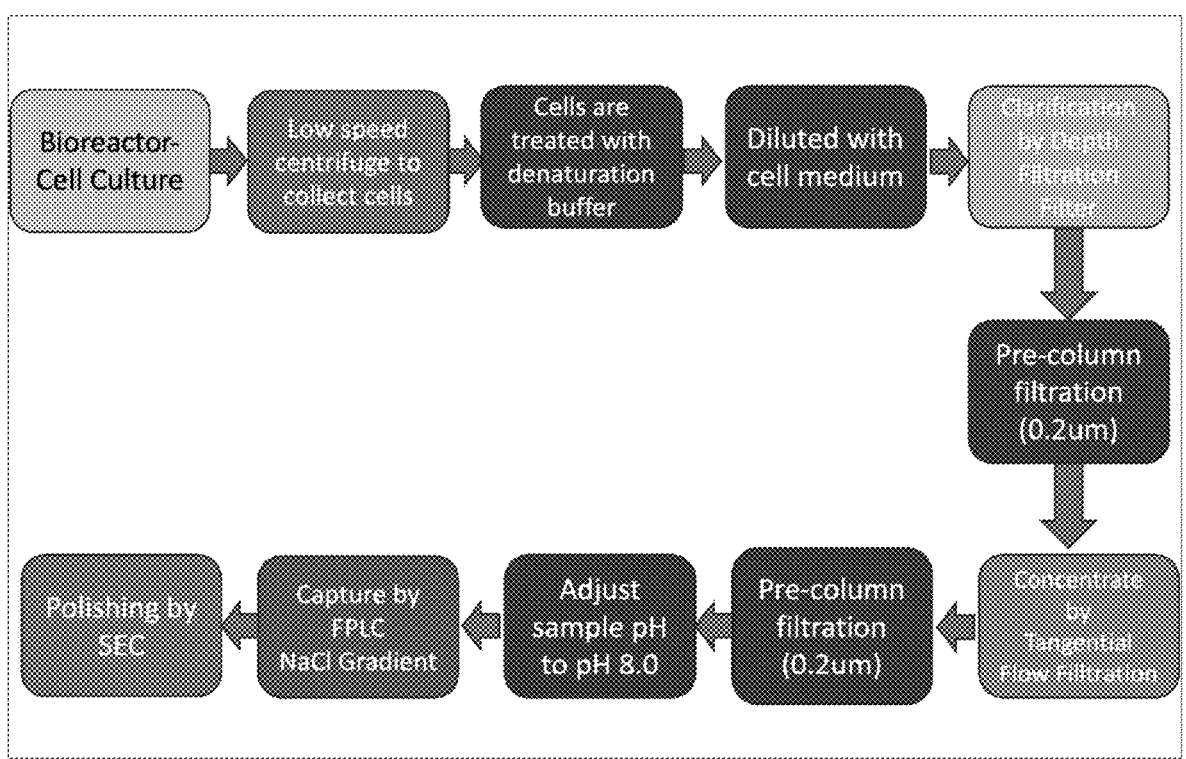
FIG. 7: sets forth an illustration entitled "Purification process with Capture/purification steps by salt-gradient-based ion exchange methods".

FIG. 7: Sets Forth an Illustration Entitled "Purification Process with Capture/Purification Steps by Salt-Gradient-Based Ion Exchange Methods".

Other approaches can also be used to purify HEV-VLPs in large quantities (scalability), with high quality (purity), high titer (potency), and in GMP-favorable manners, which include depth filtration, tangential-flow ultrafiltration (TFF), cation-exchange chromatography (IEX, FPLC) or cation-exchange membrane chromatography, and size-exclusion (SEC, FPLC) replacing the clarification, concentration, capture/purification, and polishing steps, respectively. Methods relying on separation of components from mixtures by ultracentrifugation can also be used (Xing et al. 1999; Niikura et al. 2002; Li et al. 2005a; Xing et al. 2011; Chen et al. 2018).

Generic Encapsulation Protocols

Figure 8:
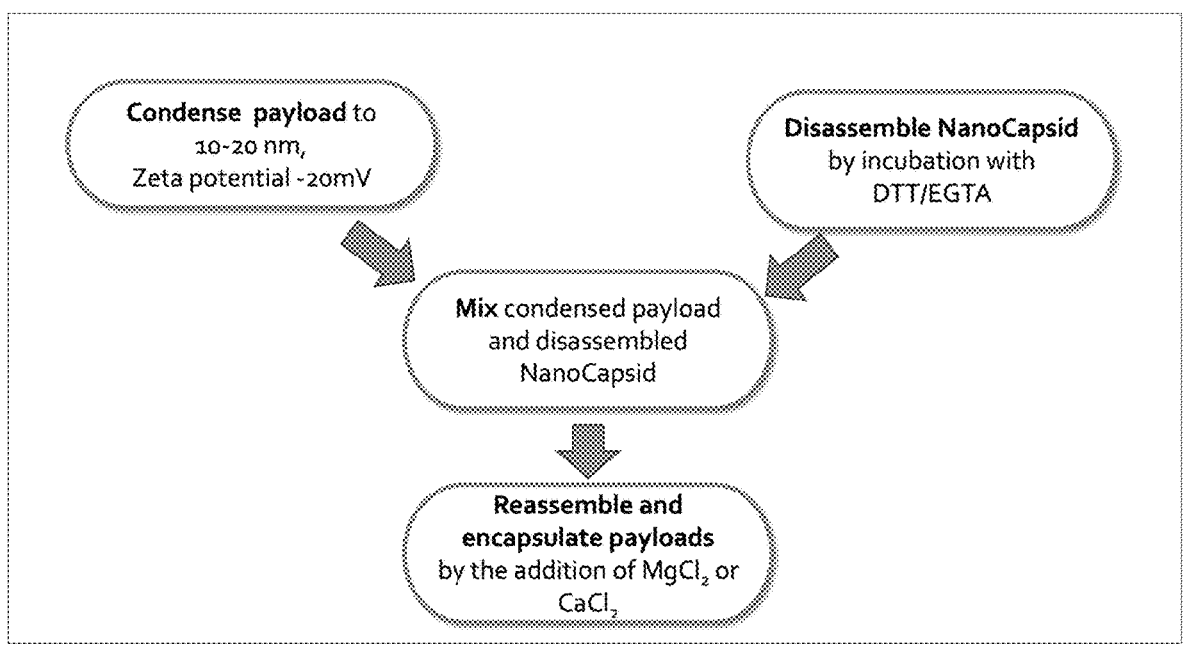
FIG. 8: sets forth an illustration entitled "Generic Encapsulation Process for HEV-VLPs".
Figure 9:
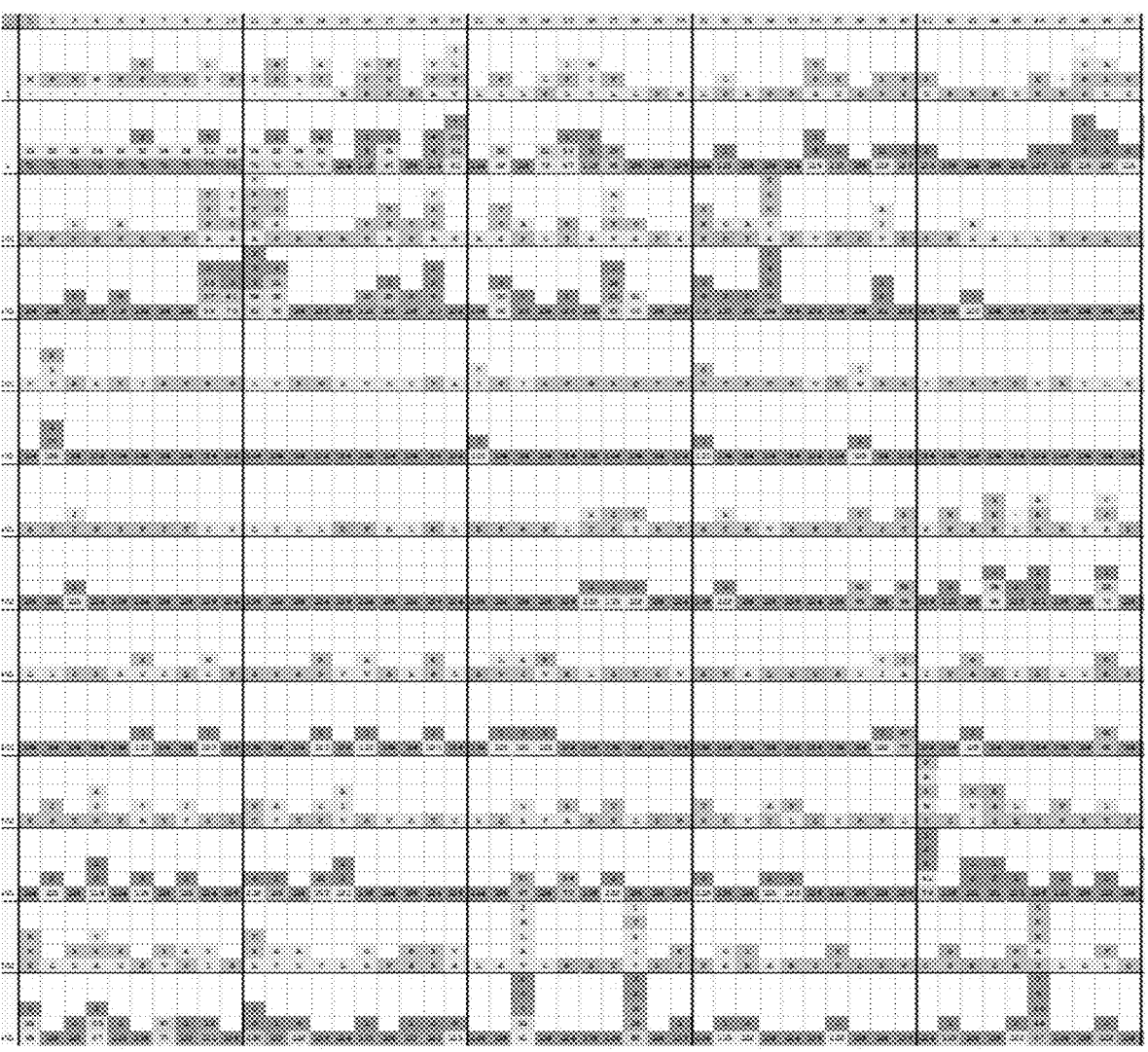
FIG. 9 and FIG. 10: set forth illustrations entitled "Distances in Number of Amino Acid Changes Across 124 HEV Sequences (Green is Lower, Red is Higher)" based on 124 different HEV capsid proteins, 93 of which are described as *Paslahepevirus balayani*, and the rest derived from other sources (including swine).

DNA encapsulation processes described in earlier studies (Barr, Keck, and Aposhian 1979; Nilsson et al. 2005) can be expanded to encapsulate different payloads, including inorganic Virus-Like Particles, DNA, mRNA, and peptides into HEV-VLPs. Disassembly and reassembly of the recombinant HEV-VLPs can be performed according to a procedure as described (Takamura et al. 2004) with minor modifications. Briefly, purified HEV-VLPs are diluted to a final concentration of 0.4-1.2 mg/mL and incubated for 1-2 hr at room temperature in a buffer containing 1-10 mM EGTA and 10-20 mM DTT. Disassembly of HEV-VLPs that are ~10 nm can be measured and confirmed by Dynamic Light Scattering (DLS) using a Malvern Anton parr, Litesizer 500 device. FIG. 8: Sets Forth an Illustration Entitled "Generic Encapsulation Process for HEV-VLPs".

Payloads at designated ratios can be added to the disassembled HEV-VLPs and mixed for >15 min. Mixtures of disassembled HEV-VLPs and payloads can be reassembled by adding ¼ volume of 4-10 mM CaCl₂) or 5-10 mM MgCl₂ every hour for four times and incubated at 4° C. overnight. The sizes of HEV-VLPs after encapsulation/reassembly reactions can be measured by DLS and confirmed by TEM.

Negatively-charged Inorganic Virus-Like Particles, like citric acid-treated ferrite NPs, can be encapsulated by HEV- VLPs regardless of their sizes. Instead of forming T=1 HEV-VLP particles that are ~27 nm, the particle sizes should vary according to the sizes of ferrite Virus-Like Particles (NP) (Chen CC 2017). Encapsulation of ferrite NPs by capsids of disassembled HEV-VLPs are primarily due to the interactions between negative-charged ferrite particles and the positively-charged residues within capsid particles (Takamura et al. 2004; Cheng and Xing 2014).

Alternative Encapsulation Process Examples:

Example 1: The encapsulation process can be performed at 37° C. to reduce the process time and improve encapsulation efficiency. In general, the payloads, such as DNA plasmid and mRNA, at designated ratios can be added to the disassembled HEV-VLPs and mixed for >15 min. Mixtures of disassembled HEV-VLPs and payloads can be reassembled by adding CaCl2) or MgCl2 to final concentration of 5-10 mM at 37° C. for one hour, followed by incubating at 4° C. overnight. The sizes of HEV-VLPs after encapsulation/reassembly reactions can be measured by DLS and confirmed by TEM.

Example 2: The encapsulation process can be performed by microfluidic process, which has been widely used in Lipid Nano Particles (LNP) (Ward 2015) to achieve automation and GMP favored process. In general, the payloads, such as DNA plasmid, mRNA etc., at designated ratios can be mixed with the disassembled HEV-VLPs in microfluid device. Similarly, mixtures of disassembled HEV-VLPs and payloads can be reassembled in microfluidic device by adding CaCl2) or MgCl2 to final concentration of 2-10 mM at 25-37° C. The sizes of HEV-VLPs after encapsulation/reassembly reactions can be measured by DLS and confirmed by TEM.

Payload Condensation and Encapsulation Procedures

Payloads generally need to be condensed to preferred size ~10 nm to enhance the efficiencies of encapsulation process steps. DNA condensation and charge inversions usually occur in solutions of multivalent counterions. Organic monovalent ions of tetraphenyl chloride arsenic (Ph₄As+) can induce DNA compaction at low Ph₄As+ concentrations of ~1 μM (Xia et al. 2017). When the concentration of Ph₄As+ is increased to 1 mM, steps disappeared in the pulling curves, and globular structures could be found in the corresponding AFM image (Xia et al. 2017), suggesting that payloads of plasmids can be condensed to ~10 nm using ~1-2 mM Ph₄As+, such as 2 mM tetra-phenyl-arsonium chloride that are incubated overnight at 4° C. The sizes of the plasmid payloads after condensation can be measured by DLS.

Generic insulin is small (MW 5.8 kDa) and has a negative surface charge, making it an attractive payload for use in HEV-VLP systems (Chen, Baikoghli, and Cheng 2018), compared to long chain-linked insulins which may be extruded out of the assembled particles. Generic insulins prepared without an aggregation step could not be encapsulated into HEV-VLP despite their size <10 nm and negatively-charged surface, suggesting that payload condensation will be critical for the successful encapsulation by HEV-VLP capsids. Structural data confirmed that insulin hexamer conformation changes can be induced by Zn+2 (Olsen et al. 2003), suggesting that generic insulins at 0.2-1.0 mg/ml can be condensed in 2 mM ZnCl2 to reduce the payload size to ~10 nm, before encapsulation. Insulin-encapsulated HEV-VLPs will be analyzed by DLS and confirmed by TEM. The content of insulin can be analyzed by ELISA analysis.

Evaluation of DNA Samples Inside HEV-VLPs

HEV-VLPs can be viewed as nucleic acid binding proteins that can form DNA/protein or RNA/protein complexes upon mixing. The resulting samples would contain a mixture of components, including empty HEV-VLPs, HEV-VLPs containing DNA, plus unincorporated DNA and capsid protein molecules. DNA encapsulated HEV-VLPs need to be efficiently separated from empty shells. Plasmid DNAs can be condensed by >1 mM Ph₄As+ before encapsulation. Reagents like Ph₄As+, however, are considered biohazard reagents. Size exclusion columns (SEC, with a cutoff size of 50-400 kDa) can be used to isolate HEV-VLPs carrying DNA payloads to reduce the concentration Ph4As+ and other solutes to safe levels.

Encapsulation of plasmid DNAs plasmids can be performed by following general procedures. Plasmid encapsulated HEV-VLPs can be concentrated by filtering through a 100 kDa centrifugal filter (Amicon Ultra-0.5 Centrifugal Filter Device). The concentrated samples are applied to a gravity size-exclusion column (SEC) (e.g., GE Sephacryl S-500 resin or TOSOH TSK gel G6000 SEC column). Collected fractions can be measured by spectrophotometry, DLS, and confirmed by TEM. The encapsulated DNA contents can be estimated by comparing amplifications of fragments by semiquantitative PCR analyses of serial dilutions of unbound plasmid DNA samples separated on 1% agarose gels.

Encapsulation of RNA Samples Inside HEV-VLPs

Small RNA molecules can be encapsulated into HEV-VLPs using a protocol that is similar noted above for plasmid DNAs, without the nucleic acid condensation step. CleanCap™ eGFP mRNA, 996 nt (TriLink Biotechnology, San Diego, CA, USA) can be used as a control, encapsulated into HEV-VLPs. Free mRNAs can be cleaned by passing through a size-exclusion column (SEC), such as a Capto™ Core 400 multimodal chromatography column (Cytiva). Samples from collected fractions can be analyzed by UV spectrophotometry, DLS (Anton parr Litesizer 500), and TEM.

HEV-VLPs containing encapsulated RNAs are also treated with RNase to confirm that RNAs are protected and packaged within the Virus-Like Particle. Reactions can be terminated by adding an RNase inhibitor, and the sample pelleted to remove the RNase and the RNase inhibitor. TEM analyses and UV spectrophotometry measurements are also used to confirm that the treatment did not disintegrate RNA molecules encapsulated within HEV-VLP. HEV-VLPs comprising RNA molecules can be disassembled, resulting in an increase in the concentration of nucleic acids, that can be detected as bands on agarose gels.

Encapsulation of Mixtures Comprising One or More Nucleic Acids or Polypeptides Inside HEV-VLPs Strategies for disassembly, assembly, and encapsulation noted above can also be used to prepare HEV-VLPs that contain one or more molecules that are not covalently associated with capsid proteins, per se. The mixtures can comprise nucleic acids such as a single-stranded RNA, a double-stranded RNA, a single-stranded DNA, a double stranded DNA, plus short peptides, longer polypeptides, and complexes between one or more peptides or polypeptides and a single- or double-stranded RNA or DNA molecule, including components of CRISPR-based systems, such as a Cas protein complexed with a guide RNA molecule.

In Vitro Potency Assay Using the Inoculation of Mammalian Cells with DNA and mRNA Payloads from Encapsulated HEV-VLPs PC-3 cells grown in monolayers in DMEM medium (GIBCO) supplemented with 10% fetal bovine serum (FBS), 100 IU/ml penicillin and 100 µg/ml streptomycin can be seeded in 12-well plates (Nunc, Life Technologies) and grown to 80% of confluence (~4×10⁵ cells/well). Cells can be washed with PBS. Samples of 50 ul of DNA encapsulated HEV-VLPs diluted in 100 ul of PBS can be added to wells, and allowed to incubate for 1 h at 37° C. After this step, 1 ml of DMEM supplemented with 10% FBS will be added, and the cells will be incubated for 48 and 72 h at 37° C. GFP expression and activity levels are measured by comparing the number of fluorescent and non-fluorescent cells using a Cellometer device.

Transmission Electron Microscopy (TEM)

The purified VLPs can be loaded onto a glow-discharged, carbon-coated EM grid and stained with 2% uranyl acetate. The formation of HEV-VLPs can be examined under transmission electron microscope (TEM) at the magnifications of 10,000×-30,000×.

Example 1: Deriving a Consensus Sequence from Related Hepatitis E Virus ORF2 Capsid Sequences A variety of methods can be used to design and assemble viral capsids based on known sequences deposited into sources of publicly-accessible nucleotide and amino acid databases, such as GenBank. In many cases, basic research is carried out with a limited set of vectors comprising nucleotide sequences encoding peptides or polypeptides of interest, and their variants, to facilitate the characterization of direct relationships between structural and functional features of molecules, such as binding of repressors or activators to DNA, RNA stability, and folding, assembly, and catalytic activity of monomeric proteins or oligomeric complexes of subunits encoded from the same or different genes. Some strategies, such as saturation mutagenesis across segments of nucleotide sequences of interest, are generally more likely to occur in applied research settings, when resources are not limiting, to generate large amounts of data that become valuable for understanding structural and functional relationships of molecules involved in chronic and acute diseases, including cancer, infectious diseases, and immunological deficiencies, that are needed to facilitate the discovery, development, and commercialization of novel drug products, including compositions comprising therapeutic agents, vaccines, and components of cell and gene therapy vector systems.

More than 2200 nucleotide sequences have been deposited into GenBank that are described as encoding components of Hepatitis E virus, many based on clinical samples collected from patients in hospitals or from veterinary samples around the world. Deciding where to begin, and which sequences to use, are often challenging when prototype viruses, despite being studied for decades, do not appear to be clinically-relevant, or amenable for mutagenesis, expression, and propagation in cultured cells, to characterize key components that will lead to the development of vaccines, or as Virus-Like Particles that can encapsulate nucleic acids, proteins, or small molecules, or be conjugated to other molecules suitable for use in diagnostic procedures or as therapeutic drug products.

This application discloses methods for the design and characterization of novel viral capsids derived from one or more consensus sequences obtained by comparing lineups of many related HEV ORF2 capsid polypeptide sequences. In the examples noted below, the frequencies of amino acids at each position across 660 or 674 amino acids derived from the ORF2 capsid protein from 124 related HEV genomes were determined. These strategies should lead to the discovery and development of new capsids that are functional in a variety of human cells, as Virus-Like Particles that can efficiently deliver a variety of other molecules, encapsulated by or conjugated to a particle that is bound to and absorbed by specific kinds of host cells. Virus-Like Particles based on a consensus sequence derived from HEV, or variants thereof, do not appear to be disclosed or suggested in publicly-available sequence, journal article, or patent document databases.

Tables and figures summarizing the frequencies of variants derived from lineups of nucleotide or polypeptide sequences allow you to identify segments comprising "a sea" of highly conserved residues interspersed with segments comprising "islands" of two or more residues, taking into account their biochemical properties, such as position of a nucleotide within a codon, or properties of side chains of amino acids observed at any given position. If a segment of one or more amino acids comprises a mixture of aliphatic, hydrophobic, positively-, or negatively-charged residues, then that segment may tolerate many kinds of amino acids, that are not necessarily observed in frequency tables. If they are all hydrophobic or negatively-charged, for example, then the tolerance for alterations may be lower, and only biochemically-similar amino acids may be substituted.

Site-specific mutagenesis or directed evolution experiments can also be performed, where one or more amino acids are substituted, inserted, or deleted at specific positions and assessed, to determine if the properties of the capsid are altered in a desirable fashion. The sequences of genes encoding the variant capsid proteins can be determined, and combined with one or several other variants to generate other desirable sequences, that may not occur in nature, but have similar or unexpected properties compared to those disclosed in GenBank or other publicly-available nucleotide or amino acid sequence databases.

Thousands of sequences of HEV or HEV-like viruses have been deposited in GenBank, and it is useful to compare multiple sequence alignments of related sequences determine the locations of segments of amino acids that were identical, highly conserved, or variable, across the entire length of the capsid protein.

A series of tables and figures are noted below based on a query in GenBank, and then extracting those sequences and preparing multiple sequence lineups using ClustalP (Sievers, 2011), and determining the frequencies of variant amino acids at different positions across the entire length of the protein. Raw lineups of sequences were pasted into Excel, in groups of 60 to 100 amino acids, and tables prepared that compare the frequency of amino acids in each aligned column of 100 sequences in each group. Some amino acids occurred only once (such as the starting methionine), while others had a variety of amino acids, up to 6 different kinds for an initial set of 124 highly similar sequences. Fewer or more sequences can be analyzed, using the data generated from other kinds of search queries.

Table 3: Search Query and Sources of 124 Related HEV Capsid Proteins in Gen Bank*

Search Straategy: (txid 291484 [organism:exp] AND (capsid[ALL Fields ] AND complete "All Fields ])) AND "Paslahepevirus balayani" [porgn] AND ("651"[SLEN]: "675"[SLEN]),

*Records 116 to 124 also contain the same supplemental annotations: "RecName: Full =Pro-secreted protein ORF2;

AltName: Full=Protein ORF2; Short=pORF2; Contains: RecName: Full=Secreted protein ORF2; Short=ORF2s Flags; Precursur".

Figures were also prepared that sorted the number of different amino acids at each position which were then analyzed using several algorithms, comparing their biochemical properties based on hydrophobicity, charge, size, and other properties, with numerical values that differ for each algorithm.

If all of the amino acids in a column are the same, that position is highly conserved, suggesting that residue is critical with respect to expression (amino terminal Met), transport (signal peptides), catalytic, or other structural or functional features of the protein.

If the amino acids vary, but have similar biochemical properties, then substitutions at those positions suggest a higher tolerance for other amino acids of the same chemical class, but not necessarily those represented in the set of sequences being analyzed.

If the amino acids vary, but have very different biochemical properties, then a wide variety of substitutions, or even insertions and deletions may be tolerated, at that position or nearby positions, perhaps because that amino acid or segments of contiguous amino acids nearby are exposed within or outside the cell, or in a disordered internal segment, such as a spacer between highly organized segments or polypeptide domains.

Figure 10:
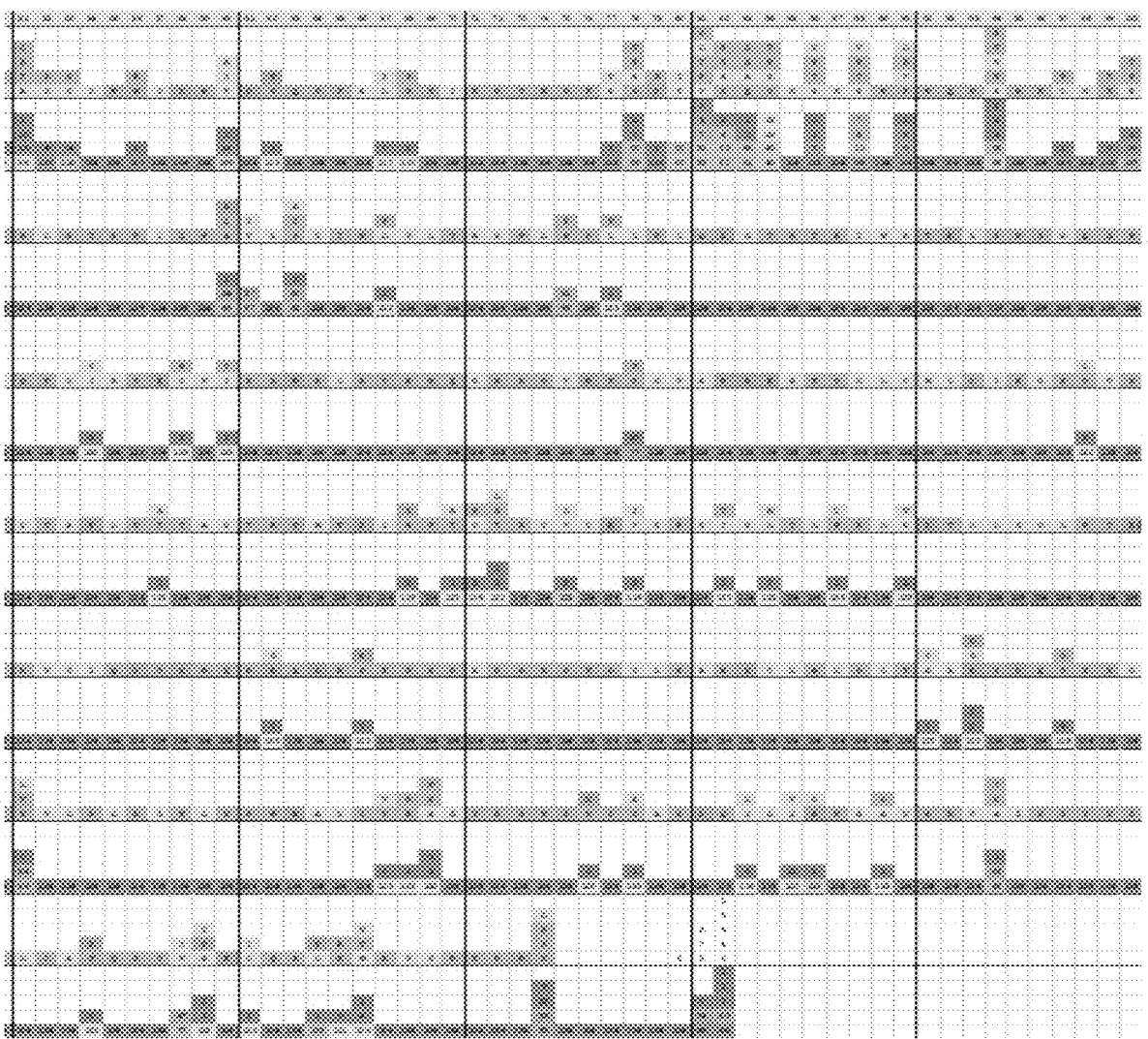
Figure 11:
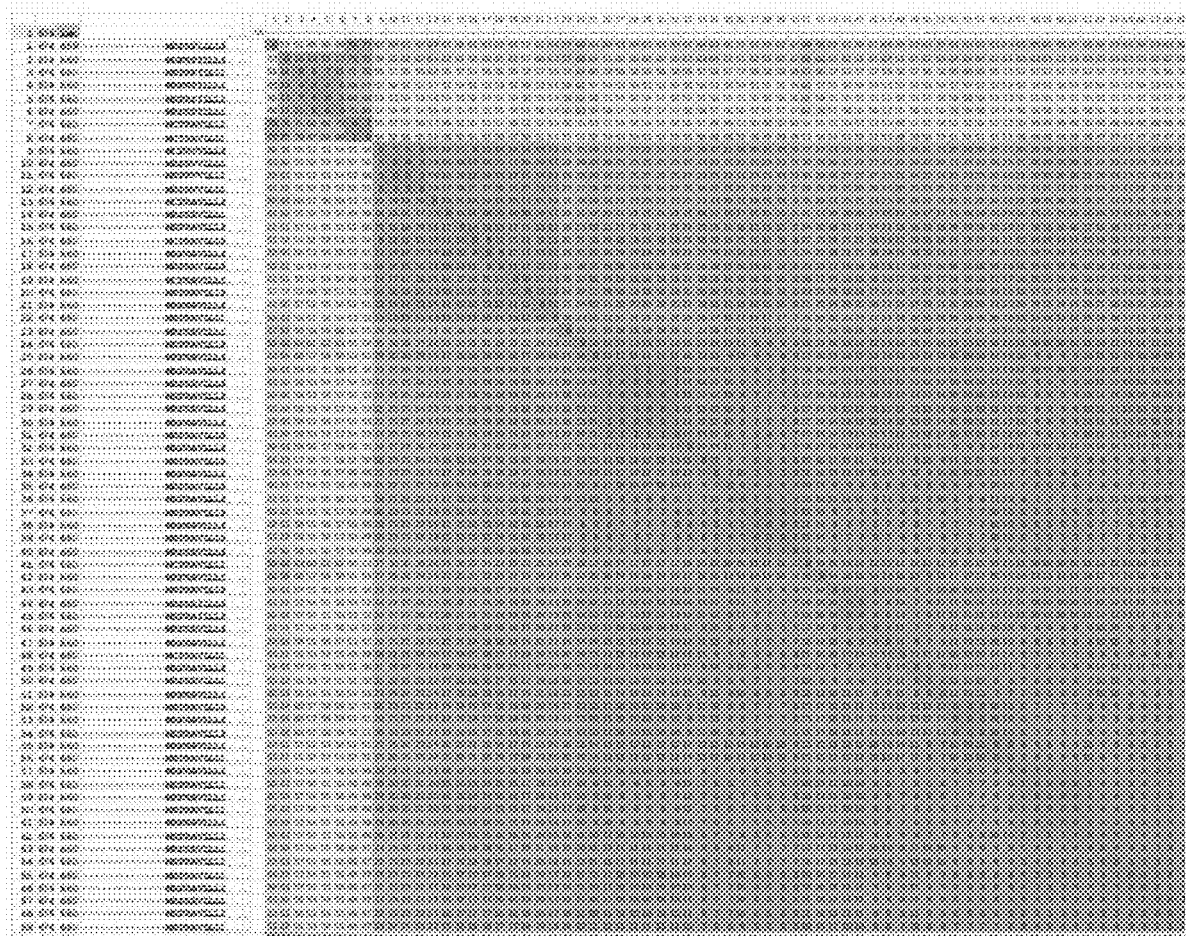
FIG. 11, FIG. 12, FIG. 13, and FIG. 14: set forth illustrations entitled "Predicted Secondary Structures For a Consensus Sequence Derived from Multiple Sequence Alignments of Related HEV ORF2 Capsid Protein".

FIG. 10 and FIG. 11: Sets Forth an Illustration Entitled "Frequencies of Amino Acid Substitutions in Related HEV ORF2 Capsid Sequences Used to Generate a Consensus Capsid Sequence" Based on 124 Different HEV Capsid Proteins, 93 of which are Described as *Paslahepevirus Balayani*, and the Rest Derived from Other Sources (Including Swine).

Note the "islands" of variability among a "sea" of highly conserved amino acids, particularly at the amino and carboxy termini of the 124 protein sequences. There are longer stretches of highly-conserved amino acids in this group of sequences, compared to the first group.

Figure 12:
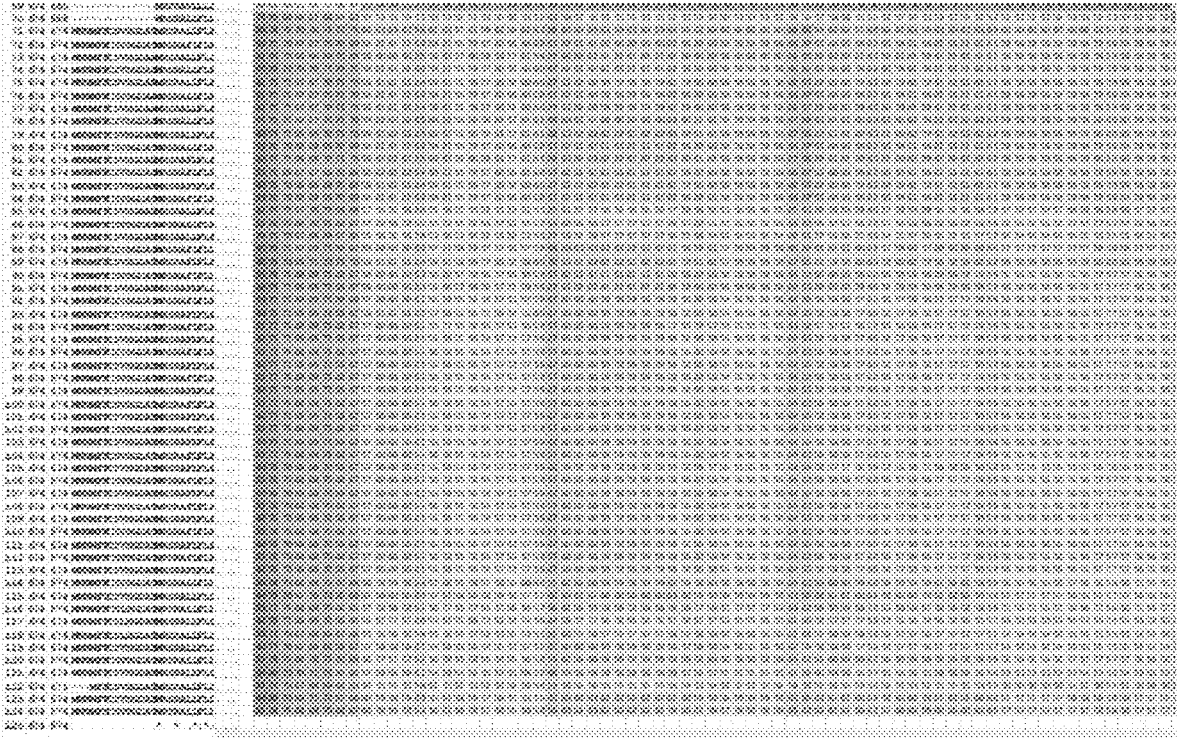
Figure 13:
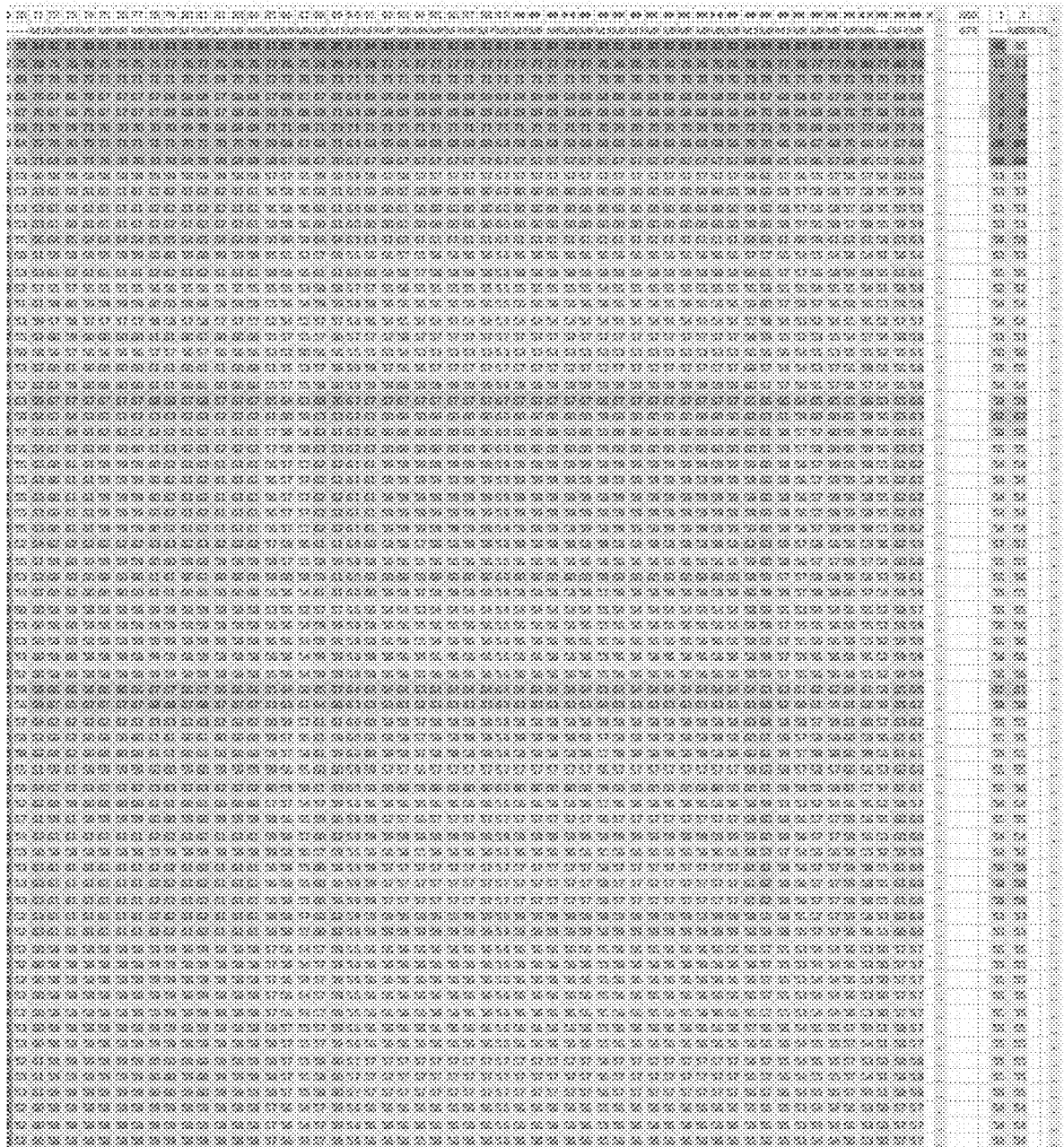
Figure 14:
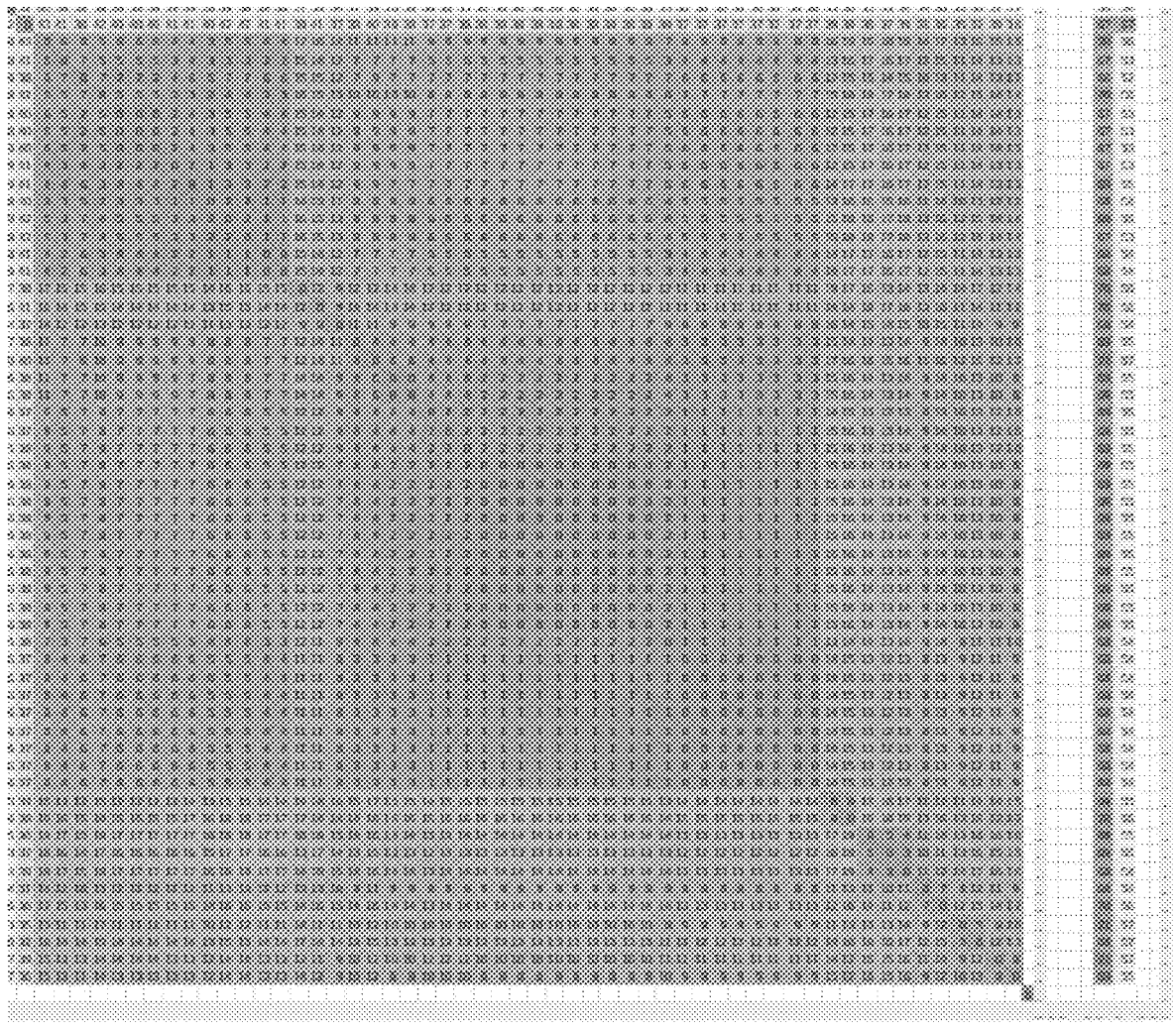

FIG. 12: Sets Forth an Illustration Entitled "Predicted Secondary Structures for a Consensus Sequence Derived from Multiple Sequence Alignments of Related HEV ORF2 Capsid Protein".

FIG. 13, FIG. 14, FIG. 15, and FIG. 16: Set Forth Illustrations Showing the Distances in Number Amino Acid Changes Across 124 Sequences (Green is Lower, Red is Higher).

This image illustrates the basic differences for the 124 sequences against each other, with a green diagonal showing equivalence between the same sequence. The big blocks illustrate sequences of 660 aa compared against 660 aa (both preceded by 15 dashes from the lineup), or 674 aa against 674 aa. The color patterns of the differences look like farm fields.

Figure 17:
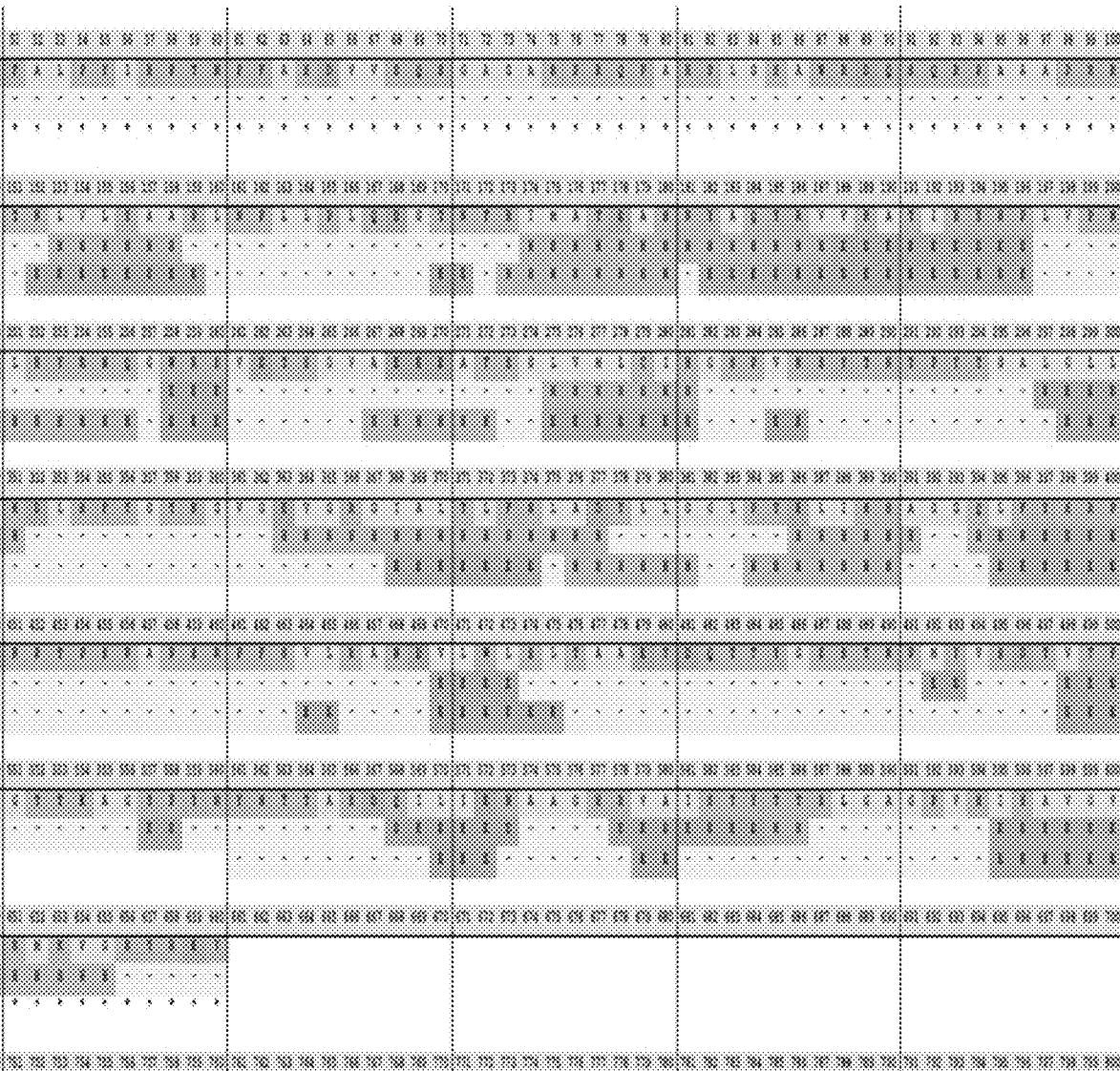

FIG. 17: Sets Forth an Illustration Showing the Frequencies of Number Amino Acid Changes Across 124 Sequences (Green is Lower, Red is Higher).

Sequence Alignment 1: Consensus Sequence NCT-660
Derived from 124 Related HEV ORF2 Capsid Sequence
(SEQ ID NO: 02)
MRPRAVLLLFLVLLPMLPAPPAGQPSGRRRGRRSGGAGGGFWGDRVDSQP

FALPYIHPTNPFASDVVSQSGAGARPRQPARPLGSAWRDQSQRPAAAPRR

RSAPAGAAPLTAVAPAPDTAPVPDVDSRGAILRRQYNLSTSPLTSSVASG

33

-continued

```
TNLVLYAAPLNPLLPLQDGTNTHIMATEASNYAQYRVVRATIRYRPLVPN

AVGGYAISISFWPQTTTTPTSVDMNSITSIDVRILVQPGIASELVIPSER

LHYRNQGWRSVETSGVAEEEATSGLVMLCIHGSPVNSYTNTPYTGALGLL

DFALELEFRNLTPGNINTRVSRYSSTARHRLRRGADGTAELTTTAATRFM

KDLHFTGINGVGEVGRGIALTLFNLADTLLGGLPTELISSAGGQLFYSRP

VVSANGEPTVKLYTSVENAQQDKGIAIPHDIDLGESRVVIQDYDNQHEQD

RPTPSPAPSRPFSVLRANDVLWLSLTAAEYDQTTYGSSTNPMYVSDTVTF

VNVATGAQAVARSLDWSKVTLDGRPLTTIQQYSKTFYVLPLRGKLSFWEA

GTTKAGYPYNYNTTASDQILIENAAGHRVAISTYTTSLGAGPVSISAVGV

LAPHSALAVLEDTVDYPARAHTFDDFCPECRTLGLQGCAFQSTVAELQRL

KMKVGKTREY
```

Clear patterns of variability from these analyses are valuable in the design of vectors encoding consensus sequences and their variants derived from HEV, where one or more amino acids are substituted, inserted, or deleted at specific positions, and assessed to determine if the properties of the capsid are altered in a desirable fashion. The sequences of genes encoding variant capsid proteins can be determined, and combined with those of other desirable sequences encoding variants, that may not occur in nature, and have altered or improved properties for particular applications in the development and commercialization of clinically-relevant therapeutic drug products, vaccines, and as components of cell and gene therapy vector systems, as described in other Examples noted below.

Note that the depictions of variable and invariable sequences depend heavily on the query sequence submitted to a nucleotide or polypeptide sequence database and the results that are returned, based on the algorithms used to identify similar sequences. A query that is highly similar to many other sequences represented in the database, will return sets of sequences that may show many invariable, identical, or highly conserved regions and fewer variable regions compared to a query that is less similar to other sequences represented in the database, that would return more regions of variability and fewer regions of invariable, identical, or highly conserved sequences.

Capsids derived from HEV consensus sequences, and variants thereof, comprising one or more amino acid substitutions, insertions, or deletions that are "functionally similar" in this context, refer to the ability of polypeptides to be expressed in prokaryotic or eukaryotic host cell systems that can assemble and form VLPs or Virus-Like Particles that have desirable properties, such as the ability to form three dimensional structures that are similar to those observed for wild-type viruses using electron microscopy and Virus-Like Particle counting equipment, and the ability to encapsulate nucleic acids, such as RNA molecules encoding viral proteins, or heterologous polypeptides, based on amino acid side chains within the shell of a capsid that can attract and specifically or non-specifically bind to an RNA molecule.

Capsids derived from HEV consensus sequences, and variants thereof, comprising one or more amino acid substitutions, insertions, or deletions that have enhanced properties in this context, also refer to the ability to encapsulate and bind dsDNA molecules, polypeptides, or be altered to contain residues on exterior or interior surfaces that facilitate conjugation to other molecules, for use as vaccines, or as agents used to target and deliver non-covalently associated nucleic acids, polypeptides, or small therapeutic drug products to a cell.

Identifying and displaying regions of variability among a sea of conserved residues in a consensus sequence derived from HEV ORF2 capsid proteins, dramatically accelerates the discovery, development, and commercialization of a wide variety of products for use as therapeutic or diagnostic agents, avoiding the need to design, express, and test hundreds of variants by traditional methods that have the desirable properties for specific applications.

Example 2: Developing HEV-VLPS for Hydrophobic Drug Delivery Systems

Applications based on Virus-Like Particles for targeted delivery of drug products have dramatically increased in recent years. While many types of nanocarriers, such as synthetic polymers, liposomes, and telodendrimers, have been designed and evaluated over the last 20 years, limitations such as toxicity, inability to accumulate enough molecules to the cytoplasm, and lack of biodegradability, still need to be addressed (Sebestik, Niederhafner et al. 2011, Jian, Zhang et al. 2012). Liposomal carriers (e.g. Doxil®, 5-fluorouricil, etc.) do not possess the ability to target specific types of cells, but tend to accumulate in solid tumors due to the features of the tumor region, such as large pore spaces in newly-synthesized blood vessels (EPR effect) (Shi, van der Meel et al. 2020). Drug leakage during circulation, resulting in undesired side effects and stability issues are significant concerns (Russell, Hultz et al. 2018).

Lipid-based Virus-Like Particle delivery systems are micelles, liposomes, polymersomes, polymeric nanospheres, and dendrimers have been used as vehicles for the targeted and controlled delivery of various agents, including small and large molecule therapeutics, genes, and diagnostic imaging agents (Hughes, Misra et al. 2023). Vaccines comprising mRNA have gained tremendous attention for their ability to protect against the SARS-COV-2 virus. Compositions comprising mRNA vaccines also contain lipid nanocarriers, which not only encapsulate mRNA, but also protect the mRNA from degradation in vivo, and transport it precisely to the cytoplasm of the cells (Zeng, Zhang et al. 2022). COVID vaccines comprising protein-based Virus-Like Particles, including one developed by Novavax, have also being evaluated in clinical trials (Anselmo and Mitragotri 2021).

Many diseases, such as cancer, can benefit from therapeutic agents that modulate the activities of intracellular targets. All the FDA-approved intracellular targeting Virus-Like Particle delivery systems utilize the parenteral route of administration. Doxorubicin (DOX), an anthracycline chemotherapeutic agent, which was first approved in 1995 with a liposomal delivery system formulated with surface PEG coating, is the most widely used doxorubicin formulation (Anselmo and Mitragotri 2016). Other FDA-approved chemotherapeutic liposomal Virus-Like Particle formulations include vincristine, irinotecan, mifamurtide, daunorubicin, cytarabine, and cisplatin (Anselmo and Mitragotri 2016).

Clinical trials and vaccinations of COVID 19 mRNA vaccines present with very high protection levels and varying degrees of side effects. Lipid Virus-Like Particles (LNPs) used in many preclinical studies are highly inflammatory in mice. Intradermal injection of LNPs led to rapid and robust inflammatory responses, characterized by massive neutrophil infiltration, activation of diverse inflammatory pathways, and production of various inflammatory cytokines and chemokines. The same dose of LNP delivered intranasally led to similar inflammatory responses in the lung and resulted in a high mortality rate (Ndeupen, Qin et al. 2021). LNPs may be not the best delivery system for mRNAs used in vaccines and other gene therapy applications. Comparable safety concerns would appear to apply to lipid-based systems for the delivery of intracellular cancer therapeutics.

Other strategies to deliver biomolecules to cells are needed, including those using viral capsids alone as protein-based carriers. The intrinsic capacity of virus capsids to encapsulate nucleic acids, small molecules, and proteins makes them ideal carriers for the delivery of therapeutic anti-cancer agents. Viral capsids can penetrate cells by active endocytosis, and undergo proteolytic decay after delivery.

Hepatitis E Virus-Like Particles (HEV-VLPs), derived from HEV, are non-infectious, self-assembling capsids capable of cell-binding and entry. HEV-VLPs appear to maintain their structural integrity in low pH environments (Zafrullah, Khursheed et al. 2004), an advantage for intra-tumoral penetration. Primary routes of HEV infection are through the fecal-oral routes. HEV-VLPs are also resistant to proteolytic and acidic mucosal conditions, making them an ideal mucosal delivery capsule (Jariyapong, Xing et al. 2013; Chen, Baikoghli et al. 2018; Shizuo G. Kamita 2019).

HEV-VLPs can be expressed and purified from High-Five insect cells at a high yields (Kawano, Xing et al. 2011). The structures of HEV-VLPs were determined by X-ray crystallography and cryo-electron microscopy (cryo-EM) (Xing, Kato et al. 1999; Xing, Li et al. 2010). The major capsid protein, open reading frame 2 (ORF2, ~500 amino acids) is composed of the 3 domains with the Shell and Middle domains of the N-terminus form the base of the shell. The remaining ~150 amino acids of C-terminal domain (protrusion domain or P-domain) consists of the major binding and antibody sites for neutralizing antibodies and receptors.

The P domain forms surface-exposed spikes atop the icosahedral base, while the flexible hinge makes it possible to modify the P domain, by inserting a foreign peptide via genetic engineering (Jariyapong, Xing et al. 2013) or by chemical conjugating (Chen, Xing et al. 2016), without compromising the base icosahedral structure. Three surface variable loops on the P domain and the C terminal of the HEV capsid protein, ORF2, are designed and engineered as conjugation sites for at least one or more bioactive agents for they are well-exposed on HEV-VLP surface (Cheng, Xing et al. 2015, Chen, Xing et al. 2016, R. Holland Cheng 2017).

One major concern with many protein-based delivery systems is their non-reusable nature, due to generation of immune responses during the delivery process. Determinants of antigenicity of HEV-VLPs are exclusively within the surface P domain (Holla, Baikoghli et al. 2017, Baikoghli 2018). Surface modifications of the P domain, such as by point mutations, chemical conjugations, and amino acid insertions, can eliminate or significantly reduce immune responses against HEV-VLPs by pre-existing HEV antibodies (Chen, Xing et al. 2016). Geometrical constraints of the middle domain (M domain) provide a physical barrier for antibody binding, which may help HEV-VLPs avoid immune system surveillance by HEV-specific antibodies. Taken together, structural characteristics of HEV-VLPs make them valuable as components of reusable delivery platforms (Shizuo G. Kamita 2019).

HEV-VLPs have the endogenous ability to deliver heterologous epitopes to and through mucosal surfaces without the need for any potentially deleterious, exogenous enhancers such as mucosal breakdown enzyme, pH regulators or uptake cofactors.

Several characteristics make HEV-VLPs ideal vehicles for targeted and mucosal delivery of other molecules (Kawano, Xing et al. 2011, Shizuo G., Kamita 2019):

(i) Surface plasticity. The HEV-VLP surface can be genetically or chemically modified while leaving the core structure intact. Different locations on the P domain can be engineered for site-specific attachment or insertion of the epitope(s). Chemical grafting of tumor targeting ligands onto the surface of HEV-VLPs enhanced in vivo tumor targeting properties (Chen, Xing et al. 2016). The P domain also carries the antigenic sites of HEV-VLPs, neutralizing the immunogenicity against HEV-VLPs with modifications of the P domain.

(ii) Signal amplification. Each HEV-VLP is composed of 30 dimer building blocks in which the antigen presentation can be potentially amplified to 60-fold.

(iii) Gastrointestinal (GI) tract stability. Surface-modified HEV-VLPs that remain stable under the harsh conditions of low pH and proteolytic enzymes found in the GI tract can be used in oral deliveries of epitopes. HEV-VLPs also have the potential to directly target the mucosal lining of the GI tract, small intestine; nasal cavity, lungs and colon (Chen, Baikoghli et al. 2021).

(iv) Packaging capability. The modularized theranostic HEV-VLP can involve utilizing the interior attributes besides its functionalized surface. The HEV-VLP sequence has been optimized not to encapsulate virus-RNA, forming highly stable non-infectious capsids capable of reversible in vitro assembly through cation mediation (Xing, Li et al. 2010).

FIG. 18: Sets Forth an Illustration Entitled "Classes of Therapeutic and Delivery Paradigms"

HEV-VLPs can be switched back and forth in self-assembly through chemical reduction and cation chelation. This property is illustrated by methods to encapsulate theranostic nanomaterials in vitro. HEV-VLPs can be disassembled in the presence of reducing and chelating reagents such as dithiothreitol (DTT) and ethylenediaminetetraacetic acid (EDTA) or ethylene glycol-bis($\beta$-aminoethyl ether)-N, N,N',N'-tetraacetic acid (EGTA), with reassembly reactions initiated by addition of calcium or magnesium ions.

Encapsulation of HEV-VLP is a charge-based interaction, such that negative-charged nucleic acids, nano-sized proteins, and inorganic molecules can be packaged for use in therapeutic applications (Chen, Baikoghli et al. 2018, Shizuo G. Kamita 2019). Oral delivery capability of exogenous genes using HEV-VLPs can be used to deliver plasmid cDNAs to the epithelial cells of the small intestine for transient expression of cDNA encoded antigen (Takamura, Niikura et al. 2004, Cheng and Xing 2014). HEV-VLPs, encapsulating magnetic ferrite NPs, can also be used in procedures such as MRI imaging and tumor-targeted hyperthermia induced by radiofrequency electromagnetic radiation (Roemer 1999).

Encapsulation of molecules by HEV-VLPs has the potential to impact many fields requiring drug and gene delivery systems (Stark and Cheng 2016). HEV-VLPs comprising surface-bound ligands that target specific types of cancer cells also have the potential to cure or ameliorate the conditions of many types of cancer.

New generations of therapeutics, including proteins and peptides, monoclonal antibodies (mAbs), nucleic acids and live cells, have provided new therapeutic functions. HEV- VLPs have been proposed as drug delivery systems (DDS) including dsDNA vectors and RNAs for gene therapy applications. Many primary classes of therapeutics, small-molecule drugs, could not be packed into HEV-VLPs due to their hydrophobicity. In this example, we disclose methods to extend the ability of HEV-VLP's encapsulate hydrophobic cancer drugs by modifying HEV-VLPs at their N termini. NCT-002: Hydrophobic Peptide Inserted in Proposed Consensus Sequence Derived from 160 Sequences (Cys Insertion Between 490aa and 491aa)

HEV-VLPs have icosahedral structures with two-, three- and five-fold axes of symmetry (Shizuo G. Kamita 2019). The capsid of Hepatitis E virus, PORF2, has features of a typically secreted protein: an N-terminal signal sequence and conserved glycosylation sites. The N-terminal 111 amino acids show maximum sequence divergence among HEV genotypes, and expressing full length ORF2 in insect cells usually results in proteolytic cleaving of this region. The virion has a T=3 symmetry, with 180 monomers, while truncated pORF folds into a T=1 particle with 60 subunits and 30 protruding spikes, which has been promoted as drug delivery system (Shizuo G. Kamita 2019). In structural studies, the extra mass could be detected inside the VLP, which could correspond to the foreign peptide been fused to the C terminus of ORF2 (Wang, Miyazaki et al. 2008).

In this example, a hydrophobic peptide designated NS5A (1-31), underlined, (represented by amino acids 2-33 of SEQ ID NO: 8) which is expected to help encapsulate hydrophobic drugs more efficiently, was chosen for the insertion to the C-terminus of ORF2 to generate HEV-NS5A-VLP (Buehler, Marsden et al. 2014). A cysteine residue (C) inserted between amino acids N490 and P491 can be used to conjugate ligands to facilitate targeting of the VLP to the desired types of cells. The VLP is expected to have a size between 20-27 nm.

FIG. 19: Sets Forth an Illustration Entitled "Peptide Hydrophobicity/Hydrophilicity Analysis".

```
Sequence Alignment 2: AA sequence of the proposed
NCT-002: HEV-NS5A-VLPs
                                        (SEQ ID NO: 08)
                 MAGSWLRDIWDWICEVLSDFKT
WLKAKAKLMPTM

LTAVAPAPDTAPVPDVDSRGAILRRQYNLSTSPLTSSV

ASGTNLVLYAAPLNPLLPLQDGTNTHIMATEASNYAQYRVVRATI

RYRPLVPNAVGGYAISISFWPQTTTTPTSVDMNSITSTDVRILVQ

PGIASELVIPSERLHYRNQGWRSVETSGVAEEEATSGLVMLCIHG

SPVNSYTNTPYTGALGLLDFALELEFRNLTPGNTNTRVSRYSSTA

RHRLRRGADGTAELTTTAATRFMKDLHFTGINGVGEVGRGIALTL

FNLADTLLGGLPTELISSAGGQLFYSRPVVSANGEPTVKLYTSVE

NAQQDKGIAIPHDIDLGESRVVIQDYDNQHEQDRPTPSPAPSRPF

SVLRANDVLWLSLTAAEYDQTTYGSSTNCPMYVSDTVTFVNVATG

AQAVARSLDWSKVTLDGRPLTTIQQYSKTFYVLPLRGKLSFWEAG

TTKAGYPYNYNTTASDQILIENAAGHRVAISTYTTSLGAGPVSIS

AVGVLAPHSALA
```

VLPs comprising a hydrophobic polypeptide at their amino terminus can be expressed in baculovirus-infected insect cells, followed by purification steps involving clarification, concentration, purification, and polishing, to generate material suitable for use in a variety of structural and functional studies, including TEM to confirm the conformation of the HEV-NS5A-VLP particles. The ability of HEV-NS5A-VLPs to encapsulate hydrophobic drug products, such as Doxorubicin, is tested by mixing the payloads with the disassembled HEV-NS5A-VLP and gradually adding calcium or magnesium ions to reassemble functional Virus-Like Particles.

Example 3: Developing Theranostic HEV-VLP for Medical Applications

Hepatitis E Virus-Like Particles (HEV-VLPs), derived from HEV, are non-infectious, self-assembling capsids capable of cell-binding and entry. HEV-VLPs appear to maintain their structural integrity in low-pH environments (Zafrullah, Khursheed et al. 2004), an advantage for intratumoral penetration. HEV infections occur primarily through fecal and oral routes. HEV-VLPs are also resistant to proteolytic and acidic mucosal conditions, making them ideal for use as mucosal delivery capsules (Jariyapong, Xing et al. 2013, Chen, Baikoghli et al. 2018). HEV-VLPs also possess a surface-exposed protrusion (P) domain connected to a stable icosahedral base through a flexible hinge. Engineered HEV-VLPs form a hollow nano-scale capsid composed of 60 identical units (Xing, Kato et al. 1999), which are highly stable during storage and under harsh physiological conditions. Surface engineering, substituting or adding cysteine residues on the P domain as chemical conjugation sites, may reduce the responses of HEV-VLPs to pre-existing antibodies (Chen, Xing et al. 2016). With 60 repeated units, single site-specific modifications on the P domain results in 60 symmetric sites on an assembled capsid for conjugation and presentation of many foreign molecules.

Cancer theranostics require direct drug contact with pathological foci. HEV-VLP-based theranostic agents had high affinities for human malignant breast tumor cells after being conjugated with LXY30 (Xiao, Li et al. 2016), and showed specific targeting to breast tumor cells in vitro and in vivo, demonstrating that HEV-VLPs can be manipulated to facilitate the targeted delivery of diagnostic or therapeutic reagents to pathologic foci (Chen, Xing et al. 2016). HEV-VLPs also accumulated at the abdominal organs including liver (Chen, Xing et al. 2016), suggesting that they can be used as liver-specific Positron emission tomography (PET) imaging agents conjugated with radioactive gallium-68 [68Ga] (Lambidis, Chen et al. 2022, Lambidis, Chen et al. 2022).

Modularized theranostic agents can be designed expanded by modifying interior cavities of HEV-VLPs. They can be reversibly disassembled and reassembled through chemical reduction and chelation, providing a method to encapsulate theranostics nanomaterials in vitro. HEV-VLPs will disassemble in the presence of reducing and chelating reagents such as dithiothreitol (DTT), ethylenediaminetetraacetic acid (EDTA), or ethylene glycol-bis($\beta$-aminoethyl ether)-N, N,N', N'-tetra-acetic acid (EGTA). A cation concentration can trigger the VLP reassembly. HEV-VLPs are also capable of encapsulation of negatively-charged insulin peptides for oral insulin application (Chen, Baikoghli et al. 2018), and magnetic Virus-Like Particles such as ferrite Virus-Like Particles for both diagnosis under MRI and tumor-targeted hyperthermia induced by the alternative magnetic field (AMF) (Ito, Honda et al. 2006, Chen CC 2017).

Passive encapsulation of different payloads is usually done by mixing the payloads with the disassembled HEV-VLPs and gradually adding calcium or magnesium ions to form the Virus-Like Particles. Magnetic iron oxide Virus-Like Particles that are nontoxic, biocompatible, and stable can be synthesized into different shapes and sizes (Cassim, Giustini et al. 2011). When the magnetic Virus-Like Particles are placed in an AMF, they can generate heat according to several established physic theories (Wu, Zhuo et al. 2015, Attar and Haghpanahi 2016, Espinosa, Di Corato et al. 2016, Kaur, Aliru et al. 2016). Encapsulation of HEV-VLPs with such attributes can enhance magnetic resonance imaging (MRI) by producing darker signals on T2-weighted images than in surrounding tissue sections (Serkova 2017).

The alternating magnetic field (AMF) induced heating capability of ferrite Virus-Like Particles has been demonstrated (Ito, Shinkai et al. 2003; Ito, Honda et al. 2006). Magnetic Virus-Like Particles injected into targeted cancer tissue will rapidly heat when activated by an external alternating magnetic field (AMF). Necrosis of the microenvironment occurs, if the concentration of particles and AMF amplitude are sufficient. Tumor-specific hyperthermia treatment induced necrotic cell death via heat shock protein (HSP) expression, inducing antitumor immunity (Ito, Shinkai et al. 2003).

HIFU is a noninvasive method for treating solid tumors and metastatic disease. HIFU has effectively treated various solid malignant tumors in the pancreas, liver, prostate, breast, uterine fibroids, and soft-tissue sarcomas in clinical settings. Long procedure times and collateral damage still remain as challenges in HIFU medical procedures. Unintended damage during HIFU procedures, such as skin burns and damage to overlying tissues, has been reported due to high-energy intensity. The gastrointestinal (GI) tract, considered heat-susceptible tissue, remains challenging for HIFU hyperthermia treatment. One strategy to reduce the required acoustic intensity and consequent side effects relies on hyperthermia-enhancing agents. Ferrite and gold Virus-Like Particles both reduce the acoustic intensity and exposure time required during HIFU thermal-ablation procedures (Kosheleva, Lai et al. 2016, Devarakonda, Myers et al. 2017, Devarakonda, Myers et al. 2017, Devarakonda, Myers et al. 2018, Kaczmarek, Hornowski et al. 2018). Magnetic ferrite Virus-Like Particles also can be used as magnetic resonance imaging (MRI) agents for tracking guidance and temperature monitoring. Magnetic resonance imaging-guided high-intensity focused ultrasound (MRg-HIFU) therapy has expanded to secure safe and effective treatment during pre-hyperthermia and post-hyperthermia treatment (Kim 2015). Virus-Like Particles can only be injected into tumor sites to enhance the intensity of heating, partly due to their lack of cancer targeting capability.

The encapsulation of HEV-VLP is a charge-based interaction such that negative-charged nucleic acids, nano-sized protein, inorganic Virus-Like Particles can be packaged for therapeutic applications (Chen, Baikoghli et al. 2018; Shizuo G. Kamita 2019). In this example, we outline strategies to enhance the ability of HEV-VLPs to encapsulate negatively-charged payloads by modifying the N terminus of HEV-VLP by adding positively-charged peptides.

NCT-001: N&C Truncated Version of Proposed Consensus Sequence Derived from 160 Sequences (99a-608aa, Cys Insertion Between 490aa and 491aa)

The icosahedral viral structure of HEV-VLP has two-, three- and five-fold axes of symmetry (Shizuo G. Kamita 2019). The capsid of Hepatitis E virus, PORF2, has features of a typically secreted protein: an N-terminal signal sequence and conserved glycosylation sites. The N-terminal 111 amino acids show maximum sequence divergence among HEV genotypes, and expressing full length ORF2 in insect cells usually results in proteolytic cleavage in this region. The virion has a T=3 symmetry, with 180 monomers, while truncated pORF folds into a T=1 particle with 60 subunits and 30 protruding spikes (Shizuo G. Kamita 2019). Extra mass could be detected inside the VLPs, which could correspond to the foreign peptide been fused to the C terminus of ORF2 (Wang, Miyazaki et al. 2008).

FIG. 20: Sets Forth an Illustration Entitled "Hydrophobicity/Hydrophilicity Analysis of Peptide NS5A (1-31)".

The negative-charged peptide of ORF2 (99-111aa) (Underlined protein sequence.

RRRSAPAGAAPLT, represented by amino acids 2-14 of SEQ ID NO 10) is chosen for the genetic insertion to the C-terminus of ORF2 to generate HEV-ORF2 (99-608)-VLP. Insertion of a cysteine residue after 490 aa on the P domain of the HEV-VLPs can be used as a chemical conjugation site for foreign peptides/ligands for antigen or specific cell targeting. The 490 aa is within one of the three flexible loops of the P domain which are non-structural essential, and could be genetically engineered without affecting the forming of VLPs (Chen et al. 2016). A Cys (C) inserted after position 490 aa of the HEV-VLP (HEV-Cys VLP) is chosen to demonstrate production of a modularized theranostic capsule. The HEV-Cys VLPs can utilize two different conjugation methods: thiol-selective conjugation between maleimide and cysteine, and amine-selective conjugation between amine group and NHS-ester.

```
Sequence Alignment 3: NCT-001-N and C terminus
deleted ORF2 (99-608 aa)
                                    (SEQ ID NO: 10)
MRRRSAPAGAAPLT

AVAPAPDTAPVPDVDSRGAILRRQYNLSTSPLTSSVASGTNLVLY

AAPLNPLLPLQDGTNTHIMATEASNYAQYRVVRATIRYRPLVPNA

VGGYAISISFWPQTTTTPTSVDMNSITSTDVRILVQPGIASELVI

PSERLHYRNQGWRSVETSGVAEEEATSGLVMLCIHGSPVNSYTNT

PYTGALGLLDFALELEFRNLTPGNTNTRVSRYSSTARHRLRRGAD

GTAELTTTAATRFMKDLHFTGTNGVGEVGRGIALTLFNLADTLLG

GLPTELISSAGGQLFYSRPVVSANGEPTVKLYTSVENAQQDKGIA

IPHDIDLGESRVVIQDYDNQHEQDRPTPSPAPSRPFSVLRANDVL

WLSLTAAEYDQTTYGSSTNCPMYVSDTVTFVNVATGAQAVARSLD

WSKVTLDGRPLTTIQQYSKTFYVLPLRGKLSFWEAGTTKAGYPYN

YNTTASDQILIENAAGHRVAISTYTTSLGAGPVSISAVGVLAPHS

ALA
```

Expected results: T=1, VLP conformation, 27 nm; the extended

RRRSAPAGAAPLT, positively charged peptide at the N terminal end will help to encapsulate negatively-charged drugs, DNA, RNA, and Fe3O4 NPs more efficiently.

Ligands can be chemically conjugated to maleimide linked peptide/ligands to the Cys mutated site on HEV-Cys VLPs and maleimide-linked peptide/ligands (20 μM-200

μM) by reacting HEV-Cys VLPs (4 μM-40 M) in 0.01M PBS, pH7.2 at 4° C. overnight. Unbound maleimide-peptide/ligands can then be removed using 7,000 MWCO or similar desalting columns (Zeba Spin Desalting Columns, Thermo Scientific).

Example 4: Developing HEV-VLP for Cancer/Tissue Targeted Drug Delivery System A fundamental challenge in the development of gene-based therapy systems is ensuring that the carriers or vectors are safe and effective. Although many kinds of viruses that have been evaluated for use in gene therapy vector systems are highly efficient in delivering genes to cells, many applications have been limited by concerns relating to carcinogenesis, immunogenicity, and biomanufacturing of these vectors. Non-viral, synthetic carriers, based on lipid Virus-Like Particles, have also been developed to enhance the delivery of therapeutic nucleic acids to their sites of action. Only a few synthetic carrier systems have been approved for clinical use, generally facing obstacles such as low delivery efficiencies compared to viral vector systems. While viruses have evolved to efficiently target and deliver their genomes to mammalian cells, many synthetic vector or carrier systems are unable to transport their payloads effectively past multiple barriers that confront them.

Hepatitis E Virus-Like Particles (HEV-VLPs) are non-infectious, self-assembling particles comprising capsid proteins capable of binding and entry into cells. HEV-VLPs also appear to maintain their structural integrity in low-pH environments (Zafrullah, Khursheed et al. 2004), an advantage for intratumoral penetration. The primary route of HEV infection is through the fecal-oral routes. HEV-VLPs are resistant to proteolytic and acidic mucosal conditions, making them an ideal mucosal delivery capsule (Jariyapong, Xing et al. 2013, Chen, Baikoghli et al. 2018, Shizuo G. Kamita 2019). HEV-VLPs can be purified from *Trichoplusia ni* insect cells infected with baculovirus expression vectors at a high yields (Kawano, Xing et al. 2011).

Modularized theranostic HEV-VLPs can bind molecules encapsulated in their interior, or to amino acids or other moieties exposed on their surfaces. HEV-VLP sequences have been optimized not to encapsulate virus-RNA, forming highly stable non-infectious capsids capable of reversible in vitro assembly through cation mediation (Xing, Li et al. 2010). HEV-VLPs can be switched back and forth in self-assembly through chemical reduction and cation chelation. This property provides a method to encapsulate theranostic nanomaterials in vitro. HEV-VLPs could be disassembled in the presence of reducing and chelating reagents such as dithiothreitol (DTT), ethylenediaminetetraacetic acid (EDTA), or ethylene glycol-bis(β-aminoethyl ether)-N,N,N', N'-tetraacetic acid (EGTA), and reassembly reactions triggered by the calcium or magnesium ions. Encapsulation of HEV-VLPs occur through charge-based interactions such that negative-charged nucleic acids, nano-sized proteins, inorganic Virus-Like Particles can be packaged for therapeutic applications (Chen, Baikoghli et al. 2018, Shizuo G. Kamita 2019). Oral deliveries of plasmid cDNAs comprising exogenous genes to the epithelial cells of the small intestine were demonstrated by showing transient expression of cDNA-encoded antigens (Takamura, Niikura et al. 2004, Cheng and Xing 2014). HEV-VLPs encapsulating magnetic ferrite NPs are suitable for use in MRI imaging and tumor-targeted hyperthermia induced by radiofrequency electromagnetic radiation (Roemer 1999). Encapsulation of molecules by HEV-VLPs suggests many applications for use in drug and gene delivery systems (Stark and Cheng 2016). Binding cancer cell-targeting ligands to their surfaces could also impact many applications focused on cell and gene therapy vector systems.

Chemotherapy is normally recommended to patients with intermediate or advanced stage cancer. Conventional therapies are often limited due to non-specific delivery of chemotherapeutic agents. Drug delivery system can effectively target and deliver cytotoxic agents to tumor sites should enhance efficacy and reduce undesirable side effects.

Cancer theranostics requires direct contact of drug with pathological foci, often requiring a capsule carrying specific ligands is preferential for targeted delivery of anti-cancer reagents. To assess the targeting and diagnostic capability, a breast cancer cell targeting ligand, LXY30, was chemically cycloadded to the surface of HEV-VLPs through cysteine-anchored melamine-alkyne. In vivo NIR optical imaging was used to investigate the distribution of the HEV-VLPs in nude mice bearing MDA-MB-231 breast cancer xenografts, as a criterion to evaluate the specificity of tumor targeting. Both Cy5.5 labeled LXY30-HEV-VLPs and the Cy5.5 labeled wild type VLPs were intravenously injected via tail vein in nude mice bearing MDA-MB-231 xenografts, respectively. Both Cy5.5-labeled wild type VLPs and LXY30-HEV-VLPs distributed throughout the body of the mice immediately after the intravenous injection, and accumulated into liver. Tumor uptake was observed for LXY30-HEV-VLP but not for the wild type VLPs. Retention of LXY30-HEV-VLP at tumor started as early as one hour post injection and lasted up to six hours post injection. HEV, as an enteric transmitted hepatitis virus, preferentially enters hepatocytes in liver. It is not surprising to observe HEV-VLP accumulation in abdominal organs including liver.

Zwitterionic-based materials are receiving great attention to resist nonspecific protein absorption due to their effectiveness, robustness, and stability. An ultra-low fouling surface can be achieved when the surface contains a nanometer-scale homogenous mixture of balanced charged groups either from zwitterionic moieties (both positively and negatively charged moieties connected in the same group), such as poly EK peptides. Nonspecific binding of HEV-VLPs in liver may be reduced by either chemical conjugating a low fouling peptide, poly EK, onto the P domain of HEV-VLPs, or genetically inserting poly EK at the well-exposed C terminal of HEV-VLPs.

Hepatitis E Virus-Like Particles (HEV-VLPs), derived from a modified form of the HEV capsid protein, are non-infectious, self-assembling capsids capable of cell-binding and entry. Like the native virus, HEV-VLP is stable in acidic environment and resistant to proteolytic digestion, thus it poses a great advantage as an oral delivery vehicle. HEV-VLPs can be manufactured cost-effectively using a system that has been used in manufacturing biomolecules that have been approved by the FDA. The major capsid protein, open reading frame 2 (ORF2, ~500 amino acids) is composed of the 3 domains with the Shell and Middle domains of the N-terminus form the base of the shell. While the remaining ~150 amino acids of C-terminal domain (protrusion domain or P-domain) consists of the major binding and antibody sites for neutralizing antibodies and receptors.

The P domain forms surface-exposed spikes atop the icosahedral base, while the flexible hinge makes it possible to modify the P domain, either inserting a foreign peptide via genetic engineering (Jariyapong, Xing et al. 2013) or chemical conjugating (Chen, Xing et al. 2016), without compromising the base icosahedral structure. Three surface variable loops on the P domain and the C terminal of the HEV capsid protein, ORF2, are designed and genetically engineered and/or chemical conjugation sites for at least one or more bioactive agents for they are well-exposed on HEV-VLP surface (Cheng, Xing et al. 2015, Chen, Xing et al. 2016, R. Holland Cheng 2017).

NCT-003: RGD Peptide Fused at the C Terminal of the N/C Terminus Deleted Version of Proposed Consensus Sequence Derived from 160 Sequences (Cys Insertion Between 490aa and 491aa)

The icosahedral viral structure of HEV-VLP has two-, three- and fivefold axes of symmetry (Shizuo G. Kamita 2019). The capsid of Hepatitis E virus, PORF2, has features of a typically secreted protein: an N-terminal signal sequence and conserved glycosylation sites. Interestingly, the N-terminal 111 amino acids show maximum sequence divergence among HEV genotypes, and expressing full length ORF2 in insect cells usually results in proteolytic cleaving of this region. The virion has a T=3 symmetry, with 180 monomers, while truncated pORF folds into a T=1 particle with 60 subunits and 30 protruding spikes, which is HEV-VLP has been promoted as drug delivery system (Shizuo G. Kamita 2019). In the prior structural research (Wang et al. 2008), the C terminus of ORF2 is exposed on the surface of HEV-VLPs. In this example, an RGD peptide (CFTPRGDMPGPYC)

with a HSV linker (QPELAPEDPED)

and poly EKEK, are fused to the VLP to reduce liver uptake.

Sequence Alignment 4: NCT-003: RGD peptide fused at the C terminal of the N/C terminus deleted version)

(SEQ ID NO: 12)

MRRR

SAPAGAAPLTAVAPAPDTAPVPDVDSRGAILRRQYNLSTSPLTSS

VASGTNLVLYAAPLNPLLPLQDGTNTHIMATEASNYAQYRVVRAT

IRYRPLVPNAVGGYAISISFWPQTTTTPTSVDMNSITSTDVRILV

QPGIASELVIPSERLHYRNQGWRSVETSGVAEEEATSGLVMLCIH

GSPVNSYTNTPYTGALGLLDFALELEFRNLTPGNTNTRVSRYSST

ARHRLRRGADGTAELTTTAATRFMKDLHFTGINGVGEVGRGIALT

LFNLADTLLGGLPTELISSAGGQLFYSRPVVSANGEPTVKLYTSV

ENAQQDKGIAIPHDIDLGESRVVIQDYDNQHEQDRPTPSPAPSRP

FSVLRANDVLWLSLTAAEYDQTTYGSSTNCPMYVSDTVTFVNVAT

GAQAVARSLDWSKVTLDGRPLTTIQQYSKTFYVLPLRGKLSFWEA

GTTKAGYPYNYNTTASDQILIENAAGHRVAISTYTTSLGAGPVSI

SAVGVLAPHSALAQPELAPEDPEDEKEKCFTPRGDMPGPYC

Amino acids 99-111 contain RRR which could enhance the encapsulation rate of negatively-charged payloads;
    Cys (C) is inserted between 490aa N and 491aa as Chemical conjugation site;
    The HSV linker-EKEK-RGD peptide,

QPELAPEDPEDEKEKCFTPRGDMPGPYC is fused to the C terminal for cancer targeting.

Expected results:
T=1,
VLP conformation, 27 nm;
    the additional HSV linker-EKEK-RGD peptide at the C terminal will help to bind to cancer cells;
    EKEK peptide between HSV linker and RGD peptide may reduce liver binding; and
    the Cys insertion between positions 490 aa and 491 aa can be used as chemical conjugation site for cell targeting ligands.

The passive encapsulation of different payloads will be done by mixing the payloads with the disassembled HEV-RGD-VLP and then gradually adding calcium or magnesium ions to form the Virus-Like Particles.

Key issues that need to be addressed to develop HEV-RGD-VLPs as mucosal drug delivery agents include: (1) the optimal quantities of payload per Virus-Like Particle; (2) the relative costs and efficiencies of encapsulation for different payloads; (3) effective separation of the unpacked drug/payload from the encapsulated HEV-VLPs, needed to meet GMP standards for products to be used in clinical trials; and (4) optimization of the HEV-RGD-VLP encapsulation procedures for different types of payloads.

Example 5: Developing Theragnostic HEV-VLPS (T=3 Virion Particles) for Medical Applications HEV consists of a non-enveloped icosahedral capsid and a single-stranded, positive-strand RNA genome of 7.2 kb that encodes three open reading frames (ORFs) (Tam, Smith et al. 1991). The capsid protein, encoded by the ORF2, is composed of 660 amino acids and responsible for most capsid-related functions, such as virion assembly, host interaction, and immunogenicity. The N-terminal 111 amino acids show maximum sequence divergence among HEV genotypes, and expressing full length ORF2 in insect cells usually results in proteolytic cleaving of this region.

The virion has a T=3 symmetry, with 180 monomers, while truncated pORF2 (amino acids 112-608) folds into a T=1 particle with 60 subunits and 30 protruding spikes (Xing, Kato et al. 1999). The essential element of PORF2 protein for T=1 VLP assembly includes amino acids 125-600 (Li, Takeda et al. 2005). VLPs expressed and purified from insect cells comprising amino acids 14-608 had T=3 VLP structures, having a diameter of 410 Å and an inner radius of 170 Å, that is considerably larger than the T=1 VLP (Xing, Li et al. 2010).

Three linear domains form distinct structural elements: S, the continuous capsid shell; M, the threefold protrusions; and P, the twofold spikes. The S domain (amino acids 118-317) adopts a jelly-roll β-barrel fold commonly observed in small RNA viruses. The M (amino acids 318-451) and P domains (amino acids 452-606) both adopt β-barrel folds. The P domain contains binding sites for neutralizing antibodies and receptors. HEV-VLPs with a (T=1) structure have a surface-exposed protrusion (P) domain connected to a stable icosahedral base through a flexible hinge.

An engineered HEV-VLP presented a high affinity for human malignant breast tumor cells after being conjugated with LXY30 and showed specific targeting to breast tumor cells both in vitro and in vivo (Xiao, Li et al. 2016). These results suggest that HEV-VLPs can be manipulated to facilitate the targeted delivery of diagnostic or therapeutic reagents to pathologic foci (Chen, Xing et al. 2016). HEV-(T=1) VLPs also accumulated in abdominal organs, including the liver (Chen, Xing et al. 2016). HEV-(T=1) VLPs were recently proposed as liver-specific Positron emission tomography (PET) imaging agents by chemically conjugating them with radioactive gallium-68 [68Ga] (Lambidis, Chen et al. 2022, Lambidis, Chen et al. 2022), supporting the continued development of HEV-(T=1) VLPs as theranostic nanocarriers, particularly for therapies that target liver cells.

In this example, we propose to improve the payload encapsulation capacity of HEV-VLP by adopting the T=3 VLP with a diameter of 410 Å and inner radius of 170 Å, compared to the T=1 VLP with a diameter of 270 Å and inner radius of 110 Å. The encapsulation capability of HEV-(T=3) VLP will be enhanced by charge-based interactions such that negative-charged nucleic acids, nano-sized proteins, and inorganic Virus-Like Particles can be packaged for therapeutic applications (Chen, Baikoghli et al. 2018, Shizuo G. Kamita 2019). Cancer/tissue targeting capabilities will be enhanced by inserting extra Cysteine residues on their surfaces, exemplified by NCT-001: HEV (T=1) VLP.

NCT-004: 13aa Deleted N terminus of Full Length of Proposed Consensus Sequence Derived From 124 Sequences (14aa-660aa, Cys Insertion Between 490aa and 491aa)

HEV consists of a non-enveloped icosahedral capsid and a single-stranded, positive-strand RNA genome of 7.2 kb that encodes three open reading frames (ORFs) (2). The capsid protein, encoded by the ORF2, is composed of 660 amino acids and responsible for most capsid-related functions, such as virion assembly, host interaction, and immunogenicity. In this example, NCT-004 comprising amino acids 14-608 of ORF2 is disclosed which should generate a T=3 VLP with diameter of 410 Å and an inner radius of 170 Å, that is considerably larger than the T=1 VLP reported earlier (Xing, Li, Mayazaki, et al. 2010).

FIG. 21: Sets Forth an Illustration Entitled "NCT-002: HEV-NS5A-VLP".

```
Sequence Alignment 5: NCT-004: Near Full length
ORF2
                                    (SEQ ID NO: 04)
    MLPMLPAPPAGQPSGRRRGRRSGGAGGGFWGDRVDS

QPFALPYIHPTNPFASDVVSQSGAGARPRQPARPLGSAWRDQSQR

PAAAPRRRSAPAGAAPLTAVAPAPDTAPVPDVDSRGAILRRQYNL

STSPLTSSVASGTNLVLYAAPLNPLLPLQDGTNTHIMATEASNYA

QYRVVRATIRYRPLVPNAVGGYAISISFWPQTTTTPTSVDMNSIT

STDVRILVQPGIASELVIPSERLHYRNQGWRSVETSGVAEEEATS

GLVMLCIHGSPVNSYTNTPYTGALGLLDFALELEFRNLTPGNTNT

RVSRYSSTARHRLRRGADGTAELTTTAATRFMKDLHFTGTNGVGE

VGRGIALTLFNLADTLLGGLPTELISSAGGQLFYSRPVVSANGEP

TVKLYTSVENAQQDKGIAIPHDIDLGESRVVIQDYDNQHEQDRPT

PSPAPSRPFSVLRANDVLWLSLTAAEYDQTTYGSSTNCPMYVSDT

VTFVNVATGAQAVARSLDWSKVTLDGRPLTTIQQYSKTFYVLPLR

GKLSFWEAGTTKAGYPYNYNTTASDQILIENAAGHRVAISTYTTS

LGAGPVSISAVGVLAPHSALAVLEDTVDYPARAHTFDDFCPECRT

LGLQGCAFQSTVAELQRLKMKVGKTREY
```

Expected results: T=3, VLP conformation, and 40 nm.

The additional size might help to encapsulate negatively-charged drugs, DNA, RNA, Insulin, and $Fe_3O_4$ NPs.

The insertion of a Cysteine residue (C) between aa positions 490 and 491 can be used as a site for chemically-conjugating cell targeting ligands.

Example 6: P Domain Replacement: HHV of Mab Replace the P Domain of the N/C Terminus Deleted Version of Proposed Consensus Sequence Derived from Consensus Sequence HEV consists of a non-enveloped icosahedral capsid and a single-stranded, positive-strand RNA genome of 7.2 kb that encodes three open reading frames (ORFs) (Tam, Smith et al. 1991). The capsid protein, encoded by ORF2, is composed of 660 amino acids and responsible for most capsid-related functions, such as virion assembly, host interaction, and immunogenicity. The N-terminal 111 amino acids show maximum sequence divergence among HEV genotypes, and expressing full length ORF2 in insect cells usually results in proteolytic cleaving of this region.

The virion has a T=3 symmetry, with 180 monomers, while truncated pORF2 (amino acids 112-608) folds into a T=1 particle with 60 subunits and 30 protruding spikes (Xing, Kato et al. 1999). The essential element of PORF2 protein for T=1 VLP assembly includes amino acids 125-600 (Li, Takeda et al. 2005). When expressed and purified from baculovirus-infected insect cells, a capsid protein comprising amino acids 14-608 yielded a T=3 VLP with diameter of 410 Å and inner radius of 170 Å, that is considerably larger than the T=1 VLP (Xing, Li et al. 2010).

Three linear domains form distinct structural elements: S, the continuous capsid shell; M, the threefold protrusions; and P, the twofold spikes. The S domain (amino acids 118-317) adopts a jelly-roll β-barrel fold commonly observed in small RNA viruses. The M (amino acids 318-451) and P domains (amino acids 452-606) both adopt β-barrel folds. The P domain contains binding sites for neutralizing antibodies and receptors. The M domain of HEVNP interacts strongly with the S domain and connects to the P domain via a long proline-rich hinge (amino acids 445-463), which appears to have an impact on the formation of the dimer, the building block of HEVNP (Xing, Li et al. 2010).

In this example, a partial P-domain (amino acids 463-608) i s replaced by a sequence of a nanobody of 120 aa derived from the HHV of Pembrolizumab, an FDA-approved anti-PD-1 drug product (Sun, Yan et al. 2018, Jeong, Lee et al. 2022), to generate a chimeric nanobody-HEVNP. A deletion of ~145 amino acids in the capsid protein is similar to the size of added nanobody segment.

The β-barrel folds of the nanobody are expected to form a building block with a dimeric ring structure capable of forming T=1 VLPs. The 3D structure of pembrolizumab (PDB: 5GGS) suggests that HCD3, the active domain, will be facing inward after fusing to the S&M domain of ORF2. The expected tertiary structure of the HHV fused ORF2 could hinder the presentation of the HCD3 of pembrolizumab, even if it is capable of forming VLPs in the chimeric molecule.

FIG. 22: Sets Forth an Illustration Entitled "PDB 5GGS (120 aa) Inserted after 364 aa P (484 aa) HHV Pembrolizumab 1-120aa)".

FIG. 23: Sets Forth an Illustration Entitled "the Schematic of the Secondary Structural Interactions in the HHV of Pembrolizumab According to its X-Ray Crystal Structure (PDB: 5GGS)".

Sequence Alignment 6: NCT-005-ORF2 (99-452 aa) fused with HHV-pembrolizumab
1-120 aa (PDB: 5GGS) (1-120 aa), Total 474 aa, (ORF2 99-608 aa, 510 aa)
AA Sequence:

(SEQ ID NO: 14)

MRRRSAPAGAAPLTAVAPA

PDTAPVPDVD SRGAILRRQY NLSTSPLTSS VASGTNLV LYAAPLNPLL PLQDGTNTHI MATEASNYAQ

YRVVRATIRY RPLVPNAVGG YAISISFWPQ TTTTPTSVDM NSITSTDVRI LVQPGIASEL VIPSERLHYR

NQGWRSVETS GVAEEEATSG LVMLCIHGSP VNSYTNTPYT GALGLLDFAL ELEFRNLTPG NTNTRVSRYS

STARHRLRRG ADGTAELTTT AATRFMKDLH FTGTNGVGEV GRGIALTLFN LADTLLGGLP TELISSAGGQ

LFYSRPVVSA NGEPTVKLYT SVENAQQDKG IAIPHDIDLG ESRVVIQDYD NQHEQDRPTP SPAPSRP

QVQLVQSGVE VKKPGASVKV SCKASGYTFT NYYMYWVRQA PGQGLEWMGG

INPSNGGTNF NEKFKNRVTL TTDSSTTTAY MELKSLQFDD TAVYYCARRD YRFDMGFDYW GQGTTVTVSS

Underlined amino acids 99-111aa contain RRR to
enhance the encapsulation rate of negatively-charged payloads;
    Double underlined: beta sheet structure by secondary
structure prediction by PredictProtein.
    PDB: 5GGS (120aa) inserted after 364aa P (484aa) (HHV
pembrolizumab 1-120aa)

QVQLVQSGVE VKKPGASVKV SCKASGYTFT NYYMYWVRQA PGQGLEWMGG

INPSNGGTNF NEKFKNRVTL TTDSSTTTAY MELKSLQFDD TAVYYCARRD YRFDMGFDYW GQGTTVTVSS

MRRRSAPAGAAPLTAVAPAPDTAPVPDVDSRGAILRRQYNLST

SPLTSSVASGTNLVLYAAPLNPLLPLQDGTNTHIMATEASNYAQY

RVVRATIRYRPLVPNAVGGYAISISFWPQTTTTPTSVDMNSITST

DVRILVQPGIASELVIPSERLHYRNOGWRSVETSGVAEEEATSGL

VMLCIHGSPVNSYTNTPYTGALGLLDFALELEFRNLTPGNTNTRV

SRYSSTARHRLRRGADGTAELTTTAATRFMKDLHFTGINGVGEVG

RGIALTLFNLADTLLGGLPTELISSAGGQLFYSRPVVSANGEPTV

KLYTSVENAQQDKGIAIPHDIDLGESRVVIQDYDNQHEQDRPTPS

PAPSRPQVQLVQSGVEVKKPGASVKVSCKASGYTFTNYYMYWVRQ

APGQGLEWMGGINPSNGGTNFNEKFKNRVTLTTDSSTTTAYMELK

SLQFDDTAVYYCARRDYRFDMGFDYWGQGTTVTVSS

Figure 25:
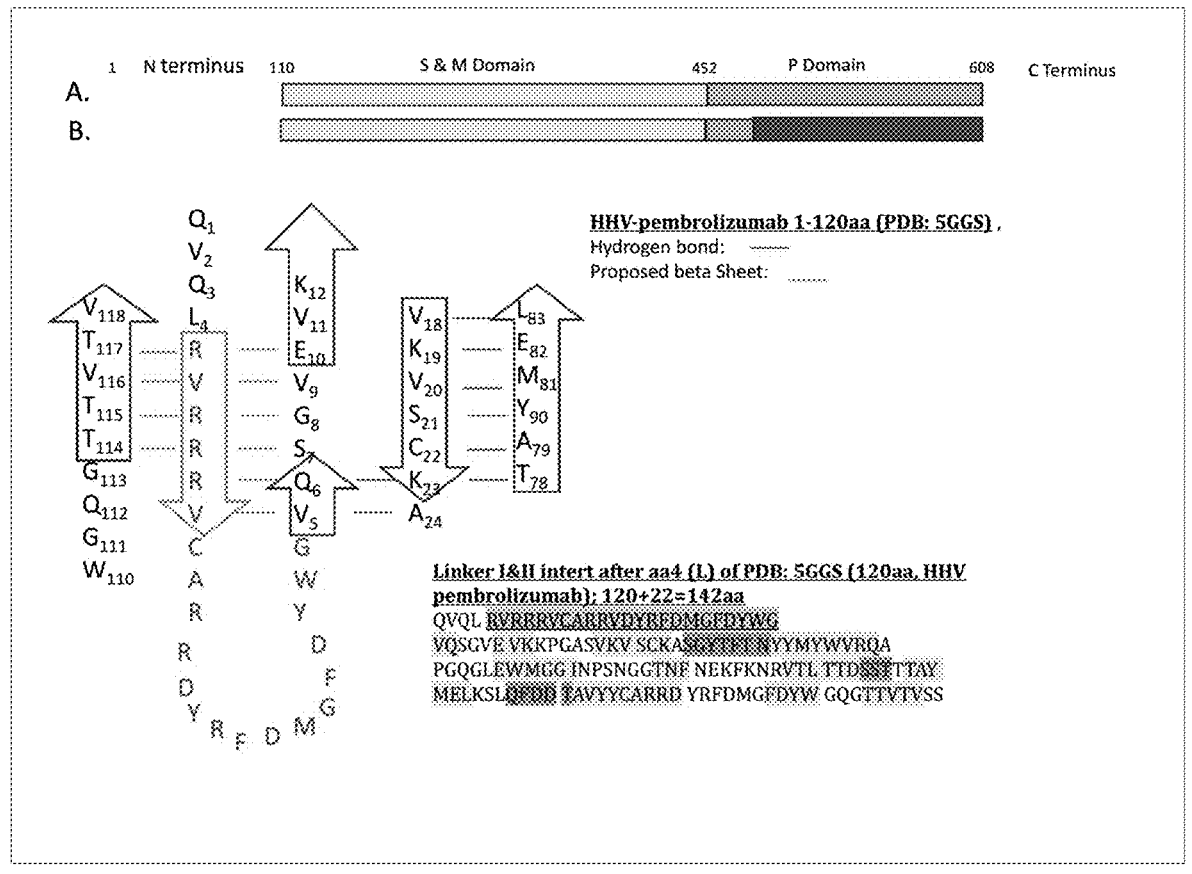
FIG. 25: sets forth an illustration entitled "NCT-006: HHV of mAb plus additional linker replace the P domain of the N/C terminus deleted version of Proposed Consensus Sequence".

Secondary structural features generated by the Predict
Protein program suggest that double underlined regions will
have beta sheet structures shown in PDB: 5GGS by X ray
analysis, and Italic underlined regions will have alpha heli-
cal structures as shown in PDB, and 5GGS by X ray
analyses.
FIG. 24: Sets Forth an Illustration Entitled "NCT-005: HHV
of mAb Replace the P Domain of the N/C Terminus Deleted
Variant of Consensus Sequence"
FIG. 25: Sets Forth an Illustration Entitled "NCT-006: HHV
of mAb Plus Additional Linker Replace the P Domain of the
N/C Terminus Deleted Version of Proposed Consensus
Sequence"

Sequence Alignment 7: NCT-006-PORF2 (99-452 aa) fused with HHV-pembrolizumab
1-120 aa (PDB: 5GGS) with linker (22 aa), Total 496Gret: aa, (ORF2 99-608 aa,
510 aa)
AA Sequence:

(SEQ ID NO: 16)

MRRRSAPAGA APLTAVAPA PDTAPVPDVD SRGAILRRQY NLSTSPLTSS VASGTNLV LYAAPLNPLL

-continued

```
PLQDGTNTHI MATEASNYAQ YRVVRATIRY RPLVPNAVGG YAISISFWPQ TTTTPTSVDM NSITSTDVRI

LVQPGIASEL VIPSERLHYR NQGWRSVETS GVAEEEATSG LVMLCIHGSP VNSYTNTPYT GALGLLDFAL

ELEFRNLTPG NTNTRVSRYS STARHRLRRG ADGTAELTTT AATRFMKDLH FTGTNGVGEV GRGIALTLFN

LADTLLGGLP TELISSAGGQ LFYSRPVVSA NGEPTVKLYT SVENAQQDKG IAIPHDIDLG ESRVVIQDYD

NQHEQDRPTP SPAPSRP

QVQLRVRRRVCARRVDYRFDMGFDYWGVQSGVE VKKPGASVKV SCKASGYTFT NYYMYWVRQA

PGQGLEWMGGINPSNGGTNF NEKFKNRVTL TTDSSTTTAY MELKSLQFDD TAVYYCARRD YRFDMGFDYW

GQGTTVTVSS
```

```
                                                      MRR

RSAPAGAAPLTAVAPAPDTAPVPDVDSRGAILRRQYNLSTSPLTS

SVASGTNLVLYAAPLNPLLPLQDGTNTHIMATEASNYAQYRVVRA

TIRYRPLVPNAVGGYAISISFWPQTTTTPTSVDMNSITSTDVRIL

VQPGIASELVIPSERLHYRNQGWRSVETSGVAEEEATSGLVMLCI

HGSPVNSYTNTPYTGALGLLDFALELEFRNLTPGNTNTRVSRYSS

TARHRLRRGADGTAELTTTAATRFMKDLHFTGTNGVGEVGRGIAL

TLFNLADTLLGGLPTELISSAGGQLFYSRPVVSANGEPTVKLYTS

VENAQQDKGIAIPHDIDLGESRVVIQDYDNQHEQDRPTPSPAPSR

PQVQLRVRRRVCARRVDYRFDMGFDYWGVQSGVEVKKPGASVKVS

CKASGYTFTNYYMYWVRQAPGQGLEWMGGINPSNGGTNFNEKFKN

RVTLTTDSSTTTAYMELKSLQFDDTAVYYCARRDYRFDMGFDYWG

QGTTVTVSS
```

Amino acids 99-111 (RRRSAPAGAAPLT) contains RRR that could enhance the encapsulation rate of negatively-charged payloads;

Underlines: Linker I and Linker II

Double underlines: beta sheet structure by secondary structure prediction by PredictProtein. Linker I and II: (to form additional beta sheet (I) and Hairpin (II) to turn the HCDR3 of HHV to face outward):

RVRRRV    (forming    beta    sheet);    and
    CARRDYRFDMGFDYWG (forming hairpin, HCDR-3).

Linker I&II insert after aa4 (L) of PDB: 5GGS (120aa, HHV pembrolizumab); 120+22=142aa The ability of chimeric nanobody-HEVNPs to bind and deliver of compounds to specific target sites on different kinds of cells, including breast cancer cells expressing HER2 antigens will be evaluated in a variety of established in vitro and in vivo assay systems. The ability to encapsulate different kinds of payloads, such as DNA, mRNA, tRNA, RNP, and inorganic molecules within Virus-Like Particles, are evaluated using established protocols. Routes of administration are evaluated in animals, including delivery to mucosal membranes by intranasal or oral means, or by intravenous injection methods.

```
QVQL RVRRRVCARRVDYRFDMGFDYWG.

VQSGVE VKKPGASVKV SCKASGYTFT NYYMYWVRQA PGQGLEWMGG

INPSNGGTNF NEKFKNRVTL TTDSSTTTAY MELKSIQFDD T AVYYCARRD YRFDMGFDYW GQGTTVTVSS
```

Underlines: Linker I and Linker II;

Double underlines: beta sheet structure shown in PDB: 5GGS by X ray;

Italic Underlines: alpha Helix structure shown in PDB and 5GGS by X ray analyses.

The HCDR3 region directed against PD-1 may be facing outward after inserting additional peptides that form beta sheets that stabilize the structure of the nanobody.

Statements Regarding Specific Aspects, Various Modifications, and Alternatives, are Meant to be Illustrative and not Limiting as to the Scope of the Invention While specific aspects of the invention have been described in detail, it will be appreciated by those skilled in the art that various modifications and alternatives to those details could be developed in light of the overall teachings of the disclosure. It is recognized that a number of variations can be made to this invention as it is currently described but which do not depart from the scope and spirit of the invention without compromising any of its advantages. These include substitution of different genetic elements particularly for improving the expression of heterologous genes in the host cell, including genetic elements for expression in eukaryotic cells other than those specified. Accordingly, the particular arrangements disclosed are meant to be illustrative only, and not limiting as to the scope of the invention, which is to be given the full breadth of the appended claims, and any equivalent thereof.

BIBLIOGRAPHY

Statement Regarding Incorporation by Reference of Journal Articles and Patent Documents All references, patents, or applications cited herein are incorporated by reference in their entirety, as if written herein.

PATENT DOCUMENTS

CHENG, R. H. and XING, L. (2014) Proteolysis-resistant capsid of chimeric hepatitis E virus as an oral delivery vector. U.S. Pat. No. 8,906,863 B2.

CHENG, R. H., XING, L., CHEN, C. C. and STARK, M. C. (2015) Chemically-activated nanocapsid functionalized for cancer targeting. WO 2017/0107261 A2.

JOURNAL ARTICLES

ANSELMO, A. C. and MITRAGOTRI, S. (2016) Virus-Like Particles in the clinic. Bioeng Transl Med 1 (1): 10-29.

ANSELMO, A. C. and MITRAGOTRI, S. (2021) Virus-Like Particles in the clinic: An update post covid-19 vaccines. Bioeng Transl Med 6 (3): e10246.

ATTAR, M. M. and HAGHPANAHI, M. (2016) Effect of heat dissipation of superparamagnetic Virus-Like Particles in alternating magnetic field on three human cancer cell lines in magnetic fluid hyperthermia. Electromagn Biol Med 35 (4): 305-320.

BAIKOGHLI, M. A. C., C. C.; CHENG, R. H. (2018) Hepatitis E Virus-Like Particle: A capsid-based platform for non-invasive vaccine delivery and imaging-guided cancer treatment. Advanced Research in Gastroenterology & Hepatology 9 (1).

BARR, S. M., KECK, K. and APOSHIAN, H. V. (1979) Cell-free assembly of a polyoma-like particle from empty capsids and DNA. Virology 96:656-9.

BUEHLER, D. C., MARSDEN, M. D., SHEN, S., TOSO, D. B., WU, X., LOO, J. A., ZHOU, Z. H., KICKHOEFER, V. A., WENDER, P. A., ZACK, J. A. and ROME, L. H. (2014) Bioengineered vaults: Self-assembling protein shell-lipophilic core Virus-Like Particles for drug delivery. ACS Nano 8 (8): 7723-7732.

CASSIM, S. M., GIUSTINI, A. J., BAKER, I. and HOOPES, P. J. (2011) Development of novel magnetic Virus-Like Particles for hyperthermia cancer therapy. Proc SPIE Int Soc Opt Eng 7901:790115.

CHEN C C, S. M., BAIKOGHLI M A, CHENG R H (2017) Virus-Like Particle encapsulating nano-theranostic reagent as modularized capsule. Adv Res Gastroentero Hepatol 5 (5): 555674.

CHEN, C. C., BAIKOGHLI, M. A., and CHENG, R. H. (2018) Tissue targeted nanocapsids for oral insulin delivery via drink. Pharm Pat Anal, 7:121-27.

CHEN, C. C., STARK, M., BAIKOGHLI, L. and CHENG, R. H. (2018) Surface Functionalization of Hepatitis E Virus-Like Particles Using Chemical Conjugation Methods. JoVE (Journal of Visualized Experiments) 135: e57020.

CHEN, C. C., BAIKOGHLI, M. A. and CHENG, R. H. (2018) Tissue targeted nanocapsids for oral insulin delivery via drink. Pharm Pat Anal 7 (3): 121-127.

CHEN, C. C., BAIKOGHLI, M. A. and CHENG, R. H. (2021) Protein-based nanoplatform for detection of tumorigenic polyps in the colon via noninvasive mucosal routes. Pharm Pat Anal 10 (1): 13-24.

CHEN, C. C., XING, L., STARK, M., OU, T., HOLLA, P., XIAO, K., KAMITA, S. G., HAMMOCK, B. D., LAM, K. and CHENG, R. H. (2016) Chemically-activatable viral capsid functionalized for cancer targeting. Nanomedicine (Lond) 11 (4): 377-390.

DEVARAKONDA, S. B., MYERS, M. R. and BANERJEE, R. K. (2018) Comparison of heat transfer enhancement between magnetic and gold Virus-Like Particles during HIFU sonication. J Biomech Eng 140 (8).

DEVARAKONDA, S. B., MYERS, M. R., GIRIDHAR, D., DIBAJI, S. A. and BANERJEE, R. K. (2017) Enhanced thermal effect using magnetic nano-particles during high-intensity focused ultrasound. PLoS One 12 (4): e0175093.

DEVARAKONDA, S. B., MYERS, M. R., LANIER, M., DUMOULIN, C. and BANERJEE, R. K. (2017) Assessment of gold Virus-Like Particle-mediated-enhanced hyperthermia using MR-guided high-intensity focused ultrasound ablation procedure. Nano Lett 17 (4): 2532-2538.

ESPINOSA, A., DI CORATO, R., KOLOSNJAJ-TABI, J., FLAUD, P., PELLEGRINO, T. and WILHELM, C. (2016) Duality of iron oxide Virus-Like Particles in cancer therapy: Amplification of heating efficiency by magnetic hyperthermia and photothermal bimodal treatment. ACS Nano 10 (2): 2436-2446.

FATH-GOODIN, A., KROEMER, J., MARTIN, S., REEVES, K., and WEBB., B. A. (2006) Polydnavirus Genes that Enhance the Baculovirus Expression Vector System. in, Advances in Virus Research (Academic Press).

GALAWAY, F. A., and STOCKLEY. P. G. (2013) MS2 virus-like particles: a robust, semisynthetic targeted drug delivery platform. Mol Pharm 10:59-68.

GLASEL, J. A. (1995) Validity of nucleic acid purities monitored by 260 nm/280 nm absorbance ratios. Biotechniques 18:62-3.

GUU, T., LIU, Z., YE, Q., MATA, D., LI, K., LIN, C., ZHANG, J. and Y TAO, T. (2009) Structure of the hepatitis E virus-like particle suggests mechanisms for virus assembly and receptor binding. Proc Natl Acad Sci USA 106:12992-97.

HIYOSHI, M., KAGESHIMA, A, KATO, T., and PARK, E. Y. (2007) Construction of a cysteine protease deficient Bombyx mori multiple nucleopolyhedrovirus bacmid and its application to improve expression of a fusion protein. J Virol Methods 144:91-7.

HOLLA, P., BAIKOGHLI, M. A., SOONSAWAD, P. and CHENG, R. H. (2017) Chapter 16-Toward mucosal DNA delivery: Structural modularity in vaccine platform design. Micro and nanotechnology in vaccine development. SKWARCZYNSKI, M. and TOTH, I., William Andrew Publishing: 303-326.

HOM, L. G., OHKAWA, T., TRUDEAU, D., and VOLKMAN, L. E. (2002) *Autographa californica* M nucleopolyhedrovirus ProV-CATH is activated during infected cell death. *Virology* 296:212-8.

HUGHES, K. A., MISRA, B., MAGHAREH, M. and BOBBALA, S. (2023) Use of stimulatory responsive soft Virus-Like Particles for intracellular drug delivery. *Nano Res:* 1-17.

HUTCHINSON, E. G., SESSIONS, R. B., THORNTON, J. M. and WOOLFSON, D. N. (1998) Determinants of strand register in antiparallel beta-sheets of proteins. *Protein Sci* 7 (11): 2287-2300.

ITO, A., HONDA, H. and KOBAYASHI, T. (2006) Cancer immunotherapy based on intracellular hyperthermia using magnetite Virus-Like Particles: A novel concept of "heat-controlled necrosis" with heat shock protein expression. *Cancer Immunol Immunother* 55 (3): 320-328.

ITO, A., SHINKAI, M., HONDA, H., YOSHIKAWA, K., SAGA, S., WAKABAYASHI, T., YOSHIDA, J. and KOBAYASHI, T. (2003) Heat shock protein 70 expression induces antitumor immunity during intracellular hyperthermia using magnetite Virus-Like Particles. *Cancer Immunol Immunother* 52 (2): 80-88.

JARIYAPONG, P., XING, L., VAN HOUTEN, N. E., LI, T. C., WEERACHATYANUKUL, W., HSIEH, B., MOSCOSO, C. G., CHEN, C. C., NIIKURA, M. and CHENG, R. H. (2013) Chimeric hepatitis e virus-like particle as a carrier for oral-delivery. *Vaccine* 31 (2): 417-424.

JEONG, T.-J., LEE, H.-T., GU, N., JANG, Y.-J., CHOI, S.-B., PARK, U.-B., LEE, S.-H. and HEO, Y.-S. (2022) The high-resolution structure reveals remarkable similarity in pd-1 binding of cemiplimab and dostarlimab, the FDA-approved antibodies for cancer immunotherapy. *Biomedicines* 10 DOI: 10.3390/biomedicines10123154.

JIAN, F., ZHANG, Y., WANG, J., BA, K., MAO, R., LAI, W. and LIN, Y. (2012) Toxicity of biodegradable nanoscale preparations. *Curr Drug Metab* 13 (4): 440-446.

KABA, S. A., SALCEDO, A. M., WAFULA, P. O., VLAK, J. M., and VAN OERS, M. M. (2004) Development of a chitinase and v-cathepsin negative bacmid for improved integrity of secreted recombinant proteins. *Journal of Virological Methods* 122:113-18.

KACZMAREK, K., HORNOWSKI, T., DOBOSZ, B. and JOZEFCZAK, A. (2018) Influence of magnetic Virus-Like Particles on the focused ultrasound hyperthermia. *Materials (Basel)* 11 (9).

KAUR, P., ALIRU, M. L., CHADHA, A. S., ASEA, A. and KRISHNAN, S. (2016) Hyperthermia using Virus-Like Particles-promises and pitfalls. *International journal of hyperthermia: The official journal of European Society for Hyperthermic Oncology, North American Hyperthermia Group* 32 (1): 76-88.

KAWANO, M., XING, L., LAM, K. S., HANDA, H., MIYAMURA, T., BARNETT, S., SRIVASTAVA, I. K. and CHENG, R. H. (2011) Design platforms of nanocapsules for human therapeutics or vaccines. *Development of vaccines*, John Wiley & Sons, Inc.: 125-139.

KIM, Y. S. (2015) Advances in MR image-guided high-intensity focused ultrasound therapy. *Int J Hyperthermia* 31 (3): 225-232.

KITTS, P. A., AYRES, M. D., and POSSEE, R. D. (1990) Linearization of baculovirus DNA enhances the recovery of recombinant virus expression vectors. *Nucleic Acids Res* 18 (19): 5667-5672.

KOSHELEVA, O. K., LAI, T.-C., CHEN, N. G., HSIAO, M. and CHEN, C.-H. (2016) Selective killing of cancer cells by Virus-Like Particle-assisted ultrasound. *Journal of Nanobiotechnology* 14 (1): 46.

LAMBIDIS, E., CHEN, C. C., BAIKOGHLI, M., IMLIMTHAN, S., KHNG, Y. C., SARPARANTA, M., CHENG, R. H. and AIRAKSINEN, A. J. (2022) Development of (68) Ga-labeled Hepatitis E Virus-Like Particles for targeted drug delivery and diagnostics with pet. *Mol Pharm* 19 (8): 2971-2979.

LAMBIDIS, E., CHEN, C.-C., LUMÉN, D., SÁNCHEZ, A. I. F., SARPARANTA, M., CHENG, R. H. and AIRAKSINEN, A. J. (2022) Biological evaluation of integrin a3B1-targeted 68ga-labeled HEVNPS in HCT 116 colorectal tumor-bearing mice. *European Journal of Pharmaceutical Sciences:* 106336.

LI, T. C., YAMAKAWA, Y., SUZUKI, K., TATSUMI, M., RAZAK, M. A., UCHIDA, T., TAKEDA, N., AND MIYAMURA, T. (1997) Expression and self-assembly of empty virus-like particles of hepatitis E virus. *J Virol* 71:7207-13.

LI, T. C., TAKEDA, N., MIYAMURA, T., MATSUURA, Y., WANG, J. C., ENGVALL, H., HAMMAR, L., XING, L. and CHENG, R. H. (2005) Essential elements of the capsid protein for self-assembly into empty virus-like particles of hepatitis e virus. *J Virol* 79 (20): 12999-13006.

LI, T.-C., SUZAKI, Y., AMI, Y., DHOLE, T. N., MIYAMURA, T., and TAKEDA, N. (2004) Protection of cynomolgus monkeys against HEV infection by oral administration of recombinant hepatitis E virus-like particles. *Vaccine,* 22:370-77.

LUDWIG, C., and WAGNER, R. (2007) Virus-like particles-universal molecular toolboxes. *Curr Opin Biotechnol* 18:537-45.

MA, Y., NOLTE, R. J., and CORNELISSEN, J. J. (2012) 'Virus-based nanocarriers for drug delivery', Adv Drug Deliv Rev, 64:811-25.

MCINTIRE, J. J., UMETSU, S. E. MACAUBAS, C. HOYTE, E. G. CINNIOGLU, C. CAVALLI-SFORZA, L. L. BARSH, G. S. HALLMAYER, J. F. UNDERHILL, P. A. RISCH, N. J. FREEMAN, G. J. DEKRUYFF, R. H. and UMETSU, D. T. (2003). Immunology: Hepatitis A virus link to atopic disease. *Nature* 425:576.

MULVANIA, T., HAYES, B., and HEDIN, D. (2004) A Flow Cytometric Assay for Rapid, Accurate Determination of Baculovirus Titers. *The BioProcessing Journal* (BPJ), 3:6.

NDEUPEN, S., QIN, Z., JACOBSEN, S., ESTANBOULI, H., BOUTEAU, A. and IGYÁRTÓ, B. Z. (2021) The mRNA-LNP platform's lipid Virus-Like Particle component used in preclinical vaccine studies is highly inflammatory. *iScience* 24 (12): 103479. PMC8604799.

NIIKURA, M., TAKAMURA, S., KIM, G., KAWAI, S., SAIJO, M., MORIKAWA, S., KURANE, I., LI, T. C., TAKEDA, N., and YASUTOMI, Y. (2002) Chimeric recombinant hepatitis E virus-like particles as an oral vaccine vehicle presenting foreign epitopes. *Virology* 293:273-80.

NILSSON, J., MIYAZAKI, N., XING, L., WU, B., HAMMAR, L., LI, T. C., TAKEDA, N., MIYAMURA, T.,

and CHENG, R. H. (2005) Structure and assembly of a T=1 virus-like particle in BK polyomavirus. *J Virol* 79:5337-45.

OLSEN, H. B., LEUENBERGER-FISHER, M. R., KADIMA, W., BORCHARDT, D. KAARSHOLM, N. C., and DUNN, M. F. (2003) Structural signatures of the complex formed between 3-nitro-4-hydroxybenzoate and the Zn(II)-substituted R(6) insulin hexamer. *Protein Sci* 12:1902-13.

PANDA, S. K., KAPUR, N., PALIWAL, D. and DURGAPAL, H. (2015) Recombinant Hepatitis E virus like particles can function as RNA nanocarriers. *Journal of Nanobiotechnology* 13:44.

PEYRET, H. (2015) A protocol for the gentle purification of virus-like particles produced in plants. *J Virol Methods* 225:59-63.

PURCEL, R. H. (1996) 'Hepatitis E virus.' in B. N. Fields, D. M. Knipe and P. M. Howley (eds.), Fields Virology (Lippincott-Raven Publishers: Philadelphia)

RICHAUD, A. D., ZHAO, G., HOBLOSS, S. and ROCHE, S. P. (2021) Folding in place: Design of β-strap motifs to stabilize the folding of hairpins with long loops. *J Org Chem* 86 (19): 13535-13547.

ROEMER, R. B. (1999) Engineering aspects of hyperthermia therapy. *Annu Rev Biomed Eng* 1:347-376.

RUSSELL, L. M., HULTZ, M. and SEARSON, P. C. (2018) Leakage kinetics of the liposomal chemotherapeutic agent doxil: The role of dissolution, protonation, and passive transport, and implications for mechanism of action. *Journal of controlled release: Official journal of the Controlled Release Society* 269:171-176.

SCHOFIELD, D. J., GLAMANN, J., EMERSON, S. U., and PURCELL, R. H. (2000) Identification by phage display and characterization of two neutralizing chimpanzee monoclonal antibodies to the hepatitis E virus capsid protein. *J Virol* 74:5548-55.

SEBESTIK, J., NIEDERHAFNER, P. and JEZEK, J. (2011) Peptide and glycopeptide dendrimers and analogous dendrimeric structures and their biomedical applications. *Amino Acids* 40 (2): 301-370.

SERKOVA, N. J. (2017) Virus-Like Particle-based magnetic resonance imaging on tumor-associated macrophages and inflammation. *Front Immunol* 8:590.

SHI, Y., VAN DER MEEL, R., CHEN, X. and LAMMERS, T. (2020) The EPR effect and beyond: Strategies to improve tumor targeting and cancer nanomedicine treatment efficacy. *Theranostics* 10 (17): 7921-7924.

SHIZUO G., KAMITA, M. A. B., LUIS M. DE LA MAZA, and CHENG, R. H. (2019) A noninvasive, orally stable, mucosa-penetrating polyvalent vaccine platform based on Hepatitis E Virus-Like Particle. Synthetic *Biology-New Interdisciplinary Science.*

SIEVERS F., WILM A., DINEEN D., GIBSON T. J., KARPLUS K., LI W., LOPEZ R., MCWILLIAM H., REMMERT M., SODING J., THOMPSON J. D. AND HIGGINS D. G. (2011) Fast, scalable generation of high-quality protein multiple sequence alignments using Clustal Omega. *Mol. Syst. Biol.* 7:539.

STARK, M. and CHENG, R. H. (2016) Surface modulatable nanocapsids for targeting and tracking toward nanotheranostic delivery. *Pharm Pat Anal* 5 (5): 307-317.

STARK, M. C., BAIKOGHLI, M. A, LAHTINEN, T., MALOLA, S., XING, L., NGUYEN, M., NGUYEN, M., SIKAROUDI, A., MARJOMAKI, V., HAKKINEN, H., and CHENG, R. H. (2017) Structural char-

56 acterization of site-modified nanocapsid with monodispersed gold clusters. *Sci Rep* 7:17048.

STARK, M., and Cheng, R. H. (2016) Surface modulatable nanocapsids for targeting and tracking toward nanotheranostic delivery. *Pharm Pat Anal* 5:307-17.

SUN, X., YAN, X., ZHUO, W., GU, J., ZUO, K., LIU, W., LIANG, L., GAN, Y., HE, G., WAN, H., GOU, X., SHI, H. and HU, J. (2018) Pd-l1 nanobody competitively inhibits the formation of the pd-1/pd-l1 complex: Comparative molecular dynamics simulations. *Int J Mol Sci* 19 (7)

TAKAMURA, S., NIIKURA, M., LI, T. C., TAKEDA, N., KUSAGAWA, S., TAKEBE, Y., MIYAMURA, T. and YASUTOMI, Y. (2004) DNA vaccine-encapsulated virus-like particles derived from an orally transmissible virus stimulate mucosal and systemic immune responses by oral administration. *Gene Ther* 11 (7): 628-635.

TAM, A. W., SMITH, M. M., GUERRA, M. E., HUANG, C. C., BRADLEY, D. W., FRY, K. E. and REYES, G. R. (1991) Hepatitis E virus (HEV): Molecular cloning and sequencing of the full-length viral genome. *Virology* 185 (1): 120-131.

VAN OERS, M. M. 2011. Opportunities and challenges for the baculovirus expression system. *Journal of Invertebrate Pathology* 107: S3-S15.

VARGASON, A. M., ANSELMO, A. C. and MITRAGOTRI, S. (2021) The evolution of commercial drug delivery technologies. *Nature Biomedical Engineering* 5 (9): 951-967.

WANG, C. Y., MIYAZAKI, N., YAMASHITA, T., HIGASHIURA, A., NAKAGAWA, A., LI, T. C., TAKEDA, N., XING, L., HJALMARSSON, E., FRIBERG, C., LIOU, D. M., SUNG, Y. J., TSUKIHARA, T., MATSUURA, Y., MIYAMURA, T. and CHENG, R. H. (2008) Crystallization and preliminary X-ray diffraction analysis of recombinant hepatitis e virus-like particle. *Acta Crystallogr Sect F Struct Biol Cryst Commun* 64 (Pt 4): 318-322.

WARD, K, FAN, Z. H. (2015) Mixing in microfluid devices and enhancement methods. *J Micromech Microeng,* 25 (9).

WU, Z., ZHUO, Z., CAI, D., WU, J., WANG, J. and TANG, J. (2015) An induction heating device using planar coil with high amplitude alternating magnetic fields for magnetic hyperthermia. *Technol Health Care* 23 Suppl 2: S203-209.

XIA, W., WANG, Y., YANG, A. and YANG, G. (2017) DNA Compaction and Charge Inversion Induced by Organic Monovalent Ions. *Polymers (Basel)* 9.

XIAO, W., LI, T., BONONI, F. C., LAC, D., KEKESSIE, I. A., LIU, Y., SANCHEZ, E., MAZLOOM, A., MA, A. H., LIN, J., TRAN, J., YANG, K., LAM, K. S. and LIU, R. (2016) Discovery and characterization of a high-affinity and high-specificity peptide ligand Ixy30 for in vivo targeting of alpha3 integrin-expressing human tumors. *EJNMMI Res* 6 (1): 18.

XING, L, LI, T. C., MIYAZAKI, N., SIMON, M. N., WALL, J. S., MOORE, M., WANG, C. Y., TAKEDA, N. WAKITA, T., MIYAMURA, T., and CHENG, R. H. (2010) Structure of hepatitis E virion-sized particle reveals an RNA-dependent viral assembly pathway. *J Biol Chem* 285:33175-83.

XING, L., WANG, J. C., LI, T. C., YASUTOMI, Y., LARA, J., KHUDYAKOV, Y., SCHOFIELD, D., EMERSON, S. U., PURCELL, R. H., TAKEDA, N.,

MIYAMURA, T., and CHENG, R. H. (2011) Spatial configuration of hepatitis E virus antigenic domain. *J Virol* 85:1117-24.

XING, L., KATO, K., LI, T., TAKEDA, N., MIYAMURA, T., HAMMAR, L. and CHENG, R. H. (1999) Recombinant hepatitis E capsid protein self-assembles into a dual-domain T=1 particle presenting native virus epitopes. *Virology* 265 (1): 35-45.

XING, L., LI, T. C., MAYAZAKI, N., SIMON, M. N., WALL, J. S., MOORE, M., WANG, C. Y., TAKEDA, N., WAKITA, T., MIYAMURA, T. and CHENG, R. H. (2010) Structure of hepatitis e virion-sized particle reveals an RNA-dependent viral assembly pathway. *J Biol Chem* 285 (43): 33175-33183.

YAMASHITA, T., MORI, Y., MIYAZAKI, N., CHENG, H., YOSHIMURA, M., UNNO, H., SHIMA, R., MORIISHI, K., TSUKIHARA, T., LI, T. C., TAKEDA,

N., MIYAMURA, T., and MATSUURA, Y. (2009) Biological and immunological characteristics of hepatitis E virus-like particles based on the crystal structure. *Proc Natl Acad Sci USA* 106:12986-91.

YU, H., LI, S. YANG, C. Y., WEI, M., SONG, C., ZHENG, Z., GU, Y., DU, H., ZHANG, J., and XIA, N. S. (2010) Homology model and potential virus-capsid binding site of a putative HEV receptor Grp78. *J Mol Model* (*In press*).

ZAFRULLAH, M., KHURSHEED, Z., YADAV, S., SAHGAL, D., JAMEEL, S. and AHMAD, F. (2004) Acidic pH enhances structure and structural stability of the capsid protein of Hepatitis E virus. *Biochem Biophys Res Commun* 313 (1): 67-73.

ZENG, C., ZHANG, C., WALKER, P. G. and DONG, Y. (2022) Formulation and delivery technologies for mRNA vaccines. *Curr Top Microbiol Immunol* 440:71-110.

SEQUENCE LISTING

```
Sequence total quantity: 16
SEQ ID NO: 1            moltype = DNA  length = 1983
FEATURE                 Location/Qualifiers
source                  1..1983
                        mol_type = other DNA
                        organism = synthetic construct
SEQUENCE: 1
atgagaccca gagcagtact tctgttgttc ctggtactgc ttccaatgct tcctgcgccg   60
ccagctggcc aaccgtcggg tcgccgtcgt ggtagacgct ctggtggagc aggtggaggc   120
ttttggggcg atagggtaga cagccaaccg tttgcgctcc catatatcca ccccacgaat   180
ccattcgcgt cagacgttgt cagtcaatcg ggagcaggcg cccgtccaag acaacctgcg   240
agacctttgg gttccgcctg gagggatcaa tcacagcgtc cggcggctgc gccgagacgc   300
agatctgcac cagcgggtgc cgctcccctg acagctgtcg cgcctgcacc ggatacagca   360
cccgtccctg atgtcgattc tagaggcgcg atattgcgca ggcagtacaa tctttctaca   420
tcgcctctca caagctctgt agccagtggt actaacctcg tactttacgc cgcgcccctg   480
aatccgttgc tccccctgca agacggcacg aacacgcaca taatggctac ggaggcctcg   540
aattacgcgc agtatcgcgt ggtcagggcc acgattagat acaggcctct cgtacctaac   600
gcagttggag gatacgccat atctatctcg ttctggcccc agactacgac gacaccgacg   660
agtgtcgaca tgaattctat taccagcacg gatgtacgca tcctcgtgca gcctggaatc   720
gcctcggagc tggtgatccc ttccgaaagg ctgcattacc gcaaccaggg ctggaggagt   780
gtggaaacca gcggtgtggc agaggaggag gcaacgtcag gactcgtaat gctgtgcata   840
cacggcagcc ctgtaaattc gtatacaaac acaccataca ccggtgcatt gggtctgctt   900
gattttgctc tcgagctgga gttcaggaat ctcactccag gtaatacaaa tacgcgcgtc   960
agcagatatt cgagtacggc gcgccatagg ctcagacgtg gtgccgacgg cacagcggaa   1020
ctcacaacca ccgcagccac gcgtttatg aaagatcttc attttacggg taccaatggc   1080
gtcggagaag taggtagggg tattgcactc actcttttca atcttgcaga cactctgctc   1140
ggaggccttc ctaccgaact tatttctagc gctggtggtc agctctttta tagcaggccg   1200
gtggtctctg ccaacggaga acctacagta aaactttata cttctgttga gaatgcgcag   1260
caagataagg gcatcgctat accacacgac atagacctcg gtgagtctcg tgtcgtaatc   1320
caggattatg acaatcagca cgaacaggat cgccctactc catcgccagc cccttcccgt   1380
ccgtttagtg tccttcgcgc caatgacgta ttgtggctta gtctcactgc ggcagaatac   1440
gatcagacaa catatggatc gtcgactaat cctatgtacg taagcgacac ggtcacattc   1500
gtaaatgttg ctaccggagc ccaagctgtt gcaaggtctc ttgattggag caaggtcacg   1560
ttggacggtc gcccgttgac taccattcag cagtactcca agaccttta tgtcttgcct   1620
ttgcgcggaa aacttagctt ttgggaggca ggaacgacca aagcaggcta tccttacaac   1680
tacaacacca ccgccagcga tcagatactt atagaaaacg ctgccggtca tagagttgca   1740
atctcgacgt ataccacttc tttgggcgca ggaccagtgt ccatatctgc tgttggtgtt   1800
ttggccccac actcagctct cgcggtcctc gaggacacag ttgactatcc cgctagggct   1860
cataccttcg acgatttctg tcccgagtgt cgtacgctcg gacttcaagg ctgcgctttc   1920
caatctactg tggccgaact gcagagactc aagatgaaag tgggaaaaac gcgcgagtac   1980
taa                                                                 1983

SEQ ID NO: 2            moltype = AA  length = 660
FEATURE                 Location/Qualifiers
source                  1..660
                        mol_type = protein
                        organism = synthetic construct
SEQUENCE: 2
MRPRAVLLLF LVLLPMLPAP PAGQPSGRRR GRRSGGAGGG FWGDRVDSQP FALPYIHPTN   60
PFASDVVSQS GAGARPRQPA RPLGSAWRDQ SQRPAAAPRR RSAPAGAAPL TAVAPAPDTA   120
PVPDVDSRGA ILRRQYNLST SPLTSSVASG TNLVLYAAPL NPLLPLQDGT NTHIMATEAS   180
NYAQYRVVRA TIRYRPLVPN AVGGYAISIS FWPQTTTTPT SVDMNSITST DVRILVQPGI   240
ASELVIPSER LHYRNQGWRS VETSGVAEEE ATSGLVMLCI HGSPVNSYTN TPYTGALGLL   300
DFALELEFRN LTPGNTNTRV SRYSSTARHR LRRGADGTAE LTTTAATRFM KDLHFTGTNG   360
VGEVGRGIAL TLFNLADTLL GGLPTELISS AGGQLFYSRP VVSANGEPTV KLYTSVENAQ   420
```

```
QDKGIAIPHD IDLGESRVVI QDYDNQHEQD RPTPSPAPSR PFSVLRANDV LWLSLTAAEY    480
DQTTYGSSTN PMYVSDTVTF VNVATGAQAV ARSLDWSKVT LDGRPLTTIQ QYSKTFYVLP    540
LRGKLSFWEA GTTKAGYPYN YNTTASDQIL IENAAGHRVA ISTYTTSLGA GPVSISAVGV    600
LAPHSALAVL EDTVDYPARA HTFDDFCPEC RTLGLQGCAF QSTVAELQRL KMKVGKTREY    660

SEQ ID NO: 3              moltype = DNA   length = 1950
FEATURE                   Location/Qualifiers
source                    1..1950
                          mol_type = other DNA
                          organism = synthetic construct
SEQUENCE: 3
atgctcccca tgctgccggc accccctgcg ggccagccat ctggacgacg acgcggaagg    60
cgtagtggag gcgcgggcgg tggtttctgg ggtgatagag tcgactcaca accttttgct    120
cttccgtata tacatcctac aaacccttc gcgtctgatg tggtgagcca gtcgggcgcg     180
ggcgctcgtc cacggcaacc agccagacct cttgggtcgg catggcgtga ccagagtcaa    240
cggccagctg cagcacctcg acgtaggagt gcacctgccg gagctgcccc cttgactgcc    300
gtggcgcctg cccctgacac cgctccggta cctgatgttg attccagagg tgcgattcta    360
agacgccagt ataatttgag cacttcgcct ttgacttcca gtgtagcgtc tggaactaac    420
cttgttctgt acgccgcccc gttaaatccg ctccttccct tacaggacgg caccaatacg    480
cacattatgg cgactgaggc ttccaactat gctcaatatc gagtggtgag agcaacgatc    540
cgatacagac cactggttcc gaatgccgtt ggagggtatg ccatttcaat aagtttctgg    600
ccacaaacca cgacaacccc gacgtcagta gacatgaact ccataacctc gaccgatgtg    660
cgcatcttgg ttcagcccgg tattgcttct gaactcgtga tacccagcga aagactgcat    720
tataggaacc aaggctggcg gtcagtcgaa acaagcggcg tcgccgagga ggaagctacc    780
tccggcctgg ttatgttgtg catccatggt tcaccggtca acagttacac taatactccc    840
tacacgggtg cgctagggtt actggacttc gcactagaat tggagtttcg taatttaacg    900
ccaggaaata ccaacactcg cgtatccagg tacagttcga cggctcgaca ccggttcgcg    960
cgtggtgctg atggaacggc tgagctcaca actactgcag caactcgctt tatgaaggac    1020
ctacacttta cgggcacaaa tggtgtcgga gaagtcggcc gtggaatcgc attaacactt    1080
tttaatctag ctgatacttt gctaggcggg ctcccaacgg agctgatctc aagcgctgga    1140
gggcagcttt tctattctcg gcctgtggta tctgcgaatg gcgaaccac ggttaaactt     1200
tatacatccg tagaaaacgc tcaacaggat aaaggcatag cgattccaca tgatatagat    1260
ctaggggaaa gtcgagttgt aatccaggac tatgataacc agcacgagca agaccggccc    1320
acgccgtcac ctgccccatc gcgaccattc tccgtgctac gggcgaatga cgtactatgg    1380
ctctcccctca cagccgcgga atacgatcaa accacatatg gaagtagcac gaattgtccc   1440
atgtacgtaa gcgacaccgt gacatttgtt aacgtcgcaa ctggtgcaca agctgttgcg    1500
aggagcttag actggtcaaa ggtcacattg gatgggcgcc cgctcactac catccaacaa    1560
tattctaaaa ctttctacgt gctgccgctg cgtgggaagc tctcattctg ggaagctggg    1620
acgacaaagg caggataccc ttataactat aacacgacgg catccgatca gatttttaata   1680
gagaacgcag ccggacatag agtcgccatt tcgacataca caacctcgtt aggtgctgga    1740
cctgtctcga tttctgctgt tggggtcctt gcgccgcatt ctgcacttgc agtgcttgag    1800
gacaccgtag attaccccgc ccgcgcgcac accttcgacg acttttgtcc agagtgtagg    1860
acattagggc tccaaggttg cgcctttcag agcaccgtag cggagctgca gcggcttaaa    1920
atgaaagttg ggaagaccag ggaatactaa                                     1950

SEQ ID NO: 4              moltype = AA   length = 649
FEATURE                   Location/Qualifiers
source                    1..649
                          mol_type = protein
                          organism = synthetic construct
SEQUENCE: 4
MLPMLPAPPA GQPSGRRRGR RSGGAGGGFW GDRVDSQPFA LPYIHPTNPF ASDVVSQSGA    60
GARPRQPARP LGSAWRDQSQ RPAAAPRRRS APAGAAPLTA VAPAPDTAPV PDVDSRGAIL    120
RRQYNLSTSP LTSSVASGTN LVLYAAPLNP LLPLQDGTNT HIMATEASNY AQYRVVRATI    180
RYRPLVPNAV GGYAISISFW PQTTTTPTSV DMNSITSTDV RILVQPGIAS ELVIPSERLH    240
YRNQGWRSVE TSGVAEEEAT SGLVMLCIHG SPVNSYTNTP YTGALGLLDF ALELEFRNLT    300
PGNTNTRVSR YSSTARHRLR RGADGTAELT TTAATRFMKD LHFTGTNGVG EVGRGIALTL    360
FNLADTLLGG LPTELISSAG GQLFYSRPVV SANGEPTVKL YTSVENAQQD KGIAIPHDID    420
LGESRVVIQD YDNQHEQDRP TPSPAPSRPF SVLRANDVLW LSLTAAEYDQ TTYGSSTNCP    480
MYVSDTVTFV NVATGAQAVA RSLDWSKVTL DGRPLTTIQQ YSKTFYVLPL RGKLSFWEAG    540
TTKAGYPYNY NTTASDQILI ENAAGHRVAI STYTTSLGAG PVSISAVGVL APHSALAVLE    600
DTVDYPARAH TFDDFCPECR TLGLQGCAFQ STVAELQRLK MKVGKTREY                649

SEQ ID NO: 5              moltype = DNA   length = 1497
FEATURE                   Location/Qualifiers
source                    1..1497
                          mol_type = other DNA
                          organism = synthetic construct
SEQUENCE: 5
atggccgttg ctccagctca cgacacgcct ccggttccag acgtcgattc gagaggggcc    60
atattgcgaa gacaatataa tctttcaacg tcacccctaa caagttctgt ggctacggga    120
acaaatctgg tactctacgc ggcgcccctt cgccactac taccctcca agacggcacc      180
aacacccata tcatggccac agaagcatct aattacgcac aatatcgcgt ggcacgcgct    240
accataagat acaggcctct ggtaccgaac gccgtaggag gttacgcgat ttccatttca    300
ttctggcctc agacaacaac tacgccaacg tcagtggata tgaactcaat tactagcacg    360
gatgtgcgga tttttagtcca gcctgggatt gctagtgagc tagtaatccc gagcgaaagg    420
cttcactatc gaaccagggg ctggcggtcc gttgagacga gcggcgtagc ggaagaggag    480
gccacctccg gtttggtcat gctgtgtata catggatcat tggtaaacag ttacactaac    540
acaccgtata cgggtgccct aggcctactt gatttcgcgt tagagctcga gtttaggaat    600
```

-continued

```
ctcacgcccg gaaatactaa tacacgggtg tcccgttatt ctagtaccgc aaggcatcga  660
ctgcggcgtg gtgcagatgg gacggccgaa ctgacgacga ccgccgcaac acgcttcatg  720
aaggacctat actttaccag caccaatggg gtcggggaaa ttggacgtgg gattgccctc  780
acccttttta acttggctga cacactgttg ggcgggttac ccactgaact aatatcttcc  840
gcaggcggtc agctttttta ttctagacca gtagtgtctg ctaacggtga acctactgtg  900
aagttgtaca cgtcagtcga aaacgctcag caagacaagg gtatcgcaat accacatgac  960
atcgatctcg gcgagagtcg ggtagtgatc caggattacg ataatcaaca tgagcaagac  1020
cgtcccaccc cgagccccgc tcctagccgc ccgttctcgg tgctgcgtgc gaacgacgtt  1080
ctttggctga gtttaactgc ggcggagtat gaccaaagta cttatggctc tagtacaggg  1140
cctgtttacg tatcggatag cgtaactttg gtcaatgttg ctacaggcgc tcaggccgtg  1200
gcgaggtcgc ttgactggac taaggttact ctcgatggac gaccgctatc gactatacaa  1260
cagtattcta aaaccttctt tgtcctgcca ttgcgaggaa aattatcatt ttgggaagca  1320
ggtacaacca aagccggata tccgtacaat tataatacca cagcctccga tcaactctta  1380
gttgagtgcg ccgcgggaca ccgcgtcgcg atcagcactt cacgacttc cttaggtgca  1440
gggcccgtct cgatatcggc agtggcggtt ttggctccac actccgcatt agcctaa     1497

SEQ ID NO: 6                  moltype = AA  length = 498
FEATURE                       Location/Qualifiers
source                        1..498
                              mol_type = protein
                              organism = synthetic construct
SEQUENCE: 6
MAVAPAHDTP PVPDVDSRGA ILRRQYNLST SPLTSSVATG TNLVLYAAPL SPLLPLQDGT  60
NTHIMATEAS NYAQYRVARA TIRYRPLVPN AVGGYAISIS FWPQTTTTPT SVDMNSITST  120
DVRILVQPGI ASELVIPSER LHYRNQGWRS VETSGVAEEE ATSGLVMLCI HGSLVNSYTN  180
TPYTGALGLL DFALELEFRN LTPGNTNTRV SRYSSTARHR LRRGADGTAE LTTTAATRFM  240
KDLYFTSTNG VGEIGRGIAL TLFNLADTLL GGLPTELISS AGGQLFYSRP VVSANGEPTV  300
KLYTSVENAQ QDKGIAIPHD IDLGESRVVI QDYDNQHEQD RPTPSPAPSR PFSVLRANDV  360
LWLSLTAAEY DQSTYGSSTG PVYVSDSVTL VNVATGAQAV ARSLDWTKVT LDGRPLSTIQ  420
QYSKTFFVLP LRGKLSFWEA GTTKAGYPYN YNTTASDQLL VECAAGHRVA ISTYTTSLGA  480
GPVSISAVAV LAPHSALA                                                498

SEQ ID NO: 7                  moltype = DNA  length = 1605
FEATURE                       Location/Qualifiers
source                        1..1605
                              mol_type = other DNA
                              organism = synthetic construct
SEQUENCE: 7
atggccggtt cctggctacg agacatctgg gactggatat gtgaagtttt gtccgatttc  60
aaaacctggc tgaaggcaaa agccaaactt atgccgacaa tgcttactgc ggtggctcca  120
gcacccgata ccgcaccggt gccagacgtt gattccagag gggctatttt acgtcgccaa  180
tacaacctct ctacatcgcc tctaacaagc tcagttgcta gcgggactaa cttagtacta  240
tatgctgcgc ctttaaatcc cctgctgcca ctgcaggatg ggactaacac acatataatg  300
gcgaccgagg caagtaacta cgcccaatat cgcgtggtaa gagcaaccat acggtacagg  360
cctttggtgc cgaatgctgt aggcgggtat gctatatcta tttcgttctg gccccagacg  420
acaactaccc caacttctgt ggatatgaac tccatcactt ctactgatgt gcgtatactc  480
gtccaacccg gtatcgctag tgaactagta atcccctcgg agagattgca ctatcgcaat  540
cagggttggc gaagcgtcga aacctcaggt gtagcggaag aggaagcaac ttccgggtta  600
gtgatgctgt gtatccacgg atcaccggtg aattcttata caaatacgcc gtatacggga  660
gccctcggac tcctcgactt cgcattggag cttgaattca ggaacctaac tccaggaaat  720
acaaacacca gggtttcccg ctacagttcc acagcccggc atcggcttcg gcgtggtgca  780
gacggcactg cagagttgac cacaacagcc gctactcggt ttatgaagga ccttcatttt  840
acagggacga atggagttgg agaggttggg cgtggcatag ccttgacctt gttcaactta  900
gcggatacgc tcctaggagg cctcccgacc gaacttattt cgtcggctgg cggccagctg  960
ttctattctc gaccagtcgt ctcggcaaac ggcgaaccta cagtgaagct ctatacgtca  1020
gttgagaacg cccaacaaga caaaggtatt gctatcccgc atgatatcga ccttggagag  1080
agccgagtcg taattcagga ttatgacaac cagcacgaac aggatcgccc cacgccatca  1140
cccgctccta gccgtccgtt tagcgtattg cgagcgaatg atgtactctg ttaagccta   1200
acggccgcgg aatatgatca aacgacgtac ggttcatcca ctaactgccc aatgtacgta  1260
tcagacacag tgacctttgt caatgtcgcg actggagccc aagcagtcgc taggagtctt  1320
gactggagta aggtcacgtt ggatggcaga cctctgacga caattcagca atacagtaaa  1380
accttttatg tactaccact tagaggtaag ttatcgtttt gggaggcagg caccacgaag  1440
gcgggttacc cctacaatta caatactacc gcctctgacc agatactgat cgagaatgcc  1500
gcgggacaca gggttgccat aagcacctac acgacgtctc taggcgcggg gcctgttagt  1560
attagtgctg ttggggtatt agcccctcat tcagcactcg cgtaa                 1605

SEQ ID NO: 8                  moltype = AA  length = 534
FEATURE                       Location/Qualifiers
source                        1..534
                              mol_type = protein
                              organism = synthetic construct
SEQUENCE: 8
MAGSWLRDIW DWICEVLSDF KTWLKAKAKL MPTMLTAVAP APDTAPVPDV DSRGAILRRQ  60
YNLSTSPLTS SVASGTNLVL YAAPLNPLLP LQDGTNTHIM ATEASNYAQY RVVRATIRYR  120
PLVPNAVGGY AISISFWPQT TTTPTSVDMN SITSTDVRIL VQPGIASELV IPSERLHYRN  180
QGWRSVETSG VAEEEATSGL VMLCIHGSPV NSYTNTPYTG ALGLLDFALE LEFRNLTPGN  240
TNTRVSRYSS TARHRLRRGA DGTAELTTTA ATRFMKDLHF TGTNGVGEVG RGIALTLFNL  300
ADTLLGGLPT ELISSAGGQL FYSRPVVSAN GEPTVKLYTS VENAQQDKGI AIPHDIDLGE  360
SRVVIQDYDN QHEQDRPTPS PAPSRPFSVL RANDVLWLSL TAAEYDQTTY GSSTNCPMYV  420
```

```
SDTVTFVNVA TGAQAVARSL DWSKVTLDGR PLTTIQQYSK TFYVLPLRGK LSFWEAGTTK    480
AGYPYNYNTT ASDQILIENA AGHRVAISTY TTSLGAGPVS ISAVGVLAPH SALA          534

SEQ ID NO: 9              moltype = DNA   length = 1539
FEATURE                   Location/Qualifiers
source                    1..1539
                          mol_type = other DNA
                          organism = synthetic construct
SEQUENCE: 9
atgcgccgta gatcggcgcc ggccggtgcg gcacctctaa cagctgtcgc gccggctccg    60
gatacagcac cggttccaga tgtagattcc cgtggtgcaa tcctacgacg tcaatataat    120
ctctccacgt caccgctcac ttccagcgta gcaagtggaa cgaatttagt tttgtacgct    180
gcccccctaa accccttgtt acctttacaa gacggaacaa atacccacat catggctact    240
gaggcttcta actatgcgca atataggggt gtaagggcaa ctattcgtta tagacctctc    300
gtacctaatg ctgttggagg ttatgctatc agcatctcgt tttggcccca gactacgact    360
acgcccactt ccgtagatat gaacagcatt acttcaactg acgtgcgcat actggtacag    420
cccggcatcg caagtgaact tgtcatcccc agcgagcgtt acattaccg caatcaggga     480
tggagatcag tggaaacatc tggagtggcc gaagaagagg ccacatcggg gctcgttatg    540
ctgtgcattc atgggtcgcc ggtaaatagt tacactaaca cgccatatac cggtgcgttg    600
gggctactcg atttcgcgct ggaattagaa tttcgaaacc tcacgccagg taacactaat    660
acgcgagtat ccaggtatag tagtaccgca cgccatcggc tgcggagggg agctgatggg    720
acagctgagc tgaccacaac tgcggccacc cgtttcatga aggatcttca cttcacagga    780
accaacggtg tcggtgaggt cggcagaggg atagccattga ccttattcaa tctggcggac    840
accttacttg gagggcttcc tacggaactg ataagtagtg ccggggggcca gctattttac    900
tctagaccag tcgtctcagc gaatggtgaa cctactgtga agttatatac aagcgttgag    960
aacgctcagc aagacaaagg catagctatt ccgcacgaca tagacttggg cgaaagccga    1020
gttgtcatac aagattatga taaccaacac gagcaggacc ggccaacccc ttctccggca    1080
ccctcaaggc cctttcggt tttgcggggcc aatgacgtac tgtggttatc gcttacggca    1140
gcggaatacg atcaaactac ctacggttca tccacaaact gtccaatgta cgtctctgat    1200
acggtaacct ttgtgaatgt tgcgacgggc gcccaagcgg tggctcgctc actcgactgg    1260
agcaaagtta cgctagacgg acggccacta acgacaattc aacagtactc caagactttc    1320
tacgttctcc ctttgcgagg aaagctttcg ttctgggagg ccgggacaac caaagccggt    1380
tacccgtata actacaacac aaccgcatct gaccagattc taatagagaa tgccgcaggc    1440
catcgagtgg ccatctcaac atataccacg tctcttggcg cagggccagt ctccatttcg    1500
gctgtgggcg tgttggcacc tcatagtgcc ctcgcgtaa                          1539

SEQ ID NO: 10             moltype = AA   length = 512
FEATURE                   Location/Qualifiers
source                    1..512
                          mol_type = protein
                          organism = synthetic construct
SEQUENCE: 10
MRRRSAPAGA APLTAVAPAP DTAPVPDVDS RGAILRRQYN LSTSPLTSSV ASGTNLVLYA    60
APLNPLLPLQ DGTNTHIMAT EASNYAQYRV VRATIRYRPL VPNAVGGYAI SISFWPQTTT    120
TPTSVDMNSI TSTDVRILVQ PGIASELVIP SERLHYRNQG WRSVETSGVA EEEATSGLVM    180
LCIHGSPVNS YTNTPYTGAL GLLDFALELE FRNLTPGNTN TRVSRYSSTA RHRLRRGADG    240
TAELTTTAAT RFMKDLHFTG TNGVGEVGRG IALTLFNLAD TLLGGLPTEL ISSAGGQLFY    300
SRPVVSANGE PTVKLYTSVE NAQQDKGIAI PHDIDLGESR VVIQDYDNQH EQDRPTPSPA    360
PSRPFSVLRA NDVLWLSLTA AEYDQTTYGS STNCPMYVSD TVTFVNVATG AQAVARSLDW    420
SKVTLDGRPL TTIQQYSKTF YVLPLRGKLS FWEAGTTKAG YPYNYNTTAS DQILIENAAG    480
HRVAISTYTT SLGAGPVSIS AVGVLAPHSA LA                                 512

SEQ ID NO: 11             moltype = DNA   length = 1623
FEATURE                   Location/Qualifiers
source                    1..1623
                          mol_type = other DNA
                          organism = synthetic construct
SEQUENCE: 11
atgagacgac gaagtgcccc ggccggggcg gcacccctca cggctgtcgc acctgctccc    60
gacacagctc ccgtccctga tgttgattcc cgcggagcga tcttaaggcg gcagtataac    120
ttgtccactt caccactcac gagctcggtg gccagcggta ctaatctggt attatacgct    180
gcaccgttaa atccgttgct gccactccag gatggcacga acacgcacat tatggctaca    240
gaggcatcaa actacgcgca ataccgagta gtccgggcaa ctattagata tcgtccacta    300
gtccctaatg ctgttggcgg ctacgctata tcgatctcgt tctggcctca gacaacaact    360
actccgacct ctgtggatat gaactcgatc acctccaccg acgtgcggat tctagtccaa    420
ccaggcatcg ccagcgaact ggttattccc tctgaacgtc ttcattacag gaaccagggg    480
tggagatcgg tagagacaag tggtgtggcg gaggaagaag cgaccagtgg cttggtaatg    540
ttatgtatac acggatcacc tgtaaacagt tacactaaca ctccctatac tgggggctctg    600
ggtctgctcg atttcgcgct ggagctagag ttcagaaatc tgacgccggg gaacacaaat    660
acgcgagtat cccgctatag cagtacggcc cgccataggc tgcgccgagg ggctgacggg    720
acggcggagc ttacgaccac agccgcgact cgtttttatga aggacttgca ttttaccggc    780
accaacggag ttgggaagt cggtcgtggt atagccctaa cgctatttaa tttggcggac    840
acccttcttg gaggactacc gacagagctc ataagcagtc aggcggaca gttattctat    900
tcacgcccg tagtctctgc gaatggtgaa ccaaccgtta aactctacac ctctgtagag    960
aatgcgcaac aagataaggg catcgccata ccgcacgaca tagatcttgg agaatcccgt    1020
gttgtaattc aagactacga caaccagcac gaacaggaca ggcctacccc ctctccagca    1080
ccttccaggc cattctccgt gctaagagcc aatgacgtct tgtggctttc attaactgcc    1140
gctgaatacg accaaaccac atatggcagt tccacgaatt gccccatgta tgtgtcagac    1200
acggtcacat ttgtgaatgt agctactggt gctcaagcgg tggcgcgctc actcgattgg    1260
```

```
tctaaagtga cattggatgg acggccactc actacaatcc aacagtattc aaagactttt    1320
tatgttctcc cattgcgtgg taagctttcg ttttgggagg ctggaacgac taaggcaggt    1380
tacccgtaca actacaacac caccgcaagc gatcaaattc tcatcgaaaa tgctgccggt    1440
caccgggttg caataagtac atatacaacg tctttaggcg cagggccagt ttcaatttcg    1500
gcggtggggg tcttggcacc tcatagcgcc ttagcccagc ctgagcttgc gcctgaggac    1560
ccggaggatg aaaaagaaaa atgtttcacc ccacggggag atatgccggg gccctattgc    1620
taa                                                                  1623

SEQ ID NO: 12              moltype = AA   length = 540
FEATURE                    Location/Qualifiers
source                     1..540
                           mol_type = protein
                           organism = synthetic construct
SEQUENCE: 12
MRRRSAPAGA APLTAVAPAP DTAPVPDVDS RGAILRRQYN LSTSPLTSSV ASGTNLVLYA    60
APLNPLLPLQ DGTNTHIMAT EASNYAQYRV VRATIRYRPL VPNAVGGYAI SISFWPQTTT    120
TPTSVDMNSI TSTDVRILVQ PGIASELVIP SERLHYRNQG WRSVETSGVA EEEATSGLVM    180
LCIHGSPVNS YTNTPYTGAL GLLDFALELE FRNLTPGNTN TRVSRYSSTA RHRLRRGADG    240
TAELTTTAAT RFMKDLHFTG TNGVGEVGRG IALTLFNLAD TLLGGLPTEL ISSAGGQLFY    300
SRPVVSANGE PTVKLYTSVE NAQQDKGIAI PHDIDLGESR VVIQDYDNQH EQDRPTPSPA    360
PSRPFSVLRA NDVLWLSLTA AEYDQTTYGS STNCPMYVSD TVTFVNVATG AQAVARSLDW    420
SKVTLDGRPL TTIQQYSKTF YVLPLRGKLS FWEAGTTKAG YPYNYNTTAS DQILIENAAG    480
HRVAISTYTT SLGAGPVSIS AVGVLAPHSA LAQPELAPED PEDEKEKCFT PRGDMPGPYC    540

SEQ ID NO: 13              moltype = DNA   length = 1455
FEATURE                    Location/Qualifiers
source                     1..1455
                           mol_type = other DNA
                           organism = synthetic construct
SEQUENCE: 13
atgagaagga ggagcgctcc agcgggagcg gctcctctta cagccgtagc accggcacct    60
gacacagcac cggtgcctga tgttgactcg cgtggtgcca tactgaggcg gcagtataat    120
ctatcgactt cgccgctcac ctctagtgtt gcatcgggca caaatctcgt gctatacgcc    180
gctccattga acccgttatt gccattacaa gatgggacga atacgcatat tatggcgact    240
gaagcaagta attacgcgca atatagagtg gtccgggcaa ccatccgtta tcgcccactc    300
gtgcctaatg ctgtaggggg ttacgcgatc tcaatatcct tttggcccca gacaacaacc    360
acacctacgt ccgtcgatat gaacagtatt acttcaactg atgtccgaat attagtgcaa    420
cccggaatag cgagtgaact ggtgatcccc tctgagcgcc ttcactatcg aaaccaaggt    480
tggcgatccg tcgagacctc cggggttgct gaggaagagg cgacatccgg cctcgttatg    540
ctgtgtatcc acggaagccc cgttaacagt tacacgaaca cccccctatac aggagcctta    600
ggcttgcttg actttgctct ggaactagaa ttccggaatc taacgcctgg aaataccaac    660
acccgcgttt ctaggtactc ttctaccgct aggcatcgac tcagacgagg cgccgacgga    720
acggctgagc ttactacaac tgctgcgact cgctttatga aagacttgca tttcaccggg    780
acgaatggcg ttggggaagt cgggagaggg attgccctga cacttttcaa tctagcagat    840
actctattgg gtggactacc gactgagctg atatcaagtg ctggagggca acttttttac    900
agccgacctg tggtatctgc caacggagag ccaacagtaa agctttacac gtcggtagag    960
aacgcccaac aggacaaagg tattgcaata ccacatgaca ttgacctggg tgaatcacgg    1020
gtggttatcc aggactatga taaccagcac gaacaagatc gtccgacgcc cagcccggca    1080
ccatccaggc cacaagtaca gttggttcag agcggcgtgg aagtcaagaa gcccgggggca    1140
tcggtgaaag tatcgtgcaa ggcatccggt tatacattta cgaattacta catgtattgg    1200
gtacgtcagg ccccgggtca aggcttggag tggatggggg ggatcaatcc ttcaaatgga    1260
ggtacgaact tcaacgaaaa atttaagaac cgggtcactt taaccaccga ctccagtacg    1320
accactgcgt acatggagct caaatcttta caatttgatg ataccgcggt atattactgt    1380
gcccgccgtg attatagatt cgatatgggc ttcgactatt ggggccaggg cacaactgtc    1440
acggtcagct cataa                                                     1455

SEQ ID NO: 14              moltype = AA   length = 484
FEATURE                    Location/Qualifiers
source                     1..484
                           mol_type = protein
                           organism = synthetic construct
SEQUENCE: 14
MRRRSAPAGA APLTAVAPAP DTAPVPDVDS RGAILRRQYN LSTSPLTSSV ASGTNLVLYA    60
APLNPLLPLQ DGTNTHIMAT EASNYAQYRV VRATIRYRPL VPNAVGGYAI SISFWPQTTT    120
TPTSVDMNSI TSTDVRILVQ PGIASELVIP SERLHYRNQG WRSVETSGVA EEEATSGLVM    180
LCIHGSPVNS YTNTPYTGAL GLLDFALELE FRNLTPGNTN TRVSRYSSTA RHRLRRGADG    240
TAELTTTAAT RFMKDLHFTG TNGVGEVGRG IALTLFNLAD TLLGGLPTEL ISSAGGQLFY    300
SRPVVSANGE PTVKLYTSVE NAQQDKGIAI PHDIDLGESR VVIQDYDNQH EQDRPTPSPA    360
PSRPQVQLVQ SGVEVKKPGA SVKVSCKASG YTFTNYYMYW VRQAPGQGLE WMGGINPSNG    420
GTNFNEKFKN RVTLTTDSST TTAYMELKSL QFDDTAVYYC ARRDYRFDMG FDYWGQGTTV    480
TVSS                                                                 484

SEQ ID NO: 15              moltype = DNA   length = 1455
FEATURE                    Location/Qualifiers
source                     1..1455
                           mol_type = other DNA
                           organism = synthetic construct
SEQUENCE: 15
atgagaagga ggagcgctcc agcgggagcg gctcctctta cagccgtagc accggcacct    60
```

-continued

```
gacacagcac cggtgcctga tgttgactcg cgtggtgcca tactgaggcg gcagtataat   120
ctatcgactt cgccgctcac ctctagtgtt gcatcgggca caaatctcgt gctatacgcc   180
gctccattga acccgttatt gccattacaa gatgggacga atacgcatat tatggcgact   240
gaagcaagta attacgcgca atatagagtg gtccgggcaa ccatccgtta tcgcccactc   300
gtgcctaatg ctgtaggggg ttacgcgatc tcaatatcct tttggcccca gacaacaacc   360
acacctacgt ccgtcgatat gaacagtatt acttcaactg atgtccgaat attagtgcaa   420
cccggaatag cgagtgaact ggtgatcccc tctgagcgcc ttcactatcg aaaccaaggt   480
tggcgatccg tcgagacctc cggggttgct gaggaagagg cgacatccgg cctcgttatg   540
ctgtgtatcc acggaagccc cgttaacagt tacacgaaca ccccctatac aggagcctta   600
ggcttgcttg actttgctct ggaactagaa ttccggaatc taacgcctgg aaataccaac   660
acccgcgttt ctaggtactc ttctaccgct aggcatcgac tcagacgagg cgccgacgga   720
acggctgagc ttactacaac tgctgcgact cgctttatga aagacttgca tttcaccggg   780
acgaatggcg ttggggaagt cgggagaggt attgccctga cacttttcaa tctagcagat   840
actctattgg gtggactacc gactgagctg atatcaagtg ctggagggca actttttac    900
agccgacctg tggtatctgc caacggagag ccaacagtaa agctttacac gtcggtagag   960
aacgcccaac aggacaaagg tattgcaata ccacatgaca ttgacctggg tgaatcacgg   1020
gtggttatcc aggactatga taaccagcac gaacaagatc gtccgacgcc cagcccggcg   1080
ccatccaggc cacaagtaca gttggttcag agcggcgtgg aagtcaagaa gcccggggca   1140
tcggtgaaag tatcgtgcaa ggcatccggt tatacattta cgaattacta catgtattgg   1200
gtacgtcagg ccccgggtca aggcttggag tggatggggg ggatcaatcc ttcaaatgga   1260
ggtacgaact tcaacgaaaa atttaagaac cgggtcactt taaccaccga ctccagtacg   1320
accactgcgt acatggagct caaatcttta caatttgatg ataccgcggt atattactgt   1380
gcccgccgtg attatagatt cgatatgggc ttcgactatt ggggccaggg cacaactgtc   1440
acggtcagct cataa                                                    1455
```

```
SEQ ID NO: 16          moltype = AA   length = 484
FEATURE                Location/Qualifiers
source                 1..484
                       mol_type = protein
                       organism = synthetic construct
SEQUENCE: 16
MRRRSAPAGA APLTAVAPAP DTAPVPDVDS RGAILRRQYN LSTSPLTSSV ASGTNLVLYA   60
APLNPLLPLQ DGTNTHIMAT EASNYAQYRV VRATIRYRPL VPNAVGGYAI SISFWPQTTT   120
TPTSVDMNSI TSTDVRILVQ PGIASELVIP SERLHYRNQG WRSVETSGVA EEEATSGLVM   180
LCIHGSPVNS YTNTPYTGAL GLLDFALELE FRNLTPGNTN TRVSRYSSTA RHRLRRGADG   240
TAELTTTAAT RFMKDLHFTG TNGVGEVGRG IALTLFNLAD TLLGGLPTEL ISSAGGQLFY   300
SRPVVSANGE PTVKLYTSVE NAQQDKGIAI PHDIDLGESR VVIQDYDNQH EQDRPTPSPA   360
PSRPQVQLVQ SGVEVKKPGA SVKVSCKASG YTFTNYYMYW VRQAPGQGLE WMGGINPSNG   420
GTNFNEKFKN RVTLTTDSST TTAYMELKSL QFDDTAVYYC ARRDYRFDMG FDYWGQGTTV   480
TVSS                                                                484
```

What is claimed is:

1. A nucleotide sequence encoding a polypeptide sequence derived from a consensus of variable and invariable domains of Hepeviridae capsid proteins represented by SEQ ID NO: 02, or a variant comprising one to ten amino acid substitutions, insertions, or deletions, in islands of variability corresponding to amino acids at or spanning positions 2-3; 5-6; 8; 10-13; 18; 22-23; 25-27; 32-33-39; 42; 46;48;53-54; 63-70; 72; 74; 76; 80; 83; 85-86; 89; 91; 95-98;102-105; 108-109; 111; 113-114; 117-120; 125; 129; 146-147; 149; 153; 161; 163; 188; 207; 217; 224; 240; 244; 246; 264; 284; 289; 312-314; 318; 324; 326; 328; 330-332; 335; 343; 354; 356-358; 361; 364; 368; 370; 373; 376; 392; 395; 400; 402; 405; 408-410; 425-426; 429; 435; 448; 452; 477; 479; 483; 488; 490; 492; 494; 497-498; 500-501; 509; 511; 513; 517; 520-521; 527; 529-531; 533; 535; 537; 553-555; 562; 564; 569; 571-572; 575; 580; 587; 589-591; 593-595; 597-599; 602; 604-606; 609; 614; 616; 618-619; 623; 628; 631-632; 635; 640; 644-645; 647; 650-652; and 660; wherein said consensus polypeptide or its variant is capable of forming a Virus-Like Particle (VLP), wherein said VLP encapsulates or is conjugated to one or more molecules selected from the group consisting of nucleic acids, polypeptides, inorganic nanoparticles, or small molecule drug products.

2. The nucleotide sequence of claim 1, wherein said consensus of Hepeviridae capsid proteins is derived from the subfamily Orthohepevirinae.

3. The nucleotide sequence of claim 2, wherein said consensus of Hepeviridae capsid proteins is derived from the subfamily Orthohepevirinae, species *Paslahepevirus balayani*.

4. The nucleotide sequence of claim 1, wherein said polypeptide sequence comprises one or more conservative amino acid substitutions in variable or invariable domains of the consensus sequence.

5. The nucleotide sequence of claim 4, wherein said polypeptide sequence comprises one to ten conservative amino acid substitutions in variable domains of the consensus sequence.

6. The nucleotide sequence of claim 4, wherein said polypeptide sequence comprises one to ten conservative amino acid substitutions in invariable domains of the consensus sequence.

7. The nucleotide sequence of claim 1, wherein said polypeptide sequence comprises one to ten amino acid deletions.

8. The nucleotide sequence of claim 7, wherein said polypeptide sequence comprises a deletion at the amino, carboxy, or amino and carboxy termini of the consensus sequence.

9. The nucleotide sequence of claim 7, wherein said polypeptide sequence comprises one to ten deletions in variable domains of the consensus sequence.

10. The nucleotide sequence of claim 1, wherein said polypeptide sequence comprises one to ten amino acid insertions.

11. The nucleotide sequence of claim 10, wherein said polypeptide sequence comprises one to ten insertions in variable domains of the consensus sequence.

12. The nucleotide sequence of claim 10, wherein said polypeptide sequence one to ten insertions in invariable domains of the consensus sequence.

13. The nucleotide sequence of claim 1, wherein said polypeptide sequence comprises one to ten conservative amino acid substitutions, one to ten insertions, or one to ten deletions in variable or invariable domains of the consensus sequence.

14. The nucleotide sequence of claim 13, wherein all of said conservative amino acid substitutions, insertions or deletions are in variable domains of the consensus sequence.

15. The nucleotide sequence of claim 1, further comprising one or more insertions of DNA segments encoding heterologous polypeptides selected from the group consisting of nucleic acid binding domains, hydrophobic binding domains, hydrophilic binding domains, polypeptide binding domain, and antibody binding domains.

16. A vector comprising a nucleotide sequence of claim 1, encoding a consensus polypeptide sequence capable of forming a Virus-Like Particle.

17. The vector of claim 16, wherein said vector is baculovirus expression vector comprising a baculovirus promoter operably-linked to a nucleotide sequence encoding a consensus polypeptide sequence capable of forming a Virus-Like Particle.

18. A polypeptide sequence derived from a consensus of variable and invariable domains of Hepeviridae capsid proteins represented by SEQ ID NO: 02, or a variant comprising one to ten amino acid substitutions, insertions, or deletions, in islands of variability corresponding to amino acids at or spanning positions 2-3; 5-6; 8; 10-13; 18; 22-23; 25-27; 32-33-39; 42; 46; 48; 53-54; 63-70; 72; 74; 76; 80; 83;85-86; 89; 91; 95-98; 102-105; 108-109; 111; 113-114; 117-120; 125; 129; 146-147; 149; 153; 161; 163; 188; 207; 217; 224; 240; 244; 246; 264; 284; 289; 312-314; 318; 324; 326; 328; 330-332; 335; 343; 354; 356-358; 361; 364; 368; 370; 373; 376; 392; 395; 400; 402; 405; 408-410; 425-426; 429; 435; 448; 452; 477; 479; 483; 488; 490; 492; 494; 497-498; 500-501; 509; 511; 513; 517; 520-521; 527; 529-531; 533; 535; 537; 553-555 ; 562; 564; 569; 571-572; 575; 580; 587; 589-591; 593-595; 597-599; 602; 604-606; 609; 614; 616; 618-619; 623; 628; 631-632; 635; 640; 644-645; 647; 650-652; and 660; capable of forming a Virus-Like Particle, wherein said Virus-Like Particle encapsulates or is conjugated to one or more molecules selected from the group consisting of a nucleic acid, a polypeptide, an inorganic nanoparticle, and a small molecule drug product.

19. A Virus-Like Particle derived from a consensus of variable and invariable domains of Hepeviridae capsid proteins represented by SEQ ID NO: 02, or a variant comprising one to ten amino acid substitutions, insertions, or deletions, in islands of variability corresponding to amino acids at or spanning positions 2-3; 5-6; 8; 10-13; 18; 22-23; 25-27; 32-33-39; 42; 46; 48; 53-54; 63-70; 72; 74; 76; 80; 83; 85-86; 89; 91; 95-98; 102-105; 108-109; 111; 113-114; 117-120; 125; 129; 146-147; 149; 153; 161; 163; 188; 207; 217; 224; 240; 244; 246; 264; 284; 289; 312-314; 318; 324; 326; 328; 330-332; 335; 343; 354; 356-358; 361; 364; 368; 370; 373; 376; 392; 395; 400; 402; 405; 408-410; 425-426; 429; 435; 448; 452; 477; 479; 483; 488; 490; 492; 494; 497-498; 500-501; 509; 511; 513; 517; 520-521; 527; 529-531; 533; 535; 537; 553-555; 562; 564; 569; 571-572; 575; 580; 587; 589-591; 593-595; 597-599; 602; 604-606; 609; 614; 616; 618-619; 623; 628; 631-632; 635; 640; 644-645; 647; 650-652; and 660; wherein said Virus-Like Particle encapsulates or is conjugated to one or more molecules selected from the group consisting of a nucleic acid, a polypeptide, an inorganic nanoparticle, and a small molecule drug product.

20. A method of isolating Virus-Like Particles derived from a consensus of variable and invariable domains of Hepeviridae capsid proteins represented by SEQ ID NO: 2, or a variant comprising one to ten amino acid substitutions, insertions, or deletions in islands of variability corresponding to amino acids at or spanning positions 2-3; 5-6; 8; 10-13; 18; 22-23; 25-27; 32-33-39; 42; 46; 48; 53-54; 63-70; 72; 74; 76; 80; 83; 85-86; 89; 91; 95-98;102-105;108- 109; 111; 113-114; 117-120; 125; 129; 146-147; 149; 153; 161; 163; 188; 207; 217; 224; 240; 244; 246; 264; 284; 289; 312-314; 318; 324; 326; 328; 330-332; 335; 343; 354; 356-358; 361; 364; 368; 370; 373; 376; 392; 395; 400; 402; 405; 408-410; 425-426; 429; 435; 448; 452; 477; 479; 483; 488; 490; 492; 494; 497-498; 500-501; 509; 511; 513; 517; 520-521; 527; 529-531; 533; 535; 537; 553-555; 562; 564; 569; 571-572; 575; 580; 587; 589-591; 593-595; 597-599; 602; 604-606; 609; 614; 616; 618-619; 623; 628; 631-632; 635; 640; 644-645; 647; 650-652; and 660; comprising the steps of (a): infecting susceptible insect cells with a baculovirus expression vector comprising a nucleotide sequence encoding a Virus-Like Particle under the control of a baculovirus promoter; (2) monitoring the expression of capsid proteins over time; (3) concentrating, binding, and eluting purified capsid proteins; and (4) forming Virus-Like Particles.

21. The polypeptide sequence of claim 1, derived from a consensus of variable and invariable domains of Hepeviridae capsid proteins represented by SEQ ID NO: 02, or a variant selected from the group consisting of SEQ ID NOS: 04, 06, 08, 10, 12, 14, and 16.

22. The nucleotide sequence of claim 1, encoding a polypeptide sequence derived from a consensus of variable and invariable domains of Hepeviridae capsid proteins represented by SEQ ID NO: 2, or a variant selected from the group consisting of SEQ ID NOS: 04, 06, 08, 10, 12, 14, and 16.

23. A nucleotide sequence encoding the polypeptide sequence of claim 22.

24. The nucleotide sequence of claim 23 selected from the group consisting of SEQ ID NOS: 01, 03, 05, 07, 09, 11, 13, and 15.

25. A vector comprising the nucleotide sequence of claim 24, comprising a nucleotide sequence encoding a consensus polypeptide represented by SEQ ID NO: 2, or a variant selected from the group consisting of SEQ ID NOS: 04, 06, 08, 10, 12, 14, and 16.

26. A cell harboring the vector of claim 16.

27. An insect cell susceptible to infection by a baculovirus expression vector harboring the vector of claim 17.

28. A method of isolating Virus-Like Particles comprising the polypeptide sequence of claim 27 comprising the steps of (a): infecting susceptible insect cells with a baculovirus expression vector comprising a nucleotide sequence encoding a Virus-Like Particle under the control of a baculovirus promoter; (2) monitoring the expression of capsid proteins over time; (3) concentrating, binding, and eluting purified capsid proteins; and (4) forming Virus-Like Particles.

29. A Virus-Like Particle isolated by the method of claim 28.

30. The Virus-Like Particle of claim 19, comprising a consensus polypeptide represented by SEQ ID NO: 02, or a variant selected from the group consisting of SEQ ID NO: 04, 06, 08, 10, 12, 14, and 16.

* * * * *